US012024551B1

United States Patent
Harmon et al.

(10) Patent No.: US 12,024,551 B1
(45) Date of Patent: Jul. 2, 2024

(54) CORONAVIRUS NEUTRALIZING HUMANIZED ANTIBODIES AND USES THEREOF

(71) Applicant: National Technology & Engineering Solutions of Sandia, LLC, Albuquerque, NM (US)

(72) Inventors: Brooke Nicole Harmon, Livermore, CA (US); Maxwell Stefan, Pleasanton, CA (US); Yooli Kim Light, Pleasanton, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 249 days.

(21) Appl. No.: 17/191,764

(22) Filed: Mar. 4, 2021

(51) Int. Cl.
| C07K 16/10 | (2006.01) |
| A61K 39/42 | (2006.01) |
| A61K 47/68 | (2017.01) |
| A61P 31/14 | (2006.01) |

(52) U.S. Cl.
CPC .............. *C07K 16/10* (2013.01); *A61K 39/42* (2013.01); *A61K 47/6841* (2017.08); *A61P 31/14* (2018.01); *C07K 2317/24* (2013.01); *C07K 2317/31* (2013.01); *C07K 2317/567* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| 9,803,238 | B1 | 10/2017 | Koh et al. |
| 10,590,477 | B2 | 3/2020 | Koh et al. |
| 10,624,949 | B1 | 4/2020 | Begrete et al. |
| 10,724,091 | B1 | 7/2020 | Meagher et al. |
| 10,787,501 | B1 * | 9/2020 | Babb ..................... A61K 39/15 |

OTHER PUBLICATIONS

Janeway, Charles A. "Immunobiology: The Immune System in Health and Disease." 2001 (Year: 2001).*
Stryer, Biochemistry 4th, WH Freeman, New York. 1995 (Year: 1995).*
Colman, Research in Immunology 145.1 (1994): 33-36 (Year: 1994).*
Ghahroudi et al., FEBS Letters Sep. 15, 1997; 414(3): 521-526. (Year: 1997).*
Sela-Culang, Inbal et al. Frontiers in immunology vol. 4 302. Oct. 8, 2013 (Year: 2013).*
Vincke, Cecile, et al. "General strategy to humanize a camelid single-domain antibody and identification of a universal humanized nanobody scaffold." Journal of Biological Chemistry 284.5 (2009): 3273-3284. (Year: 2009).*
Arbabi Ghahroudi, M et al. "Selection and identification of single domain antibody fragments from camel heavy-chain antibodies." FEBS letters vol. 414,3 (1997): 521-6. doi:10.1016/s0014-5793(97)01062-4 (Year: 1997).*
Kipriyanov, Sergey M., and Fabrice Le Gall. "Generation and production of engineered antibodies." Molecular biotechnology 26.1 (2004): 39-60. (Year: 2004).*
McMahon, C. et al., "Yeast surface display platform for rapid discovery of conformationally selective nanobodies," Nature Structural & Molecular Biology Mar. 2018;25(3):289-296 (26 pp.).
McMahon, C. et al., Supplementary Information for "Yeast surface display platform for rapid discovery of conformationally selective nanobodies," Nature Structural & Molecular Biology Mar. 2018;25(3):289-296 (28 pp.).
Schoof, M. et al., "An ultrapotent synthetic nanobody neutralizes SARS-CoV-2 by stabilizing inactive Spike," Science Dec. 18, 2020;370(6523):1473-1479.
Schoof, M. et al., Supplementary Materials for "An ultrapotent synthetic nanobody neutralizes SARS-CoV-2 by stabilizing inactive Spike," Science Dec. 18, 2020;370(6523):1473-1479 (33 pp.).
Xiang, Y. et al., "Versatile and multivalent nanobodies efficiently neutralize SARS-CoV-2," Science Dec. 18, 2020;370(6523):1479-1484.
Xiang, Y. et al., Supplementary Materials for "Versatile and multivalent nanobodies efficiently neutralize SARS-CoV-2," Science Dec. 18, 2020;370(6523):1479-1484 (39 pp.).
Stefan MA et al., "Development of potent and effective synthetic SARS-CoV-2 neutralizing nanobodies," MAbs. 2021;13(1): Article No. e1958663 (13 pages).
Stefan MA et al., "Development of potent and effective SARS-CoV-2 neutralizing nanobodies," Sandia Report No. SAND2021-3736C (Mar. 1, 2021), Proposed for presentation at the PEGS: The Essential Protein Engineering & Cell Therapy Summit held May 11, 2021.
Harmon B, "Generation of highly effective SARS-CoV-2 neutralizing humanized nanobodies," Sandia Report No. SAND2021-0573C (Jan. 1, 2021), Proposed for presentation at the NVBL Molecular Design Symposium held Feb. 1, 2021.

* cited by examiner

*Primary Examiner* — Michael Szperka
*Assistant Examiner* — Lia E Taylor
(74) *Attorney, Agent, or Firm* — Fish & Richardson; Madelynne J. Farber; Samantha Updegraff

(57) ABSTRACT

The present disclosure relates to an isolated or purified antibody, or a fragment thereof, having a binding domain that binds to a coronavirus (e.g., SARS-COV-2) or a portion thereof. In other embodiments, the antibody includes a binding domain that competes with binding to angiotensin converting enzyme 2 (ACE2) or a portion thereof. Methods of using such antibodies are also described herein, such as methods of treating or delaying the progression of a disease associated with a coronavirus.

8 Claims, 24 Drawing Sheets
Specification includes a Sequence Listing.

```
>SP1B4 (SEQ ID NO:1)
EVQLQASGGGFVQPGGSLRLSCAASGRAFGIYRMGWFRQAPGKEREFVSAISGGDAGHTRYADSVKGRFTISRDNSK
NTVYLQMNSLRAEDTATYYCAYWDYNGVVPFFKYWGQGTQVTVSS

>SP1D9 (SEQ ID NO:2)
EVQLQASGGGFVQPGGSLRLSCAASGRYDSYVRMGWFRQAPGKEREFVSAISGGGDKSTWYADSVKGRFTISRDNSK
NTVYLQMNSLRAEDTATYYCANAQLGPAYDKIGYWGQGTQVTVSS

>SP3A5 (SEQ ID NO:3)
EVQLQASGGGFVQPGGSLRLSCAASGRTSGQYRMGWFRQAPGKEREFVSAISAWGGGSAKYADSVKGRFTISRDNSK
NTVYLQMNSLRAEDTATYYCAAWYFEQIFRADVKTEYWGQGTQVTVSS

>SP3H4 (SEQ ID NO:4)
EVQLQASGGGFVQPGGSLRLSCAASGTAYGWSRMGWFRQAPGKEREFVSAISRASAGYAQYADSVKGRFTISRDNSK
NTVYLQMNSLRAEDTATYYCAFPLHDQGEPYGWYWGQGTQVTVSS

>SP1A2 (SEQ ID NO:5)
EVQLQASGGGFVQPGGSLRLSCAASGHTFDAYQMGWFRQAPGKEREFVSAISAGDGAASYYADSVKGRFTISRDNSK
NTVYLQMNSLRAEDTATYYCAKFSKWHSRVQAEYWGQGTQVTVSS

>SP1A11 (SEQ ID NO:6)
EVQLQASGGGFVQPGGSLRLSCAASGRTFSFLPMGWFRQAPGKEREFVSAISDWSGGHTYYADSVKGRFTISRDNSK
NTVYLQMNSLRAEDTATYYCAPNPQAAVYENEWPIVYWGQGTQVTVSS

>SP1E1 (SEQ ID NO:7)
EVQLQASGGGFVQPGGSLRLSCAASGHTFDAHRMGWFRQAPGKEREFVSAISTWAGDSARYADSVKGRFTISRDNSK
NTVYLQMNSLRAEDTATYYCASFLWDREQWYWGQGTQVTVSS

>SP1E4 (SEQ ID NO:8)
EVQLQASGGGFVQPGGSLRLSCAASGQPYTQYRMGWFRQAPGKEREFVSAISTWAGDSARYADSVKGRFTISRDNSK
NTVYLQMNSLRAEDTATYYCADFRSASEDIARWYWGQGTQVTVSS

>SP1F2 (SEQ ID NO:9)
EVQLQASGGGFVQPGGSLRLSCAASGHSFGQHRMGWFRQAPGKEREFVSAISSGGSGHTRYADSVKGRFTISRDNSK
NTVYLQMNSLRAEDTATYYCAPLYWVHQVSNEVWRQYWGQGTQVTVSS

>SP1F6 (SEQ ID NO:10)
EVQLQASGGGFVQPGGSLRLSCAASGRTSGQYRMGWFRQAPGKEREFVSAISDTAGQSTTYADSVKGRFTISRDNSK
NTVYLQMNSLRAEDTATYYCALRGVGWPDSNLELQWYWGQGTQVTVSS

>SP1G7 (SEQ ID NO:11)
EVQLQASGGGFVQPGGSLRLSCAASGRAFGIYRMGWFRQAPGKEREFVSAISSSAGGYKTYADSVKGRFTISRDNSK
NTVYLQMNSLRAEDTATYYCAFRGTIDGNYYWGQGTQVTVSS

>SP2A7 (SEQ ID NO:12)
EVQLQASGGGFVQPGGSLRLSCAASGSSFGIRRMGWFRQAPGKEREFVSAISTTSGETTRYADSVKGRFTISRDNSK
NTVYLQMNSLRAEDTATYYCAQRFVTGTHWYWGQGTQVTVSS

>SP2D8 (SEQ ID NO:13)
EVQLQASGGGFVQPGGSLRLSCAASGSFDTSQRMGWFRQAPGKEREFVSAISAWSGDSFRYADSVKGRFTISRDNSK
NTVYLQMNSLRAEDTATYYCAATQRLDADAFGWYWGQGTQVTVSS

>SP3D6 (SEQ ID NO:14)
EVQLQASGGGFVQPGGSLRLSCAASGRADGITQMGWFRQAPGKEREFVSAISSGSAGQTDYADSVKGRFTISRDNSK
NTVYLQMNSLRAEDTATYYCAGWFTELKLPGRVFRIYWGQGTQVTVSS
```

FIG. 2A

\>SP3D11 (SEQ ID NO:15)
EVQLQASGGGFVQPGGSLRLSCAASGGPAQDYRMGWFRQAPGKEREFVSAISGWSDASTYYADSVKGRFTISRDNSK
NTVYLQMNSLRAEDTATYYCASIRNFAPQWYWGQGTQVTVSS

\>SP3F9 (SEQ ID NO:16)
EVQLQASGGGFVQPGGSLRLSCAASGSTFDQYIMGWFRQAPGKEREFVSAISAGDGAASYYADSVKGRFTISRDNSK
NTVYLQMNSLRAEDTATYYCALFSNQRVEPTDSYWGQGTQVTVSS

\>SP3H10 (SEQ ID NO:17)
EVQLQASGGGFVQPGGSLRLSCAASGGTADSYRMGWFRQAPGKEREFVSAISAGSGDFKHYADSVKGRFTISRDNSK
NTVYLQMNSLRAEDTATYYCANRDNKWPFLYQEYWGQGTQVTVSS

\>SP4A5 (SEQ ID NO:18)
EVQLQASGGGFVQPGGSLRLSCAASGFFFGSYRMGWFRQAPGKEREFVSAISTTSGETTRYADSVKGRFTISRDNSK
NTVYLQMNSLRAEDTATYYCASFLWDRELWYWGQGTQVTVSS

\>SP4B5 (SEQ ID NO:19)
EVQLQASGGGFVQPGGSLRLSCAASGGTFGQWRMGWFRQAPGKEREFVSAISGGDAGHTRYADSVKGRFTISRDNSK
NTVYLQMNSLRAEDTATYYCARRDLAGAQYYWGQGTQVTVSS

\>SP1A6 (SEQ ID NO:20)
EVQLQASGGGFVQPGGSLRLSCAASGRSFGFYRMGWFRQAPGKEREFVSAISSWGGTSAHYADSVKGRFTISRDNSK
NTVYLQMNSLRAEDTATYYCATYATQDNGQVNVYWGQGTQVTVSS

\>SP1D8 (SEQ ID NO:21)
EVQLQASGGGFVQPGGSLRLSCAASGSIFGDFQMGWFRQAPGKEREFVSAISGGYGQSTQYADSVKGRFTISRDNSK
NTVYLQMNSLRAEDTATYYCARAAWDQVIGYWGQGTQVTVSS

\>SP1E2 (SEQ ID NO:22)
EVQLQASGGGFVQPGGSLRLSCAASGGTFGQWRMGWFRQAPGKEREFVSAISDADARFTRYADSVKGRFTISRDNSK
NTVYLQMNSLRAEDTATYYCAVLFPFTTIRYWGQGTQVTVSS

\>SP1E8 (SEQ ID NO:23)
EVQLQASGGGFVQPGGSLRLSCAASGGTFDAFQMGWFRQAPGKEREFVSAISGGTGEATYYADSVKGRFTISRDNSK
NTVYLQMNSLRAEDTATYYCAGWESYFISRHYRDHTYWGQGTQVTVSS

\>SP1F5 (SEQ ID NO:24)
EVQLQASGGGFVQPGGSLRLSCAASGRTFDESRMGWFRQAPGKEREFVSAISAADGGWSYYADSVKGRFTISRDNSK
NTVYLQMNSLRAEDTATYYCAERRIVRGEPYGWYWGQGTQVTVSS

\>SP1G9 (SEQ ID NO:25)
EVQLQASGGGFVQPGGSLRLSCAASGHTFGRYRMGWFRQAPGKEREFVSAISSWSGGSARYADSVKGRFTISRDNSK
NTVYLQMNSLRAEDTATYYCAPLVGPEDQWNFNYWGQGTQVTVSS

\>SP2A3 (SEQ ID NO:26)
EVQLQASGGGFVQPGGSLRLSCAASGGTFQGLRMGWFRQAPGKEREFVSAISASAATFVAYADSVKGRFTISRDNSK
NTVYLQMNSLRAEDTATYYCAPAISGYDHPYWGQGTQVTVSS

\>SP2A12 (SEQ ID NO:27)
EVQLQASGGGFVQPGGSLRLSCAASGTFASQLTMGWFRQAPGKEREFVSAISATSGGFAYYADSVKGRFTISRDNSK
NTVYLQMNSLRAEDTATYYCARYQFPGHRSYWGQGTQVTVSS

\>SP2B4 (SEQ ID NO:28)
EVQLQASGGGFVQPGGSLRLSCAASGRYFGTYRMGWFRQAPGKEREFVSAISDTQGQATWYADSVKGRFTISRDNSK
NTVYLQMNSLRAEDTATYYCAAREYFYGHKDREVQYYWGQGTQVTVSS

FIG. 2B

```
>SP2D6 (SEQ ID NO:29)
EVQLQASGGGFVQPGGSLRLSCAASGGTAGQLRMGWFRQAPGKEREFVSAISASAATFVAYADSVKGRFTISRDNSK
NTVYLQMNSLRAEDTATYYCAAQSHEADGHYWGQGTQVTVSS

>SP2F7 (SEQ ID NO:30)
EVQLQASGGGFVQPGGSLRLSCAASGQTASWQWMGWFRQAPGKEREFVSAISAAAGGTDSYADSVKGRFTISRDNSK
NTVYLQMNSLRAEDTATYYCAGLIHESEGTSNDYWGQGTQVTVSS

>SP3C2 (SEQ ID NO:31)
EVQLQASGGGFVQPGGSLRLSCAASGRTYDAWHMGWFRQAPGKEREFVSAISSSSGSAKYYADSVKGRFTISRDNSK
NTVYLQMNSLRAEDTATYYCAAYTTTTVPHYWGQGTQVTVSS

>SP3C8 (SEQ ID NO:32)
EVQLQASGGGFVQPGGSLRLSCAASGFFDREYAMGWFRQAPGKEREFVSAISSQYQGPTAYADSVKGRFTISRDNSK
NTVYLQMNSLRAEDTATYYCALRNNDEIEFYWGQGTQVTVSS

>SP3D5 (SEQ ID NO:33)
EVQLQASGGGFVQPGGSLRLSCAASGGPFGTYRMGWFRQAPGKEREFVSAISHWSGESVKYADSVKGRFTISRDNSK
NTVYLQMNSLRAEDTATYYCAIWRWGLQDSQVLYWGQGTQVTVSS

>SP3E1 (SEQ ID NO:34)
EVQLQASGGGFVQPGGSLRLSCAASGRPFTQSRMGWFRQAPGKEREFVSAISAWGGGSAKYADSVKGRFTISRDNSK
NTVYLQMNSLRAEDTATYYCAAVLPEFGRHYWGQGTQVTVSS
```

FIG. 2C

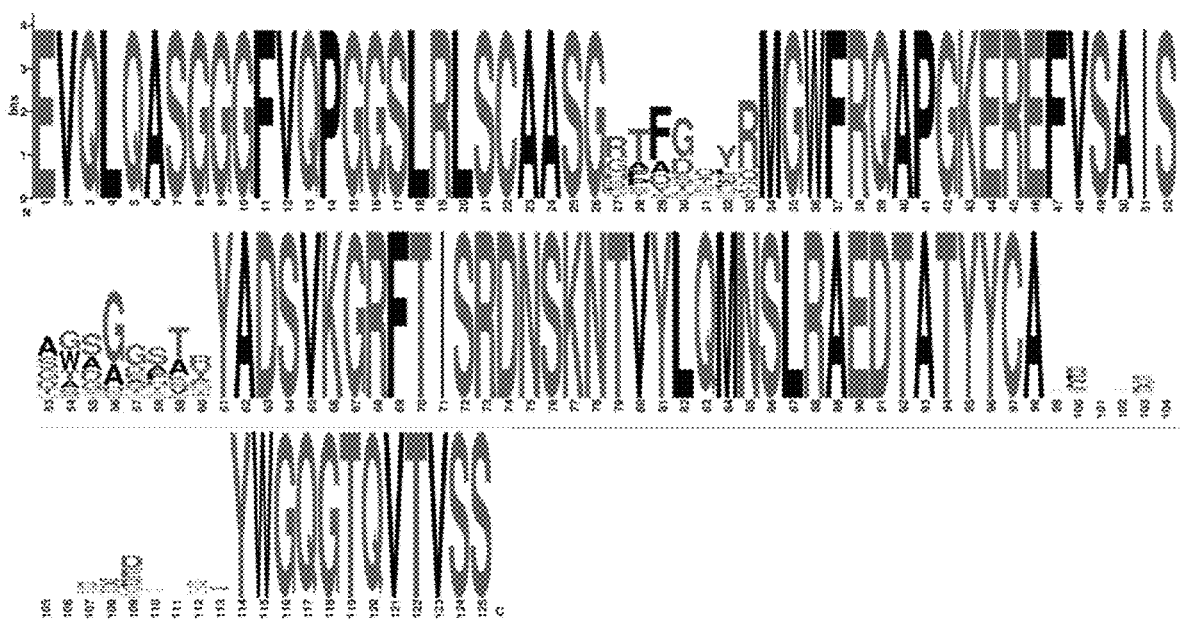

FIG. 3

| Name | CDR1 | SEQ ID NO: | CDR2 | SEQ ID NO: | CDR3 | SEQ ID NO: |
|---|---|---|---|---|---|---|
| SP1B4 | RAFGIYR | 40 | GGDAGHTR | 74 | YWDYNGVVPFFK | 108 |
| SP1D9 | RYDSYVR | 41 | GGGDKSTW | 75 | NAQLGPAYDKIG | 109 |
| SP3A5 | RTSGQYR | 42 | AWGGGSAK | 76 | AWYFEQIFRADVKTE | 110 |
| SP3H4 | TAYGWSR | 43 | RASAGYAQ | 77 | FPLHDQGEPYGW | 111 |
| SP1A2 | HTFDAYQ | 44 | AGDGAASY | 78 | KFSKWHSRVQAE | 112 |
| SP1A11 | RTFSFLP | 45 | DWSGGHTY | 79 | PNPQAAVYENEWPIV | 113 |
| SP1E1 | HTFDAHR | 46 | TWAGDSAR | 80 | SFLWDREQW | 114 |
| SP1E4 | QPYTQYR | 47 | TWAGDSAR | 81 | DFRSASEDIARW | 115 |
| SP1F2 | HSFGQHR | 48 | SGGSGHTR | 82 | PLYWVHQVSNEVWRQ | 116 |
| SP1F6 | RTSGQYR | 49 | DTAGQSTT | 83 | LRGVGWPDSNLELQW | 117 |
| SP1G7 | RAFGIYR | 50 | SSAGGYKT | 84 | FRGTIDGNY | 118 |
| SP2A7 | SSFGIRR | 51 | TTSGETTR | 85 | QRFVTGTHW | 119 |
| SP2D8 | SFDTSQR | 52 | AWSGDSFR | 86 | ATQRLDADAFGW | 120 |
| SP3D6 | RADGITQ | 53 | SGSAGQTD | 87 | GWFTELKLPGRVFRI | 121 |
| SP3D11 | GPAQDYR | 54 | GWSDASTY | 88 | SIRNFAPQW | 122 |
| SP3F9 | STFDQYI | 55 | AGDGAASY | 89 | LFSNQRVEPTDS | 123 |
| SP3H10 | GTADSYR | 56 | AGSGDFKH | 90 | NRDNKWPFLYQE | 124 |
| SP4A5 | FFFGSYR | 57 | TTSGETTR | 91 | SFLWDRELW | 125 |
| SP4B5 | GTFGQWR | 58 | GGDAGHTR | 92 | RRDLAGAQY | 126 |
| SP1A6 | RSFGFYR | 59 | SWGGTSAH | 93 | TYATQDNGQVNV | 127 |
| SP1D8 | SIFGDFQ | 60 | GGYGQSTQ | 94 | RAAWDVIG | 128 |
| SP1E2 | GTFGQWR | 61 | DADARFTR | 95 | VLFPFTTIR | 129 |
| SP1E8 | GTFDAFQ | 62 | GGTGEATY | 96 | GWESYFISRHYRDHT | 130 |
| SP1F5 | RTFDESR | 63 | AADGGWSY | 97 | ERRIVRGEPYGW | 131 |
| SP1G9 | HTFGRYR | 64 | SWSGGSAR | 98 | PLVGPEDWNFN | 132 |
| SP2A3 | GTFQGLR | 65 | ASAATFVA | 99 | PAISGYDHP | 133 |
| SP2A12 | TFASQLT | 66 | ATSGGFAY | 100 | RYQFPGHRS | 134 |
| SP2B4 | RYFGTYR | 67 | DTQGQATW | 101 | AREYFYGHKDREVQY | 135 |
| SP2D6 | GTAGQLR | 68 | ASAATFVA | 102 | AQSHEADGH | 136 |
| SP2F7 | QTASWQW | 69 | AAAGGTDS | 103 | GLIHESEGTSND | 137 |
| SP3C2 | RTYDAWH | 70 | SSSGSAKY | 104 | AYTTTTVPH | 138 |
| SP3C8 | FFDREYA | 71 | SQYQGPTA | 105 | LRNNDEIEF | 139 |
| SP3D5 | GPFGTYR | 72 | HWSGESVK | 106 | IWRWGLQDSQVL | 140 |
| SP3E1 | RPFTQSR | 73 | AWGGGSAK | 107 | AVLPEFGRH | 141 |

FIG. 4

|        | CDR1      | SEQ ID NO:       |
|--------|-----------|------------------|
| SP1A11 | RTFSFLP-  | (SEQ ID NO:45)   |
| SP1D9  | --RYDSYVR | (SEQ ID NO:41)   |
| SP3D11 | GPAQDYR-  | (SEQ ID NO:54)   |
| SP3H10 | GTADSYR-  | (SEQ ID NO:56)   |
| SP2D8  | -SFDTSQR  | (SEQ ID NO:52)   |
| SP1E4  | QPYTQYR-  | (SEQ ID NO:47)   |
| SP3H4  | TAYGWSR-  | (SEQ ID NO:43)   |
| SP3F9  | STFDQYI-  | (SEQ ID NO:55)   |
| SP1F2  | HSFGQHR-  | (SEQ ID NO:48)   |
| SP1A2  | HTFDAYQ-  | (SEQ ID NO:44)   |
| SP1E1  | HTFDAHR-  | (SEQ ID NO:46)   |
| SP4B5  | GTFGQWR-  | (SEQ ID NO:58)   |
| SP2D6  | GTAGQLR-  | (SEQ ID NO:68)   |
| SP4A5  | FFFGSYR-  | (SEQ ID NO:57)   |
| SP3D6  | RADGITQ-  | (SEQ ID NO:53)   |
| SP2A7  | SSFGIRR-  | (SEQ ID NO:51)   |
| SP1B4  | RAFGIYR-  | (SEQ ID NO:40)   |
| SP1G7  | RAFGIYR-  | (SEQ ID NO:50)   |
| SP3A5  | RTSGQYR-  | (SEQ ID NO:42)   |
| SP1F6  | RTSGQYR-  | (SEQ ID NO:49)   |
|        | XTXGXYR   | (SEQ ID NO:150)  |
|        | XTFGXYR   | (SEQ ID NO:151)  |
|        | XTSGXYR   | (SEQ ID NO:152)  |
|        | XAFGXYR   | (SEQ ID NO:153)  |
|        | XFFGXYR   | (SEQ ID NO:154)  |
|        | XXYGXYR   | (SEQ ID NO:155)  |

FIG. 5B

|  | CDR2 | SEQ ID NO: |
|---|---|---|
| SP3H4 | RASAGYAQ--- | (SEQ ID NO:77) |
| SP1E2 | DADA---RFTR | (SEQ ID NO:95) |
| SP1B4 | ----GGDAGHTR | (SEQ ID NO:74) |
| SP4B5 | ----GGDAGHTR | (SEQ ID NO:92) |
| SP1F2 | ---SGGSGHTR | (SEQ ID NO:82) |
| SP3D6 | ---SGSAGQTD | (SEQ ID NO:87) |
| SP3H10 | ----AGSGDFKH | (SEQ ID NO:90) |
| SP1A2 | ---AGDGAASY | (SEQ ID NO:78) |
| SP3F9 | ---AGDGAASY | (SEQ ID NO:89) |
| SP3A5 | -AWGGGSAK-- | (SEQ ID NO:76) |
| SP1E1 | -TWAGDSAR-- | (SEQ ID NO:80) |
| SP1E4 | -TWAGDSAR-- | (SEQ ID NO:81) |
| SP2D8 | -AWSGDSFR-- | (SEQ ID NO:86) |
| SP2A7 | -TTSG-ETTR- | (SEQ ID NO:85) |
| SP4A5 | -TTSG-ETTR- | (SEQ ID NO:91) |
| SP1G7 | ---SSAGGYKT | (SEQ ID NO:84) |
| SP1F6 | -DTAGQSTT-- | (SEQ ID NO:83) |
| SP1A11 | -DWSGGHTY-- | (SEQ ID NO:79) |
| SP1D9 | -GGGDKSTW-- | (SEQ ID NO:75) |
| SP3D11 | -GWSDASTY-- | (SEQ ID NO:88) |
|  | SXSGXSTR | (SEQ ID NO:160) |
|  | XGXXGHTR | (SEQ ID NO:161) |
|  | XAXAGYAQ | (SEQ ID NO:162) |
|  | GXXDXSTX | (SEQ ID NO:163) |
|  | XWXGXSAX | (SEQ ID NO:164) |
|  | XWXGXSXX | (SEQ ID NO:165) |
|  | TXXGXXXR | (SEQ ID NO:166) |
|  | TXXG-XXXX | (SEQ ID NO:167) |

FIG. 6B

|        | CDR3                              | SEQ ID NO:       |
|--------|-----------------------------------|------------------|
| SP3F9  | ------------------------LFSNQRVEPTDS | (SEQ ID NO:123) |
| SP3H4  | ---------FPLHD--QGEPYGW-------------- | (SEQ ID NO:111) |
| SP3H10 | ----------------NRDNKWPFLYQE--------- | (SEQ ID NO:124) |
| SP1F6  | -LRG------VGWPD--SNLELQW------------- | (SEQ ID NO:117) |
| SP1G7  | -FRG------T--ID--GNY----------------- | (SEQ ID NO:118) |
| SP1A11 | -----------PNPQAAVYENEWPIV----------- | (SEQ ID NO:113) |
| SP2A7  | ---------------QRFVTGTHW------------- | (SEQ ID NO:119) |
| SP1B4  | ------YWDYNGVVPF--------FK----------- | (SEQ ID NO:108) |
| SP2D8  | ATQRLDADAFGW------------------------- | (SEQ ID NO:120) |
| SP4B5  | -RRDLAGAQY--------------------------- | (SEQ ID NO:126) |
| SP1F2  | ----PLY-------WVH--QVSNEVWRQ--------- | (SEQ ID NO:116) |
| SP1D9  | ----------------NAQLGPAYDKIG--------- | (SEQ ID NO:109) |
| SP3D11 | ---SIRNFAPQW------------------------- | (SEQ ID NO:122) |
| SP3D6  | ---------GWFTELKLPGRVFRI------------ | (SEQ ID NO:121) |
| SP1E4  | DFRSASEDIARW------------------------- | (SEQ ID NO:115) |
| SP1A2  | ---------KFSKWHSR--VQAE-------------- | (SEQ ID NO:112) |
| SP3A5  | ------AWYFEQIFRADVKTE--------------- | (SEQ ID NO:110) |
| SP1E1  | ---SFLWDREQW------------------------- | (SEQ ID NO:114) |
| SP4A5  | ---SFLWDRELW------------------------- | (SEQ ID NO:125) |
|        | XWXXEXXFXXXXVXXE                    | (SEQ ID NO:170) |
|        | NAQLGPXXDKIG                        | (SEQ ID NO:171) |
|        | XWDXXGXXXX-------FX                 | (SEQ ID NO:172) |
|        | YWXXNGXXPF-------XX                 | (SEQ ID NO:173) |
|        | FPXXD--XXXXXXW                      | (SEQ ID NO:174) |
|        | FPLXD---XXXXXGW                     | (SEQ ID NO:175) |

FIG. 7B

FIG. 8A

```
XVQLXXSGXXXXXXXXXLXLXCXXSGXXXX-CDR1-XXWXXXXXXXXXXXXXXX-CDR2-
XXXXXXXXXXXXXXDXXXXXXXXXXXXXXXXDXXXYXCXX-CDR3-XXGXGTXXXVSX        (SEQ ID NO:180)

XXXLXXXGXXXXXPXXXXXXXCXXXX-CDR1-XXWXXXXXXXXXXEXXXXXX-CDR2-
XXXXXXXXXXXXXXXXXXXXXXXXXXXXXXXXDXXXYXXXX-CDR3-XWGXXXXXXXVSX      (SEQ ID NO:181)

XVXLXXSGGGXXXXGXSLXLSCAASG-CDR1-XXWXRXXPXXXXXXXXXXX-CDR2-
XYXXXXXXRFXXSXDXXXXXXXLXXXXXXXXDTXXYKCAK-CDR3-XXGXGTXVTVSX        (SEQ ID NO:182)

EVQLQASGGGFVQPGGSLRLSCAASG-CDR1-MGWFRQAPGKEREFVSAIS-CDR2-
YADSVKGRFTISRDNSKNTVYLQMNSLRAEDTATYYCA-CDR3-YWGQGTQVTVSS          (SEQ ID NO:183)

EVQLQASGGGFVQPGGSLRLSCAASG-CDR1-MGWFRQAPGKEREFVSAIS-CDR2-
YADSVKGRFTISRDNSKNTVYLQMNSLRAEDTATYYCA-CDR3-YWGQGTQVTVSS          (SEQ ID NO:184)

EVQLQASGGGFVQAGGSLRLSCAASG-CDR1-MGWFRQAPGKEREFVAAIS-CDR2-
YYADSVKGRFTISRDNAKNTVYLQMNSLKPEDTATYYCA-CDR3-YWGQGTQVTVSS         (SEQ ID NO:185)

EVQLQASGGGFVQAGGSLRLSCAASG-CDR1-MGWFRQAPGKEREFVAAIS-CDR2-
YYADSVKGRFTISRDNAKNTVYLQMNSLKPEDTATYYCA-CDR3-YWGQGTQVTVSS         (SEQ ID NO:186)
```

FIG. 8B

```
FR1
EVQLQASGGGFVQAGGSLRLSCAASG              (SEQ ID NO:190)
EVQLQASGGGFVQPGGSLRLSCAASG              (SEQ ID NO:191)
QVQLVESGGGSVQAGGSLRLSCTASGGSEY          (SEQ ID NO:192)
QVQLVESGGGSVQAGGSLRLSCTASG              (SEQ ID NO:193)
QVQLVESGGGSVQAGGSLRLSCTASGFSRE          (SEQ ID NO:194)
QVQLQESGPSLVRPSQTLSLTCTISGFSRE          (SEQ ID NO:195)
QVQLQESGPSLVRPSQTLSLTCTISG              (SEQ ID NO:196)
QVQLVESGGNLVQPGGSLRLSCAASGFTFG          (SEQ ID NO:197)
QVQLVESGGNLVQPGGSLRLSCAASG              (SEQ ID NO:198)
QVQLVESGGALVQPGGSLRLSCAASGFPVN          (SEQ ID NO:199)
QVQLVESGGALVQPGGSLRLSCAASGFTFG          (SEQ ID NO:200)
QVQLVESGGGLVQPGGSLRLSCAASGFTFG          (SEQ ID NO:201)
QVQLVESGGALVQPGGSLRLSCAASG              (SEQ ID NO:202)
QVQLVESGGGLVQAGGSLRLSCAASG              (SEQ ID NO:203)
QVQLVESGGGLMQAGGSLRLSCAVSG              (SEQ ID NO:204)
QVQLQESGGGLVQAGGSLRLSCAASG              (SEQ ID NO:205)
HVQLVESGGGLVQAGGSLRLSCAASG              (SEQ ID NO:206)
DVQLVESGGGLVQAGGSLRLSCAASG              (SEQ ID NO:207)
EVQLVESGGGLVQAGGSLRLSCAASG              (SEQ ID NO:208)
EVQLVESGGGVVQPGRSLRLSCAASGFTFD          (SEQ ID NO:209)
EVQLVESGGGVVQPGRSLRLSCAASG              (SEQ ID NO:210)
DVQLQASGGGLVQAGGSLRLSCAASGFKIT          (SEQ ID NO:211)
DVQLQASGGGLVQAGGSLRLSCAASG              (SEQ ID NO:212)

XVQLXXSGXXXXXXXXXLXLCXXSGXXXX           (SEQ ID NO:213)
XXXLXXXGXXXXXXXXXXXXXCXXX               (SEQ ID NO:214)
XVQLXXSGXXXXXXXXXLXLCXXSG               (SEQ ID NO:215)
QVQLVESGGGLVQXGGSLRLSCAASGXXXX          (SEQ ID NO:216)
QVQLVESGGGLVQXGGSLRLSCAASG              (SEQ ID NO:217)
```

FIG. 9A

```
FR2
MGWFRQAPGKEREFVAAIS        (SEQ ID NO:220)
MGWFRQAPGKEREFVSAIS        (SEQ ID NO:221)
--WFRQAPGQEREAVA           (SEQ ID NO:222)
--WFRQAPGQEREAVAAIA        (SEQ ID NO:223)
--WVRQAPGKALEWLG           (SEQ ID NO:224)
--WVRQAPGKALEWLGRI         (SEQ ID NO:225)
--WFRQAPGQEREWLG           (SEQ ID NO:226)
--WFRQAPGQEREWLGRI         (SEQ ID NO:227)
--WVRQAPGGGLEWVA           (SEQ ID NO:228)
--WYRQATGKEREWVA           (SEQ ID NO:229)
MSWYRQATGKEREWVA           (SEQ ID NO:230)
MGWFRQAPGKEREFVAAIR        (SEQ ID NO:231)
MGWFRQAPGKEREFVAAI         (SEQ ID NO:232)
MGWFRQAPGKEREFVA           (SEQ ID NO:233)
MGWYRQAPGKERELVA           (SEQ ID NO:234)
MGWYRQAPGKERELVAA          (SEQ ID NO:235)
MGWYRQAPGKERELVAAID        (SEQ ID NO:236)
MGWYRQAPGKERELVAVIS        (SEQ ID NO:237)
MGWFRQAPGKEREGVA           (SEQ ID NO:238)
--WFRQAPGKEREGVA           (SEQ ID NO:239)
MGWFRQAPGKEREFVA           (SEQ ID NO:240)
--WFRQAPGKEREFVA           (SEQ ID NO:241)
--WVRQAPGKGPEWVA           (SEQ ID NO:242)
--WFRQAPGKEREFVS           (SEQ ID NO:243)

XXWXXXXXXXXXXXXXXX         (SEQ ID NO:244)
XXWXPQAXGXXXEXXXXXX        (SEQ ID NO:245)
XXWXPQAXGXXXEXXX           (SEQ ID NO:246)
MXWFRQAPGKEREWVAXXX        (SEQ ID NO:247)
MXWFRQAPGKEREWVA           (SEQ ID NO:248)
```

FIG. 9B

```
FR3
-YADSVKGRFTISRDNAKNTVYLQMNSLKPEDTATYYCA-          (SEQ ID NO:250)
YYADSVKGRFTISRDNAKNTVYLQMNSLKPEDTATYYCA-          (SEQ ID NO:251)
-YADSVKGRFTISRDNSKNTVYLQMNSLRAEDTATYYCA-          (SEQ ID NO:252)
YYADSVKGRFTISRDNSKNTVYLQMNSLRAEDTATYYCA-          (SEQ ID NO:253)
----------RFTISRDNAKNTVTLQMNNLKPEDTAIYYCA-        (SEQ ID NO:254)
----------RFTISRDNAKNTVTLQMNNLKPEDTAIYYCAA        (SEQ ID NO:255)
----------RLTITRDISKSQVSLSLSSVTLEDTAEYYCV-        (SEQ ID NO:256)
----------RLTITRDISKSQVSLSLSSVTLEDTAEYYCVY        (SEQ ID NO:257)
----------RFTISRDIAKNTVTLQMNNLKPEDTAIYYVY-        (SEQ ID NO:258)
----------RFTISRDIAKNTVTLQMNNLKPEDTAIYYVYA        (SEQ ID NO:259)
YYADSVKGRFTISRDNAKNTVTLQMNNLKPEDTAIYYCA-          (SEQ ID NO:260)
YYADSVKGRFTISRDNAKNTVTLQMNNLKPEDTAIYYCAA          (SEQ ID NO:261)
-YEDSVKGRFCISRDDARNTVYLQMNSLKPEDTAVYYCNV          (SEQ ID NO:262)
-YEDSVKGRFCISRDDARNTVYLQMNSLKPEDTAVYYCN-          (SEQ ID NO:263)
-YADSVKGRFTISRDNAKNSVYLQMNSLRVEDTAVYYCAR          (SEQ ID NO:264)
-YADSVKGRFTISRDNAKNSVYLQMNSLRVEDTAVYYCA-          (SEQ ID NO:265)
-YADSVKGRFTISRDNARNTVYLQMNSLKPEDTAVYYCAR          (SEQ ID NO:266)
-YADSVKGRFTISRDNARNTVYLQMNSLKPEDTAVYYCA-          (SEQ ID NO:267)
-YADSVKGRFTISRDNARNTVYLQMNSLKPEDTAVYYCAR          (SEQ ID NO:268)
----------RFTISRDNARNTVYLQMNSLKPEDTAVYYCAR        (SEQ ID NO:269)
-YADSVKGRFTISRDKGKNTVYLQMDSLKPEDTATYYCAA          (SEQ ID NO:270)
----------RFTISRDKGKNTVYLQMDSLKPEDTATYYCAA        (SEQ ID NO:271)
-YADSVKGRFTISRDKGKNTVYLQMDSLKPEDTATYYCA-          (SEQ ID NO:272)
----------RFTISRDKGKNTVYLQMDSLKPEDTATYYCA-        (SEQ ID NO:273)
YYADSVKGRFTISRDKAKNTVYLQMNSLKYEDTAVYYCA-          (SEQ ID NO:274)
-YADSVKGRFTISRDKAKNTVYLQMNSLKYEDTAVYYCA-          (SEQ ID NO:275)
YYADSVKGRFTISRDNAKNTVYLQMNSLKPEDTAVYYCA-          (SEQ ID NO:276)
LHNPALKSRLTITRDISKSQVSLSLSSVTLEDTAEYYCV-          (SEQ ID NO:277)
LHNPALKSRLTITRDISKSQVSLSLSSVTLEDTAEYYCVY          (SEQ ID NO:278)
LHNPALKSRFTISRDIAKNTVTLQMNNLKPEDTAIYYVYA          (SEQ ID NO:279)
-YADSVKGRFTISRDNAKNTVYLQMNSLKPEDTAVYYCAA          (SEQ ID NO:280)
-YADSVKGRFTISRDNAKNTVYLQMNSLKPEDTAVYYCA-          (SEQ ID NO:281)
YYADSVKGRFTISRDNAKNTVYLQMNSLKPEDTAVYYCAA          (SEQ ID NO:282)
----------RFTISRDNSKNTLYLQMNSLRAEDTAVYYCAK        (SEQ ID NO:283)
----------RFTISRDNAKNTVYLQMNSLKPEDTADYYCAA        (SEQ ID NO:284)

XXXXXXXXXXXXDXXXXXXXXXXXXXXXXXDXXXYXCXX           (SEQ ID NO:285)
XXXXXXXXRXXIXRDXXXXXXVXLXXXXXXXEDTAXYYXXX         (SEQ ID NO:286)
XXXXXXXXRXXIXRDXXXXXXVXLXXXXXXXEDTAXYYXX          (SEQ ID NO:287)
XYADSVKGRFTISRDNAKNTVYLQMNSLKPEDTAVYYCAX          (SEQ ID NO:288)
XYADSVKGRFTISRDNAKNTVYLQMNSLKPEDTAVYYCA           (SEQ ID NO:289)
```

FIG. 9C

FR4
YWGQGTQVTVSS    (SEQ ID NO:290)
-WGQGTQVTVSS    (SEQ ID NO:291)
VWGPGLLLTVSS    (SEQ ID NO:292)
-WGPGLLLTVSS    (SEQ ID NO:293)
-WGQGTLVTVS-    (SEQ ID NO:294)
-WGQGTLVTVSS    (SEQ ID NO:295)
-WGQGTQVTVS-    (SEQ ID NO:296)
-WGQGTQVTVSS    (SEQ ID NO:297)
QWGQGTQVTVSS    (SEQ ID NO:298)
YWGQGTQVTVS-    (SEQ ID NO:299)
-WGQGTTVVVSS    (SEQ ID NO:300)
-WGKGTQVTVSS    (SEQ ID NO:301)

XWGXGXXXTVSX    (SEQ ID NO:302)
XWGXGXXXTVS     (SEQ ID NO:303)
 WGXGXXXTVSX    (SEQ ID NO:304)
XXGXGTXXXVSX    (SEQ ID NO:305)
XWGQGTQVTVSS    (SEQ ID NO:306)
XWGQGTQVTVS     (SEQ ID NO:307)

FIG. 9D

Binding of SARS-CoV-2 Spike to Ace2

FIG. 10A rVSV-SARS-CoV-2 GFP

FIG. 10B

Neutralization of Wildtype SARS-CoV-2 (BSL-3)

|       | MM57   | anti-VSV | SP3D1  | SP1E1 | SP1E4  | SP1F6 | SP3D6 | SP3F9 |
|-------|--------|----------|--------|-------|--------|-------|-------|-------|
| IC50  | 0.4142 | Unstable | 0.5256 | 2.069 | 0.8050 | 6.427 | 4.267 | 1.564 |

```
P0DTC2      MFVFLVLLPLVS-SQ---CVNLTTRTQLPPAYTNSFTRGVYYPDKVFRSSVLHSTQDLFL    56
A0A6B9WHD3  MFVFLVLLPLVS-SQ---CVNLTTRTQLPPAYTNSSTRGVYYPDKVFRSSVLHLTQDLFL    56
P59594      MFIFLLFLTLTSGSDLDRCTTFDDVQAPNYTQHTSSMRGVYYPDEIFRSDTLYLTQDLFL    60
Q5GDB5      MFIFLLFLTLTSGSDLDRCTTFDDVQAPNYTQHTSSMRGVYYPDEIFRSDTLYLTQDLFL    60
Q3LZX1      MKILIFAFLANLAKAQEGCGIISRKPQPKMAQVSSSRRGVYYNDDIFRSDVLHLTQDYFL    60
Q3I5J5      MKILILAFLASLAKAQEGCGIISRKPQPKMAQVSSSRRGVYYNDDIFRSNVLHLTQDYFL    60
Q0Q475      MKVLIFALLFSLAKAQEGCGIISRKPQPKMEKVSSSRRGVYYNDDIFRSDVLHLTQDYFL    60
            * ::. :           . *  :            .* **** *.:.**..*: *** **
            XXXXXCXXXXXXXXXXXXXXXXSXXRGVYYXDXXFRSXXLXXTQDXFL

P0DTC2      PFFSNVTWFHAIHVSGTNGTKRFDNPVLPFNDGVYFASTEKSNIIRGWIFGTTLDSKTQS   116
A0A6B9WHD3  PFFSNVTWFHAIHVSGTNGIKRFDNPVLPFNDGVYFASTEKSNIIRGWIFGTTLDSKTQS   116
P59594      PFYSNVTGFHTIN-------HTFGNPVIPFKDGIYFAATEKSNVVRGWVFGSTMNNKSQS   113
Q5GDB5      PFYSNVTGFHTIN-------HTFDNPVIPFKDGIYFAATEKSNVVRGWVFGSTMNNKSQS   113
Q3LZX1      PFDSNLTQYFSLNVDS-DRYTYFDNPILDFGDVYFAATEKSNVIRGWIFGSSFDNTTQS   119
Q3I5J5      PFDSNLTQYFSLNVDS-DRFTYFDNPILDFGDVYFAATEKSNVIRGWIFGSTFDNTTQS   119
Q0Q475      PFDSNLTQYFSLNIDS-NKYTYFDNPILDFGDVYFAATEKSNVIRGWIFGSSFDNTTQS   119
            ** **:*  :.:::          *.**:: *  *:***:****:.***:*:::..:**
            PFXSNXTXXXXXXXXXXXXXXXFXNPXXXFXDGXYFAXTEKSNXXRGWXFGXXXXXXXQS

P0DTC2      LLIVNNATNVVIKVCEFQFCNDPFLGVYYHKNNKSWMESEFRVYSSANNCTFEYVSQPFL   176
A0A6B9WHD3  LLIVNNATNVVIKVCEFQFCNDPFLGVYYHKNNKSWMESEFRVYSSANNCTFEYVSQPFL   176
P59594      VIIINNSTNVVIRACNFELCDNPFFAVSKPMG-----TQTHTMIFDNAFNCTFEYISDAFS  169
Q5GDB5      VIIINNSTNVVIRACNFELCDNPFFVVSKPMG-----TRTHTMIFDNAFNCTFEYISDAFS  169
Q3LZX1      AVIVNNSTHIIIRVCNFNLCKEPMYTVSR--G-----TQQNAWVYQSAFNCTYDRVEKSFQ  173
Q3I5J5      AVIVNNSTHIIIRVCNFNLCKEPMYTVSR--G-----AQQSSWVYQSAFNCTYDRVEKSFQ  173
Q0Q475      AIIVNNSTHIIIRVCNFNLCKEPMYTVSK--G-----TQQSSWVYQSAFNCTYDRVEKSFQ  173
             :*:**:*:::*:.:.*:*:*:.:*  *       .       ::..* ***:: :.. *
            XXIXNNXTXXXIXXCXFXCXXPXXXVXXXXXXXXXXXXXXXXXXXXXANCTXXXXXXXFX

P0DTC2      MDLEGKQGNFKNLREFVFKNIDGYFKIYSKHTPINLVRDLPQGFSALEPLVDLPIGINIT   236
A0A6B9WHD3  MDLEGKQGNFKNLREFVFKNIDGYFKIYSKHTPINLVRDLPPGFSALEPLVDLPIGINIT   236
P59594      LDVSEKSGNFKHLREFVFKNKDGFLYVYKGYQPIDVVRDLPSGFNTLKPIFKLPLGINIT   229
Q5GDB5      LDVSEKSGNFKHLREFVFKNKDGFLYVYKGYQPIDVVRDLPSGFNTLKPIFKLPLGINIT   229
Q3LZX1      LDTTPKTGNFKDLREYVFKNRDGFLSVYQTYTAVNLPRGLPTGFSVLKPILKLPFGINIT   233
Q3I5J5      LDTAPKTGNFKDLREYVFKNRDGFLSVYQTYTAVNLPRGLPIGFSVLRPILKLPFGINIT   233
Q0Q475      LDTAPKTGNFKDLREYVFKNRDGFLSVYQTYTAVNLPRGFPAGFSVLRPILKLPFGINIT   233
            :*    * **** ,***:****  **::  :*,  :    ::: *.:*  **,.,*.*:..**:*****
            XDXXXKXGNFKXLREXVFKNXDGXXXXYXXXXXXXXXXRXXPXGFXXLXPXXXLPXGINIT

P0DTC2      RFQTLLALHRSYLTPGDSSSGWTAGAAAYYVGYLQPRTFLLKYNENGTITDAVDCALDPL   296
A0A6B9WHD3  RFQTLLALHRSYLTPGDSSSGWTAGAAAYYVGYLQPRTFLLKYNENGTITDAVDCALDPL   296
P59594      NFRAILTAFS------PAQDIWGTSAAAYFVGYLKPTTFMLKYDENGTITDAVDCSQNPL   283
Q5GDB5      NFRAILTAFS------PAQDTWGTSAAAYFVGYLKPTTFMLKYDENGTITDAVDCSQNPL   283
Q3LZX1      SYRVVMAMFS------QTTSNFLPESAAYYVGNLKYSTFMLRFNENGTITDAVDCSQNPL   287
Q3I5J5      SYRVVMAMFS------QTTSNFLPESAAYYVGNLKYTTFMLSFNENGTITNAIDCAQNPL   287
Q0Q475      SYRVVMTMFS------QFNSNFLPESAAYYVGNLKYTTFMLSFNENGTITDAVDCSQNPL   287
            ::,.::: .            . :  :***:** *:   **:*  ::*****:;:*:: :**
            XXXXXXXXXXXXXXXXXXXXXXXXXXXXAAYXVGXLXXXTFXLXXXENGTITXAXDCXXXPL

P0DTC2      SETKCTLKSFTVEKGIYQTSNFRVQPTESIVRFPNITNLCPFGEVFNATRFASVYAWNRK   356
A0A6B9WHD3  SETKCTLKSFTVEKGIYQTSNFRVQPTDSIVRFPNITNLCPFGEVFNATTFASVYAWNRK   356
P59594      AELKCSVKSFEIDKGIYQTSNFRVVPSGDVVRFPNITNLCPFGEVFNATKFPSVYAWERK   343
Q5GDB5      AELKCSVKSFEIDKGIYQTSNFRVVPSGDVVRFPNITNLCPFGEVFNATKFPSVYAWERK   343
Q3LZX1      AELKCTIKNFNVDKGIYQTSNFRVSPTQEVIRFPNITNRCPFDKVFNATRFPNVYAWERT   347
Q3I5J5      AELKCTIKNFNVSKGIYQTSNFRVSPTQEVIRFPNITNRCPFDKVFNATRFPNVYAWERT   347
Q0Q475      AELKCTIKNFNVSKGIYQTSNFRVTPTQEVVRFPNITNRCPFDKVFNASRFPNVYAWERT   347
            :* **::*.* ,:*********  *:  .;:******  ***.:****; * ,****:*.
            XEXKCXXKXFXXXKGIYQTSNFRVXPXXXXXXRFPNITNXCPFXXVFNAXXFXXVYAWXRX
```

FIG. 12A

```
P0DTC2       RISNCVADYSVLYNSASFSTFKCYGVSPTKLNDLCFTNVYADSFVIRGDEVRQIAPGQTG   416
A0A6B9WHD3   RISNCVADYSVLYNSTSFSTFKCYGVSPTKLNDLCFTNVYADSFVITGDEVRQIAPGQTG   416
P59594       KISNCVADYSVLYNSTFFSTFKCYGVSATKLNDLCFSNVYADSFVVKGDDVRQIAPGQTG   403
Q5GDB5       RISNCVADYSVLYNSTFSTFKCYGVSATKLNDLCFSNVYADSFVVKGDDVRQIAPGQTG    403
Q3LZX1       KISDCVADYTVLYNSTSFSTFKCYGVSPSKLIDLCFTSVYADTFLIRSSEVRQVAPGETG   407
Q3I5J5       KISDCVADYTVLYNSTSFSTFKCYGVSPSKLIDLCFTSVYADTFLIRSSEVRQVAPGETG   407
Q0Q475       KISDCVADYTVLYNSTSFSTFKCYGVSPSKLIDLCFTSVYADTFLIRSSEVRQVAPGETG   407
             :**:*****:*****:   **********:** ****:.****:*::  ..:***:***:**
             XISXCVADYXVLYNSXXFSTFKCYGVSXXKLXDLCFXXVYADXFXXXXXXVRQXAPGXTG

P0DTC2       KIADYNYKLPDDFTGCVIAWNSNNLDSKVGGNYNYLYRLFRKSNLKPFERDISTEIYQAG   476
A0A6B9WHD3   KIADYNYKLPDDFTGCVIAWNSKHIDAKEGGNFNYLYRLFRKANLKPFERDISTEIYQAG   476
P59594       VIADYNYKLPDDFMGCVLAWNTRNIDATSTGNYNYKYRYLHGKLRPFERDISNVPFSPD   463
Q5GDB5       VIADYNYKLPDDFMGCVLAWNTRNIDATSTGNYNYKYPYLHGKLRPFERDISNVPFSPD   463
Q3LZX1       VIADYNYKLPDDFTGCVIAWNTAKHDT---G--NYYYRSHRKTKLKPFERDLSSDD----  458
Q3I5J5       VIADYNYKLPDDFTGCVIAWNTAKQDQ---G--QYYYRSHRKTKLKPFERDLSSD-----  457
Q0Q475       VIADYNYKLPDDFTGCVIAWNTAQQDQ---G--QYYYRSYRKEKLKPFERDLSSD-----  457
             :*********** ***:***:  :      *  :*  *:  *: :*:*****:*.
             XIADYNYKLPDDFXGCVXAWNXXXXDXXXXGXXXYXYRXXRXXLXPFERDXSXXXXXXX

P0DTC2       STPCNGVEGFNCYFPLQSYGFQPTNGVGYQPYRVVVLSFELLHAPATVCGPKKSTNLVKN   536
A0A6B9WHD3   SKPCNGQTGLNCYYPLYRYGFYPTDGVGHQPYRVVVLSFELLNAPATVCGPKKSTNLVKN   536
P59594       GKPCTPP-ALNCYWPLNDYGFYTTTGIGYQPYRVVVLSFELLNAPATVCGPKLSTDLIKN  522
Q5GDB5       GKPCTPP-APNCYWPLNGYGFYTTSGIGYQPYRVVVLSFELLNAPATVCGPKLSTDLIKN  522
Q3LZX1       ---------GNGVYTLSTYDFNPNVPVAYQATRVVVLSFELLNAPATVCGPKLSTELVKN  509
Q3I5J5       ---------ENGVRTLSTYDFYPSVPVAYQATRVVVLSFELLNAPATVCGPKLSTQLVKN  508
Q0Q475       ---------ENGVYTLSTYDFYPSIPVEYQATRVVVLSFELLNAPATVCGPKLSTQLVKN  508
                      *    * .*  : :*  **********:********** ***:;*:**
             XXXXXXXXXXXXXXXXLXXXYXFXXXXXXXXQXXRVVVLSFELLXAPATVCGPKXSTXLXKN

P0DTC2       KCVNFNFNGLTGTGVLTESNKKFLPFQQFGRDIADTTDAVRDPQTLEILDITPCSFGGVS   596
A0A6B9WHD3   KCVNFNFNGLTGTGVLTESNKKFLPFQQFGRDIADTTDAVRDPQTLEILDITPCSFGGVS   596
P59594       QCVNFNFNGLTGTGVLTPSSKRFQPFQQFGRDVSDFTDSVRDPKTSEILDISPCSFGGVS   582
Q5GDB5       QCVNFNFNGLTGTGVLTPSSKRFQPFQQFGRDVSDFTDSVRDPKTSEILDISPCSFGGVS   582
Q3LZX1       QCVNFNFNGLKGTGVLTSSSKRFQSFQQFGRDTSDFTDSVRDPQTLEILDISPCSFGGVS   569
Q3I5J5       QCVNFNFNGLKGTGVLTESSKRFQSFQQFGRDTSDFTDSVRDPQTLEILDISPCSFGGVS   568
Q0Q475       QCVNFNFNGLRGTGVLTTSSKRFQSFQQFGRDTSDFTDSVRDPQTLEILDISPCSFGGVS   568
             :*********  ****** *.*:* ******  :* **:****:* ****:*********
             XCVNFNFNGLXGTGVLTXSXKXFXXFQQFGRDXXDXTDXVRDPXTXEILDIXPCSFGGVS

P0DTC2       VITPGTNTSNQVAVLYQDVNCTEVPVAIHADQLTPTWRVYSTGSNVFQTRAGCLIGAEHV   656
A0A6B9WHD3   VITPGTNASNQVAVLYQDVNCTEVPVAIHADQLTPTWRVYSTGSNVFQTRAGCLIGAEHV   656
P59594       VITPGTNASSEVAVLYQDVNCTDVSTAIHADQLTPAWRIYSTGNNVFQTQAGCLIGAEHV   642
Q5GDB5       VITPGTNASSEVAVLYQDVNCTDVSTLIHAEQLTPAWRIYSTGNNVFQTQAGCLIGAEHV   642
Q3LZX1       VITPGTNASSEVAVLYQDVNCTDVPTAIRADQLTPAWRVYSTGVNVFQTQAGCLIGAEHV   629
Q3I5J5       VITPGTNASSEVAVLYQDVNCTDVPAAIHADQLTPAWRVYSTGTNVFQTQAGCLIGAEHV   628
Q0Q475       VITPGTNASSEVAVLYQDVNCTDVPTSIHADQLTPAWRVYSTGVNVFQTQAGCLIGAEHV   628
             *******:*..:********** .  :**:*****:**:****.****:**********
             VITPGTNXSXXVAVLYQDVNCTXVXXXIXAXQLTPXWRXYSTGXNVFQTXAGCLIGAEHV

P0DTC2       NNSYECDIPIGAGICASYQTQTNSPRRARSVASQSIIAYTMSLGAENSVAYSNNSIAIPT   716
A0A6B9WHD3   NNSYECDIPIGAGICASYQTQTNS----RSVASQSIIAYTMSLGAENSVAYSNNSIAIPT   712
P59594       DTSYECDIPIGAGICASYHTVS----LLRSTSQKSIVAYTMSLGADSSIAYSNNTIAIPT   698
Q5GDB5       DTSYECDIPIGAGICASYHTVS----SLRSTSQKSIVAYTMSLGADSSIAYSNNTIAIPT   698
Q3LZX1       NASYECDIPIGAGICASYHTAS----VLRSTGQKSIVAYTMSLGAENSIAYANNSIAIPT   685
Q3I5J5       NASYECDIPIGAGICASYHTAS----TLRSVGQKSIVAYTMSLGAENSIAYANNSIAIPT   684
Q0Q475       NASYECDIPIGAGICASYHTAS----VLRSTGQKSIVAYTMSLGAENSIAYANNSIAIPT   684
              :*************:*:  :       **..:**::*********::*:**:**:*****
             XXSYECDIPIGAGICASYXTXXXXXXXXRSXXXSIXAYTMSLGAXXSXAYXNNXIAIPT
```

FIG. 12B

```
P0DTC2       NFTISVTTEILPVSMTKTSVDCTMYICGDSTECSNLLLQYGSFCTQLNRALTGIAVEQDK    776
A0A6B9WHD3   NFTISVTTEILPVSMTKTSVDCTMYICGDSTECSNLLLQYGSFCTQLNRALTGIAVEQDK    772
P59594       NFSISITTEVMPVSMAKTSVDCNMYICGDSTECANLLLQYGSFCTQLNRALSGIAAEQDR    758
Q5GDB5       NFSISITTEVMPVSMAKTSVDCNMYICGDSTECANLLLQYGSFCRQLNRALSGIAAEQDR    758
Q3LZX1       NFSISVTTEVMPVSMAKTAVDCMYICGDSLECSNLLLQYGSFCTQLNRALTGIAIEQDK    745
Q3I5J5       NFSISVTTEVMPVSMAKTSVDCTMYICGDSLECSNLLLQYGSFCTQLNRALSGIAIEQDK    744
Q0Q475       NFSISVTTEVMPVSIAKTSVDCTMYICGDSLECSNLLLQYGSFCTQLNRALTGIAIEQDK    744
             **:**:****:.***.***.***:*******:**.**************.***:***.***:
             NFXISXTTEXXPVSXXKTXVDCXMYICGDSXECXNLLLQYGSFCXQLNRALXGIAXEQDX

P0DTC2       NTQEVFAQVKQIYKTPPIKDFGGFNFSQILPDPSKPSKRSFIEDLLFNKVTLADAGFIKQ    836
A0A6B9WHD3   NTQEVFAQVKQIYKTPPIKDFGGFNFSQILPDPSKPSKRSFIEDLLFNKVTLADAGFIKQ    832
P59594       NTREVFAQVKQMYKTPTLKYFGGFNFSQILPDPLKPTKRSFIEDLLFNKVTLADAGFMKQ    819
Q5GDB5       NTREVFVQVKQMYKTPTLKDFGGFNFSQILPDPLKPTKRSFIEDLLFNKVTLADAGFMKQ    818
Q3LZX1       NTQEVFAQVKQMYKTPAIKDFGGFNFSQILPDPSKPTKRSFIEDLLFNKVTLADAGFMKQ    805
Q3I5J5       NTQEVFAQVKQMYKTPAIKDFGGFNFSQILPDPSKPTKRSFIEDLLFNKVTLADAGFMKQ    804
Q0Q475       NTQEVFAQVKQMYKTPAIKDFGGFNFSQILPDPSKPTKRSFIEDLLFNKVTLADAGFMKQ    804
             **:***.****:****  :* ************** **:*********************:**
             NTXEVFXQVKQXYKTPXXKXFGGFNFSQILPDPXKPXKRSFIEDLLFNKVTLADAGFXKQ

P0DTC2       YGDCLGDIAARDLICAQKFNGLTVLPPLLTDEMIAQYTSALLAGTITSGWTFGAGAALQI    896
A0A6B9WHD3   YGDCLGDIAARDLICAQKFNGLTVLPPLLTDEMIAQYTSALLAGTITSGWTFGAGAALQI    892
P59594       YGECLGDINARDLICAQKFNGLTVLPPLLTDDMIAAYTAALVSGTATAGWTFGAGAALQI    878
Q5GDB5       YGECLGDINARDLICAQKFNGLTVLPPLLTDDMIAAYTAALVSGTATAGWTFGAGAALQI    878
Q3LZX1       YGDCLGDVSARDLICAQKFNGLTVLPPLLTDEMVAAYTAALVSGTATAGWTFGAGAALQI    865
Q3I5J5       YGECLGDISARDLICAQKFNGLTVLPPLLTDEMIAAYTAALVSGTATAGWTFGAGSALQI    864
Q0Q475       YGECLGDISARDLICAQKFNGLTVLPPLLTDEMIAAYTAALVSGTATAGWTFGAGSALQI    864
             **:****:  **************.****:*:*:.**:**:.**:*.:*******.****
             YGXCLGDXXARDLICAQKFNGLTVLPPLLTDXMXAXYTXALXXGTXTXGWTFGAGXALQI

P0DTC2       PFAMQMAYRFNGIGVTQNVLYENQKLIANQFNSAIGKIQDSLSSTASALGKLQDVVNQNA    956
A0A6B9WHD3   PFAMQMAYRFNGIGVTQNVLYENQKLIANQFNSAIGKIQDSLSSTASALGKLQDVVNQNA    952
P59594       PFAMQMAYRFNGIGVTQNVLYENQKQIANQFNKAISQIQESLTTTSTALGKLQDVVNQNA    938
Q5GDB5       PFAMQMAYRFNGIGVTQNVLYENQKQIANQFNKAISQIQESLTTTSTALGKLQDVVNQNA    938
Q3LZX1       PFAMQMAYRFNGIGVTQNVLYENQKLIANQFNSAIGKIQESLSSTASALGKLQDVVNQNA    925
Q3I5J5       PFAMQMAYRFNGIGVTQNVLYENQKQIANQFNKAISQIQESLTTTSTALGKLQDVVNQNA    924
Q0Q475       PFAMQMAYRFNGIGVTQNVLYENQKQIANQFNKAISQIQESLTTTSTALGKLQDVVNDNA    924
             ************************ ******.**..**:**:.*::***********:**
             PFAMQMAYRFNGIGVTQNVLYENQKXIANQFNKAIXXIQXSLXXTXXALGKLQDVVNXNA

P0DTC2       QALNTLVKQLSSNFGAISSVLNDILSRLDKVEAEVQIDRLITGRLQSLQTYVTQQLIRAA    1016
A0A6B9WHD3   QALNTLVKQLSSNFGAISSVLNDILSRLDKVEAEVQIDRLITGRLQSLQTYVTQQLIRAA    1012
P59594       QALNTLVKQLSSNFGAISSVLNDILSRLDKVEAEVQIDRLITGRLQSLQTYVTQQLIRAA    998
Q5GDB5       QALNTLVKQLSSNFGAISSVLNDILSRLDKVEAEVQIDRLITGRLQSLQTYVTQQLIRAA    998
Q3LZX1       QALNTLVKQLSSNFGAISSVLNDILSRLDKVEAEVQIDRLITGRLQSLQTYVTQQLIRAA    985
Q3I5J5       QALNTLVKQLSSNFGAISSVLNDILSRLDKVEAEVQIDRLITGRLQSLQTYVTQQLIRAA    984
Q0Q475       QALNTLVKQLSSNFGAISSVLNDILSRLDKVEAEVQIDRLITGRLQSLQTYVTQQLIRAA    984
             ************************************************************
             QALNTLVKQLSSNFGAISSVLNDILSRLDKVEAEVQIDRLITGRLQSLQTYVTQQLIRAA

P0DTC2       EIRASANLAATKMSECVLGQSKRVDFCGKGYHLMSFPQSAPHGVVFLHVTYVPAQEKNFT    1076
A0A6B9WHD3   EIRASANLAATKMSECVLGQSKRVDFCGKGYHLMSFPQSAPHGVVFLHVTYVPAQEKNFT    1072
P59594       EIRASANLAATKMSECVLGQSKRVDFCGKGYHLMSFPQAAPHGVVFLHVTYVPSQERNFT    1058
Q5GDB5       EIRASANLAATKMSECVLGQSKRVDFCGKGYHLMSFPQAAPHGVVFLHVTYVPSQERNFT    1058
Q3LZX1       EIRASANLAATKMSECVLGQSKRVDFCGKGYHLMSFPQSAPHGVVFLHVTYVPSQEKNFT    1045
Q3I5J5       EIRASANLAATKMSECVLGQSKRVDFCGKGYHLMSFPQAAPHGVVFLHVTYVPSQERNFT    1044
Q0Q475       EIRASANLAATKMSECVLGQSKRVDFCGKGYHLMSFPQAAPHGVVFLHVTYVPSQERNFT    1044
             **************************************:*************.**:***
             EIRASANLAATKMSECVLGQSKRVDFCGKGYHLMSFPQXAPHGVVFLHVTYVPXQEXNFT
```

FIG. 12C

```
P0DTC2      TAPAICHDGKAHFPREGVFVSNGTHWFVTQRNFYEPQIITTDNTFVSGNCDVVIGIVNNT   1136
A0A6B9WHD3  TAPAICHDGKAHFPREGVFVSNGTHWFVTQRNFYEPQIITTDNTFVSGSCDVVIGIVNNT   1132
P59594      TAPAICHEGKAYFPREGVFVFNGTSWFITQRNFFSPQIITTDNTFVSGNCDVVIGIINNT   1118
Q5GDB5      TAPAICHEGKAYFPREGVFVFNGTSWFITQRNFFSPQIITTDNTFVSGNCDVVIGIINNT   1118
Q3LZX1      TAPAICHEGKAYFPREGVFVSNGTSWFITQRNFYSPQLITTDNTFVSGNCDVVIGIINNT   1105
Q3I5J5      TAPAICHEGKAYFPREGVFVSNGTSWFITQRNFYSPQIITTDNTFVAGSCDVVIGIINNT   1104
Q0Q475      TAPAICHEGKAYFPREGVFVSNGTSWFITQRNFYSPQIITTDNTFVAGNCDVVIGIINNT   1104
            ******:***:********  ***  **:*****: .**:********:*.*******:***
            TAPAICHXGKAXFPREGVFVXNGTXWFXTQRNFXXPQXITTDNTFVXGXCDVVIGIXNNT

P0DTC2      VYDPLQPELDSFKEELDKYFKNHTSPDVDLGDISGINASVVNIQKEIDRLNEVAKNLNES   1196
A0A6B9WHD3  VYDPLQPELDSFKEELDKYFKNHTSPDVDLGDISGINASVVNIQKEIDRLNEVAKNLNES   1192
P59594      VYDPLQPELDSFKEELDKYFKNHTSPDVDLGDISGINASVVNIQKEIDRLNEVAKNLNES   1178
Q5GDB5      VYDPLQPELDSFKEELDKYFKNHTSPDVDLGDISGINASVVNIQEEIDRLNEVAKNLNES   1178
Q3LZX1      VYDPLQPELDSFKEELDKYFKNHTSPDVDLGDISGINASVVNIQKEIDRLNEVAKNLNES   1165
Q3I5J5      VYDPLQPELDSFKEELDKYFKNHTSPDVDLGDISGINASVVNIQKEIDRLNEVAKNLNES   1164
Q0Q475      VYDPLQPELDSFKEELDKYFKNHTSPDVDLGDISGINASVVNIQKEIDRLNEVAKNLNES   1164
            ********************************************:**************
            VYDPLQPELDSFKEELDKYFKNHTSPDVDLGDISGINASVVNIQXEIDRLNEVAKNLNES

P0DTC2      LIDLQELGKYEQYIKWPWYIWLGFIAGLIAIVMVTIMLCCMTSCCSCLKGCCSCGSCCKF   1256
A0A6B9WHD3  LIDLQELGKYEQYIKWPWYIWLGFIAGLIAIIMVTIMLCCMTSCCSCLKGCCSCGSCCKF   1252
P59594      LIDLQELGKYEQYIKWPWYVWLGFIAGLIAIVMVTILLCCMTSCCSCLKGACSCGSCCKF   1238
Q5GDB5      LIDLQELGKYEQYIKWPWYVWLGFIAGLIAIVMVTILLCCMTSCCSCLKGACSCGSCCKF   1238
Q3LZX1      LIDLQELGKYEQYIKWPWYVWLGFIAGLIAIVMVTILLCCMTSCCSCLKGACSCGSCCKF   1225
Q3I5J5      LIDLQELGKYEQYIKWPWYVWLGFIAGLIAIVMVTILLCCMTSCCSCLKGACSCGSCCKF   1224
Q0Q475      LIDLQELGKYEQYIKWPWYVWLGFIAGLIAIVMVTILLCCMTSCCSCLKGACSCGSCCKF   1224
            ******************:***********:***:*:***********.********
            LIDLQELGKYEQYIKWPWYXWLGFIAGLIAIXMVTIXLCCMTSCCSCLKGXCSCGSCCKF

P0DTC2      DEDDSEPVLKGVKLHYT   1273    (SEQ ID NO:320)
A0A6B9WHD3  DEDDSEPVLKGVKLHYT   1269    (SEQ ID NO:321)
P59594      DEDDSEPVLKGVKLHYT   1255    (SEQ ID NO:322)
Q5GDB5      DEDDSEPVLKGVKLHYT   1255    (SEQ ID NO:323)
Q3LZX1      DEDDSEPVLKGVKLHYT   1242    (SEQ ID NO:324)
Q3I5J5      DEDDSEPVLKGVKLHYT   1241    (SEQ ID NO:325)
Q0Q475      DEDDSEPVLKGVKLHYT   1241    (SEQ ID NO:326)
            *****************
            DEDDSEPVLKGVKLHYT           (SEQ ID NO:327)
```

FIG. 12D

```
P0DTC2      RVQPTESIVRFPNITNLCPFGEVFNATRFASVYAWNRKRISNCVADYSVLYNSASFSTFK   378
A0A6B9WHD3  RVQPTDSIVRFPNITNLCPFGEVFNATTFASVYAWNRKRISNCVADYSVLYNSTSFSTFK   378
P59594      RVVPSGDVVRFPNITNLCPFGEVFNATKFPSVYAWERKKISNCVADYSVLYNSTFFSTFK   365
Q5GDB5      RVVPSGDVVRFPNITNLCPFGEVFNATKFPSVYAWERKRISNCVADYSVLYNSTSFSTFK   365
Q3LZX1      RVSPTQEVIRFPNITNRCPFDKVFNATRFPNVYAWERTKISDCVADYTVLYNSTSFSTFK   369
Q3I5J5      RVSPTQEVIRFPNITNRCPFDKVFNATRFPNVYAWERTKISDCVADYTVLYNSTSFSTFK   369
Q0Q475      RVTPTQEVVRFPNITNRCPFDKVFNASRFPNVYAWERTKISDCVADYTVLYNSTSFSTFK   369
            ** *:  .::******** ***.:****:  *  ,****:*.:.**:****:*****: *****
            RVXPXXXXXRFPNITNXCPFXXXFNAXXFXXVYAWXRXXISXCVADYXVLYNSXXFSTFK

P0DTC2      CYGVSPTKLNDLCFTNVYADSFVIRGDEVRQIAPGQTGKIADYNYKLPDDFTGCVIAWNS   438
A0A6B9WHD3  CYGVSPTKLNDLCFTNVYADSFVITGDEVRQIAPGQTGKIADYNYKLPDDFTGCVIAWNS   438
P59594      CYGVSATKLNDLCFSNVYADSFVVKGDDVRQIAPGQTGVIADYNYKLPDDFMGCVLAWNT   425
Q5GDB5      CYGVSATKLNDLCFSNVYADSFVVKGDDVRQIAPGQTGVIADYNYKLPDDFMGCVLAWNT   425
Q3LZX1      CYGVSPSKLIDLCFTSVYADTFLIRSSEVRQVAPGETGVIADYNYKLPDDFTGCVIAWNT   429
Q3I5J5      CYGVSPSKLIDLCFTSVYADTFLIRSSEVRQVAPGETGVIADYNYKLPDDFTGCVIAWNT   429
Q0Q475      CYGVSPSKLIDLCFTSVYADTFLIRSSEVRQVAPGETGVIADYNYKLPDDFTGCVIAWNT   429
            ****  :**  ****:.****:*: :  .:***:***:** *************  ***:***:
            CYGVSXXKLXDLCFXXVYADXFXXXXXXVRQXAPGXTGXIADYNYKLPDDFXGCVXXWNX
                                                                         NX

P0DTC2      NNLDSKVGGNYNYLYRLFRKSNLKPFERDISTEIYQAGSTPCNGVEGFNCYFPLQSYGFQ   498
A0A6B9WHD3  KHIDAKEGGNFNYLYRLFRKANLKPFERDISTEIYQAGSKPCNGQTGLNCYYPLYRYGFY   498
P59594      RNIDATSTGNYNYKYRYLRHGKLRPFERDISNVPFSPDGKPCTPP-ALNCYWPLNDYGFY   484
Q5GDB5      RNIDATSTGNYNYKYRYLRHGKLRPFERDISNVPFSPDGKPCTPP-APNCYWPLNGYGFY   484
Q3LZX1      AKHDT----G---NYYYRSHRKTKLKPFERDLSSDD---------------GNGVYTLSTYDFN   471
Q3I5J5      AKQDQ----G---QYYYRSHRKTKLKPFERDLSSD----------------ENGVRTLSTYDFY   470
Q0Q475      AQQDQ----G---QYYYRSYRKEKLKPFERDLSSD----------------ENGVYTLSTYDFY   470
              : *      *    :* **  *; :*:*****:*.         *      *  *,*
            XXXDXXXGXXXYXYPXXRXXXLXPFERDXSXXXXXXXXXXXXXXXXXNXXXLXXYXFX
            XXXDXXXXGXXXYXYRXXRXXXLXPFERDXSXXXXXXXXXXXXXXXXXXNXXXLXXYXFX

P0DTC2      PTNGVGYQPYRVVVLSFELLHAPATVCGPKKSTNLVKNKCVNF   541  (SEQ ID NO:328)
A0A6B9WHD3  PTDGVGHQPYRVVVLSFELLNAPATVCGPKKSTNLVKNKCVNF   541  (SEQ ID NO:329)
P59594      TTTGIGYQPYRVVVLSFELLNAPATVCGPKLSTDLIKNQCVNF   527  (SEQ ID NO:330)
Q5GDB5      TTSGIGYQPYRVVVLSFELLNAPATVCGPKLSTDLIKNQCVNF   527  (SEQ ID NO:331)
Q3LZX1      PNVPVAYQATRVVVLSFELLNAPATVCGPKLSTELVKNQCVNF   514  (SEQ ID NO:332)
Q3I5J5      PSVPVAYQATRVVVLSFELLNAPATVCGPKLSTQLVKNQCVNF   513  (SEQ ID NO:333)
Q0Q475      PSIPVEYQATRVVVLSFELLNAPATVCGPKLSTQLVKNQCVNF   513  (SEQ ID NO:334)
             .  :  :*  ********** ********* **:*:**:****
            XXXXXXXQXXRVVVLSFELLXAPATVCGPKXSTXLXKNXCVNF    (SEQ ID NO:335)
            XXXXXXXQXX                                     (SEQ ID NO:336)
```

FIG. 12E

CORONAVIRUS NEUTRALIZING HUMANIZED ANTIBODIES AND USES THEREOF

STATEMENT OF GOVERNMENT INTEREST

This invention was made with Government support under Contract No. DE-NA0003525 awarded by the United States Department of Energy/National Nuclear Security Administration. The U.S. Government has certain rights in the invention

REFERENCE TO A SEQUENCE LISTING APPENDIX

A sequence listing appendix including an ASCII formatted file accompanies this application. The appendix includes a file named "SANDP010_ST25.txt," created on Feb. 19, 2021 (size of 256 kilobytes), which is hereby incorporated by reference in its entirety.

FIELD OF THE INVENTION

The present disclosure relates to an isolated or purified antibody, or a fragment thereof, having a binding domain that binds to a coronavirus (e.g., SARS-COV-2 or a portion thereof). In other embodiments, the antibody includes a binding domain that competes with binding to angiotensin converting enzyme 2 (ACE2) or a portion thereof. Methods of using such antibodies are also described herein, such as methods of treating, prophylactically treating, or delaying the progression of a disease associated with a coronavirus.

BACKGROUND OF THE INVENTION

Severe acute respiratory syndrome coronavirus 2 (SARS-COV-2) remains a challenging public health issue. There is a need for further strategies and efforts to control disease associated with this virus.

SUMMARY OF THE INVENTION

The present invention relates to use of an isolated or purified antibody, or a fragment thereof, that binds to SARS-COV-2 or a portion thereof (e.g., the spike protein or receptor-binding domain (RBD) of the spike protein). Such antibodies, in some instances, can also be characterized as competing (e.g., with SARS-COV-2) for binding with angiotensin converting enzyme 2 (ACE2). In particular, provided herein are complementarity determining regions (CDRs) that provide such binding. The antibody can have any useful form, such as a single variable domain (VHH) or nanobody, a single-chain variable-fragment (scFv) antibody, a monoclonal antibody (mAb), an antigen-binding fragment (Fab), a heavy-chain only antibody (HcAb), an Immunoglobulin G (IgG) antibody, as well as bivalent, biparatropic, bispecific, chimeric, and humanized forms thereof. Additional details follow.

Accordingly, in a first aspect the present disclosure features an isolated or purified antibody or fragment thereof, including a first binding domain, wherein the first binding domain includes: a first complementarity determining region including a polypeptide sequence having at least 90% sequence identity to any one of SEQ ID NOs: 150-155; a second complementarity determining region including a polypeptide sequence having at least 90% sequence identity to any one of SEQ ID NOs: 160-167; and/or a third complementarity determining region including a polypeptide sequence having at least 90% sequence identity to any one of SEQ ID NOs: 170-175.

In some embodiments, the first complementarity determining region includes a polypeptide sequence having at least 90% sequence identity to any one of SEQ ID NOs:40-73. In other embodiments, the second complementarity determining region includes a polypeptide sequence having at least 90% sequence identity to any one of SEQ ID NOs:74-107. In yet other embodiments, the third complementarity determining region includes a polypeptide sequence having at least 90% sequence identity to any one of SEQ ID NOs: 108-141.

In some embodiments, the antibody or fragment thereof further includes: a first framework region attached to an N-terminus of the first complementarity determining region; a second framework region disposed between the first and second complementarity determining regions; a third framework region disposed between the second and third complementarity determining regions; and a fourth framework region attached to a C-terminus of the third complementarity determining region.

In some embodiments, the antibody or fragment thereof includes a polypeptide sequence having at least 90% sequence identity to any one of SEQ ID NOs: 1-34 or a fragment thereof.

In some embodiments, the antibody or fragment thereof includes a polypeptide sequence having at least 90% sequence identity to any one of SEQ ID NOs: 180-186, wherein CDR1 includes the first complementarity determining region, wherein CDR2 includes the second complementarity determining region, and wherein CDR3 includes the third complementarity determining region.

In other embodiments, the first framework region includes a polypeptide sequence having at least 90% sequence identity to any one of SEQ ID NOs:213-217. In yet other embodiments, the second framework region includes a polypeptide sequence having at least 90% sequence identity to any one of SEQ ID NOs:244-248. In other embodiments, the third framework region includes a polypeptide sequence having at least 90% sequence identity to any one of SEQ ID NOs:285-289. In yet other embodiments, the fourth framework region includes a polypeptide sequence having at least 90% sequence identity to any one of SEQ ID NOs:302-307.

In some embodiments, the first framework region includes a polypeptide sequence having at least 90% sequence identity to any one of SEQ ID NOs: 190-212. In other embodiments, the second framework region includes a polypeptide sequence having at least 90% sequence identity to any one of SEQ ID NOs:220-243. In yet other embodiments, the third framework region includes a polypeptide sequence having at least 90% sequence identity to any one of SEQ ID NOs:250-284. In some embodiments, the fourth framework region includes a polypeptide sequence having at least 90% sequence identity to any one of SEQ ID NOs: 290-301.

In some embodiments, the first complementarity determining region includes a polypeptide sequence having at least 90% sequence identity to any one of SEQ ID NOs:40-73; and/or the second complementarity determining region includes a polypeptide sequence having at least 90% sequence identity to any one of SEQ ID NOs:74-107; and/or the third complementarity determining region includes a polypeptide sequence having at least 90% sequence identity to any one of SEQ ID NOs: 108-141.

In any embodiment herein, the antibody or fragment thereof includes a nanobody.

In any embodiment herein, a binding domain of the antibody or fragment thereof (e.g., the first binding domain and/or the second binding domain) binds to a spike protein of a coronavirus or a receptor-binding domain of a coronavirus. In some embodiments, the coronavirus is SARS-CoV-2. In other embodiments, the spike protein includes a polypeptide sequence having at least 90% sequence identity to any one of SEQ ID NOs:320-327 or a fragment thereof. In yet other embodiments, the receptor-binding domain includes a polypeptide sequence having at least 90% sequence identity to any one of SEQ ID NOs:328-336 or a fragment thereof.

In any embodiment herein, the antibody or fragment thereof further includes a second binding domain that binds to a coronavirus or a portion thereof. In some embodiments, the second binding domain includes: a first complementarity determining region including a polypeptide sequence having at least 90% sequence identity to any one of SEQ ID NOs: 150-155; and/or a second complementarity determining region including a polypeptide sequence having at least 90% sequence identity to any one of SEQ ID NOs: 160-167; and/or a third complementarity determining region including a polypeptide sequence having at least 90% sequence identity to any one of SEQ ID NOs:170-175.

In some embodiments, the antibody or fragment thereof further includes a linker disposed between the first and second binding domains. Non-limiting linkers include any described herein, such as SEQ ID NOs:310-319.

In any embodiment herein, the antibody or fragment thereof further includes a therapeutic agent or a diagnostic agent attached directly or indirectly to the first binding domain.

In a second aspect, the present disclosure features a method of treating or prophylactically treating a viral infection. In some embodiments, the method includes: administering an isolated or purified antibody or fragment thereof (e.g., any described herein) to a subject in need thereof. In other embodiments, the isolated or purified antibody or fragment thereof is provided as a pharmaceutical composition having a pharmaceutically acceptable carrier (e.g., as described herein). Such a composition can be provided as a medication (e.g., a vaccine optionally including any useful adjuvant).

In some embodiments, the viral infection includes an infection from a coronavirus. In other embodiments, the coronavirus is SARS-COV-2 or a variant or a mutant thereof.

In some embodiments, the isolated or purified antibody or fragment thereof includes a first complementarity determining region including a polypeptide sequence having at least 90% sequence identity to any one of SEQ ID NOs:40-73; and/or a second complementarity determining region including a polypeptide sequence having at least 90% sequence identity to any one of SEQ ID NOs:74-107; and/or a third complementarity determining region including a polypeptide sequence having at least 90% sequence identity to any one of SEQ ID NOs: 108-141. Additional details follow.

Definitions

As used herein, the term "about" means +/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., J. Mol. Biol. 1990; 215:403-10; Zhang J et al., Genome Res. 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., Adv. Appl. Math. 1981; 2(4):482-9.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones. Non-limiting amino acids include glycine (Gly, G), alanine (Ala, A), valine (Val, V), isoleucine (Ile, I), leucine (Leu, L), cysteine (Cys, C), methionine (Met, M), aspartic acid (Asp, D), glutamic acid (Glu, E), arginine (Arg, R), histidine (His, H), lysine (Lys, K), asparagine (Asn, N), glutamine (Gln, Q), serine (Ser, S), threonine (Thr, T), proline (Pro, P), phenylalanine (Phe, F), tyrosine (Tyr, Y), tryptophan (Trp, W), selenocysteine (Sec, U), and pyrrolysine (Pyl, O).

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T);

a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); and a group of amino acids having sulfur containing side chains consists of cysteine (Cys, C) and methionine (Met, M). Exemplary conservative amino acid substitution groups are valine-leucine-isoleucine, phenylalanine-tyrosine, lysine-arginine, alanine-valine, glycine-serine, glutamate-aspartate, and asparagine-glutamine. The present disclosure encompasses any sequence having a conservative amino acid sequence of any polypeptide sequence described herein.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., J. Mol. Biol. 1981; 147:195-7) and BLAST (Basic Local Alignment Search Tool; Altschul S F et al., J. Mol. Biol. 1990; 215:403-10). These and other alignment algorithms are accessible using publicly available computer software such as "Best Fit" (Smith T F et al., Adv. Appl. Math. 1981; 2(4):482-9) as incorporated into GeneMatcher Plus.™. (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

By an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an antiviral agent, an effective amount of an agent is, for example, an amount sufficient to achieve a reduction in viral load or a mitigation of a symptom related to a viral infection or a delay in a symptom related to a viral infection, as compared to the response obtained without administration of the agent.

By "subject" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and/or remission (whether partial or total), whether detectable or undetectable.

By "attached," "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIGS. 2A-2C provide non-limiting sequences for nanobodies, in which complementarity determining regions (CDRs) are underlined. Provided are (A) sequences for SEQ ID NOs: 1-14, (B) sequences for SEQ ID NOs: 15-28, and (C) sequences for SEQ ID NOs:29-34.

FIG. 3 provides a non-limiting sequence logo for nanobody sequences provided as SEQ ID NOs: 1-34. The sequence logo was generated with WebLogo.

FIG. 4 provides non-limiting sequences for CDRs, including sequences for complementarity determining region 1 (CDR1, SEQ ID NOs:40-73), complementarity determining region 2 (CDR2, SEQ ID NOs:74-107), and complementarity determining region 3 (CDR3, SEQ ID NOs:108-141).

FIGS. 5A-5B provide (A) a non-limiting phylogenetic tree constructed from CDR1 sequences (SEQ ID NOs:40-73) and (B) a sequence alignment of non-limiting CDR1 sequences (SEQ ID NOs:40-58 and 68) and non-limiting consensus sequences (SEQ ID NOs:150-155).

FIGS. 6A-6B provide (A) a non-limiting phylogenetic tree constructed from CDR2 sequences (SEQ ID NOs:74-107) and (B) a sequence alignment of non-limiting CDR2 sequences (SEQ ID NOs:74-92 and 95) and non-limiting consensus sequences (SEQ ID NOs: 160-167).

FIGS. 7A-7B provide (A) a non-limiting phylogenetic tree constructed from CDR3 sequences (SEQ ID NOs: 108-141) and (B) a sequence alignment of non-limiting CDR3 sequences (SEQ ID NOs: 108-126) and non-limiting consensus sequences (SEQ ID NOs: 170-175).

FIGS. 8A-8B provide (A) a non-limiting schematic of an antibody having framework regions (FRs) interspersed with complementarity determining regions (CDRs), in which a nanobody can include framework regions 1-4 (FR1, FR2, FR3, and FR4) with interspersed CDR1, CDR2, and CDR3; and (B) non-limiting sequences (SEQ ID NOs: 180-186) for framework regions with interspersed CDR1, CDR2, and CDR3 sequences (e.g., any described herein, such as SEQ ID NOs:40-141, 150-155, 160-167, and 170-175).

FIGS. 9A-9D provide (A) a sequence alignment of non-limiting FR1 sequences (SEQ ID NOs: 190-212) and non-limiting consensus sequences (SEQ ID NOs:213-217); (B) a sequence alignment of non-limiting FR2 sequences (SEQ ID NOs:220-243) and non-limiting consensus sequences (SEQ ID NOs:244-248); (C) a sequence alignment of non-limiting FR3 sequences (SEQ ID NOs:250-284) and non-limiting consensus sequences (SEQ ID NOs:285-289); and (D) a sequence alignment of non-limiting FR4 sequences (SEQ ID NOs:290-301) and non-limiting consensus sequences (SEQ ID NOs:302-307).

FIGS. 10A-10C show mechanism of inhibition of viral infections with non-limiting nanobodies. Provided are results from (A) a competition ELISA with human ACE2 and full length SARS-COV-2 spike protein with particular nanobodies (SP1D9, SP3A5, SP3H4, and SP1B4); (B) a neutralization assay showing relative infection of green monkey kidney cells (vero) with VSV-SARS-COV-2 virus in the presence of particular nanobodies (SPID9, SP3A5, SP3H4, and SP1B4) and MM57; and (C) a neutralization assay showing relative infection with wild-type SARS-COV-2 in the presence of particular nanobodies (SP1D9, SP3A5, SP3H4, and SP1B4) and MM57. Experiments were performed in triplicate, two times, with similar results.

FIGS. 11A-11C show results of neutralization assays with non-limiting nanobodies. Provided are results for (A) SP3D11, SPIE1, SPIE4, SPIF6, SP3D6, SP3F9, MM57, and anti-VSV; (B) SP4B5, SPID8, SP1F2, SP1G7, SP2A7, SP2D8, and MM57; and (C) SP1A11, SP1A2, SP3H10, SP4A5, and MM57-2. Experiments were performed in triplicate, two times, with similar results.

FIGS. 12A-12E show (A-D) a sequence alignment of non-limiting sequences for spike glycoproteins (SEQ ID NOs:320-326) and a non-limiting consensus sequence (SEQ ID NOs:327) and (E) a sequence alignment of non-limiting sequences for RBDs of spike glycoproteins (SEQ ID NOs: 328-334) and non-limiting consensus sequences (SEQ ID NOs:335-336).

DETAILED DESCRIPTION OF THE INVENTION

The present invention relates to an isolated or purified antibody or fragment thereof, that binds to SARS-COV-2 or a portion thereof (e.g., the spike protein or receptor-binding domain (RBD) of the spike protein). We have identified CDRs that provide enhanced efficacy, as determined by reducing infectivity of a coronavirus and/or exhibiting binding to the coronavirus. Such CDRs can be provided in an antibody having any useful format, such as a nanobody or other forms described herein.

Figure 1:
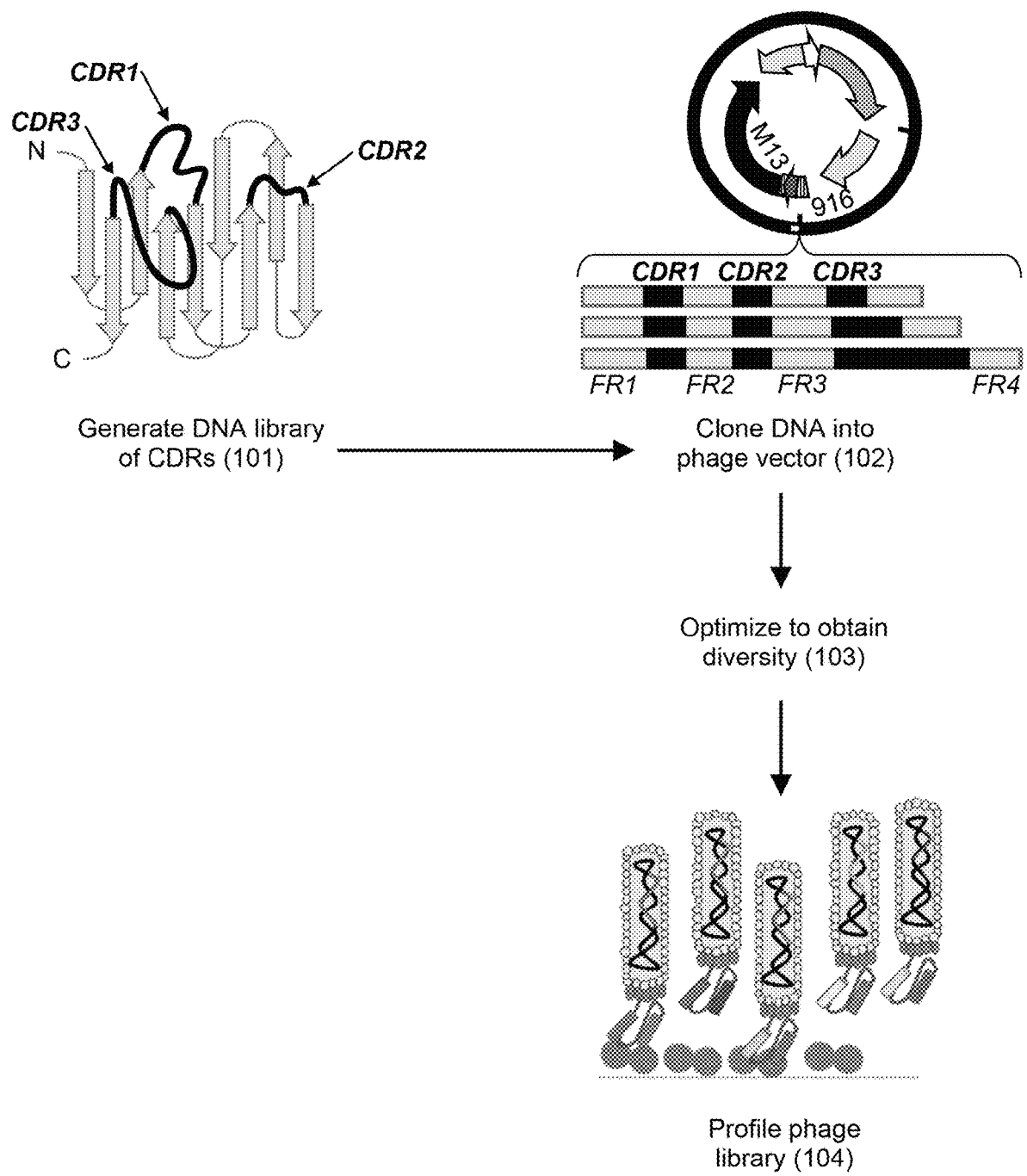
FIG. 1 shows a schematic of a non-limiting method for providing illustrative antibodies.

CDRs can be identified by using a phage library (FIG. 1). Such a library can be constructed by generating 101 a DNA library of CDRs with high diversity, cloning 102 the DNA into a phage vector to express nanobodies as fusion proteins with the phage coat protein, optimizing 103 the transformation to obtain phages having sufficient diversity, and profiling 104 the phage library by sequencing. Diversity can include distribution in both the amino acid content and the length of the CDRs.

The selections from the phage library can be screened. Such screening can include testing by various assays, including a competition enzyme-linked immunosorbent assay (ELISA), a binding assay with the coronavirus or a portion thereof (e.g., SARS-COV-2, the spike protein of SARS-COV-2, or the RBD of SARS-COV-2), a competition assay including the coronavirus (or a portion thereof) and a target of the coronavirus (e.g., human ACE2 or another receptor that binds to SARS-COV-2), and/or a neutralization assay including coronavirus-expressing cells.

The antibody can have any useful form, such as one or more of the following domains: a single variable domain (VHH) or nanobody, a variable heavy domain (VH), a variable light domain (VL), a single-chain variable-fragment (scFv) antibody, a monoclonal antibody (mAb), an antigen-binding fragment (Fab), a fragment crystallizable region (Fc region), a heavy-chain only antibody (HcAb), an Immunoglobulin G (IgG) antibody, as well as bivalent, trivalent, tetravalent, multivalent, biparatopic, bispecific, multispecific chimeric, and humanized forms thereof. Any of the forms can include a linker between a first amino acid sequence (any domain herein, e.g., such as VH) and a second amino acid sequence (any domain herein, e.g. such as VL).

The constructs herein can be employed as a nanobody, preferably human or humanized. In some embodiments, the nanobody has a molecular weight of about 12-15 kDa. In some embodiments, the nanobody can include a single VHH domain. In other embodiments, the nanobody can include a plurality of VHH domains, in which each VHH domain can be the same or different. Furthermore, each VHH domain can bind to the same target, the same portion of the same target, different targets, or different portions of the same target. Non-limiting targets are described herein.

One or more VHH domains can be fused to any useful amino acid sequence, such as a Fc domain or a humanized Fc domain. The VHH domains can be fused to other humanized forms of constant domains, such as Fc, CH1, CH2, CH3, and CL domains. Such VHH domains can be sued to other forms, such as IgG1, IgG3, IgA, or IgM.

Yet other forms can include an Fc region and a Fab; or an Fc region and a VHH. The Fc region can include heavy chains present in any useful isotype (A, E, G, or M), such as Immunoglobulin G (e.g., IgG1, IgG2a, or IgG3). The Fab region can include domains from the heavy and light chains, including the variable heavy (VH) and variable light (VL) domains. Within the VH and VL domains, CDRs can be configured to bind to a target of interest. The VHH domain can include a single variable domain having CDRs configured to bind to a target of interest.

The Fc region of the constructs herein can include a native immunoglobulin, i.e., as formed by the dimeric association of the respective Fc domains (or Fc moieties) of its two heavy chains, in which a native Fc region is homodimeric and comprises two polypeptide chains; or a genetically-fused Fc region or a single-chain Fc region (scFc region), in which a synthetic dimeric Fc region comprised of Fc domains (or Fc moieties) are genetically linked within a single polypeptide chain (i.e., encoded in a single contiguous genetic sequence) as described. In one embodiment, the construct includes a complete Fc region, whether present as one polypeptide chain (an scFc molecule) or in the wild-type form as two polypeptide chains.

The Fc region can include a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

The Fc domains or moieties of a polypeptide may be from any isotype (A, E, G, or M) and may be derived from different immunoglobulin molecules. For example, an Fc domain or moiety of a polypeptide may comprise a CH2 and/or CH3 domain derived from an IgG1 molecule and a hinge region derived from an IgG3 molecule. In another example, an Fc domain or moiety can comprise a chimeric hinge region derived, in part, from an IgG1 molecule and, in part, from an IgG3 molecule. In another example, an Fc domain or moiety can comprise a chimeric hinge derived, in part, from an IgG1 molecule and, in part, from an IgG4 molecule.

The constructs herein can be modified antibodies, which includes synthetic forms of antibodies which are altered such that they are not naturally occurring, e.g., antibodies that comprise at least two heavy chain portions but not two complete heavy chains (such as, domain deleted antibodies or minibodies); engineered antibodies having synthetic linkers, such as any described herein; and multispecific forms of antibodies (e.g., bispecific, trispecific, etc., forms of any antibody, such as a nanobody) altered to bind to two or more different antigens e.g., to the RBD of a coronavirus and another therapeutically relevant target binding site.

Modified antibodies can include other types of modifications, such as chemical modification (e.g., pegylation, glycosylation, lipidation, etc.), attachment to a particle or liposome, or bonding to a protein (e.g., a serum protein, a cytokine) or a cell (e.g., a CAR-T cell).

The constructs herein can be "chimeric" or "fusion" proteins. Such proteins comprises a first amino acid sequence linked to a second amino acid sequence to which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created using methods well known in the art, for example, by chemical synthesis, or by creating and translating a polynucleotide in which the peptide regions are encoded in the desired relationship.

Such forms or fusions can include a linker disposed between any number of domains, in which non-limiting linkers are described herein. Any useful linker can be employed, such as a peptide linker that can be cleavable or non-cleavable. Linkers can include or consist of a sequence according to the formula $[(Gly)_m(Ser)]_n(Gly)_p$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. Alternatively, the linker sequence includes or consists of a sequence according to the formula $(Gly)_p[(Ser)(Gly)_m]_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. In another embodiment, the linker sequence includes or consists of a sequence according to the formula $[(Gly)_m(Ser)(Gly)_p]_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. Further non-limiting linkers include any described herein, such as in SEQ ID NOs:310-319 (Table 1).

TABLE 1

Non-limiting linkers

| Name | Sequence | SEQ ID NO: |
|---|---|---|
| $G_3$ | GGG | 310 |
| $G_3S$ | GGGS | 311 |
| $G_4$ | GGGG | 312 |
| $G_4S$ | GGGGS | 313 |
| $G_2SG$ | GGSG | 314 |
| $(G_4S)_2$ | GGGGSGGGGS | 315 |
| $(G_4S)_3$ | GGGGSGGGGSGGGGS | 316 |
| $(G_4S)_4$ | GGGGSGGGGSGGGGSGGGGS | 317 |
| $(G_2SG)_2$ | GGSGGGSG | 318 |
| $(G_2SG)_3$ | GGSGGGSGGGSG | 319 |

The constructs can include other variations. Such variations can include one or more amino acids that facilitate humanization of an initial sequence. Humanization can include use of one or more amino acids present in a human form of the constant or variable regions (e.g., frameworks regions or CDRs). In other embodiments, the variation can include a sequence that lacks Cys and Met residues. In yet other embodiments, the CDR can have an altered length, such as a length from about 4-9 amino acids, 9-12 amino acids, or 12-15 amino acids.

The construct can be characterized in any useful manner. In one instance, the construct can bind a target (e.g., any described herein), in which such binding can be characterized by a dissociation constant ($K_d$) of about 0.5 nM to 1 µM and/or a half maximal inhibitory concentration ($IC_{50}$) of about 0.001-100 nM. In other embodiments, efficacy of binding can be characterized by a half maximal effective concentration ($EC_{50}$) of about 0.001-100 nM.

Binding Domains

The binding domain can have any useful sequence. In one embodiment, the binding domain includes or is a polypeptide sequence having at least 90% sequence identity to any one of SEQ ID NOs: 1-34 (FIGS. 2A-2C) or a fragment thereof. Non-limiting fragments can include a polypeptide that is one amino acid shorter than the reference sequence of SEQ ID NOs: 1-34. The omitted amino acid can be removed from the C-terminus.

FIG. 3 shows a non-limiting sequence logo obtained for nanobody sequences of SEQ ID NOs:1-34. As can be seen, a nanobody sequence can include framework regions (amino acid at positions 1-26, 34-52, 61-98, and 114-125) and CDRs (amino acid at positions 27-33, 53-60, and 99-113).

Within the variable domain of the antibody, three CDRs can be present. Non-limiting CDRs can include a first CDR, a second CDR, and a third CDR. Any of these CDRs can include or be a polypeptide sequence having at least 90% sequence identity to SEQ ID NOs:40-141 (FIG. 4) or a fragment thereof. The fragment can include a polypeptide that is one, two, or three amino acids shorter than the reference sequence of SEQ ID NOs:40-141. The omitted amino acid(s) can be removed from the C-terminus and/or the N-terminus.

Figure 5A:
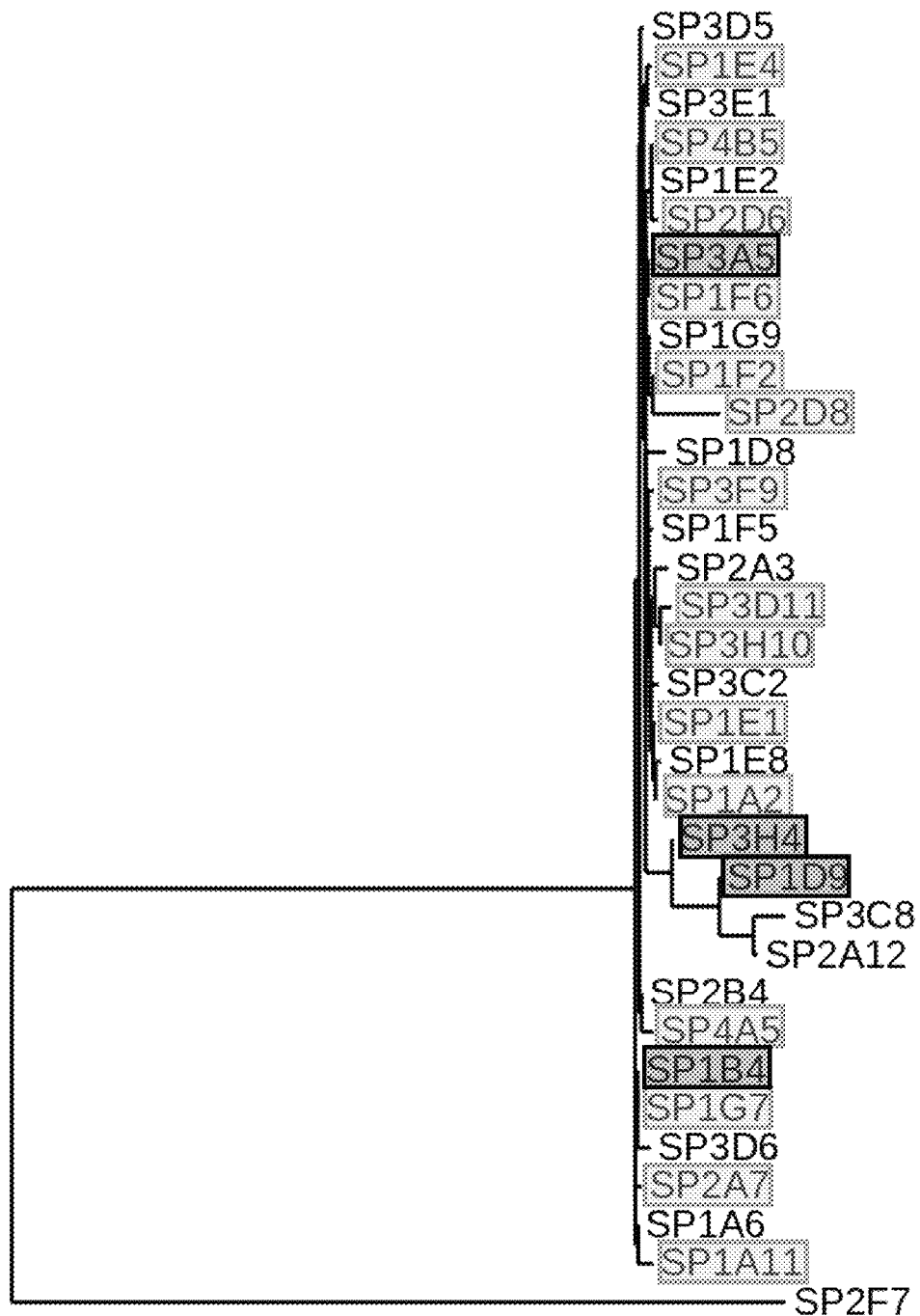

FIGS. 5A-5B provide a phylogentic tree and consensus sequences for non-limiting CDR1 sequences. In some embodiments, the first CDR includes or is a polypeptide sequence having at least 90% sequence identity to SEQ ID NO:150:

$X_1TX_3GX_5YR$, wherein:
$X_1$ is G, R, H, K, N, Q, S, T, F, Y, or absent (e.g., G, R, H, Q, S, T, F, or absent);
$X_3$ is A, V, D, E, S T, F, or Y (e.g., A, D, S, F, or Y); and
$X_5$ is G, A, V, I, L, D, E, R, H, K, N, Q, S, T, F, Y, or W (e.g., L, R, H, S, T, Y, or W).

In some embodiments, each X in SEQ ID NO: 150 can be an amino acid in any one of SEQ ID NOs:40-73 when any one of the sequences in SEQ ID NOs:40-73 is used as a reference sequence to be optimally aligned with SEQ ID NO:150. In other embodiments, each X in SEQ ID NO:150 can be an amino acid in any one of SEQ ID NOs:40-58 when any one of the sequences in SEQ ID NOs:40-58 is used as a reference sequence to be optimally aligned with SEQ ID NO:150.

In some embodiments, the first CDR includes or is a polypeptide sequence having at least 90% sequence identity to SEQ ID NOs: 151-154:

$X_1TFGX_5YR$ (SEQ ID NO:151),
$X_1TSGX_5YR$ (SEQ ID NO:152),
$X_1AFGX_5YR$ (SEQ ID NO:153), or
$X_1FFGX_5YR$ (SEQ ID NO:154), wherein:
$X_1$ is G, R, H, K, N, Q, S, T, F, Y, or absent (e.g., G, R, H, Q, S, T, F, or absent); and
$X_5$ is G, A, V, I, L, D, E, R, H, K, N, Q, S, T, F, Y, or W (e.g., L, R, H, S, T, Y, or W).

In some embodiments, each X in SEQ ID NOs: 151-154 can be an amino acid in any one of SEQ ID NOs:40-73 when any one of the sequences in SEQ ID NOs:40-73 is used as a reference sequence to be optimally aligned with SEQ ID NOs:151-154. In other embodiments, each X in SEQ ID NOs: 151-154 can be an amino acid in any one of SEQ ID NOs:40-58 when any one of the sequences in SEQ ID NOs:40-58 is used as a reference sequence to be optimally aligned with SEQ ID NOs: 151-154.

In some embodiments, the first CDR includes or is a polypeptide sequence having at least 90% sequence identity to SEQ ID NO: 155:

$X_1X_2YGX_5YR$ wherein:
$X_1$ is G, R, H, K, N, Q, S, T, F, Y, or absent (e.g., G, R, H, Q, S, T, F, or absent);
$X_2$ is A, V, I, L, R, H, K, S, T, F, Y, or P (e.g., A, R, S, T, F, or P); and
$X_5$ is G, A, V, I, L, D, E, R, H, K, N, Q, S, T, F, Y, or W (e.g., L, R, H, S, T, Y, or W).

In some embodiments, each X in SEQ ID NO: 155 can be an amino acid in any one of SEQ ID NOs:40-73 when any one of the sequences in SEQ ID NOs:40-73 is used as a reference sequence to be optimally aligned with SEQ ID NO:155. In other embodiments, each X in SEQ ID NO:155 can be an amino acid in any one of SEQ ID NOs:40-58 when any one of the sequences in SEQ ID NOs:40-58 is used as a reference sequence to be optimally aligned with SEQ ID NO: 155.

Figure 6A:
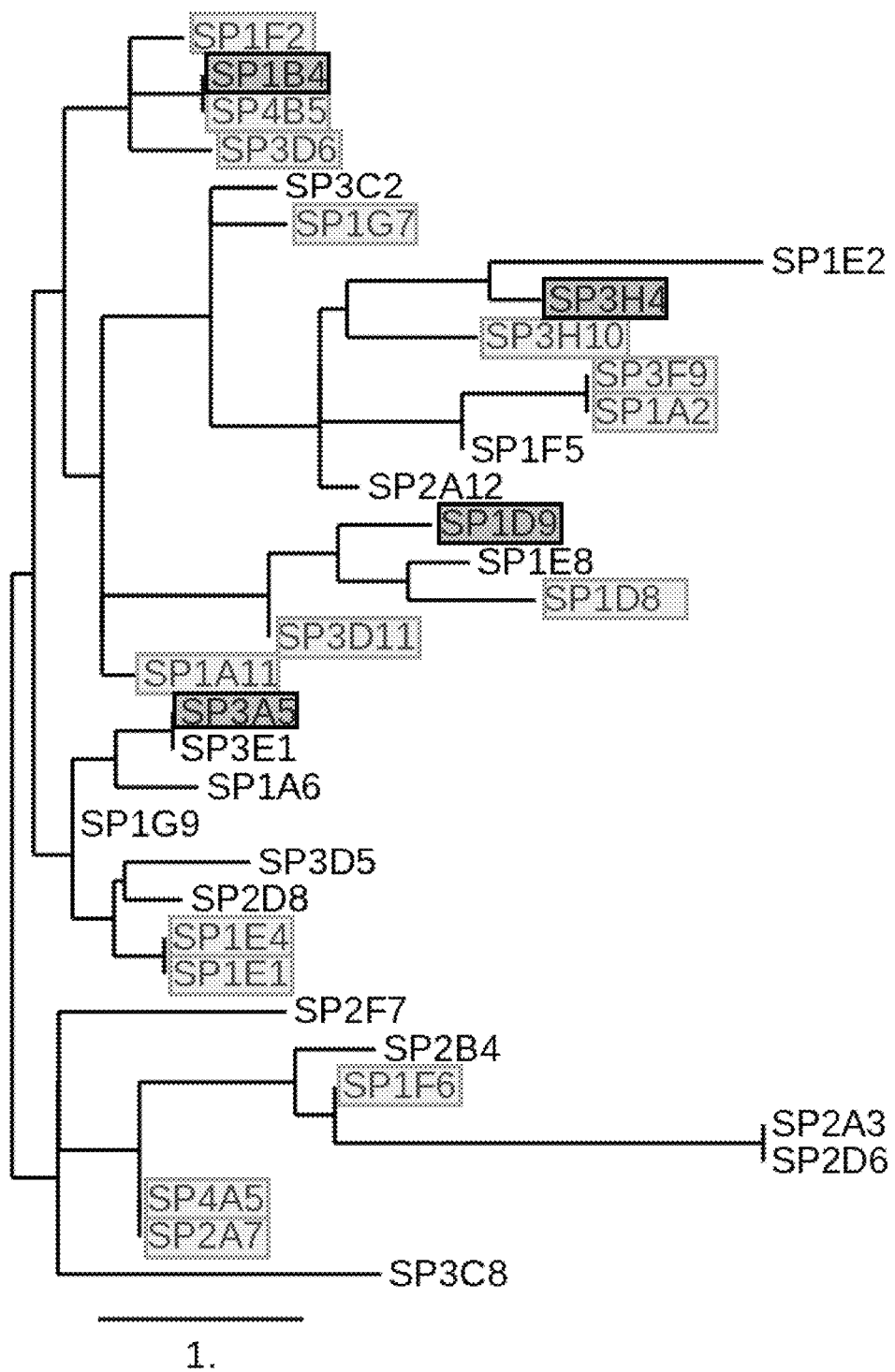

FIGS. 6A-6B provide a phylogentic tree and consensus sequences for non-limiting CDR2 sequences. In some embodiments, the second CDR includes or is a polypeptide sequence having at least 90% sequence identity to SEQ ID NO:160:

$SX_3SGX_6STR$, wherein:
$X_3$ is G, D, E, S, T, F, Y, W, or absent (e.g., G, D, S, T, W, or absent); and $X_6$ is G, A, V, D, E, R, H, K, N, Q, S, T, F, Y, or absent (e.g., G, A, D, K, Q, S, T, Y, or absent).

In some embodiments, each X in SEQ ID NO: 160 can be an amino acid in any one of SEQ ID NOs: 74-107 when any one of the sequences in SEQ ID NOs:74-107 is used as a reference sequence to be optimally aligned with SEQ ID NO:160. In other embodiments, each X in SEQ ID NO:160 can be an amino acid in any one of SEQ ID NOs: 74-92 when any one of the sequences in SEQ ID NOs: 74-92 is used as a reference sequence to be optimally aligned with SEQ ID NO:160.

In other embodiments, the second CDR includes or is a polypeptide sequence having at least 90% sequence identity to SEQ ID NO:161:

$X_5GX_7X_8GHTR$, wherein:
$X_5$ is G, D, E, S, T, or absent (e.g., G, D, S, or absent);
$X_7$ is G, A, V, I, L, D, E, R, H, K, S, T, or absent (e.g., G, A, E, H, S, or absent); and
$X_8$ is G, A, V, I, L, D, E, R, H, K, N, Q, S, T, F, or Y (e.g., G, A, D, R, Q, T, or F).

In some embodiments, each X in SEQ ID NO:161 can be an amino acid in any one of SEQ ID NOs: 74-107 when any one of the sequences in SEQ ID NOs: 74-107 is used as a reference sequence to be optimally aligned with SEQ ID NO: 161. In other embodiments, each X in SEQ ID NO:161 can be an amino acid in any one of SEQ ID NOs: 74-92 when any one of the sequences in SEQ ID NOs: 74-92 is used as a reference sequence to be optimally aligned with SEQ ID NO: 161.

In yet other embodiments, the second CDR includes or is a polypeptide sequence having at least 90% sequence identity to SEQ ID NO: 162:

$X_1AX_3AGYAQ$, wherein:
$X_1$ is G, D, E, R, H, K, or absent (e.g., D, R, or absent); and
$X_3$ is G, D, E, S, T, F, Y, W, or absent (e.g., G, D, S, T, W, or absent).

In some embodiments, each X in SEQ ID NO: 162 can be an amino acid in any one of SEQ ID NOs: 74-107 when any one of the sequences in SEQ ID NOs: 74-107 is used as a reference sequence to be optimally aligned with SEQ ID NO:162. In other embodiments, each X in SEQ ID NO:162 can be an amino acid in any one of SEQ ID NOs: 74-92 when any one of the sequences in SEQ ID NOs:74-92 is used as a reference sequence to be optimally aligned with SEQ ID NO:162.

In some embodiments, the second CDR includes or is a polypeptide sequence having at least 90% sequence identity to SEQ ID NO: 163:

$GX_3X_4DX_6STX_9$, wherein:
$X_3$ is G, D, E, S, T, F, Y, W, or absent (e.g., G, D, S, T, W, or absent);
$X_4$ is G, A, V, I, L, S, or T (e.g., G, A, or S);
$X_6$ is G, A, V, D, E, R, H, K, N, Q, S, T, F, Y, W, or absent (e.g., G, A, D, K, Q, S, T, Y, or absent); and
$X_9$ is G, A, V, I, L, R, H, K, N, Q, S, T, F, Y, W, or absent (e.g., G, A, R, H, K, Q, T, F, Y, W, or absent).

In some embodiments, each X in SEQ ID NO:163 can be an amino acid in any one of SEQ ID NOs: 74-107 when any one of the sequences in SEQ ID NOs: 74-107 is used as a reference sequence to be optimally aligned with SEQ ID NO:163. In other embodiments, each X in SEQ ID NO: 163 can be an amino acid in any one of SEQ ID NOs: 74-92 when any one of the sequences in SEQ ID NOs: 74-92 is used as a reference sequence to be optimally aligned with SEQ ID NO: 163.

In other embodiments, the second CDR includes or is a polypeptide sequence having at least 90% sequence identity to SEQ ID NO: 164:

$X_2WX_4GX_6SAX_9$, wherein:
$X_2$ is G, A, V, I, L, D, E, S, T, or absent (e.g., G, A, D, S, T, or absent);
$X_4$ is G, A, V, I, L, S, or T (e.g., G, A, or S);
$X_6$ is G, A, V, D, E, R, H, K, N, Q, S, T, F, Y, W, or absent (e.g., G, A, D, K, Q, S, T, Y, or absent); and
$X_9$ is G, A, V, I, L, R, H, K, N, Q, S, T, F, Y, W, or absent (e.g., G, A, R, H, K, Q, T, F, Y, W, or absent).

In some embodiments, each X in SEQ ID NO:164 can be an amino acid in any one of SEQ ID NOs: 74-107 when any one of the sequences in SEQ ID NOs: 74-107 is used as a reference sequence to be optimally aligned with SEQ ID NO:164. In other embodiments, each X in SEQ ID NO:164 can be an amino acid in any one of SEQ ID NOs: 74-92 when any one of the sequences in SEQ ID NOs: 74-92 is used as a reference sequence to be optimally aligned with SEQ ID NO:164.

In yet other embodiments, the second CDR includes or is a polypeptide sequence having at least 90% sequence identity to SEQ ID NO: 165:

$X_2WX_4GX_6SX_8X_9$, wherein:
$X_2$ is G, A, V, I, L, D, E, S, T, or absent (e.g., G, A, D, S, T, or absent);
$X_4$ is G, A, V, I, L, S, or T (e.g., G, A, or S);
$X_6$ is G, A, V, D, E, R, H, K, N, Q, S, T, F, Y, W, or absent (e.g., G, A, D, K, Q, S, T, Y, or absent);
$X_8$ is G, A, V, I, L, D, E, R, H, K, N, Q, S, T, F, Y, or W (e.g., G, A, D, R, Q, T, or F); and
$X_9$ is G, A, V, I, L, R, H, K, N, Q, S, T, F, Y, W, or absent (e.g., G, A, R, H, K, Q, T, F, Y, W, or absent).

In some embodiments, each X in SEQ ID NO: 165 can be an amino acid in any one of SEQ ID NOs: 74-107 when any one of the sequences in SEQ ID NOs: 74-107 is used as a reference sequence to be optimally aligned with SEQ ID NO:165. In other embodiments, each X in SEQ ID NO:165 can be an amino acid in any one of SEQ ID NOs: 74-92 when any one of the sequences in SEQ ID NOs: 74-92 is used as a reference sequence to be optimally aligned with SEQ ID NO: 165.

In other embodiments, the second CDR includes or is a polypeptide sequence having at least 90% sequence identity to SEQ ID NO:166:

$TX_3X_4GX_6X_7X_8R$, wherein:
$X_3$ is G, D, E, S, T, F, Y, W, or absent (e.g., G, D, S, T, W, or absent);
$X_4$ is G, A, V, I, L, S, or T (e.g., G, A, or S);
$X_6$ is G, A, V, D, E, R, H, K, N, Q, S, T, F, Y, W, or absent (e.g., G, A, D, K, Q, S, T, Y, or absent);
$X_7$ is G, A, V, I, L, D, E, R, H, K, S, T, or absent (e.g., G, A, E, H, S, or absent); and
$X_8$ is G, A, V, I, L, D, E, R, H, K, N, Q, S, T, F, Y, or W (e.g., G, A, D, R, Q, T, or F).

In some embodiments, each X in SEQ ID NO:166 can be an amino acid in any one of SEQ ID NOs: 74-107 when any one of the sequences in SEQ ID NOs: 74-107 is used as a reference sequence to be optimally aligned with SEQ ID NO:166. In other embodiments, each X in SEQ ID NO:166 can be an amino acid in any one of SEQ ID NOs: 74-92 when any one of the sequences in SEQ ID NOs: 74-92 is used as a reference sequence to be optimally aligned with SEQ ID NO:166.

In yet other embodiments, the second CDR includes or is a polypeptide sequence having at least 90% sequence identity to SEQ ID NO:167:

$TX_3X_4G-X_7X_8X_9X_{10}$, wherein:

$X_3$ is G, D, E, S, T, F, Y, W, or absent (e.g., G, D, S, T, W, or absent);

$X_4$ is G, A, V, I, L, S, or T (e.g., G, A, or S);

$X_7$ is G, A, V, I, L, D, E, R, H, K, S, T, or absent (e.g., G, A, E, H, S, or absent);

$X_8$ is G, A, V, I, L, D, E, R, H, K, N, Q, S, T, F, Y, or W (e.g., G, A, D, R, Q, T, or F);

$X_9$ is G, A, V, I, L, R, H, K, N, Q, S, T, F, Y, W, or absent (e.g., G, A, R, H, K, Q, T, F, Y, W, or absent); and $X_{10}$ is G, S, T, R, H, K, or absent (e.g., S, T, R, H, K, or absent).

In some embodiments, each X in SEQ ID NO: 167 can be an amino acid in any one of SEQ ID NOs: 74-107 when any one of the sequences in SEQ ID NOs: 74-107 is used as a reference sequence to be optimally aligned with SEQ ID NO: 167. In other embodiments, each X in SEQ ID NO:167 can be an amino acid in any one of SEQ ID NOs: 74-92 when any one of the sequences in SEQ ID NOs: 74-92 is used as a reference sequence to be optimally aligned with SEQ ID NO: 167.

Figure 7A:
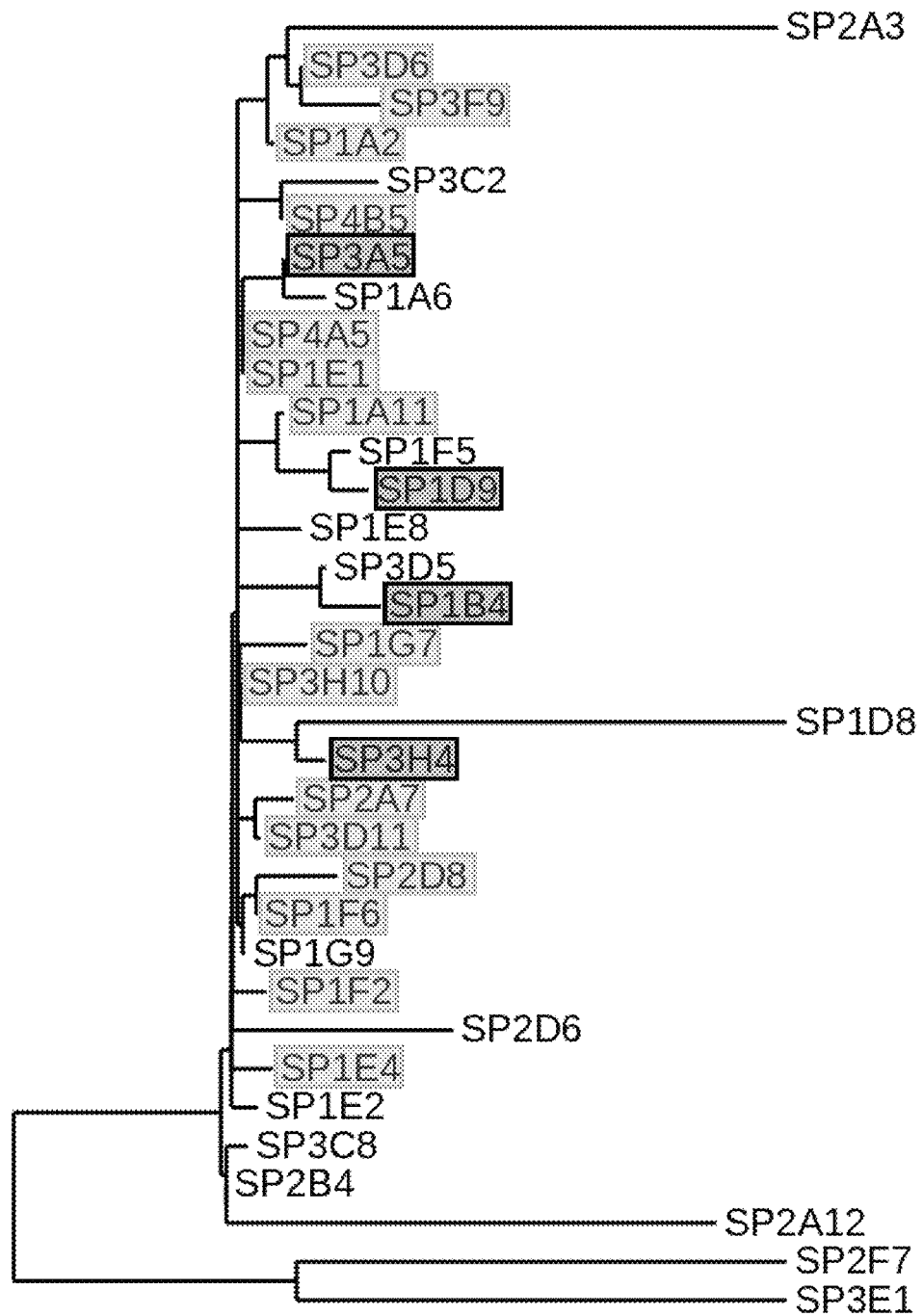
Figure 11B:
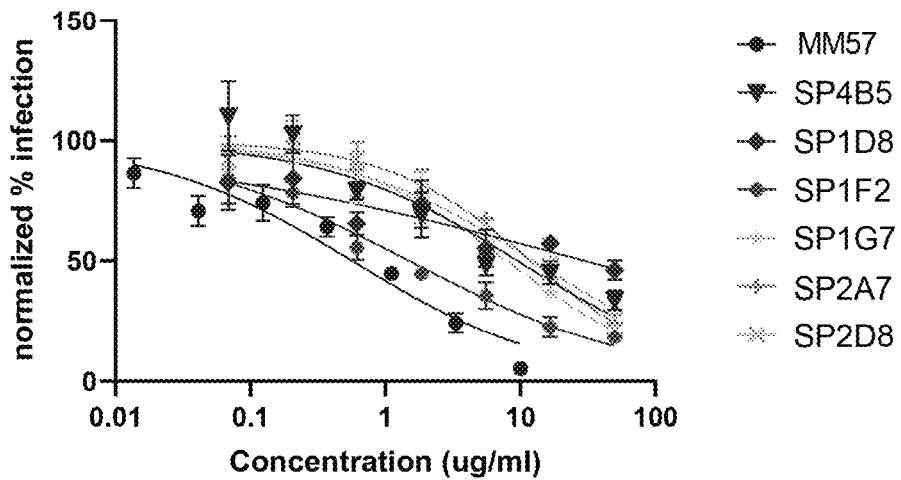
Figure 11C:
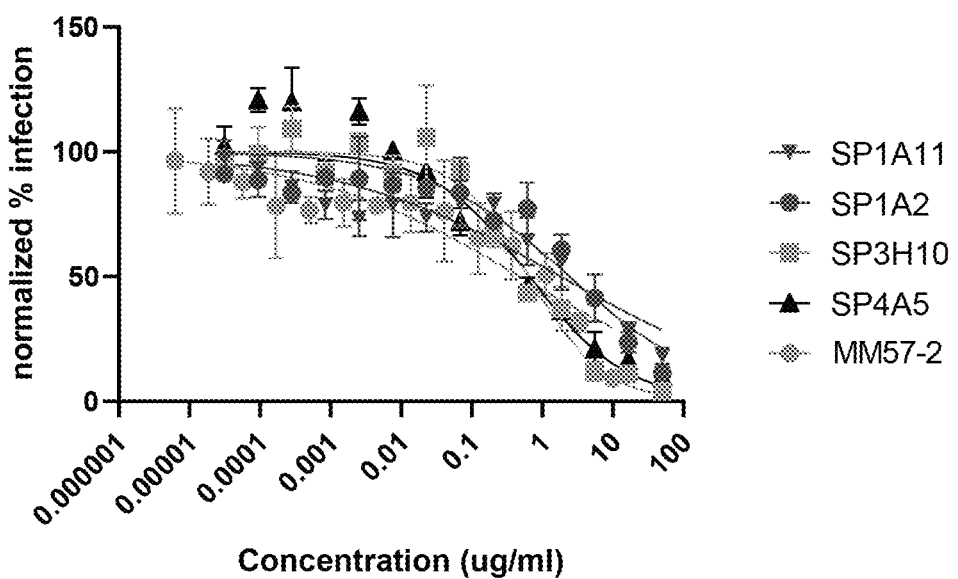

FIGS. 7A-7B provide a phylogentic tree and consensus sequences for non-limiting CDR3 sequences. In some embodiments, the third CDR includes or is a polypeptide sequence having at least 90% sequence identity to SEQ ID NO:170:

$X_6WX_8X_9EX_{11}X_{12}FX_{14}X_{15}X_{16}X_{17}VX_{19}X_{20}E$, wherein:

$X_6$ is G, A, V, I, L, D, E, R, H, K, S, T, P, F, Y, or absent (e.g., A, L, D, R, S, Y, or absent);

$X_8$ is G, A, V, I, L, D, E, R, H, K, P, F, Y, or absent (e.g., A, D, K, F, Y, or absent);

$X_9$ is G, A, V, I, L, R, H, K, N, Q, P, F, Y, or absent (e.g., A, I, R, Q, F, Y, or absent);

$X_{11}$ is G, A, V, I, L, R, H, K, N, Q, P, F, Y, or absent (e.g., G, L, R, K, Q, P, or absent);

$X_{12}$ is G, A, V, I, L, P, F, Y, W, or absent (e.g., V, I, L, P, W, or absent);

$X_{14}$ is D, E, R, H, K, S, T, P, F, Y, W, or absent (e.g., D, R, H, S, T, P, or absent);

$X_{15}$ is A, V, I, L, D, E, R, H, K, N, Q, P, F, Y, W, or absent (e.g., A, E, R, Q, F, or absent);

$X_{16}$ is A, V, I, L, D, E, R, H, K, N, Q, or absent (e.g., A, L, D, R, N, or absent);

$X_{17}$ is G, A, V, I, L, R, H, K, N, Q, S, T, P, F, Y, W, or absent (e.g., G, A, V, R, Q, S, F, or absent);

$X_{19}$ is A, V, I, L, D, E, R, H, K, S, T, P, F, Y, W, or absent (e.g., A, L, E, R, S, T, P, Y, or absent); and $X_{20}$ is G, D, E, N, Q, P, F, Y, W, or absent (e.g., G, D, E, N, P, or absent).

In some embodiments, each X in SEQ ID NO: 170 can be an amino acid in any one of SEQ ID NOs: 108-141 when any one of the sequences in SEQ ID NOs: 108-141 is used as a reference sequence to be optimally aligned with SEQ ID NO:170. In other embodiments, each X in SEQ ID NO:170 can be an amino acid in any one of SEQ ID NOs: 108-126 when any one of the sequences in SEQ ID NOs: 108-126 is used as a reference sequence to be optimally aligned with SEQ ID NO:170.

In some embodiments, the third CDR includes or is a polypeptide sequence having at least 90% sequence identity to SEQ ID NO:171:

$NAQLGPX_{22}X_{23}DKIG$, wherein:

$X_{22}$ is G, A, V, I, L, D, E, R, H, K, N, Q, or absent (e.g., G, A, V, E, H, K, Q, or absent); and $X_{23}$ is P, F, Y, W, or absent (e.g., F, Y, W, or absent).

In some embodiments, each X in SEQ ID NO: 171 can be an amino acid in any one of SEQ ID NOs: 108-141 when any one of the sequences in SEQ ID NOs: 108-141 is used as a reference sequence to be optimally aligned with SEQ ID NO:171. In other embodiments, each X in SEQ ID NO:171 can be an amino acid in any one of SEQ ID NOs: 108-126 when any one of the sequences in SEQ ID NOs: 108-126 is used as a reference sequence to be optimally aligned with SEQ ID NO: 171.

In other embodiments, the third CDR includes or is a polypeptide sequence having at least 90% sequence identity to SEQ ID NO:172:

$X_6WDX_9X_{10}GX_{12}X_{13}X_{14}X_{15}$-------$FX_{24}$, wherein:

$X_6$ is G, A, V, I, L, D, E, R, H, K, S, T, P, F, Y, or absent (e.g., A, L, D, R, S, Y, or absent);

$X_9$ is G, A, V, I, L, R, H, K, N, Q, P, F, Y, or absent (e.g., A, I, R, Q, F, Y, or absent);

$X_{10}$ is G, A, V, I, L, D, E, N, Q, S, T, P, F, Y, W, or absent (e.g., V, A, E, N, Q, S, T, P, F, Y, or absent);

$X_{12}$ is G, A, V, I, L, P, F, Y, W, or absent (e.g., V, I, L, P, W, or absent);

$X_{13}$ is G, A, V, I, L, N, Q, R, H, K, P, F, Y, W, or absent (e.g., I, V, N, H, P, F, or absent);

$X_{14}$ is D, E, R, H, K, S, T, P, F, Y, W, or absent (e.g., D, R, H, S, T, P, or absent);

$X_{15}$ is A, V, I, L, D, E, R, H, K, N, Q, P, F, Y, W, or absent (e.g., A, E, R, Q, F, or absent); and $X_{24}$ is D, E, R, H, K, P, F, Y, W, or absent (e.g., D, R, K, P, or absent).

In some embodiments, each X in SEQ ID NO: 172 can be an amino acid in any one of SEQ ID NOs: 108-141 when any one of the sequences in SEQ ID NOs: 108-141 is used as a reference sequence to be optimally aligned with SEQ ID NO:172. In other embodiments, each X in SEQ ID NO:172 can be an amino acid in any one of SEQ ID NOs: 108-126 when any one of the sequences in SEQ ID NOs: 108-126 is used as a reference sequence to be optimally aligned with SEQ ID NO:172.

In other embodiments, the third CDR includes or is a polypeptide sequence having at least 90% sequence identity to SEQ ID NO:173:

$YWX_8X_9NGX_{12}X_{13}PF$-----$X_{23}X_{24}$, wherein:

$X_8$ is G, A, V, I, L, D, E, R, H, K, P, F, Y, or absent (e.g., A, D, K, F, Y, or absent);

$X_9$ is G, A, V, I, L, R, H, K, N, Q, P, F, Y, or absent (e.g., A, I, R, Q, F, Y, or absent);

$X_{12}$ is G, A, V, I, L, P, F, Y, W, or absent (e.g., V, I, L, P, W, or absent);

$X_{13}$ is G, A, V, I, L, N, Q, R, H, K, P, F, Y, W, or absent (e.g., I, V, N, H, P, F, or absent);

$X_{23}$ is P, F, Y, W, or absent (e.g., F, Y, W, or absent); and $X_{24}$ is D, E, R, H, K, P, F, Y, W, or absent (e.g., D, R, K, P, or absent).

In some embodiments, each X in SEQ ID NO:173 can be an amino acid in any one of SEQ ID NOs: 108-141 when any one of the sequences in SEQ ID NOs: 108-141 is used as a reference sequence to be optimally aligned with SEQ ID NO:173. In other embodiments, each X in SEQ ID NO:173 can be an amino acid in any one of SEQ ID NOs: 108-126 when any one of the sequences in SEQ ID NOs:108-126 is used as a reference sequence to be optimally aligned with SEQ ID NO:173.

In other embodiments, the third CDR includes or is a polypeptide sequence having at least 90% sequence identity to SEQ ID NO:174:

$FPX_{12}X_{13}D$--$X_{17}X_{18}X_{19}X_{20}X_{21}X_{22}W$, wherein:

$X_{12}$ is G, A, V, I, L, P, F, Y, W, or absent (e.g., V, I, L, P, W, or absent);

$X_{13}$ is G, A, V, I, L, N, Q, R, H, K, P, F, Y, W, or absent (e.g., I, V, N, H, P, F, or absent);

$X_{17}$ is G, A, V, I, L, R, H, K, N, Q, S, T, P, F, Y, W, or absent (e.g., G, A, V, R, K, Q, S, F, or absent);

$X_{18}$ is G, A, V, I, L, R, H, K, N, Q, or absent (e.g., G, V, L, K, N, Q, or absent);

$X_{19}$ is A, V, I, L, D, E, R, H, K, S, T, P, F, Y, W, or absent (e.g., A, L, E, R, S, T, P, Y, or absent);

$X_{20}$ is G, D, E, N, Q, P, F, Y, W, or absent (e.g., G, D, E, N, P, or absent);

$X_{21}$ is A, V, I, L, R, H, K, D, E, S, T, N, Q, P, F, Y, W, or absent (e.g., L, R, E, T, N, P, Y, or absent); and $X_{22}$ is G, A, V, I, L, D, E, R, H, K, N, Q, or absent (e.g., G, A, V, E, H, K, Q, or absent).

In some embodiments, each X in SEQ ID NO:174 can be an amino acid in any one of SEQ ID NOs: 108-141 when any one of the sequences in SEQ ID NOs: 108-141 is used as a reference sequence to be optimally aligned with SEQ ID NO:174. In other embodiments, each X in SEQ ID NO:174 can be an amino acid in any one of SEQ ID NOs: 108-126 when any one of the sequences in SEQ ID NOs: 108-126 is used as a reference sequence to be optimally aligned with SEQ ID NO: 174.

In yet other embodiments, the third CDR includes or is a polypeptide sequence having at least 90% sequence identity to SEQ ID NO:175:

$FPLX_{13}D$--$X_{17}X_{18}X_{19}X_{20}X_{21}GW$, wherein:

$X_{13}$ is G, A, V, I, L, N, Q, R, H, K, P, F, Y, W, or absent (e.g., I, V, N, H, P, F, or absent);

$X_{17}$ is G, A, V, I, L, R, H, K, N, Q, S, T, P, F, Y, W, or absent (e.g., G, A, V, R, K, Q, S, F, or absent);

$X_{18}$ is G, A, V, I, L, R, H, K, N, Q, or absent (e.g., G, V, L, K, N, Q, or absent);

$X_{19}$ is A, V, I, L, D, E, R, H, K, S, T, P, F, Y, W, or absent (e.g., A, L, E, R, S, T, P, Y, or absent);

$X_{20}$ is G, D, E, N, Q, P, F, Y, W, or absent (e.g., G, D, E, N, P, or absent); and $X_{21}$ is A, V, I, L, R, H, K, D, E, S, T, N, Q, P, F, Y, W, or absent (e.g., L, R, E, T, N, P, Y, or absent).

In some embodiments, each X in SEQ ID NO: 175 can be an amino acid in any one of SEQ ID NOs: 108-141 when any one of the sequences in SEQ ID NOs: 108-141 is used as a reference sequence to be optimally aligned with SEQ ID NO:175. In other embodiments, each X in SEQ ID NO: 175 can be an amino acid in any one of SEQ ID NOs: 108-126 when any one of the sequences in SEQ ID NOs: 108-126 is used as a reference sequence to be optimally aligned with SEQ ID NO: 175.

The construct can include one or more binding domains. The binding domain can also be characterized by its binding affinity to a binding sequence. The terms "binding sequence," "binding domain," or "binding site", as used herein, refer to the portion, region, or site of polypeptide that mediates specific binding with a target molecule (e.g., a SARS-COV-2 as the target, including the spike protein or RBD thereof). Exemplary binding domains include an antigen binding site (e.g., a VHH, VH, and/or VL domain) or molecules comprising such a binding site (e.g., an antibody or a single domain antibody). In one instance, a plurality of CDRs can be taken together to form a binding domain for the construct.

Non-limiting constructs have CDRs and framework regions (FRs). As can be seen, each CDR can be disposed between two FRs. As seen in FIG. 8A, a non-limiting construct can include framework region 1 (FR1) attached to an N-terminus of CDR1; FR2 disposed between CDR1 and CD2; FR3 disposed between CDR2 and CDR3; and FR4 attached to a C-terminus of CDR3. Examples of sequences for CDR1, CDR2, and CDR3 include, e.g., any sequences for first CDR, second CDR, and third CDR, respectively, as described herein.

FIG. 8B shows non-limiting constructs, which provides sequences for framework regions disposed between regions indicated as CDR1, CDR2, and CDR3. SEQ ID NOs: 180-182 provide consensus sequences, in which each X in SEQ ID NOs: 180-182 can be an amino acid in any one of SEQ ID NOs: 183-186 when any one of the sequences in SEQ ID NOs: 183-186 is used as a reference sequence to be optimally aligned with one of SEQ ID NOs: 180-182.

In some embodiments, the construct includes or is a polypeptide sequence having at least 90% sequence identity to SEQ ID NO:180:

$X_1VQLX_5X_6SGX_9X_{10}X_{11}X_{12}X_{13}X_{14}X_{15}X_{16}X_{17}LX_{19}$
$LX_{21}CX_{23}X_{24}SGX_{27}X_{28}X_{29}X_{30}$-CDR1-
$X_{31}X_{32}WX_{34}X_{35}X_{36}X_{37}X_{38}X_{39}X_{40}X_{41}X_{42}X_{43}X_{44}X_{45}$
$X_{46}X_{47}X_{48}X_{49}$-CDR2-
$X_{50}X_{51}X_{52}X_{53}X_{54}X_{55}X_{56}X_{57}X_{58}X_{59}X_{60}X_{61}X_{62}X_{63}$
$DX_{65}X_{66}X_{67}X_{68}X_{69}X_{70}X_{71}X_{72}X_{73}X_{74}X_{75}$
$X_{76}X_{77}X_{78}X_{79}X_{80}DX_{82}X_{83}X_{84}YX_{86}X_{87}X_{88}X_{89}$-CDR3-
$X_{90}X_{91}GX_{93}GX_{95}X_{96}X_{97}X_{98}$
$VSX_{101}$, wherein:

$X_1$ is A, V, I, L, D, E, R, H, K, N, or Q (e.g., A, D, E, H, or Q);

$X_5$ is A, V, I, L, N, or Q (e.g., V, L, or Q);

$X_6$ is A, V, I, L, D, E, N, or Q (e.g., A, E, or Q);

$X_9$ is G, A, V, I, L, P, F, Y, or W (e.g., G, A, or P);

$X_{10}$ is G, A, V, I, L, D, E, N, Q, S, or T (e.g., G, A, E, N, or S);

$X_{11}$ is A, V, I, L, S, T, F, Y, or W (e.g., V, L, S, or F);

$X_{12}$ is A, V, I, L, R, H, K, M, S, or T (e.g., V, K, or M);

$X_{13}$ is R, H, K, N, or Q (e.g., R, K, or Q);

$X_{14}$ is A, V, I, L, F, Y, or P (e.g., A or P);

$X_{15}$ is G, S, or T (e.g., G or S);

$X_{16}$ is G, A, V, I, L, D, E, R, H, K, N, Q, S, or T (e.g., G, A, D, E, R, Q, or S);

$X_{17}$ is S, T, N, or Q (e.g., S or T);

$X_{19}$ is R, H, K, S, or T (e.g., R, K, S, or T);

$X_{21}$ is S, T, N, or Q (e.g., S or T);

$X_{23}$ is G, A, V, I, L, R, H, K, S, or T (e.g., A, V, K, or T);

$X_{24}$ is A, V, I, L, F, Y, or W (e.g., A, V, I, or F);

$X_{27}$ is G, F, Y, W, or absent (e.g., G, F, or absent);

$X_{28}$ is R, H, K, S, T, P, F, Y, W, or absent (e.g., K, S, T, P, or absent);

$X_{29}$ is A, V, I, L, D, E, R, H, K, F, Y, W, or absent (e.g., V, I, E, R, F, or absent);

$X_{30}$ is G, D, E, N, Q, S, T, F, Y, W, or absent (e.g., G, D, E, N, T, Y, or absent);

$X_{31}$ is A, V, I, L, M, S, T, F, Y, W, or absent (e.g., I, V, M, W, or absent);

$X_{32}$ is G, A, V, I, L, N, Q, R, H, K, or absent (e.g., G, A, N, H, or absent);

$X_{34}$ is A, V, I, L, P, F, Y or W (e.g., I, V, F, or Y);
$X_{35}$ is R, H, or K (e.g., R or K);
$X_{36}$ is R, H, K, N, or Q (e.g., R or Q);
$X_{37}$ is A, V, I, L, R, H, K, P, F, Y, or W (e.g., A, V, R, or P);
$X_{38}$ is R, H, K, S, T, P, F, Y, or W (e.g., H, S, T, or P);
$X_{39}$ is G, D, or E (e.g., G or E);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{43}$ is D, E, S or T (e.g., D or E);
$X_{44}$ is G, A, V, I, L, P, F, Y, or W (e.g., G, A, L, F, or W);
$X_{45}$ is A, V, I, L, M, S, or T (e.g., V, I, L, or M);
$X_{46}$ is G, A, V, I, L, S, or T (e.g., G, A, V, or S);
$X_{47}$ is A, V, I, L, R, H, K, M, S, T, or absent (e.g., A, V, I, R, S, T, or absent);
$X_{48}$ is A, V, I, L, M, S, T, or absent (e.g., V, I, L, M, or absent);
$X_{49}$ is A, V, I, L, D, E, R, H, K, M, S, T, or absent (e.g., A, D, R, S, or absent);
$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{58}$ is R, H, or K (e.g., R or K);
$X_{59}$ is A, V, I, L, F, Y, or W (e.g., A, V, L, or F);
$X_{60}$ is A, V, I, L, C, M, S, or T (e.g., A, C, S, or T);
$X_{61}$ is A, V, I, L, C, M, S, T, F, Y, or W (e.g., A, I, L, M, S, or F);
$X_{62}$ is C, M, S, or T (e.g., S or T);
$X_{63}$ is A, V, I, L, R, H, K, N, or Q (e.g., A, V, R, K, or Q);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{70}$ is A, V, I, L, C, M, F, Y, or W (e.g., A, V, L, M, or F);
$X_{71}$ is S, T, F, Y, or W (e.g., S, T, F, or Y);
$X_{72}$ is A, V, I, L, C, or M (e.g., L or M);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{80}$ is A, V, I, L, D, or E (e.g., A, D, or E);
$X_{82}$ is C, S, or T (e.g., S or T);
$X_{83}$ is G, A, V, I, or L (e.g., G or A);
$X_{84}$ is A, V, I, L, C, M, D, E, S or T (e.g., V, I, M, D, E, or T);
$X_{86}$ is S, T, F, Y, or W (e.g., T, F, or Y);
$X_{87}$ is A, V, I, L, C, or M (e.g., V or C);
$X_{88}$ is A, V, I, L, N, Q, S, T, F, Y, W, or absent (e.g., A, V, N, Q, T, Y, or absent);
$X_{89}$ is G, A, V, I, L, R, H, K, F, Y, W, or absent (e.g., G, A, V, R, K, Y, or absent);
$X_{90}$ is any amino acid or absent (e.g., V, H, Q, S, F, Y, or absent);
$X_{91}$ is R, H, K, F, Y, or W (e.g., R or W);
$X_{93}$ is R, H, K, N, Q, P, F, Y, or W (e.g., R, K, Q, or P);
$X_{95}$ is A, V, I, L, S, or T (e.g., L or T);
$X_{96}$ is A, V, I, L, C, M, N, Q, S, or T (e.g., L, M, Q, S, or T);
$X_{97}$ is A, V, I, or L (e.g., V or L);
$X_{98}$ is A, V, I, L, S, or T (e.g., V or T);
$X_{10}1$ is S, T, or absent (e.g., S or absent);
CDR1 is any CDR described herein (e.g., SEQ ID NOs: 40-73 and 150-155);
CDR2 is any CDR described herein (e.g., SEQ ID NOs: 74-107 and 160-167); and
CDR3 is any CDR described herein (e.g., SEQ ID NOs: 108-141 and 170-175).

In other embodiments, the construct includes or is a polypeptide sequence having at least 90% sequence identity to SEQ ID NO:181:

$X_1X_2X_3LX_5X_6X_7GX_9X_{10}X_{11}X_{12}X_{13}PX_{15}X_{16}X_{17}X_{18}X_{19}X_{20}X_{21}CX_{23}X_{24}X_{25}X_{26}$-CDR1-
$X_{31}X_{32}WX_{34}X_{35}X_{36}X_{37}X_{38}X_{39}X_{40}X_{41}X_{42}EX_{44}X_{45}X_{46}X_{47}X_{48}X_{49}$-CDR2-
$X_{50}X_{51}X_{52}X_{53}X_{54}X_{55}X_{56}X_{57}X_{58}X_{59}X_{60}X_{61}X_{62}X_{63}X_{64}X_{65}X_{66}X_{67}X_{68}X_{69}X_{70}X_{71}X_{72}X_{73}$
$X_{74}X_{75}X_{76}X_{77}X_{78}X_{79}X_{80}DX_{82}X_{83}X_{84}YX_{86}X_{87}X_{88}X_{89}$-CDR3-$X_{90}WGX_{93}X_{94}X_{95}X_{96}$
$X_{97}X_{98}VSX_{101}$, wherein:
$X_1$ is A, V, I, L, D, E, R, H, K, N, or Q (e.g., A, D, E, H, or Q);
$X_2$ is A, V, I, or L (e.g., V or L);
$X_3$ is N, Q, S, or T (Q or T);
$X_5$ is A, V, I, L, N, or Q (e.g., V, L, or Q);
$X_6$ is A, V, I, L, D, E, N, or Q (e.g., A, E, or Q);
$X_7$ is S, T, P, F, Y, or W (e.g., S, T, or P);
$X_9$ is G, A, V, I, L, P, F, Y, or W (e.g., G, A, or P);
$X_{10}$ is G, A, V, I, L, D, E, N, Q, S, or T (e.g., G, A, E, N, or S);
$X_{11}$ is A, V, I, L, S, T, F, Y, or W (e.g., V, L, S, or F);
$X_{12}$ is A, V, I, L, R, H, K, M, S, or T (e.g., V, K, or M);
$X_{13}$ is R, H, K, N, or Q (e.g., R, K, or Q);
$X_{15}$ is G, S, or T (e.g., G or S);
$X_{16}$ is G, A, V, I, L, D, E, R, H, K, N, Q, S, or T (e.g., G, A, D, E, R, Q, or S);
$X_{17}$ is S, T, N, or Q (e.g., S or T);
$X_{18}$ is A, V, I, or L (e.g., V, I, or L);
$X_{19}$ is R, H, K, S, or T (e.g., R, K, S, or T);
$X_{20}$ is A, V, I, or L (e.g., V, I, or L);
$X_{21}$ is S, T, N, or Q (e.g., S or T);
$X_{23}$ is G, A, V, I, L, R, H, K, S, or T (e.g., A, V, K, or T);
$X_{24}$ is A, V, I, L, F, Y, or W (e.g., A, V, I, or F);
$X_{25}$ is S or T;
$X_{26}$ is G, A, V, I, L, D, E, R, H, K, or absent (e.g., G, A, E, R, or absent);
$X_{31}$ is A, V, I, L, M, S, T, F, Y, W, or absent (e.g., I, V, M, W, or absent);
$X_{32}$ is G, A, V, I, L, N, Q, R, H, K, or absent (e.g., G, A, N, H, or absent);
$X_{34}$ is A, V, I, L, P, F, Y or W (e.g., I, V, F, or Y);

$X_{35}$ is R, H, or K (e.g., R or K);
$X_{36}$ is R, H, K, N, or Q (e.g., R or Q);
$X_{37}$ is A, V, I, L, R, H, K, P, F, Y, or W (e.g., A, V, R, or P);
$X_{38}$ is R, H, K, S, T, P, F, Y, or W (e.g., H, S, T, or P);
$X_{39}$ is G, D, or E (e.g., G or E);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{43}$ is G, A, V, I, L, P, F, Y, or W (e.g., G, A, L, F, or W);
$X_{45}$ is A, V, I, L, M, S, or T (e.g., V, I, L, or M);
$X_{46}$ is G, A, V, I, L, S, or T (e.g., G, A, V, or S);
$X_{47}$ is A, V, I, L, R, H, K, M, S, T, or absent (e.g., A, V, I, R, S, T, or absent);
$X_{48}$ is A, V, I, L, M, S, T, or absent (e.g., V, I, L, M, or absent);
$X_{49}$ is A, V, I, L, D, E, R, H, K, M, S, T, or absent (e.g., A, D, R, S, or absent);
$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{58}$ is R, H, or K (e.g., R or K);
$X_{59}$ is A, V, I, L, F, Y, or W (e.g., A, V, L, or F);
$X_{60}$ is A, V, I, L, C, M, S, or T (e.g., A, C, S, or T);
$X_{61}$ is A, V, I, L, C, M, S, T, F, Y, or W (e.g., A, I, L, M, S, or F);
$X_{62}$ is C, M, S, or T (e.g., S or T);
$X_{63}$ is A, V, I, L, R, H, K, N, or Q (e.g., A, V, R, K, or Q);
$X_{64}$ is D or E;
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{70}$ is A, V, I, L, C, M, F, Y, or W (e.g., A, V, L, M, or F);
$X_{71}$ is S, T, F, Y, or W (e.g., S, T, F, or Y);
$X_{72}$ is A, V, I, L, C, or M (e.g., L or M);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{80}$ is A, V, I, L, D, or E (e.g., A, D, or E);
$X_{82}$ is C, S, or T (e.g., S or T);
$X_{83}$ is G, A, V, I, or L (e.g., G or A);
$X_{84}$ is A, V, I, L, C, M, D, E, S or T (e.g., V, I, M, D, E, or T);
$X_{86}$ is S, T, F, Y, or W (e.g., T, F, or Y);
$X_{87}$ is A, V, I, L, C, or M (e.g., V or C);
$X_{88}$ is A, V, I, L, N, Q, S, T, F, Y, W, or absent (e.g., A, V, N, Q, T, Y, or absent);
$X_{89}$ is G, A, V, I, L, R, H, K, F, Y, W, or absent (e.g., G, A, V, R, K, Y, or absent);
$X_{90}$ is any amino acid or absent (e.g., V, H, Q, S, F, Y, or absent);
$X_{93}$ is R, H, K, N, Q, P, F, Y, or W (e.g., R, K, Q, or P);
$X_{94}$ is G, A, V, I, or L (e.g., G);
$X_{95}$ is A, V, I, L, S, or T (e.g., L or T);
$X_{96}$ is A, V, I, L, C, M, N, Q, S, or T (e.g., L, M, Q, S, or T);
$X_{97}$ is A, V, I, or L (e.g., V or L);
$X_{98}$ is A, V, I, L, S, or T (e.g., V or T);
$X_{101}$ is S, T, or absent (e.g., S or absent);
CDR1 is any CDR described herein (e.g., SEQ ID NOs: 40-73 and 150-155);
CDR2 is any CDR described herein (e.g., SEQ ID NOs: 74-107 and 160-167); and
CDR3 is any CDR described herein (e.g., SEQ ID NOs: 108-141 and 170-175).

In yet other embodiments, the construct includes or is a polypeptide sequence having at least 90% sequence identity to SEQ ID NO:182:

$X_1VX_3LX_5X_6SGGGX_{11}X_{12}X_{13}X_{14}GX_{16}SLX_{19}LSCAASG$-CDR1-$X_{31}X_{32}WX_{34}RX_{36}X_{37}PX_{39}X_{40}X_{41}X_{42}X_{43}X_{44}X_{45}X_{46}X_{47}X_{48}X_{49}$-CDR2-$X_{50}YX_{52}X_{53}X_{54}X_{55}X_{56}X_{57}RFX_{60}X_{61}SX_{63}DX_{65}X_{66}X_{67}X_{68}X_{69}X_{70}X_{71}LX_{73}X_{74}X_{75}X_{76}X_{77}X_{78}X_{79}X_{80}DTX_{83}X_{84}YX_{86}CAX_{89}$-CDR3-$X_{90}X_{91}GX_{93}GTX_{96}VTVSX_{101}$, wherein:
$X_1$ is A, V, I, L, D, E, R, H, K, N, or Q (e.g., A, D, E, H, or Q);
$X_3$ is N, Q, S, or T (Q or T);
$X_5$ is A, V, I, L, N, or Q (e.g., V, L, or Q);
$X_6$ is A, V, I, L, D, E, N, or Q (e.g., A, E, or Q);
$X_{11}$ is A, V, I, L, S, T, F, Y, or W (e.g., V, L, S, or F);
$X_{12}$ is A, V, I, L, R, H, K, M, S, or T (e.g., V, K, or M);
$X_{13}$ is R, H, K, N, or Q (e.g., R, K, or Q);
$X_{14}$ is A, V, I, L, F, Y, or P (e.g., A or P);
$X_{16}$ is G, A, V, I, L, D, E, R, H, K, N, Q, S, or T (e.g., G, A, D, E, R, Q, or S);
$X_{19}$ is R, H, K, S, or T (e.g., R, K, S, or T);
$X_{31}$ is A, V, I, L, M, S, T, F, Y, W, or absent (e.g., I, V, M, W, or absent);
$X_{32}$ is G, A, V, I, L, N, Q, R, H, K, or absent (e.g., G, A, N, H, or absent);
$X_{34}$ is A, V, I, L, P, F, Y or W (e.g., I, V, F, or Y);
$X_{36}$ is R, H, K, N, or Q (e.g., R or Q);
$X_{37}$ is A, V, I, L, R, H, K, P, F, Y, or W (e.g., A, V, R, or P);
$X_{39}$ is G, D, or E (e.g., G or E);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{43}$ is D or E;
$X_{44}$ is G, A, V, I, L, P, F, Y, or W (e.g., G, A, L, F, or W);
$X_{45}$ is A, V, I, L, M, S, or T (e.g., V, I, L, or M);
$X_{46}$ is G, A, V, I, L, S, or T (e.g., G, A, V, or S);
$X_{47}$ is A, V, I, L, R, H, K, M, S, T, or absent (e.g., A, V, I, R, S, T, or absent);

$X_{48}$ is A, V, I, L, M, S, T, or absent (e.g., V, I, L, M, or absent);
$X_{49}$ is A, V, I, L, D, E, R, H, K, M, S, T, or absent (e.g., A, D, R, S, or absent);
$X_{50}$ is A, V, I, L, D, E, R, H, K, N, Q, S, T, F, Y, W, or absent (e.g., L, D, R, N, T, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{60}$ is A, V, I, L, C, M, S, or T (e.g., A, C, S, or T);
$X_{61}$ is A, V, I, L, C, M, S, T, F, Y, or W (e.g., A, I, L, M, S, or F);
$X_{63}$ is A, V, I, L, R, H, K, N, or Q (e.g., A, V, R, K, or Q);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{70}$ is A, V, I, L, C, M, F, Y, or W (e.g., A, V, L, M, or F);
$X_{71}$ is S, T, F, Y, or W (e.g., S, T, F, or Y);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{80}$ is A, V, I, L, D, or E (e.g., A, D, or E);
$X_{83}$ is G, A, V, I, or L (e.g., G or A);
$X_{84}$ is A, V, I, L, C, M, D, E, S or T (e.g., V, I, M, D, E, or T);
$X_{86}$ is S, T, F, Y, or W (e.g., T, F, or Y);
$X_{89}$ is G, A, V, I, L, R, H, K, F, Y, W, or absent (e.g., G, A, V, R, K, Y, or absent);
$X_{90}$ is any amino acid or absent (e.g., V, H, Q, S, F, Y, or absent);
$X_{91}$ is F, Y, or W (e.g., W);
$X_{93}$ is R, H, K, N, Q, P, F, Y, or W (e.g., R, K, Q, or P);
$X_{96}$ is A, V, I, L, C, M, N, Q, S, or T (e.g., L, M, Q, S, or T);
$X_{101}$ is S, T, or absent (e.g., S or absent);
CDR1 is any CDR described herein (e.g., SEQ ID NOs: 40-73 and 150-155);
CDR2 is any CDR described herein (e.g., SEQ ID NOs: 74-107 and 160-167); and
CDR3 is any CDR described herein (e.g., SEQ ID NOs: 108-141 and 170-175).

In some embodiments, the construct includes or is a polypeptide sequence having at least 90% sequence identity to SEQ ID NOs: 183-186. In particular embodiments, CDR1 is any CDR described herein (e.g., SEQ ID NOs:40-73 and 150-155); CDR2 is any CDR described herein (e.g., SEQ ID NOs: 74-107 and 160-167); and CDR3 is any CDR described herein (e.g., SEQ ID NOs:108-141 and 170-175).

Any of the constructs herein can include any of the FRs described herein. FIG. 9A provides non-limiting FR1 sequences. In some embodiments, the first FR includes or is a polypeptide sequence having at least 90% sequence identity to SEQ ID NOs: 190-212. In other embodiments, the first FR includes or is a polypeptide sequence having at least 90% sequence identity to SEQ ID NO:213:

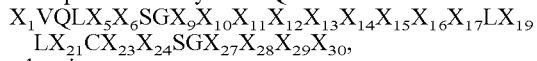
$LX_{21}CX_{23}X_{24}SGX_{27}X_{28}X_{29}X_{30}$, wherein:
$X_1$ is A, V, I, L, D, E, R, H, K, N, or Q (e.g., A, D, E, H, or Q);
$X_5$ is A, V, I, L, N, or Q (e.g., V, L, or Q);
$X_6$ is A, V, I, L, D, E, N, or Q (e.g., A, E, or Q);
$X_9$ is G, A, V, I, L, P, F, Y, or W (e.g., G, A, or P);
$X_{10}$ is G, A, V, I, L, D, E, N, Q, S, or T (e.g., G, A, E, N, or S);
$X_{11}$ is A, V, I, L, S, T, F, Y, or W (e.g., V, L, S, or F);
$X_{12}$ is A, V, I, L, R, H, K, M, S, or T (e.g., V, K, or M);
$X_{13}$ is R, H, K, N, or Q (e.g., R, K, or Q);
$X_{14}$ is A, V, I, L, F, Y, or P (e.g., A or P);
$X_{15}$ is G, S, or T (e.g., G or S);
$X_{16}$ is G, A, V, I, L, D, E, R, H, K, N, Q, S, or T (e.g., G, A, D, E, R, Q, or S);
$X_{17}$ is S, T, N, or Q (e.g., S or T);
$X_{19}$ is R, H, K, S, or T (e.g., R, K, S, or T);
$X_{21}$ is S, T, N, or Q (e.g., S or T);
$X_{23}$ is G, A, V, I, L, R, H, K, S, or T (e.g., A, V, K, or T);
$X_{24}$ is A, V, I, L, F, Y, or W (e.g., A, V, I, or F);
$X_{27}$ is G, F, Y, W, or absent (e.g., G, F, or absent);
$X_{28}$ is R, H, K, S, T, P, F, Y, W, or absent (e.g., K, S, T, P, or absent);
$X_{29}$ is A, V, I, L, D, E, R, H, K, F, Y, W, or absent (e.g., V, I, E, R, F, or absent); and
$X_{30}$ is G, D, E, N, Q, S, T, F, Y, W, or absent (e.g., G, D, E, N, T, Y, or absent).

In some embodiments, each X in SEQ ID NO:213 can be an amino acid in any one of SEQ ID NOs: 190-212 when any one of the sequences in SEQ ID NOs: 190-212 is used as a reference sequence to be optimally aligned with SEQ ID NO:213.

In other embodiments, the first FR includes or is a polypeptide sequence having at least 90% sequence identity to SEQ ID NO:214:

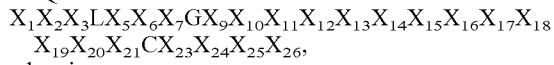
$X_{19}X_{20}X_{21}CX_{23}X_{24}X_{25}X_{26}$, wherein:
$X_1$ is A, V, I, L, D, E, R, H, K, N, or Q (e.g., A, D, E, H, or Q);
$X_2$ is A, V, I, or L (e.g., V or L);
$X_3$ is N, Q, S, or T (Q or T);
$X_5$ is A, V, I, L, N, or Q (e.g., V, L, or Q);
$X_6$ is A, V, I, L, D, E, N, or Q (e.g., A, E, or Q);
$X_7$ is S, T, P, F, Y, or W (e.g., S, T, or P);
$X_9$ is G, A, V, I, L, P, F, Y, or W (e.g., G, A, or P);
$X_{10}$ is G, A, V, I, L, D, E, N, Q, S, or T (e.g., G, A, E, N, or S);
$X_{11}$ is A, V, I, L, S, T, F, Y, or W (e.g., V, L, S, or F);
$X_{12}$ is A, V, I, L, R, H, K, M, S, or T (e.g., V, K, or M);
$X_{13}$ is R, H, K, N, or Q (e.g., R, K, or Q);
$X_{14}$ is A, V, I, L, F, Y, or P (e.g., A or P);
$X_{15}$ is G, S, or T (e.g., G or S);
$X_{16}$ is G, A, V, I, L, D, E, R, H, K, N, Q, S, or T (e.g., G, A, D, E, R, Q, or S);
$X_{17}$ is S, T, N, or Q (e.g., S or T);
$X_{18}$ is A, V, I, or L (e.g., V, I, or L);
$X_{19}$ is R, H, K, S, or T (e.g., R, K, S, or T);
$X_{20}$ is A, V, I, or L (e.g., V, I, or L);
$X_{21}$ is S, T, N, or Q (e.g., S or T);

$X_{23}$ is G, A, V, I, L, R, H, K, S, or T (e.g., A, V, K, or T);
$X_{24}$ is A, V, I, L, F, Y, or W (e.g., A, V, I, or F);
$X_{25}$ is S or T; and
$X_{26}$ is G, A, V, I, L, D, E, R, H, K, or absent (e.g., G, A, E, R, or absent).

In some embodiments, each X in SEQ ID NO:214 can be an amino acid in any one of SEQ ID NOs: 190-212 when any one of the sequences in SEQ ID NOs: 190-212 is used as a reference sequence to be optimally aligned with SEQ ID NO:214.

In yet other embodiments, the first FR includes or is a polypeptide sequence having at least 90% sequence identity to SEQ ID NO:215:
$X_1VQLX_5X_6SGX_9X_{10}X_{11}X_{12}X_{13}X_{14}X_{15}X_{16}X_{17}LX_{19}LX_{21}CX_{23}X_{24}SG$,
wherein:
$X_1$ is A, V, I, L, D, E, R, H, K, N, or Q (e.g., A, D, E, H, or Q);
$X_5$ is A, V, I, L, N, or Q (e.g., V, L, or Q);
$X_6$ is A, V, I, L, D, E, N, or Q (e.g., A, E, or Q);
$X_9$ is G, A, V, I, L, P, F, Y, or W (e.g., G, A, or P);
$X_{10}$ is G, A, V, I, L, D, E, N, Q, S, or T (e.g., G, A, E, N, or S);
$X_{11}$ is A, V, I, L, S, T, F, Y, or W (e.g., V, L, S, or F);
$X_{12}$ is A, V, I, L, R, H, K, M, S, or T (e.g., V, K, or M);
$X_{13}$ is R, H, K, N, or Q (e.g., R, K, or Q);
$X_{14}$ is A, V, I, L, F, Y, or P (e.g., A or P);
$X_{15}$ is G, S, or T (e.g., G or S);
$X_{16}$ is G, A, V, I, L, D, E, R, H, K, N, Q, S, or T (e.g., G, A, D, E, R, Q, or S);
$X_{17}$ is S, T, N, or Q (e.g., S or T);
$X_{19}$ is R, H, K, S, or T (e.g., R, K, S, or T);
$X_{21}$ is S, T, N, or Q (e.g., S or T);
$X_{23}$ is G, A, V, I, L, R, H, K, S, or T (e.g., A, V, K, or T); and
$X_{24}$ is A, V, I, L, F, Y, or W (e.g., A, V, I, or F).

In some embodiments, each X in SEQ ID NO:215 can be an amino acid in any one of SEQ ID NOs: 190-212 when any one of the sequences in SEQ ID NOs: 190-212 is used as a reference sequence to be optimally aligned with SEQ ID NO:215.

In some embodiments, the first FR includes or is a polypeptide sequence having at least 90% sequence identity to SEQ ID NO:216:
QVQLVESGGGL VQX$_{14}$GGSLRLSCAASGX$_{27}$X$_{28}$X$_{29}$X$_{30}$,
wherein:
$X_{14}$ is A, V, I, L, F, Y, or P (e.g., A or P);
$X_{27}$ is G, F, Y, W, or absent (e.g., G, F, or absent);
$X_{28}$ is R, H, K, S, T, P, F, Y, W, or absent (e.g., K, S, T, P, or absent);
$X_{29}$ is A, V, I, L, D, E, R, H, K, F, Y, W, or absent (e.g., V, I, E, R, F, or absent); and
$X_{30}$ is G, D, E, N, Q, S, T, F, Y, W, or absent (e.g., G, D, E, N, T, Y, or absent).

In other embodiments, each X in SEQ ID NO:216 can be an amino acid in any one of SEQ ID NOs: 190-212 when any one of the sequences in SEQ ID NOs: 190-212 is used as a reference sequence to be optimally aligned with SEQ ID NO:216.

In yet other embodiments, the first FR includes or is a polypeptide sequence having at least 90% sequence identity to SEQ ID NO:217:
QVQLVESGGGLVQX$_{14}$GGSLRLSCAASG,
wherein:
$X_{14}$ is A, V, I, L, F, Y, or P (e.g., A or P).

FIG. 9B provides non-limiting FR2 sequences. In some embodiments, the second FR includes or is a polypeptide sequence having at least 90% sequence identity to SEQ ID NOs:220-243. In other embodiments, the second FR includes or is a polypeptide sequence having at least 90% sequence identity to SEQ ID NO:244:
$X_{31}X_{32}WX_{34}X_{35}X_{36}X_{37}X_{38}X_{39}X_{40}X_{41}X_{42}X_{43}X_{44}X_{45}X_{46}X_{47}X_{48}X_{49}$,
wherein:
$X_{31}$ is A, V, I, L, M, S, T, F, Y, W, or absent (e.g., I, V, M, W, or absent);
$X_{32}$ is G, A, V, I, L, N, Q, R, H, K, or absent (e.g., G, A, N, H, or absent);
$X_{34}$ is A, V, I, L, P, F, Y or W (e.g., I, V, F, or Y);
$X_{35}$ is R, H, or K (e.g., R or K);
$X_{36}$ is R, H, K, N, or Q (e.g., R or Q);
$X_{37}$ is A, V, I, L, R, H, K, P, F, Y, or W (e.g., A, V, R, or P);
$X_{38}$ is R, H, K, S, T, P, F, Y, or W (e.g., H, S, T, or P);
$X_{39}$ is G, D, or E (e.g., G or E);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{43}$ is D, E, S or T (e.g., D or E);
$X_4$ is G, A, V, I, L, P, F, Y, or W (e.g., G, A, L, F, or W);
$X_{45}$ is A, V, I, L, M, S, or T (e.g., V, I, L, or M);
$X_{46}$ is G, A, V, I, L, S, or T (e.g., G, A, V, or S);
$X_{47}$ is A, V, I, L, R, H, K, M, S, T, or absent (e.g., A, V, I, R, S, T, or absent);
$X_{48}$ is A, V, I, L, M, S, T, or absent (e.g., V, I, L, M, or absent); and
$X_{49}$ is A, V, I, L, D, E, R, H, K, M, S, T, or absent (e.g., A, D, R, S, or absent).

In yet other embodiments, each X in SEQ ID NO:244 can be an amino acid in any one of SEQ ID NOs:220-243 when any one of the sequences in SEQ ID NOs:220-243 is used as a reference sequence to be optimally aligned with SEQ ID NO:244.

In some embodiments, the second FR includes or is a polypeptide sequence having at least 90% sequence identity to SEQ ID NO:245:
$X_{31}X_{32}WX_{34}RQAX_{38}GX_{40}X_{41}X_{42}EX_4X_{45}X_{46}X_{47}X_{48}X_{49}$,
wherein:
$X_{31}$ is A, V, I, L, M, S, T, F, Y, W, or absent (e.g., I, V, M, W, or absent);
$X_{32}$ is G, A, V, I, L, N, Q, R, H, K, or absent (e.g., G, A, N, H, or absent);
$X_{34}$ is A, V, I, L, P, F, Y or W (e.g., I, V, F, or Y);
$X_{38}$ is R, H, K, S, T, P, F, Y, or W (e.g., H, S, T, or P);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{44}$ is G, A, V, I, L, P, F, Y, or W (e.g., G, A, L, F, or W);
$X_{45}$ is A, V, I, L, M, S, or T (e.g., V, I, L, or M);
$X_{46}$ is G, A, V, I, L, S, or T (e.g., G, A, V, or S);
$X_{47}$ is A, V, I, L, R, H, K, M, S, T, or absent (e.g., A, V, I, R, S, T, or absent);
$X_{48}$ is A, V, I, L, M, S, T, or absent (e.g., V, I, L, M, or absent); and
$X_{49}$ is A, V, I, L, D, E, R, H, K, M, S, T, or absent (e.g., A, D, R, S, or absent).

In other embodiments, each X in SEQ ID NO:245 can be an amino acid in any one of SEQ ID NOs:220-243 when any one of the sequences in SEQ ID NOs:220-243 is used as a reference sequence to be optimally aligned with SEQ ID NO:245.

In some embodiments, the second FR includes or is a polypeptide sequence having at least 90% sequence identity to SEQ ID NO:246:

$X_{31}X_{32}WX_{34}RQAX_{38}GX_{40}X_{41}X_{42}EX_{44}X_{45}X_{46}$,
wherein:
$X_{31}$ is A, V, I, L, M, S, T, F, Y, W, or absent (e.g., I, V, M, W, or absent);
$X_{32}$ is G, A, V, I, L, N, Q, R, H, K, or absent (e.g., G, A, N, H, or absent);
$X_{34}$ is A, V, I, L, P, F, Y or W (e.g., I, V, F, or Y);
$X_{38}$ is R, H, K, S, T, P, F, Y, or W (e.g., H, S, T, or P);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{43}$ is G, A, V, I, L, P, F, Y, or W (e.g., G, A, L, F, or W);
$X_{45}$ is A, V, I, L, M, S, or T (e.g., V, I, L, or M); and
$X_{46}$ is G, A, V, I, L, S, or T (e.g., G, A, V, or S).

In other embodiments, each X in SEQ ID NO:246 can be an amino acid in any one of SEQ ID NOs:220-243 when any one of the sequences in SEQ ID NOs:220-243 is used as a reference sequence to be optimally aligned with SEQ ID NO:246.

In some embodiments, the second FR includes or is a polypeptide sequence having at least 90% sequence identity to SEQ ID NO:247:

$MX_{32}WFRQAPGKEREWVAX_{47}X_{48}X_{49}$,
wherein:
$X_{32}$ is G, A, V, I, L, N, Q, R, H, K, or absent (e.g., G, A, N, H, or absent);
$X_{47}$ is A, V, I, L, R, H, K, M, S, T, or absent (e.g., A, V, I, R, S, T, or absent);
$X_{48}$ is A, V, I, L, M, S, T, or absent (e.g., V, I, L, M, or absent); and
$X_{49}$ is A, V, I, L, D, E, R, H, K, M, S, T, or absent (e.g., A, D, R, S, or absent).

In other embodiments, each X in SEQ ID NO:247 can be an amino acid in any one of SEQ ID NOs:220-243 when any one of the sequences in SEQ ID NOs:220-243 is used as a reference sequence to be optimally aligned with SEQ ID NO:247.

In yet other embodiments, the second FR includes or is a polypeptide sequence having at least 90% sequence identity to SEQ ID NO:248:

$MX_{32}WFRQAPGKEREWVA$,
wherein:
$X_{32}$ is G, A, V, I, L, N, Q, R, H, K, or absent (e.g., G, A, N, H, or absent).

FIG. 9C provides non-limiting FR3 sequences. In some embodiments, the third FR includes or is a polypeptide sequence having at least 90% sequence identity to SEQ ID NOs:250-284. In other embodiments, the third FR includes or is a polypeptide sequence having at least 90% sequence identity to SEQ ID NO:285:

$X_{50}X_{51}X_{52}X_{53}X_{54}X_{55}X_{56}X_{57}X_{58}X_{59}X_{60}X_{61}X_{62}X_{63}$
$DX_{65}X_{66}X_{67}X_{68}X_{69}X_{70}X_{71}X_{72}X_{73}X_{74}X_{75}$
$X_{76}X_{77}X_{78}X_{79}X_{80}DX_{82}X_{83}X_{84}YX_{86}CX_{88}X_{89}$,
wherein:
$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{58}$ is R, H, or K (e.g., R or K);
$X_{59}$ is A, V, I, L, F, Y, or W (e.g., A, V, L, or F);
$X_{60}$ is A, V, I, L, C, M, S, or T (e.g., A, C, S, or T);
$X_{61}$ is A, V, I, L, C, M, S, T, F, Y, or W (e.g., A, I, L, M, S, or F);
$X_{62}$ is C, M, S, or T (e.g., S or T);
$X_{63}$ is A, V, I, L, R, H, K, N, or Q (e.g., A, V, R, K, or Q);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{70}$ is A, V, I, L, C, M, F, Y, or W (e.g., A, V, L, M, or F);
$X_{71}$ is S, T, F, Y, or W (e.g., S, T, F, or Y);
$X_{72}$ is A, V, I, L, C, or M (e.g., L or M);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{80}$ is A, V, I, L, D, or E (e.g., A, D, or E);
$X_{82}$ is C, S, or T (e.g., S or T);
$X_{83}$ is G, A, V, I, or L (e.g., G or A);
$X_{84}$ is A, V, I, L, C, M, D, E, S or T (e.g., V, I, M, D, E, or T);
$X_{86}$ is S, T, F, Y, or W (e.g., T, F, or Y);
$X_{88}$ is A, V, I, L, N, Q, S, T, F, Y, W, or absent (e.g., A, V, N, Q, T, Y, or absent); and
$X_{89}$ is G, A, V, I, L, R, H, K, F, Y, W, or absent (e.g., G, A, V, R, K, Y, or absent).

In other embodiments, each X in SEQ ID NO:285 can be an amino acid in any one of SEQ ID NOs:250-284 when any one of the sequences in SEQ ID NOs:250-284 is used as a reference sequence to be optimally aligned with SEQ ID NO:285.

In some embodiments, the third FR includes or is a polypeptide sequence having at least 90% sequence identity to SEQ ID NO:286:

$X_{50}X_{51}X_{52}X_{53}X_{54}X_{55}X_{56}X_{57}RX_{59}X_{60}IX_{62}RDX_{65}X_{66}$
$X_{67}X_{68}X_{69}VX_{71}LX_{73}X_{74}X_{75}X_{76}X_{77}X_{78}$
$X_{79}EDTAX_{84}YYX_{87}X_{88}X_{89}$,
wherein:
$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);

$X_{56}$ is D, E, R, H, K, N, Q, or absent (e.g., E, R, K, Q, or absent);
$X_{57}$ is G, D, E, S, T, or absent (e.g., G, D, S, or absent);
$X_{59}$ is A, V, I, L, F, Y, or W (e.g., A, V, L, or F);
$X_{60}$ is A, V, I, L, C, M, S, or T (e.g., A, C, S, or T);
$X_{62}$ is C, M, S, or T (e.g., S or T);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{71}$ is S, T, F, Y, or W (e.g., S, T, F, or Y);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{84}$ is A, V, I, L, C, M, D, E, S or T (e.g., V, I, M, D, E, or T);
$X_{87}$ is F, Y, or W (e.g., Y);
$X_{88}$ is A, V, I, L, N, Q, S, T, F, Y, W, or absent (e.g., A, V, N, Q, T, Y, or absent); and
$X_{89}$ is G, A, V, I, L, R, H, K, F, Y, W, or absent (e.g., G, A, V, R, K, Y, or absent).

In other embodiments, each X in SEQ ID NO:286 can be an amino acid in any one of SEQ ID NOs:250-284 when any one of the sequences in SEQ ID NOs:250-284 is used as a reference sequence to be optimally aligned with SEQ ID NO:286.

In some embodiments, the third FR includes or is a polypeptide sequence having at least 90% sequence identity to SEQ ID NO:287:
$X_{50}X_{51}X_{52}X_{53}X_{54}X_{55}X_{56}X_{57}RX_{59}X_{60}IX_{62}RDX_{65}X_{66}$
$X_{67}X_{68}X_{69}VX_{71}LX_{73}X_{74}X_{75}X_{76}X_{77}X_{78}$
$X_{79}EDTAX_{84}YYX_{87}X_{88}$,
wherein:
$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{59}$ is A, V, I, L, F, Y, or W (e.g., A, V, L, or F);
$X_{60}$ is A, V, I, L, C, M, S, or T (e.g., A, C, S, or T);
$X_{62}$ is C, M, S, or T (e.g., S or T);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{71}$ is S, T, F, Y, or W (e.g., S, T, F, or Y);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{84}$ is A, V, I, L, C, M, D, E, S or T (e.g., V, I, M, D, E, or T);
$X_{87}$ is F, Y, or W (e.g., Y); and
$X_{88}$ is A, V, I, L, N, Q, S, T, F, Y, W, or absent (e.g., A, V, N, Q, T, Y, or absent).

In other embodiments, each X in SEQ ID NO:287 can be an amino acid in any one of SEQ ID NOs:250-284 when any one of the sequences in SEQ ID NOs:250-284 is used as a reference sequence to be optimally aligned with SEQ ID NO:287.

In some embodiments, the third FR includes or is a polypeptide sequence having at least 90% sequence identity to SEQ ID NO:288:
$X_{50}$YADSVKGRFTISRDNAKNTVYLQMNSLKPEDT AVYYCAX$_{89}$,
wherein:
$X_{50}$ is A, V, I, L, D, E, R, H, K, N, Q, S, T, F, Y, W, or absent (e.g., L, D, R, N, T, Y, or absent); and
$X_{89}$ is G, A, V, I, L, R, H, K, F, Y, W, or absent (e.g., G, A, V, R, K, Y, or absent).

In other embodiments, the third FR includes or is a polypeptide sequence having at least 90% sequence identity to SEQ ID NO:289:
$X_{50}$YADSVKGRFTISRDNAKNTVYLQMNSLKPED TAVYYCA,
wherein:
$X_{50}$ is A, V, I, L, D, E, R, H, K, N, Q, S, T, F, Y, W, or absent (e.g., L, D, R, N, T, Y, or absent).

FIG. 9D provides non-limiting FR4 sequences. In some embodiments, the fourth FR includes or is a polypeptide sequence having at least 90% sequence identity to SEQ ID NOs:290-301. In other embodiments, the fourth FR includes or is a polypeptide sequence having at least 90% sequence identity to SEQ ID NO:302:
$X_{90}$WGX$_{93}$GX$_{95}$X$_{96}$X$_{97}$TVSX$_{101}$,
wherein:
$X_{90}$ is A, V, I, L, R, H, K, N, Q, S, T, F, Y, W, or absent (e.g., V, H, Q, S, F, Y, or absent);
$X_{93}$ is R, H, K, N, Q, P, F, Y, or W (e.g., R, K, Q, or P);
$X_{95}$ is A, V, I, L, S, or T (e.g., L or T);
$X_{96}$ is A, V, I, L, C, M, N, Q, S, or T (e.g., L, M, Q, S, or T);
$X_{97}$ is A, V, I, or L (e.g., V or L); and
$X_{101}$ is S, T, or absent (e.g., S or absent).

In other embodiments, each X in SEQ ID NO:302 can be an amino acid in any one of SEQ ID NOs:290-301 when any one of the sequences in SEQ ID NOs:290-301 is used as a reference sequence to be optimally aligned with SEQ ID NO:302.

In some embodiments, the fourth FR includes or is a polypeptide sequence having at least 90% sequence identity to SEQ ID NO:303:
$X_{90}$WGX$_{93}$GX$_{95}$X$_{96}$X$_{97}$TVS,
wherein:
$X_{90}$ is A, V, I, L, R, H, K, N, Q, S, T, F, Y, W, or absent (e.g., V, H, Q, S, F, Y, or absent);
$X_{93}$ is R, H, K, N, Q, P, F, Y, or W (e.g., R, K, Q, or P);

$X_{95}$ is A, V, I, L, S, or T (e.g., L or T);

$X_{96}$ is A, V, I, L, C, M, N, Q, S, or T (e.g., L, M, Q, S, or T); and $X_{97}$ is A, V, I, or L (e.g., V or L).

In other embodiments, each X in SEQ ID NO:303 can be an amino acid in any one of SEQ ID NOs:290-301 when any one of the sequences in SEQ ID NOs:290-301 is used as a reference sequence to be optimally aligned with SEQ ID NO:303.

In some embodiments, the fourth FR includes or is a polypeptide sequence having at least 90% sequence identity to SEQ ID NO:304:

$WGX_{93}GX_{95}X_{96}X_{97}TVSX_{101}$, wherein:

$X_{93}$ is R, H, K, N, Q, P, F, Y, or W (e.g., R, K, Q, or P);

$X_{95}$ is A, V, I, L, S, or T (e.g., L or T);

$X_{96}$ is A, V, I, L, C, M, N, Q, S, or T (e.g., L, M, Q, S, or T);

$X_{97}$ is A, V, I, or L (e.g., V or L); and $X_{101}$ is S, T, or absent (e.g., S or absent).

In other embodiments, each X in SEQ ID NO:304 can be an amino acid in any one of SEQ ID NOs:290-301 when any one of the sequences in SEQ ID NOs:290-301 is used as a reference sequence to be optimally aligned with SEQ ID NO:304.

In some embodiments, the fourth FR includes or is a polypeptide sequence having at least 90% sequence identity to SEQ ID NO:305:

$X_{90}X_{91}GX_{93}GTX_{96}X_{97}X_{98}VSX_{101}$, wherein:

$X_{90}$ is A, V, I, L, R, H, K, N, Q, S, T, F, Y, W, or absent (e.g., V, H, Q, S, F, Y, or absent);

$X_{91}$ is P, F, Y, or W (e.g., W);

$X_{93}$ is R, H, K, N, Q, P, F, Y, or W (e.g., R, K, Q, or P);

$X_{96}$ is A, V, I, L, C, M, N, Q, S, or T (e.g., L, M, Q, S, or T);

$X_{97}$ is A, V, I, or L (e.g., V or L);

$X_{98}$ is S or T; and $X_{101}$ is S, T, or absent (e.g., S or absent).

In other embodiments, each X in SEQ ID NO:305 can be an amino acid in any one of SEQ ID NOs:290-301 when any one of the sequences in SEQ ID NOs:290-301 is used as a reference sequence to be optimally aligned with SEQ ID NO:305.

In some embodiments, the fourth FR includes or is a polypeptide sequence having at least 90% sequence identity to SEQ ID NO:306:

$X_{90}$WGQGTQVTVSS, wherein:

$X_{90}$ is A, V, I, L, R, H, K, N, Q, S, T, F, Y, W, or absent (e.g., V, H, Q, S, F, Y, or absent).

In other embodiments, the fourth FR includes or is a polypeptide sequence having at least 90% sequence identity to SEQ ID NO:307:

$X_{90}$WGQGTQVTVS, wherein:

$X_{90}$ is A, V, I, L, R, H, K, N, Q, S, T, F, Y, W, or absent (e.g., V, H, Q, S, F, Y, or absent).

Targets

A target can be an antigen that can be bound by any construct described herein. Non-limiting targets include a coronavirus or a portion thereof. Non-limiting portions of a coronavirus includes a spike protein (e.g., a S-glycoprotein) or a receptor-binding domain (RBD). Non-limiting sequences for such spike proteins and RBDs include one or more of the following: UniProtKB No. P0DTC2 (amino acids 13-1273 for the spike glycoprotein, amino acids 13-685 for the spike protein 1, amino acids 319-541 for the RBD, or amino acids 437-508 for a receptor-binding motif that binds to human ACE2); UniProtKB No. A0A6B9WHD3 (amino acids 31-1228 for the spike glycoprotein, amino acids 31-592 for the spike protein 1, or amino acids 349-526 for the RBD); UniProtKB No. P59594 (amino acids 14-1255 for the spike glycoprotein, amino acids 14-667 for the spike protein S1, amino acids 306-527 for the RBD, or amino acids 424-494 for a receptor-binding motif that binds to human ACE2); UniProtKB No. Q5GDB5 (amino acids 14-667 for spike protein S1, amino acids 306-527 for the RBD, or amino acids 335-512 for the RBD); UniProtKB No. Q3LZX1 (amino acids 14-1242 for the spike glycoprotein, amino acids 14-654 for the spike protein S1, or amino acids 310-514 for the RBD); UniProtKB No. Q315J5 (amino acids 14-1241 for the spike glycoprotein, amino acids 14-653 for the spike protein S1, or amino acids 310-513 for the RBD); and UniProtKB No. Q0Q475 (amino acids 14-1241 for the spike glycoprotein, amino acids 14-653 for the spike protein S1, or amino acids 310-513 for the RBD).

Targets can also include a polypeptide sequence having at least 90% sequence identity to any one of SEQ ID NOs: 320-327 (FIGS. 12A-12D) or a fragment thereof. In other embodiments, each X in SEQ ID NO:327 can be an amino acid in any one of SEQ ID NOs:320-326 when any one of the sequences in SEQ ID NOs:320-326 is used as a reference sequence to be optimally aligned with SEQ ID NO:327.

In yet other embodiments, the target can include the following one or more mutations: L5F, V341I, K417N, K417T, A435S, N439K, L452R, K458R, I472V, E484K, N501Y, D614G, H655Y, R682Q, D936Y, S939F, and/or S943T, using the numbering provided for SEQ ID NO:320 or for another sequence that is optimally aligned with SEQ ID NO:320.

Targets can also include a polypeptide sequence having at least 90% sequence identity to any one of SEQ ID NOs: 328-336 (FIG. 12E) or a fragment thereof. In other embodiments, each X in SEQ ID NO:335 can be an amino acid in any one of SEQ ID NOs:328-334 when any one of the sequences in SEQ ID NOs:328-334 is used as a reference sequence to be optimally aligned with SEQ ID NO:335. In yet other embodiments, each X in SEQ ID NO:336 can be an amino acid in any one of SEQ ID NOs:328-334 when any one of the sequences in SEQ ID NOs:328-334 is used as a reference sequence to be optimally aligned with SEQ ID NO:336.

In some embodiments, the target is or includes a polypeptide sequence having at least 90% sequence identity to SEQ ID NO:335:

$RVX_{321}PX_{323}X_{324}X_{325}X_{326}X_{327}RFPNITNX_{335}CPFX_{339}$
$X_{340}X_{341}FNAX_{345}X_{346}FX_{348}$
$X_{349}VYAWX_{354}RX_{356}X_{357}ISX_{360}CVADYX_{366}$
$VLYNSX_{372}X_{373}FSTFKCYGVSX_{384}$
$X_{385}KLX_{388}DLCFX_{393}X_{394}VYADX_{399}FX_{401}X_{402}X_{403}$
$X_{404}X_{405}X_{406}VRQX_{410}APGX_{414}TGX_{417}IADYNYK$
$LPDDFX_{430}GCVX_{434}X_{435}WNX_{438}X_{439}X_{440}X_{441}$
$DX_{443}X_{444}X_{445}X_{446}G$
$X_{448}X_{449}X_{450}YX_{452}YRX_{455}X_{456}RX_{458}X_{459}X_{460}LX_{462}$
$PFERDX_{468}SX_{470}X_{471}X_{472}X_{473}$
$X_{474}X_{475}X_{476}X_{477}X_{478}X_{479}X_{480}X_{481}X_{482}X_{483}X_{484}X_{485}$
$X_{486}NX_{488}X_{489}X_{490}X_{491}LX_{493}X_{494}YX_{496}FX_{498}X_{499}$
$X_{500}X_{501}X_{502}X_{503}X_{504}X_{505}QX_{507}X_{508}RVVVLSFEL$
$LX_{519}APATVCGPKX_{529}S$
$TX_{532}LX_{534}KNX_{537}CVNF$ wherein:

$X_{321}$ is A, V, I, L, N, Q, S, or T (e.g., V, Q, S, or T);

$X_{323}$, $X_{345}$, $X_{366}$, $X_{385}$, $X_{393}$, $X_{399}$, $X_{404}$, and $X_{438}$ is, independently, G, S, or T (e.g., S or T);

$X_{324}$, $X_{339}$, $X_{354}$, $X_{360}$, $X_{414}$, and $X_{532}$ is, independently, G, D, E, N or Q (e.g., G, D, E, or Q; E or N; D or N; or E or Q);

$X_{325}$ and $X_{405}$ is, independently, D, E, S, or T (e.g., D, E, or S);

$X_{326}$, $X_{327}$, $X_{341}$, $X_{401}$, $X_{402}$, $X_{410}$, $X_{434}$, $X_{468}$, $X_{503}$, and $X_{534}$ is, independently, A, V, I, or L (e.g., V or I; or V or L);

$X_{335}$ and $X_{529}$ is, independently, A, V, I, L, R, H, or K (e.g., L or R; or V or K);

$X_{340}$ is D, E, R, H, or K (e.g., E or K);

$X_{346}$, $X_{356}$, and $X_{403}$ is, independently, R, H, K, S, or T (e.g., R, K, or T);

$X_{348}$, $X_{384}$, $X_{489}$, $X_{502}$, and $X_{507}$ is, independently, G, A, V, I, L, P, F, Y, or W (e.g., A or P; V or W; G or P; G or W);

$X_{349}$, $X_{394}$, $X_{470}$, and $X_{500}$ is, independently, N, Q, S, or T (e.g., N or S);

$X_{357}$, $X_{458}$, and $X_{462}$ is, independently, R, H, or K (e.g., R or K);

$X_{372}$ and $X_{435}$ is, independently, A, V, I, L, S, or T (e.g., A or T; or A or S);

$X_{373}$, $X_{491}$, and $X_{499}$ is, independently, S, T, P, F, Y, or W (e.g., S or F; or T or P);

$X_{388}$ is A, V, I, L, N, or Q (e.g., I or N);

$X_{406}$, $X_{496}$, and $X_{504}$ is, independently, G, A, V, I, L, D, or E (e.g., D or E; or G, A, or E);

$X_{417}$, $X_{439}$, $X_{441}$, and $X_{443}$ is, independently, A, V, I, L, R, H, K, N, Q, S, or T (e.g., V, K, N, or T; A, R, K, or N; A, Q, S, or T; or L, I, H, or Q);

$X_{430}$ is L, C, M, S, or T (e.g., M or T);

$X_{440}$, $X_{450}$, $X_{460}$, $X_{519}$, and $X_{537}$ is, independently, R, H, K, N or Q (e.g., N, K, or Q);

$X_{444}$, $X_{446}$, and $X_{478}$ is, independently, G, R, H, K, S, T, or absent (e.g., K, T, or absent; or G, T, or absent; or K, T, or absent);

$X_{445}$, $X_{459}$, $X_{471}$, $X_{476}$, $X_{477}$, and $X_{485}$ is, independently, G, A, V, I, L, D, E, S, T, or absent (e.g., V, E, S, or absent; G, A, E, S, or T; V, D, or E; G, D, E, or absent; G, S, or absent; E, T, or absent; or G, A, or absent);

$X_{448}$ is N, Q, or absent (e.g., N or absent);

$X_{449}$, $X_{473}$, $X_{479}$, and $X_{482}$ is, independently, G, P, F, Y, W, or absent (e.g., F, Y, or absent; P or absent; or G, P, or absent);

$X_{452}$, $X_{456}$, $X_{490}$, and $X_{505}$ is, independently, A, V, I, L, R, H, K, F, Y, or W (e.g., L, R, K or Y; or L, H, F, or Y; or R, F, Y, or W; or H or Y);

$X_{455}$ and $X_{508}$ is, independently, A, V, I, L, S, T, F, Y, or W (e.g., L, S, or Y; or T or Y);

$X_{472}$, $X_{475}$, and $X_{483}$ is, independently, A, V, I, L, D, E, N, Q, P, or absent (e.g., V, I, D, P, or absent; A, P, or absent; or V, Q, P, or absent);

$X_{474}$ and $X_{481}$ is, independently, N, Q, S, T, or absent (e.g., Q, S, or absent; N, T, or absent);

$X_{480}$ and $X_{488}$ is, independently, G, C, M, or absent (e.g., C or absent);

$X_{486}$ is G, A, V, I, L, D, E, P, F, Y, or W (e.g., G, L, E, P, or F);

$X_{493}$ and $X_{498}$ is, independently, N, Q, S, T, F, Y, or W (e.g., N, Q, S, or Y; or N, Q, or Y);

$X_{484}$ and $X_{494}$ is, independently, G, D, E, R, H, K, S, T, or absent (e.g., G, D, R, S, or T; or E, K, T, or absent); and $X_{501}$ is any amino acid, such as A, V, I, L, D, E, N, Q, S, T, F, Y, or W (e.g., V, I, D, N, S, T, or Y).

In yet other embodiments, the target can include the following one or more mutations: V341I, K417N, K417T, A435S, N439K, L452R, K458R, I472V, E484K, and/or N501Y using the numbering provided for SEQ ID NOs:335-336 or for another sequence that is optimally aligned with one of SEQ ID NOs:335-336.

Therapeutic or Diagnostic Agents

The present disclosure also encompasses a construct that can be directly or indirectly attached to one or more therapeutic or diagnostic agents. Such agents can include a therapeutic antibody, a complementarity determining region (CDR), a small molecule, a chemotherapeutic agent, an antiviral agent, an antibacterial agent, an anti-inflammatory agent, a scavenging agent, an imaging agent, a marker, a dye, a detectable moiety, or a label.

Any of the constructs herein (e.g., isolated or purified antibodies or fragments thereof) can be employed to bind to a target. Binding can be accomplished, e.g., by using CDRs specific for that target. In one embodiment, the therapeutic or diagnostic agent includes one or more CDRs for viral targets. Exemplary targets include a virus, such as Coronaviridae (e.g., severe acute respiratory syndrome-related coronavirus (SARS-COV), severe acute respiratory syndrome coronavirus 2 (SARS-COV-2), or variants thereof); or a portion of a virus, such as a spike protein or a receptor-binding domain (RBD) of a coronavirus.

Other non-limiting therapeutic or diagnostic agents include a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; or a lipopolysaccharide.

Non-limiting detectable moieties may be a radioisotope (e.g., 32P), a fluorescent or chemiluminescent compound such as rhodamine or luciferin, or an enzyme, such as alkaline phosphatase or horseradish peroxidase. Non-limiting labels include a radiolabel, an isotope, a visible or near-infrared fluorescent label, a reporter molecule, biotin, or the like.

The therapeutic or diagnostic agent can be a peptide, an enzyme (e.g., horseradish peroxidase, alkaline phosphatase, glucose-6-phosphatase or beta-galactosidase), a nucleic acid, a virus, a fluorophore (e.g., green fluorescent protein (GFP), blue fluorescent dyes excited at wavelengths in the ultraviolet (UV) part of the spectrum (e.g., AMCA (7-amino-4-methylcoumarin-3-acetic acid); Alexa Fluor 350), green fluorescent dyes excited by blue light (e.g., FITC, Cy2, Alexa Fluor 488), red fluorescent dyes excited by green light (e.g., rhodamines, Texas Red, Cy3, Alexa Fluor dyes 546, 564 and 594), or dyes excited with far-red light (e.g., Cy5) to be visualized with electronic detectors (CCD cameras, photomultipliers)), a heavy metal (including chelates thereof, such as those including europium, lanthanum or yttrium), a chemical entity, or a radioisotope (e.g., [$^{18}$F] fluorodeoxy glucose, $^{11}$C-, $^{125}$I-, $^{131}$I-, $^{3}$H-, $^{14}$C-, $^{35}$S-, or $^{99\text{m}}$Tc-labelled compounds).

The therapeutic or diagnostic agent can include a drug, an antigen binding fragment of an antibody molecule or portion thereof (e.g., F(ab), scFv, a VH domain, or a VL domain) (e.g., to impart, induce or block a biological response), a ligand binding portion of a receptor or a receptor binding portion of a ligand, an enzyme, therapeutically useful amino acids, peptides, proteins, nucleic acids, including but not limited to polynucleotides, oligonucleotides, carbohydrates and lipids. Yet other exemplary agents include cytokines, neurotrophic factors, growth factors, enzymes, antibodies, neurotransmitters, neuromodulators, antibiotics, antiviral agents, antifungal agents, imaging or detectable agents, isotopes, and chemotherapeutic agents, and the like. The therapeutic or diagnostic agents can also include drugs, prodrugs, and precursors that can be activated when the therapeutic agent is delivered to the target tissue.

Methods

The present disclosure also encompasses methods that employ any construct described herein. In particular embodiments, the methods include method of treatment or prophylaxis of one or more diseases or conditions. Non-limiting diseases and conditions include a viral infection.

Methods can also include use of the construct as a therapeutic or diagnostic agent, which can be administered to a subject (a mammal or a human) by injection, preferably by intravenous, intraperitoneal, intramuscular or subcutaneous injection. The constructs herein (e.g., with a therapeutic or diagnostic agent) can be used in imaging or in diagnosing viral spread.

Methods can also include providing a construct or a pharmaceutical composition thereof (e.g., as described herein) for use in the treatment of viral infections or any disorder or condition herein. A pharmaceutical composition can include any construct, described herein either with a therapeutic or diagnostic agent, and a pharmaceutically acceptable carrier.

As used herein, "pharmaceutically acceptable carrier" is intended to include any and all solvents, adjuvants, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

EXAMPLES

Example 1: Highly Effective SARS-COV-2 Neutralizing Humanized Nanobodies

A high-diversity synthetic nanobody phage library was used to identify 34 humanized nanobodies that show nanomolar to low picomolar efficacy in preventing cell infection by replicating VSV-SARSCOV-2 virus. In particular, we developed a high diversity humanized nanobody library (more than $3\times10^{10}$ nanobody variants), which was designed to have three different CDR3 lengths and incorporated the natural prevalence of amino acids at specific CDR positions for CDR1 and CDR2 derived from numerous effective nanobodies. For CDR3, all amino acids were used with the exception of cysteine and methionine.

FIG. 1 provides a non-limiting method of constructing a nanobody phage library. In particular, the library was constructed using novel DNA synthesis technology, thereby ensuring high quality and full length nanobodies with low incidence of stop codons. These attributes allowed for the identification of highly potent binders to desired targets with femtomolar to nanomolar dissociation constants. This library was cloned into the pADL20c M13 phagemid vector, which allows for expression of nanobodies as a fusion protein to coat protein gIIIp of M13 phage. This library was screening against full length soluble SARS-COV-2 stabilized spike protein for three rounds, followed by a single round against the SARS-COV-2 receptor-binding domain (RBD).

From this biopanning campaign, we identified numerous potential candidate nanobodies. Reconformation screening using nanobody-human Fc fusion proteins elucidated 34 nanobodies, which specifically prevented infection of green monkey kidney cells (vero) with VSV-SARS-COV-2 virus with enhanced efficacy. These candidates also were able to compete with human ACE2 binding on full length SARS-COV-2 spike protein in an in vitro competition enzyme-linked immunosorbent assay (ELISA). Results for the competition assays and neutralization assays are seen in FIGS. 10A-10C and FIGS. 11A-11C. Subsequent testing to validate efficacy can include testing against BSL-3 SARS-COV-2 infection of vero cells and in transgenic mouse models.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. An isolated or purified single-domain antibody comprising a variable domain, wherein the variable domain comprises:
   (i) a first complementarity determining region comprising a polypeptide sequence of SEQ ID NO:40, a second complementarity determining region comprising a polypeptide sequence of SEQ ID NO:74, and a third complementarity determining region comprising a polypeptide sequence of SEQ ID NO:108; or
   (ii) a first complementarity determining region comprising a polypeptide sequence of SEQ ID NO:41, a second complementarity determining region comprising a polypeptide sequence of SEQ ID NO:75, and a third complementarity determining region comprising a polypeptide sequence of SEQ ID NO:109; or
   (iii) a first complementarity determining region comprising a polypeptide sequence of SEQ ID NO:42, a second complementarity determining region comprising a polypeptide sequence of SEQ ID NO:76, and a third complementarity determining region comprising a polypeptide sequence of SEQ ID NO:110; or
   (iv) a first complementarity determining region comprising a polypeptide sequence of SEQ ID NO:43, a second complementarity determining region comprising a polypeptide sequence of SEQ ID NO:77, and a third complementarity determining region comprising a polypeptide sequence of SEQ ID NO:111,
   wherein the variable domain binds to a spike protein of a coronavirus or a receptor-binding domain of a coronavirus, and wherein the coronavirus is severe acute respiratory syndrome coronavirus 2.

2. The single-domain antibody of claim 1, wherein variable domain further comprises:
   a first framework region attached to an N-terminus of the first complementarity determining region;
   a second framework region disposed between the first and second complementarity determining regions;
   a third framework region disposed between the second and third complementarity determining regions; and
   a fourth framework region attached to a C-terminus of the third complementarity determining region.

3. The single-domain antibody of claim 2, wherein the variable domain comprises a polypeptide sequence of any one of SEQ ID NOS:1-4.

4. The single-domain antibody of claim 2, wherein the first framework region comprises a polypeptide sequence of SEQ ID NO:191, wherein the second framework region comprises a polypeptide sequence of SEQ ID NO:221, wherein the third framework region comprises a polypeptide sequence of SEQ ID NO:252, and wherein the fourth framework region comprises a polypeptide sequence of SEQ ID NO:290.

5. The single-domain antibody of claim 2, wherein the first framework region comprises a polypeptide sequence of SEQ ID NO:190, wherein the second framework region comprises a polypeptide sequence of SEQ ID NO:220, wherein the third framework region comprises a polypeptide sequence of SEQ ID NO:251, and wherein the fourth framework region comprises a polypeptide sequence of SEQ ID NO:290.

6. The single-domain antibody of claim 1, wherein the spike protein comprises a polypeptide sequence of any one of SEQ ID NOS:320-326; or wherein the receptor-binding domain comprises a polypeptide sequence of any one of SEQ ID NOS:328-334.

7. The single-domain antibody of claim 1, further comprising a therapeutic agent or a diagnostic agent attached directly or indirectly to the variable domain.

8. A method of treating or prophylactically treating a viral infection, the method comprising:
   administering a single-domain antibody of claim 1 to a subject in need thereof,
   wherein the viral infection comprises an infection from a coronavirus, and wherein the coronavirus is severe acute respiratory syndrome coronavirus 2.

* * * * *

SEQUENCE LISTING

```
<160> NUMBER OF SEQ ID NOS: 336

<210> SEQ ID NO 1
<211> LENGTH: 122
<212> TYPE: PRT
<213> ORGANISM: Artificial Sequence
<220> FEATURE:
<223> OTHER INFORMATION: Synthetic construct
```

<400> SEQUENCE: 1

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Ala Phe Gly Ile Tyr
            20                  25                  30

Arg Met Gly Trp Phe Arg Gln Ala Pro Gly Lys Glu Arg Glu Phe Val
        35                  40                  45

Ser Ala Ile Ser Gly Gly Asp Ala Gly His Thr Arg Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Tyr Trp Asp Tyr Asn Gly Val Val Pro Phe Phe Lys Tyr Trp
            100                 105                 110

Gly Gln Gly Thr Gln Val Thr Val Ser Ser
            115                 120
```

<210> SEQ ID NO 2
<211> LENGTH: 122
<212> TYPE: PRT
<213> ORGANISM: Artificial Sequence
<220> FEATURE:
<223> OTHER INFORMATION: Synthetic construct

<400> SEQUENCE: 2

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Tyr Asp Ser Tyr Val
            20                  25                  30

Arg Met Gly Trp Phe Arg Gln Ala Pro Gly Lys Glu Arg Glu Phe Val
        35                  40                  45

Ser Ala Ile Ser Gly Gly Gly Asp Lys Ser Thr Trp Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Asn Ala Gln Leu Gly Pro Ala Tyr Asp Lys Ile Gly Tyr Trp
            100                 105                 110

Gly Gln Gly Thr Gln Val Thr Val Ser Ser
            115                 120
```

<210> SEQ ID NO 3
<211> LENGTH: 125
<212> TYPE: PRT
<213> ORGANISM: Artificial Sequence
<220> FEATURE:
<223> OTHER INFORMATION: Synthetic construct

<400> SEQUENCE: 3

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Ser Gly Gln Tyr
            20                  25                  30

Arg Met Gly Trp Phe Arg Gln Ala Pro Gly Lys Glu Arg Glu Phe Val
        35                  40                  45
```

```
Ser Ala Ile Ser Ala Trp Gly Gly Ser Lys Tyr Ala Asp Ser
        50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Ala Trp Tyr Phe Glu Gln Ile Phe Arg Ala Asp Val Lys Thr
                100                 105                 110

Glu Tyr Trp Gly Gln Gly Thr Gln Val Thr Val Ser Ser
                115                 120                 125

<210> SEQ ID NO 4
<211> LENGTH: 122
<212> TYPE: PRT
<213> ORGANISM: Artificial Sequence
<220> FEATURE:
<223> OTHER INFORMATION: Synthetic construct

<400> SEQUENCE: 4

Glu Val Gln Leu Gln Ala Ser Gly Gly Gly Phe Val Gln Pro Gly Gly
 1               5                  10                  15

Ser Leu Arg Leu Ser Cys Ala Ala Ser Gly Thr Ala Tyr Gly Trp Ser
                 20                  25                  30

Arg Met Gly Trp Phe Arg Gln Ala Pro Gly Lys Glu Arg Glu Phe Val
             35                  40                  45

Ser Ala Ile Ser Arg Ala Ser Ala Gly Tyr Ala Gln Tyr Ala Asp Ser
        50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Phe Pro Leu His Asp Gln Gly Glu Pro Tyr Gly Trp Tyr Trp
                100                 105                 110

Gly Gln Gly Thr Gln Val Thr Val Ser Ser
            115                 120

<210> SEQ ID NO 5
<211> LENGTH: 122
<212> TYPE: PRT
<213> ORGANISM: Artificial Sequence
<220> FEATURE:
<223> OTHER INFORMATION: Synthetic construct

<400> SEQUENCE: 5

Glu Val Gln Leu Gln Ala Ser Gly Gly Gly Phe Val Gln Pro Gly Gly
 1               5                  10                  15

Ser Leu Arg Leu Ser Cys Ala Ala Ser Gly His Thr Phe Asp Ala Tyr
                 20                  25                  30

Gln Met Gly Trp Phe Arg Gln Ala Pro Gly Lys Glu Arg Glu Phe Val
             35                  40                  45

Ser Ala Ile Ser Ala Gly Asp Gly Ala Ala Ser Tyr Tyr Ala Asp Ser
        50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Lys Phe Ser Lys Trp His Ser Arg Val Gln Ala Glu Tyr Trp
```

```
                100                 105                 110
Gly Gln Gly Thr Gln Val Thr Val Ser Ser
        115                 120

<210> SEQ ID NO 6
<211> LENGTH: 125
<212> TYPE: PRT
<213> ORGANISM: Artificial Sequence
<220> FEATURE:
<223> OTHER INFORMATION: Synthetic construct

<400> SEQUENCE: 6

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Phe Ser Phe Leu
            20                  25                  30

Pro Met Gly Trp Phe Arg Gln Ala Pro Gly Lys Glu Arg Glu Phe Val
        35                  40                  45

Ser Ala Ile Ser Asp Trp Ser Gly Gly His Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Asn Pro Gln Ala Ala Val Tyr Glu Asn Glu Trp Pro Ile
            100                 105                 110

Val Tyr Trp Gly Gln Gly Thr Gln Val Thr Val Ser Ser
        115                 120                 125

<210> SEQ ID NO 7
<211> LENGTH: 119
<212> TYPE: PRT
<213> ORGANISM: Artificial Sequence
<220> FEATURE:
<223> OTHER INFORMATION: Synthetic construct

<400> SEQUENCE: 7

Glu Val Gln Leu Gln Ala Ser Gly Gly Gly Phe Val Gln Pro Gly Gly
1               5                   10                  15

Ser Leu Arg Leu Ser Cys Ala Ala Ser Gly His Thr Phe Asp Ala His
            20                  25                  30

Arg Met Gly Trp Phe Arg Gln Ala Pro Gly Lys Glu Arg Glu Phe Val
        35                  40                  45

Ser Ala Ile Ser Thr Trp Ala Gly Asp Ser Ala Arg Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ser Phe Leu Trp Asp Arg Glu Gln Trp Tyr Trp Gly Gln Gly
            100                 105                 110

Thr Gln Val Thr Val Ser Ser
        115

<210> SEQ ID NO 8
<211> LENGTH: 122
<212> TYPE: PRT
<213> ORGANISM: Artificial Sequence
<220> FEATURE:
```

<223> OTHER INFORMATION: Synthetic construct

<400> SEQUENCE: 8

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Pro Tyr Thr Gln Tyr
            20                  25                  30

Arg Met Gly Trp Phe Arg Gln Ala Pro Gly Lys Glu Arg Glu Phe Val
        35                  40                  45

Ser Ala Ile Ser Thr Trp Ala Gly Asp Ser Ala Arg Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Asp Phe Arg Ser Ala Ser Glu Asp Ile Ala Arg Trp Tyr Trp
            100                 105                 110

Gly Gln Gly Thr Gln Val Thr Val Ser Ser
        115                 120
```

<210> SEQ ID NO 9
<211> LENGTH: 125
<212> TYPE: PRT
<213> ORGANISM: Artificial Sequence
<220> FEATURE:
<223> OTHER INFORMATION: Synthetic construct

<400> SEQUENCE: 9

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly His Ser Phe Gly Gln His
            20                  25                  30

Arg Met Gly Trp Phe Arg Gln Ala Pro Gly Lys Glu Arg Glu Phe Val
        35                  40                  45

Ser Ala Ile Ser Ser Gly Gly Ser Gly His Thr Arg Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Leu Tyr Trp Val His Gln Val Ser Asn Glu Val Trp Arg
            100                 105                 110

Gln Tyr Trp Gly Gln Gly Thr Gln Val Thr Val Ser Ser
        115                 120                 125
```

<210> SEQ ID NO 10
<211> LENGTH: 125
<212> TYPE: PRT
<213> ORGANISM: Artificial Sequence
<220> FEATURE:
<223> OTHER INFORMATION: Synthetic construct

<400> SEQUENCE: 10

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Ser Gly Gln Tyr
            20                  25                  30

Arg Met Gly Trp Phe Arg Gln Ala Pro Gly Lys Glu Arg Glu Phe Val
```

```
            35                  40                  45

Ser Ala Ile Ser Asp Thr Ala Gly Gln Ser Thr Thr Tyr Ala Asp Ser
         50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Leu Arg Gly Val Gly Trp Pro Asp Ser Asn Leu Glu Leu Gln
                100                 105                 110

Trp Tyr Trp Gly Gln Gly Thr Gln Val Thr Val Ser Ser
            115                 120                 125

<210> SEQ ID NO 11
<211> LENGTH: 119
<212> TYPE: PRT
<213> ORGANISM: Artificial Sequence
<220> FEATURE:
<223> OTHER INFORMATION: Synthetic construct

<400> SEQUENCE: 11

Glu Val Gln Leu Gln Ala Ser Gly Gly Gly Phe Val Gln Pro Gly Gly
 1               5                  10                  15

Ser Leu Arg Leu Ser Cys Ala Ala Ser Gly Arg Ala Phe Gly Ile Tyr
                20                  25                  30

Arg Met Gly Trp Phe Arg Gln Ala Pro Gly Lys Glu Arg Glu Phe Val
            35                  40                  45

Ser Ala Ile Ser Ser Ser Ala Gly Gly Tyr Lys Thr Tyr Ala Asp Ser
         50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Phe Arg Gly Thr Ile Asp Gly Asn Tyr Tyr Trp Gly Gln Gly
                100                 105                 110

Thr Gln Val Thr Val Ser Ser
            115

<210> SEQ ID NO 12
<211> LENGTH: 119
<212> TYPE: PRT
<213> ORGANISM: Artificial Sequence
<220> FEATURE:
<223> OTHER INFORMATION: Synthetic construct

<400> SEQUENCE: 12

Glu Val Gln Leu Gln Ala Ser Gly Gly Gly Phe Val Gln Pro Gly Gly
 1               5                  10                  15

Ser Leu Arg Leu Ser Cys Ala Ala Ser Gly Ser Ser Phe Gly Ile Arg
                20                  25                  30

Arg Met Gly Trp Phe Arg Gln Ala Pro Gly Lys Glu Arg Glu Phe Val
            35                  40                  45

Ser Ala Ile Ser Thr Thr Ser Gly Glu Thr Thr Arg Tyr Ala Asp Ser
         50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95
```

```
Cys Ala Gln Arg Phe Val Thr Gly Thr His Trp Tyr Trp Gly Gln Gly
                100                 105                 110

Thr Gln Val Thr Val Ser Ser
        115
```

<210> SEQ ID NO 13
<211> LENGTH: 122
<212> TYPE: PRT
<213> ORGANISM: Artificial Sequence
<220> FEATURE:
<223> OTHER INFORMATION: Synthetic construct

<400> SEQUENCE: 13

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Phe Asp Thr Ser Gln
            20                  25                  30

Arg Met Gly Trp Phe Arg Gln Ala Pro Gly Lys Glu Arg Glu Phe Val
        35                  40                  45

Ser Ala Ile Ser Ala Trp Ser Gly Asp Ser Phe Arg Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Thr Gln Arg Leu Asp Ala Asp Ala Phe Gly Trp Tyr Trp
                100                 105                 110

Gly Gln Gly Thr Gln Val Thr Val Ser Ser
            115                 120
```

<210> SEQ ID NO 14
<211> LENGTH: 125
<212> TYPE: PRT
<213> ORGANISM: Artificial Sequence
<220> FEATURE:
<223> OTHER INFORMATION: Synthetic construct

<400> SEQUENCE: 14

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Ala Asp Gly Ile Thr
            20                  25                  30

Gln Met Gly Trp Phe Arg Gln Ala Pro Gly Lys Glu Arg Glu Phe Val
        35                  40                  45

Ser Ala Ile Ser Ser Gly Ser Ala Gly Gln Thr Asp Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Gly Trp Phe Thr Glu Leu Lys Leu Pro Gly Arg Val Phe Arg
                100                 105                 110

Ile Tyr Trp Gly Gln Gly Thr Gln Val Thr Val Ser Ser
            115                 120                 125
```

<210> SEQ ID NO 15
<211> LENGTH: 119
<212> TYPE: PRT
<213> ORGANISM: Artificial Sequence

```
<220> FEATURE:
<223> OTHER INFORMATION: Synthetic construct

<400> SEQUENCE: 15

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Pro Ala Gln Asp Tyr
            20                  25                  30

Arg Met Gly Trp Phe Arg Gln Ala Pro Gly Lys Glu Arg Glu Phe Val
        35                  40                  45

Ser Ala Ile Ser Gly Trp Ser Asp Ala Ser Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ser Ile Arg Asn Phe Ala Pro Gln Trp Tyr Trp Gly Gln Gly
            100                 105                 110

Thr Gln Val Thr Val Ser Ser
        115
```

```
<210> SEQ ID NO 16
<211> LENGTH: 122
<212> TYPE: PRT
<213> ORGANISM: Artificial Sequence
<220> FEATURE:
<223> OTHER INFORMATION: Synthetic construct

<400> SEQUENCE: 16

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Thr Phe Asp Gln Tyr
            20                  25                  30

Ile Met Gly Trp Phe Arg Gln Ala Pro Gly Lys Glu Arg Glu Phe Val
        35                  40                  45

Ser Ala Ile Ser Ala Gly Asp Gly Ala Ala Ser Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Leu Phe Ser Asn Gln Arg Val Glu Pro Thr Asp Ser Tyr Trp
            100                 105                 110

Gly Gln Gly Thr Gln Val Thr Val Ser Ser
        115                 120
```

```
<210> SEQ ID NO 17
<211> LENGTH: 122
<212> TYPE: PRT
<213> ORGANISM: Artificial Sequence
<220> FEATURE:
<223> OTHER INFORMATION: Synthetic construct

<400> SEQUENCE: 17

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Thr Ala Asp Ser Tyr
            20                  25                  30
```

```
Arg Met Gly Trp Phe Arg Gln Ala Pro Gly Lys Glu Arg Glu Phe Val
            35                  40                  45

Ser Ala Ile Ser Ala Gly Ser Gly Asp Phe Lys His Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Asn Arg Asp Asn Lys Trp Pro Phe Leu Tyr Gln Glu Tyr Trp
                100                 105                 110

Gly Gln Gly Thr Gln Val Thr Val Ser Ser
            115                 120
```

<210> SEQ ID NO 18
<211> LENGTH: 119
<212> TYPE: PRT
<213> ORGANISM: Artificial Sequence
<220> FEATURE:
<223> OTHER INFORMATION: Synthetic construct

<400> SEQUENCE: 18

```
Glu Val Gln Leu Gln Ala Ser Gly Gly Gly Phe Val Gln Pro Gly Gly
 1               5                  10                  15

Ser Leu Arg Leu Ser Cys Ala Ala Ser Gly Phe Phe Phe Gly Ser Tyr
                 20                  25                  30

Arg Met Gly Trp Phe Arg Gln Ala Pro Gly Lys Glu Arg Glu Phe Val
            35                  40                  45

Ser Ala Ile Ser Thr Thr Ser Gly Glu Thr Thr Arg Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Ser Phe Leu Trp Asp Arg Glu Leu Trp Tyr Trp Gly Gln Gly
                100                 105                 110

Thr Gln Val Thr Val Ser Ser
            115
```

<210> SEQ ID NO 19
<211> LENGTH: 119
<212> TYPE: PRT
<213> ORGANISM: Artificial Sequence
<220> FEATURE:
<223> OTHER INFORMATION: Synthetic construct

<400> SEQUENCE: 19

```
Glu Val Gln Leu Gln Ala Ser Gly Gly Gly Phe Val Gln Pro Gly Gly
 1               5                  10                  15

Ser Leu Arg Leu Ser Cys Ala Ala Ser Gly Gly Thr Phe Gly Gln Trp
                 20                  25                  30

Arg Met Gly Trp Phe Arg Gln Ala Pro Gly Lys Glu Arg Glu Phe Val
            35                  40                  45

Ser Ala Ile Ser Gly Gly Asp Ala Gly His Thr Arg Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95
```

Cys Ala Arg Arg Asp Leu Ala Gly Ala Gln Tyr Tyr Trp Gly Gln Gly
            100                 105                 110

Thr Gln Val Thr Val Ser Ser
        115

<210> SEQ ID NO 20
<211> LENGTH: 122
<212> TYPE: PRT
<213> ORGANISM: Artificial Sequence
<220> FEATURE:
<223> OTHER INFORMATION: Synthetic construct

<400> SEQUENCE: 20

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Ser Phe Gly Phe Tyr
            20                  25                  30

Arg Met Gly Trp Phe Arg Gln Ala Pro Gly Lys Glu Arg Glu Phe Val
        35                  40                  45

Ser Ala Ile Ser Ser Trp Gly Thr Ser Ala His Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
            85                  90                  95

Cys Ala Thr Tyr Ala Thr Gln Asp Asn Gly Gln Val Asn Val Tyr Trp
            100                 105                 110

Gly Gln Gly Thr Gln Val Thr Val Ser Ser
        115                 120

<210> SEQ ID NO 21
<211> LENGTH: 119
<212> TYPE: PRT
<213> ORGANISM: Artificial Sequence
<220> FEATURE:
<223> OTHER INFORMATION: Synthetic construct

<400> SEQUENCE: 21

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Ile Phe Gly Asp Phe
            20                  25                  30

Gln Met Gly Trp Phe Arg Gln Ala Pro Gly Lys Glu Arg Glu Phe Val
        35                  40                  45

Ser Ala Ile Ser Gly Gly Tyr Gly Gln Ser Thr Gln Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
            85                  90                  95

Cys Ala Arg Ala Ala Trp Asp Gln Val Ile Gly Tyr Trp Gly Gln Gly
            100                 105                 110

Thr Gln Val Thr Val Ser Ser
        115

<210> SEQ ID NO 22
<211> LENGTH: 119
<212> TYPE: PRT

<213> ORGANISM: Artificial Sequence
<220> FEATURE:
<223> OTHER INFORMATION: Synthetic construct

<400> SEQUENCE: 22

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Thr Phe Gly Gln Trp
            20                  25                  30

Arg Met Gly Trp Phe Arg Gln Ala Pro Gly Lys Glu Arg Glu Phe Val
        35                  40                  45

Ser Ala Ile Ser Asp Ala Asp Ala Arg Phe Thr Arg Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Val Leu Phe Pro Phe Thr Thr Ile Arg Tyr Trp Gly Gln Gly
            100                 105                 110

Thr Gln Val Thr Val Ser Ser
        115

<210> SEQ ID NO 23
<211> LENGTH: 125
<212> TYPE: PRT
<213> ORGANISM: Artificial Sequence
<220> FEATURE:
<223> OTHER INFORMATION: Synthetic construct

<400> SEQUENCE: 23

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Thr Phe Asp Ala Phe
            20                  25                  30

Gln Met Gly Trp Phe Arg Gln Ala Pro Gly Lys Glu Arg Glu Phe Val
        35                  40                  45

Ser Ala Ile Ser Gly Gly Thr Gly Glu Ala Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Gly Trp Glu Ser Tyr Phe Ile Ser Arg His Tyr Arg Asp His
            100                 105                 110

Thr Tyr Trp Gly Gln Gly Thr Gln Val Thr Val Ser Ser
        115                 120                 125

<210> SEQ ID NO 24
<211> LENGTH: 122
<212> TYPE: PRT
<213> ORGANISM: Artificial Sequence
<220> FEATURE:
<223> OTHER INFORMATION: Synthetic construct

<400> SEQUENCE: 24

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Phe Asp Glu Ser
            20                  25                  30

```
Arg Met Gly Trp Phe Arg Gln Ala Pro Gly Lys Glu Arg Glu Phe Val
            35                  40                  45

Ser Ala Ile Ser Ala Ala Asp Gly Gly Trp Ser Tyr Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Glu Arg Arg Ile Val Arg Gly Glu Pro Tyr Gly Trp Tyr Trp
                100                 105                 110

Gly Gln Gly Thr Gln Val Thr Val Ser Ser
            115                 120

<210> SEQ ID NO 25
<211> LENGTH: 122
<212> TYPE: PRT
<213> ORGANISM: Artificial Sequence
<220> FEATURE:
<223> OTHER INFORMATION: Synthetic construct

<400> SEQUENCE: 25

Glu Val Gln Leu Gln Ala Ser Gly Gly Gly Phe Val Gln Pro Gly Gly
 1               5                  10                  15

Ser Leu Arg Leu Ser Cys Ala Ala Ser Gly His Thr Phe Gly Arg Tyr
             20                  25                  30

Arg Met Gly Trp Phe Arg Gln Ala Pro Gly Lys Glu Arg Glu Phe Val
            35                  40                  45

Ser Ala Ile Ser Ser Trp Ser Gly Ser Ala Arg Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                 85                  90                  95

Cys Ala Pro Leu Val Gly Pro Glu Asp Gln Trp Asn Phe Asn Tyr Trp
                100                 105                 110

Gly Gln Gly Thr Gln Val Thr Val Ser Ser
            115                 120

<210> SEQ ID NO 26
<211> LENGTH: 119
<212> TYPE: PRT
<213> ORGANISM: Artificial Sequence
<220> FEATURE:
<223> OTHER INFORMATION: Synthetic construct

<400> SEQUENCE: 26

Glu Val Gln Leu Gln Ala Ser Gly Gly Gly Phe Val Gln Pro Gly Gly
 1               5                  10                  15

Ser Leu Arg Leu Ser Cys Ala Ala Ser Gly Gly Thr Phe Gln Gly Leu
             20                  25                  30

Arg Met Gly Trp Phe Arg Gln Ala Pro Gly Lys Glu Arg Glu Phe Val
            35                  40                  45

Ser Ala Ile Ser Ala Ser Ala Ala Thr Phe Val Ala Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
```

```
                85                  90                  95
Cys Ala Pro Ala Ile Ser Gly Tyr Asp His Pro Tyr Trp Gly Gln Gly
            100                 105                 110

Thr Gln Val Thr Val Ser Ser
        115

<210> SEQ ID NO 27
<211> LENGTH: 119
<212> TYPE: PRT
<213> ORGANISM: Artificial Sequence
<220> FEATURE:
<223> OTHER INFORMATION: Synthetic construct

<400> SEQUENCE: 27

Glu Val Gln Leu Gln Ala Ser Gly Gly Gly Phe Val Gln Pro Gly Gly
1               5                   10                  15

Ser Leu Arg Leu Ser Cys Ala Ala Ser Gly Thr Phe Ala Ser Gln Leu
            20                  25                  30

Thr Met Gly Trp Phe Arg Gln Ala Pro Gly Lys Glu Arg Glu Phe Val
        35                  40                  45

Ser Ala Ile Ser Ala Thr Ser Gly Gly Phe Ala Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Arg Tyr Gln Phe Pro Gly His Arg Ser Tyr Trp Gly Gln Gly
            100                 105                 110

Thr Gln Val Thr Val Ser Ser
        115

<210> SEQ ID NO 28
<211> LENGTH: 125
<212> TYPE: PRT
<213> ORGANISM: Artificial Sequence
<220> FEATURE:
<223> OTHER INFORMATION: Synthetic construct

<400> SEQUENCE: 28

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Tyr Phe Gly Thr Tyr
            20                  25                  30

Arg Met Gly Trp Phe Arg Gln Ala Pro Gly Lys Glu Arg Glu Phe Val
        35                  40                  45

Ser Ala Ile Ser Asp Thr Gln Gly Gln Ala Thr Trp Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Arg Glu Tyr Phe Tyr Gly His Lys Asp Arg Glu Val Gln
            100                 105                 110

Tyr Tyr Trp Gly Gln Gly Thr Gln Val Thr Val Ser Ser
        115                 120                 125

<210> SEQ ID NO 29
<211> LENGTH: 119
```

<212> TYPE: PRT
<213> ORGANISM: Artificial Sequence
<220> FEATURE:
<223> OTHER INFORMATION: Synthetic construct

<400> SEQUENCE: 29

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Thr Ala Gly Gln Leu
            20                  25                  30

Arg Met Gly Trp Phe Arg Gln Ala Pro Gly Lys Glu Arg Glu Phe Val
        35                  40                  45

Ser Ala Ile Ser Ala Ser Ala Thr Phe Val Ala Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Gln Ser His Glu Ala Asp Gly His Tyr Trp Gly Gln Gly
            100                 105                 110

Thr Gln Val Thr Val Ser Ser
            115

<210> SEQ ID NO 30
<211> LENGTH: 122
<212> TYPE: PRT
<213> ORGANISM: Artificial Sequence
<220> FEATURE:
<223> OTHER INFORMATION: Synthetic construct

<400> SEQUENCE: 30

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Thr Ala Ser Trp Gln
            20                  25                  30

Trp Met Gly Trp Phe Arg Gln Ala Pro Gly Lys Glu Arg Glu Phe Val
        35                  40                  45

Ser Ala Ile Ser Ala Ala Ala Gly Gly Thr Asp Ser Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Gly Leu Ile His Glu Ser Glu Gly Thr Ser Asn Asp Tyr Trp
            100                 105                 110

Gly Gln Gly Thr Gln Val Thr Val Ser Ser
            115                 120

<210> SEQ ID NO 31
<211> LENGTH: 119
<212> TYPE: PRT
<213> ORGANISM: Artificial Sequence
<220> FEATURE:
<223> OTHER INFORMATION: Synthetic construct

<400> SEQUENCE: 31

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Tyr Asp Ala Trp

```
                    20                  25                  30

His Met Gly Trp Phe Arg Gln Ala Pro Gly Lys Glu Arg Glu Phe Val
            35                  40                  45

Ser Ala Ile Ser Ser Ser Gly Ser Ala Lys Tyr Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                85                  90                  95

Cys Ala Ala Tyr Thr Thr Thr Thr Val Pro His Tyr Trp Gly Gln Gly
                100                 105                 110

Thr Gln Val Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Synthetic construct

<400> SEQUENCE: 32

Glu Val Gln Leu Gln Ala Ser Gly Gly Gly Phe Val Gln Pro Gly Gly
 1               5                  10                  15

Ser Leu Arg Leu Ser Cys Ala Ala Ser Gly Phe Asp Arg Glu Tyr
            20                  25                  30

Ala Met Gly Trp Phe Arg Gln Ala Pro Gly Lys Glu Arg Glu Phe Val
            35                  40                  45

Ser Ala Ile Ser Ser Gln Tyr Gln Gly Pro Thr Ala Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Thr Tyr Tyr
                85                  90                  95

Cys Ala Leu Arg Asn Asn Asp Glu Ile Glu Phe Tyr Trp Gly Gln Gly
                100                 105                 110

Thr Gln Val Thr Val Ser Ser
        115

<210> SEQ ID NO 33
<211> LENGTH: 122
<212> TYPE: PRT
<213> ORGANISM: Artificial Sequence
<220> FEATURE:
<223> OTHER INFORMATION: Synthetic construct

<400> SEQUENCE: 33

Glu Val Gln Leu Gln Ala Ser Gly Gly Gly Phe Val Gln Pro Gly Gly
 1               5                  10                  15

Ser Leu Arg Leu Ser Cys Ala Ala Ser Gly Gly Pro Phe Gly Thr Tyr
            20                  25                  30

Arg Met Gly Trp Phe Arg Gln Ala Pro Gly Lys Glu Arg Glu Phe Val
            35                  40                  45

Ser Ala Ile Ser His Trp Ser Gly Glu Ser Val Lys Tyr Ala Asp Ser
 50                  55                  60

Val Lys Gly Arg Phe Thr Ile Ser Arg Asp Asn Ser Lys Asn Thr Val
 65                  70                  75                  80
```

```
Tyr Leu Gln Met Asn Ser Leu Arg Ala Glu Asp Thr Ala Thr Tyr Tyr
                 85                  90                  95

Cys Ala Ile Trp Arg Trp Gly Leu Gln Asp Ser Gln Val Leu Tyr Trp
            100                 105                 110

Gly Gln Gly Thr Gln Val Thr Val Ser Ser
        115                 120
```

<210> SEQ ID NO 34
<211> LENGTH: 119
<212> TYPE: PRT
<213> ORGANISM: Artificial Sequence
<220> FEATURE:
<223> OTHER INFORMATION: Synthetic construct

<400> SEQUENCE: 34

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Pro Phe Thr Gln Ser
            20                  25                  30

Arg Met Gly Trp Phe Arg Gln Ala Pro Gly Lys Glu Arg Glu Phe Val
        35                  40                  45

Ser Ala Ile Ser Ala Trp Gly Gly Ser Ala Lys Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Val Leu Pro Glu Phe Gly Arg His Tyr Trp Gly Gln Gly
            100                 105                 110

Thr Gln Val Thr Val Ser Ser
        115
```

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

```
<210> SEQ ID NO 40
<211> LENGTH: 7
<212> TYPE: PRT
<213> ORGANISM: Artificial Sequence
<220> FEATURE:
<223> OTHER INFORMATION: Synthetic construct

<400> SEQUENCE: 40

Arg Ala Phe Gly Ile Tyr Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic construct

<400> SEQUENCE: 41

Arg Tyr Asp Ser Tyr Val Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic construct

<400> SEQUENCE: 42

Arg Thr Ser Gly Gln Tyr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic construct

<400> SEQUENCE: 43

Thr Ala Tyr Gly Trp Ser Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic construct

<400> SEQUENCE: 44

His Thr Phe Asp Ala Tyr Gln
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic construct

<400> SEQUENCE: 45

Arg Thr Phe Ser Phe Leu Pro
1               5

<210> SEQ ID NO 46
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 46

His Thr Phe Asp Ala His Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic construct

<400> SEQUENCE: 47

Gln Pro Tyr Thr Gln Tyr Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic construct

<400> SEQUENCE: 48

His Ser Phe Gly Gln His Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic construct

<400> SEQUENCE: 49

Arg Thr Ser Gly Gln Tyr Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic construct

<400> SEQUENCE: 50

Arg Ala Phe Gly Ile Tyr Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic construct

<400> SEQUENCE: 51

Ser Ser Phe Gly Ile Arg Arg
1               5

<210> SEQ ID NO 52
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 52

Ser Phe Asp Thr Ser Gln Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic construct

<400> SEQUENCE: 53

Arg Ala Asp Gly Ile Thr Gln
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic construct

<400> SEQUENCE: 54

Gly Pro Ala Gln Asp Tyr Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic construct

<400> SEQUENCE: 55

Ser Thr Phe Asp Gln Tyr Ile
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic construct

<400> SEQUENCE: 56

Gly Thr Ala Asp Ser Tyr Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic construct

<400> SEQUENCE: 57

Phe Phe Phe Gly Ser Tyr Arg
1               5

<210> SEQ ID NO 58
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 58

Gly Thr Phe Gly Gln Trp Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic construct

<400> SEQUENCE: 59

Arg Ser Phe Gly Phe Tyr Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic construct

<400> SEQUENCE: 60

Ser Ile Phe Gly Asp Phe Gln
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic construct

<400> SEQUENCE: 61

Gly Thr Phe Gly Gln Trp Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic construct

<400> SEQUENCE: 62

Gly Thr Phe Asp Ala Phe Gln
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic construct

<400> SEQUENCE: 63

Arg Thr Phe Asp Glu Ser Arg
1               5

<210> SEQ ID NO 64
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 64

His Thr Phe Gly Arg Tyr Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic construct

<400> SEQUENCE: 65

Gly Thr Phe Gln Gly Leu Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic construct

<400> SEQUENCE: 66

Thr Phe Ala Ser Gln Leu Thr
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic construct

<400> SEQUENCE: 67

Arg Tyr Phe Gly Thr Tyr Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic construct

<400> SEQUENCE: 68

Gly Thr Ala Gly Gln Leu Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic construct

<400> SEQUENCE: 69

Gln Thr Ala Ser Trp Gln Trp
1               5

<210> SEQ ID NO 70
<211> LENGTH: 7
<212> TYPE: PRT
<213> ORGANISM: Artificial Sequence
<220> FEATURE:
```

```
<223> OTHER INFORMATION: Synthetic construct

<400> SEQUENCE: 70

Arg Thr Tyr Asp Ala Trp His
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic construct

<400> SEQUENCE: 71

Phe Phe Asp Arg Glu Tyr Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic construct

<400> SEQUENCE: 72

Gly Pro Phe Gly Thr Tyr Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic construct

<400> SEQUENCE: 73

Arg Pro Phe Thr Gln Ser Arg
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic construct

<400> SEQUENCE: 74

Gly Gly Asp Ala Gly His Thr Arg
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic construct

<400> SEQUENCE: 75

Gly Gly Gly Asp Lys Ser Thr Trp
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic construct
```

<400> SEQUENCE: 76

Ala Trp Gly Gly Gly Ser Ala Lys
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic construct

<400> SEQUENCE: 77

Arg Ala Ser Ala Gly Tyr Ala Gln
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic construct

<400> SEQUENCE: 78

Ala Gly Asp Gly Ala Ala Ser Tyr
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic construct

<400> SEQUENCE: 79

Asp Trp Ser Gly Gly His Thr Tyr
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic construct

<400> SEQUENCE: 80

Thr Trp Ala Gly Asp Ser Ala Arg
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic construct

<400> SEQUENCE: 81

Thr Trp Ala Gly Asp Ser Ala Arg
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic construct

```
<400> SEQUENCE: 82

Ser Gly Gly Ser Gly His Thr Arg
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic construct

<400> SEQUENCE: 83

Asp Thr Ala Gly Gln Ser Thr Thr
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic construct

<400> SEQUENCE: 84

Ser Ser Ala Gly Gly Tyr Lys Thr
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic construct

<400> SEQUENCE: 85

Thr Thr Ser Gly Glu Thr Thr Arg
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic construct

<400> SEQUENCE: 86

Ala Trp Ser Gly Asp Ser Phe Arg
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic construct

<400> SEQUENCE: 87

Ser Gly Ser Ala Gly Gln Thr Asp
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic construct

<400> SEQUENCE: 88
```

```
Gly Trp Ser Asp Ala Ser Thr Tyr
1               5
```

<210> SEQ ID NO 89
<211> LENGTH: 8
<212> TYPE: PRT
<213> ORGANISM: Artificial Sequence
<220> FEATURE:
<223> OTHER INFORMATION: Synthetic construct

<400> SEQUENCE: 89

```
Ala Gly Asp Gly Ala Ala Ser Tyr
1               5
```

<210> SEQ ID NO 90
<211> LENGTH: 8
<212> TYPE: PRT
<213> ORGANISM: Artificial Sequence
<220> FEATURE:
<223> OTHER INFORMATION: Synthetic construct

<400> SEQUENCE: 90

```
Ala Gly Ser Gly Asp Phe Lys His
1               5
```

<210> SEQ ID NO 91
<211> LENGTH: 8
<212> TYPE: PRT
<213> ORGANISM: Artificial Sequence
<220> FEATURE:
<223> OTHER INFORMATION: Synthetic construct

<400> SEQUENCE: 91

```
Thr Thr Ser Gly Glu Thr Thr Arg
1               5
```

<210> SEQ ID NO 92
<211> LENGTH: 8
<212> TYPE: PRT
<213> ORGANISM: Artificial Sequence
<220> FEATURE:
<223> OTHER INFORMATION: Synthetic construct

<400> SEQUENCE: 92

```
Gly Gly Asp Ala Gly His Thr Arg
1               5
```

<210> SEQ ID NO 93
<211> LENGTH: 8
<212> TYPE: PRT
<213> ORGANISM: Artificial Sequence
<220> FEATURE:
<223> OTHER INFORMATION: Synthetic construct

<400> SEQUENCE: 93

```
Ser Trp Gly Gly Thr Ser Ala His
1               5
```

<210> SEQ ID NO 94
<211> LENGTH: 8
<212> TYPE: PRT
<213> ORGANISM: Artificial Sequence
<220> FEATURE:
<223> OTHER INFORMATION: Synthetic construct

<400> SEQUENCE: 94

```
Gly Gly Tyr Gly Gln Ser Thr Gln
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic construct

<400> SEQUENCE: 95

Asp Ala Asp Ala Arg Phe Thr Arg
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic construct

<400> SEQUENCE: 96

Gly Gly Thr Gly Glu Ala Thr Tyr
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic construct

<400> SEQUENCE: 97

Ala Ala Asp Gly Gly Trp Ser Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic construct

<400> SEQUENCE: 98

Ser Trp Ser Gly Gly Ser Ala Arg
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic construct

<400> SEQUENCE: 99

Ala Ser Ala Ala Thr Phe Val Ala
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic construct

<400> SEQUENCE: 100

Ala Thr Ser Gly Gly Phe Ala Tyr
```

```
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic construct

<400> SEQUENCE: 101

Asp Thr Gln Gly Gln Ala Thr Trp
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic construct

<400> SEQUENCE: 102

Ala Ser Ala Ala Thr Phe Val Ala
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic construct

<400> SEQUENCE: 103

Ala Ala Ala Gly Gly Thr Asp Ser
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic construct

<400> SEQUENCE: 104

Ser Ser Ser Gly Ser Ala Lys Tyr
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic construct

<400> SEQUENCE: 105

Ser Gln Tyr Gln Gly Pro Thr Ala
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic construct

<400> SEQUENCE: 106

His Trp Ser Gly Glu Ser Val Lys
1               5
```

```
<210> SEQ ID NO 107
<211> LENGTH: 8
<212> TYPE: PRT
<213> ORGANISM: Artificial Sequence
<220> FEATURE:
<223> OTHER INFORMATION: Synthetic construct

<400> SEQUENCE: 107

Ala Trp Gly Gly Gly Ser Ala Lys
1               5

<210> SEQ ID NO 108
<211> LENGTH: 12
<212> TYPE: PRT
<213> ORGANISM: Artificial Sequence
<220> FEATURE:
<223> OTHER INFORMATION: Synthetic construct

<400> SEQUENCE: 108

Tyr Trp Asp Tyr Asn Gly Val Val Pro Phe Phe Lys
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic construct

<400> SEQUENCE: 109

Asn Ala Gln Leu Gly Pro Ala Tyr Asp Lys Ile Gly
1               5                   10

<210> SEQ ID NO 110
<211> LENGTH: 15
<212> TYPE: PRT
<213> ORGANISM: Artificial Sequence
<220> FEATURE:
<223> OTHER INFORMATION: Synthetic construct

<400> SEQUENCE: 110

Ala Trp Tyr Phe Glu Gln Ile Phe Arg Ala Asp Val Lys Thr Glu
1               5                   10                  15

<210> SEQ ID NO 111
<211> LENGTH: 12
<212> TYPE: PRT
<213> ORGANISM: Artificial Sequence
<220> FEATURE:
<223> OTHER INFORMATION: Synthetic construct

<400> SEQUENCE: 111

Phe Pro Leu His Asp Gln Gly Glu Pro Tyr Gly Trp
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic construct

<400> SEQUENCE: 112

Lys Phe Ser Lys Trp His Ser Arg Val Gln Ala Glu
1               5                   10
```

<210> SEQ ID NO 113
<211> LENGTH: 15
<212> TYPE: PRT
<213> ORGANISM: Artificial Sequence
<220> FEATURE:
<223> OTHER INFORMATION: Synthetic construct

<400> SEQUENCE: 113

Pro Asn Pro Gln Ala Ala Val Tyr Glu Asn Glu Trp Pro Ile Val
1               5                   10                  15

<210> SEQ ID NO 114
<211> LENGTH: 9
<212> TYPE: PRT
<213> ORGANISM: Artificial Sequence
<220> FEATURE:
<223> OTHER INFORMATION: Synthetic construct

<400> SEQUENCE: 114

Ser Phe Leu Trp Asp Arg Glu Gln Trp
1               5

<210> SEQ ID NO 115
<211> LENGTH: 12
<212> TYPE: PRT
<213> ORGANISM: Artificial Sequence
<220> FEATURE:
<223> OTHER INFORMATION: Synthetic construct

<400> SEQUENCE: 115

Asp Phe Arg Ser Ala Ser Glu Asp Ile Ala Arg Trp
1               5                   10

<210> SEQ ID NO 116
<211> LENGTH: 15
<212> TYPE: PRT
<213> ORGANISM: Artificial Sequence
<220> FEATURE:
<223> OTHER INFORMATION: Synthetic construct

<400> SEQUENCE: 116

Pro Leu Tyr Trp Val His Gln Val Ser Asn Glu Val Trp Arg Gln
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic construct

<400> SEQUENCE: 117

Leu Arg Gly Val Gly Trp Pro Asp Ser Asn Leu Glu Leu Gln Trp
1               5                   10                  15

<210> SEQ ID NO 118
<211> LENGTH: 9
<212> TYPE: PRT
<213> ORGANISM: Artificial Sequence
<220> FEATURE:
<223> OTHER INFORMATION: Synthetic construct

<400> SEQUENCE: 118

Phe Arg Gly Thr Ile Asp Gly Asn Tyr
1               5

```
<210> SEQ ID NO 119
<211> LENGTH: 9
<212> TYPE: PRT
<213> ORGANISM: Artificial Sequence
<220> FEATURE:
<223> OTHER INFORMATION: Synthetic construct

<400> SEQUENCE: 119

Gln Arg Phe Val Thr Gly Thr His Trp
1               5

<210> SEQ ID NO 120
<211> LENGTH: 12
<212> TYPE: PRT
<213> ORGANISM: Artificial Sequence
<220> FEATURE:
<223> OTHER INFORMATION: Synthetic construct

<400> SEQUENCE: 120

Ala Thr Gln Arg Leu Asp Ala Asp Ala Phe Gly Trp
1               5                   10

<210> SEQ ID NO 121
<211> LENGTH: 15
<212> TYPE: PRT
<213> ORGANISM: Artificial Sequence
<220> FEATURE:
<223> OTHER INFORMATION: Synthetic construct

<400> SEQUENCE: 121

Gly Trp Phe Thr Glu Leu Lys Leu Pro Gly Arg Val Phe Arg Ile
1               5                   10                  15

<210> SEQ ID NO 122
<211> LENGTH: 9
<212> TYPE: PRT
<213> ORGANISM: Artificial Sequence
<220> FEATURE:
<223> OTHER INFORMATION: Synthetic construct

<400> SEQUENCE: 122

Ser Ile Arg Asn Phe Ala Pro Gln Trp
1               5

<210> SEQ ID NO 123
<211> LENGTH: 12
<212> TYPE: PRT
<213> ORGANISM: Artificial Sequence
<220> FEATURE:
<223> OTHER INFORMATION: Synthetic construct

<400> SEQUENCE: 123

Leu Phe Ser Asn Gln Arg Val Glu Pro Thr Asp Ser
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic construct

<400> SEQUENCE: 124

Asn Arg Asp Asn Lys Trp Pro Phe Leu Tyr Gln Glu
1               5                   10

<210> SEQ ID NO 125
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 125

Ser Phe Leu Trp Asp Arg Glu Leu Trp
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic construct

<400> SEQUENCE: 126

Arg Arg Asp Leu Ala Gly Ala Gln Tyr
1               5

<210> SEQ ID NO 127
<211> LENGTH: 12
<212> TYPE: PRT
<213> ORGANISM: Artificial Sequence
<220> FEATURE:
<223> OTHER INFORMATION: Synthetic construct

<400> SEQUENCE: 127

Thr Tyr Ala Thr Gln Asp Asn Gly Gln Val Asn Val
1               5                   10

<210> SEQ ID NO 128
<211> LENGTH: 9
<212> TYPE: PRT
<213> ORGANISM: Artificial Sequence
<220> FEATURE:
<223> OTHER INFORMATION: Synthetic construct

<400> SEQUENCE: 128

Arg Ala Ala Trp Asp Gln Val Ile Gly
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic construct

<400> SEQUENCE: 129

Val Leu Phe Pro Phe Thr Thr Ile Arg
1               5

<210> SEQ ID NO 130
<211> LENGTH: 15
<212> TYPE: PRT
<213> ORGANISM: Artificial Sequence
<220> FEATURE:
<223> OTHER INFORMATION: Synthetic construct

<400> SEQUENCE: 130

Gly Trp Glu Ser Tyr Phe Ile Ser Arg His Tyr Arg Asp His Thr
1               5                   10                  15

<210> SEQ ID NO 131
<211> LENGTH: 12
```

```
<212> TYPE: PRT
<213> ORGANISM: Artificial Sequence
<220> FEATURE:
<223> OTHER INFORMATION: Synthetic construct

<400> SEQUENCE: 131

Glu Arg Arg Ile Val Arg Gly Glu Pro Tyr Gly Trp
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic construct

<400> SEQUENCE: 132

Pro Leu Val Gly Pro Glu Asp Gln Trp Asn Phe Asn
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Synthetic construct

<400> SEQUENCE: 133

Pro Ala Ile Ser Gly Tyr Asp His Pro
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic construct

<400> SEQUENCE: 134

Arg Tyr Gln Phe Pro Gly His Arg Ser
1               5

<210> SEQ ID NO 135
<211> LENGTH: 15
<212> TYPE: PRT
<213> ORGANISM: Artificial Sequence
<220> FEATURE:
<223> OTHER INFORMATION: Synthetic construct

<400> SEQUENCE: 135

Ala Arg Glu Tyr Phe Tyr Gly His Lys Asp Arg Glu Val Gln Tyr
1               5                   10                  15

<210> SEQ ID NO 136
<211> LENGTH: 9
<212> TYPE: PRT
<213> ORGANISM: Artificial Sequence
<220> FEATURE:
<223> OTHER INFORMATION: Synthetic construct

<400> SEQUENCE: 136

Ala Gln Ser His Glu Ala Asp Gly His
1               5

<210> SEQ ID NO 137
<211> LENGTH: 12
<212> TYPE: PRT
```

```
<213> ORGANISM: Artificial Sequence
<220> FEATURE:
<223> OTHER INFORMATION: Synthetic construct

<400> SEQUENCE: 137

Gly Leu Ile His Glu Ser Glu Gly Thr Ser Asn Asp
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Synthetic construct

<400> SEQUENCE: 138

Ala Tyr Thr Thr Thr Thr Val Pro His
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic construct

<400> SEQUENCE: 139

Leu Arg Asn Asn Asp Glu Ile Glu Phe
1               5

<210> SEQ ID NO 140
<211> LENGTH: 12
<212> TYPE: PRT
<213> ORGANISM: Artificial Sequence
<220> FEATURE:
<223> OTHER INFORMATION: Synthetic construct

<400> SEQUENCE: 140

Ile Trp Arg Trp Gly Leu Gln Asp Ser Gln Val Leu
1               5                   10

<210> SEQ ID NO 141
<211> LENGTH: 9
<212> TYPE: PRT
<213> ORGANISM: Artificial Sequence
<220> FEATURE:
<223> OTHER INFORMATION: Synthetic construct

<400> SEQUENCE: 141

Ala Val Leu Pro Glu Phe Gly Arg His
1               5

<210> SEQ ID NO 142

<400> SEQUENCE: 142

000

<210> SEQ ID NO 143

<400> SEQUENCE: 143

000

<210> SEQ ID NO 144

<400> SEQUENCE: 144
```

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 150

Xaa Thr Xaa Gly Xaa Tyr Arg
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

```
<400> SEQUENCE: 151

Xaa Thr Phe Gly Xaa Tyr Arg
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 152

Xaa Thr Ser Gly Xaa Tyr Arg
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 153

Xaa Ala Phe Gly Xaa Tyr Arg
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 154

Xaa Phe Phe Gly Xaa Tyr Arg
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
```

```
<220> FEATURE:
<221> NAME/KEY: misc_feature
<222> LOCATION: (5)..(5)
<223> OTHER INFORMATION: Xaa can be any naturally occurring amino acid

<400> SEQUENCE: 155

Xaa Xaa Tyr Gly Xaa Tyr Arg
1               5

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 160

Ser Xaa Ser Gly Xaa Ser Thr Arg
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 161

Xaa Gly Xaa Xaa Gly His Thr Arg
1               5
```

```
<210> SEQ ID NO 162
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 162

Xaa Ala Xaa Ala Gly Tyr Ala Gln
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 163

Gly Xaa Xaa Asp Xaa Ser Thr Xaa
1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 164

Xaa Trp Xaa Gly Xaa Ser Ala Xaa
1               5

<210> SEQ ID NO 165
<211> LENGTH: 8
```

```
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 165

Xaa Trp Xaa Gly Xaa Ser Xaa Xaa
1               5

<210> SEQ ID NO 166
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 166

Thr Xaa Xaa Gly Xaa Xaa Xaa Arg
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 167

Thr Xaa Xaa Gly Xaa Xaa Xaa Xaa
1               5

<210> SEQ ID NO 168

<400> SEQUENCE: 168

000

<210> SEQ ID NO 169

<400> SEQUENCE: 169
```

000

<210> SEQ ID NO 170
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 170

Xaa Trp Xaa Xaa Glu Xaa Xaa Phe Xaa Xaa Xaa Xaa Val Xaa Xaa Glu
1               5                   10                  15

<210> SEQ ID NO 171
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (7)..(8)
<223> OTHER INFORMATION: Xaa can be any naturally occurring amino acid

<400> SEQUENCE: 171

Asn Ala Gln Leu Gly Pro Xaa Xaa Asp Lys Ile Gly
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 172

```
Xaa Trp Asp Xaa Xaa Gly Xaa Xaa Xaa Xaa Phe Xaa
1               5                   10
```

<210> SEQ ID NO 173
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 173

```
Tyr Trp Xaa Xaa Asn Gly Xaa Xaa Pro Phe Xaa Xaa
1               5                   10
```

<210> SEQ ID NO 174
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid

<400> SEQUENCE: 174

```
Phe Pro Xaa Xaa Asp Xaa Xaa Xaa Xaa Xaa Xaa Trp
1               5                   10
```

<210> SEQ ID NO 175
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid

<400> SEQUENCE: 175

```
Phe Pro Leu Xaa Asp Xaa Xaa Xaa Xaa Xaa Gly Trp
1               5                   10
```

<210> SEQ ID NO 176

<400> SEQUENCE: 176

000

<210> SEQ ID NO 177

```
<400> SEQUENCE: 177

000

<210> SEQ ID NO 178

<400> SEQUENCE: 178

000

<210> SEQ ID NO 179

<400> SEQUENCE: 179

000

<210> SEQ ID NO 180
<211> LENGTH: 104
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Can be any amino acid or amino acids (e.g., any
      CDR1 described herein)
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(50)
<223> OTHER INFORMATION: Xaa can be any naturally occurring amino acid
<220> FEATURE:
<221> NAME/KEY: MISC_FEATURE
<222> LOCATION: (51)..(51)
<223> OTHER INFORMATION: Can be any amino acid or amino acids (e.g., any
      CDR2 described herein)
<220> FEATURE:
<221> NAME/KEY: misc_feature
<222> LOCATION: (52)..(65)
<223> OTHER INFORMATION: Xaa can be any naturally occurring amino acid
<220> FEATURE:
<221> NAME/KEY: misc_feature
<222> LOCATION: (67)..(82)
```

```
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: MISC_FEATURE
<222> LOCATION: (92)..(92)
<223> OTHER INFORMATION: Can be any amino acid or amino acids (e.g., any
      CDR3 described herein)
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(101)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 180

Xaa Val Gln Leu Xaa Xaa Ser Gly Xaa Xaa Xaa Xaa Xaa Xaa Xaa Xaa
1               5                   10                  15

Xaa Leu Xaa Leu Xaa Cys Xaa Xaa Ser Gly Xaa Xaa Xaa Xaa Xaa Xaa
            20                  25                  30

Xaa Trp Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Asp Xaa Xaa Xaa Xaa Xaa Xaa Xaa Xaa Xaa Xaa Xaa Xaa Xaa Xaa
65                  70                  75                  80

Xaa Xaa Asp Xaa Xaa Xaa Tyr Xaa Cys Xaa Xaa Xaa Xaa Xaa Gly Xaa
                85                  90                  95

Gly Thr Xaa Xaa Xaa Val Ser Xaa
            100

<210> SEQ ID NO 181
<211> LENGTH: 100
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
```

```
<222> LOCATION: (15)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(39)
<223> OTHER INFORMATION: Xaa can be any naturally occurring amino acid
<220> FEATURE:
<221> NAME/KEY: misc_feature
<222> LOCATION: (41)..(46)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
<221> NAME/KEY: misc_feature
<222> LOCATION: (48)..(78)
<223> OTHER INFORMATION: Xaa can be any naturally occurring amino acid
<220> FEATURE:
<221> NAME/KEY: misc_feature
<222> LOCATION: (80)..(82)
<223> OTHER INFORMATION: Xaa can be any naturally occurring amino acid
<220> FEATURE:
<221> NAME/KEY: misc_feature
<222> LOCATION: (84)..(87)
<223> OTHER INFORMATION: Xaa can be any naturally occurring amino acid
<220> FEATURE:
<221> NAME/KEY: MISC_FEATURE
<222> LOCATION: (88)..(88)
<223> OTHER INFORMATION: Can be any amino acid or amino acids (e.g., any
      CDR3 described herein)
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (92)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 181

Xaa Xaa Xaa Leu Xaa Xaa Xaa Gly Xaa Xaa Xaa Xaa Xaa Pro Xaa Xaa
1               5                   10                  15

Xaa Xaa Xaa Xaa Xaa Cys Xaa Xaa Xaa Xaa Xaa Xaa Trp Xaa Xaa
            20                  25                  30

Xaa Xaa Xaa Xaa Xaa Xaa Xaa Glu Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Asp Xaa
65                  70                  75                  80

Xaa Xaa Tyr Xaa Xaa Xaa Xaa Xaa Xaa Trp Gly Xaa Xaa Xaa Xaa Xaa
                85                  90                  95

Xaa Val Ser Xaa
```

```
                    100

<210> SEQ ID NO 182
<211> LENGTH: 100
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(46)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(55)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(69)
<223> OTHER INFORMATION: Xaa can be any naturally occurring amino acid
```

```
<220> FEATURE:
<221> NAME/KEY: misc_feature
<222> LOCATION: (71)..(78)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: MISC_FEATURE
<222> LOCATION: (88)..(88)
<223> OTHER INFORMATION: Can be any amino acid or amino acids (e.g., any
      CDR3 described herein)
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 182

Xaa Val Xaa Leu Xaa Xaa Ser Gly Gly Gly Xaa Xaa Xaa Xaa Gly Xaa
1               5                   10                  15

Ser Leu Xaa Leu Ser Cys Ala Ala Ser Gly Xaa Xaa Xaa Trp Xaa Arg
            20                  25                  30

Xaa Xaa Pro Xaa Xaa Xaa Xaa Xaa Xaa Xaa Xaa Xaa Xaa Xaa Xaa Xaa
        35                  40                  45

Tyr Xaa Xaa Xaa Xaa Xaa Xaa Arg Phe Xaa Xaa Ser Xaa Asp Xaa Xaa
50                  55                  60

Xaa Xaa Xaa Xaa Xaa Leu Xaa Xaa Xaa Xaa Xaa Xaa Xaa Xaa Asp Thr
65                  70                  75                  80

Xaa Xaa Tyr Xaa Cys Ala Xaa Xaa Xaa Gly Xaa Gly Thr Xaa Val
                85                  90                  95

Thr Val Ser Xaa
            100

<210> SEQ ID NO 183
<211> LENGTH: 98
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
```

-continued

```
<221> NAME/KEY: MISC_FEATURE
<222> LOCATION: (86)..(86)
<223> OTHER INFORMATION: Can be any amino acid or amino acids (e.g., any
      CDR3 described herein)

<400> SEQUENCE: 183

Glu Val Gln Leu Gln Ala Ser Gly Gly Gly Phe Val Gln Pro Gly Gly
1               5                   10                  15

Ser Leu Arg Leu Ser Cys Ala Ala Ser Gly Xaa Met Gly Trp Phe Arg
            20                  25                  30

Gln Ala Pro Gly Lys Glu Arg Glu Phe Val Ser Ala Ile Ser Xaa Tyr
        35                  40                  45

Ala Asp Ser Val Lys Gly Arg Phe Thr Ile Ser Arg Asp Asn Ser Lys
    50                  55                  60

Asn Thr Val Tyr Leu Gln Met Asn Ser Leu Arg Ala Glu Asp Thr Ala
65                  70                  75                  80

Thr Tyr Tyr Cys Ala Xaa Tyr Trp Gly Gln Gly Thr Gln Val Thr Val
                85                  90                  95

Ser Ser

<210> SEQ ID NO 184
<211> LENGTH: 98
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
<221> NAME/KEY: MISC_FEATURE
<222> LOCATION: (86)..(86)
<223> OTHER INFORMATION: Can be any amino acid or amino acids (e.g., any
      CDR3 described herein)

<400> SEQUENCE: 184

Glu Val Gln Leu Gln Ala Ser Gly Gly Gly Phe Val Gln Pro Gly Gly
1               5                   10                  15

Ser Leu Arg Leu Ser Cys Ala Ala Ser Gly Xaa Met Gly Trp Phe Arg
            20                  25                  30

Gln Ala Pro Gly Lys Glu Arg Glu Phe Val Ser Ala Ile Ser Xaa Tyr
        35                  40                  45

Ala Asp Ser Val Lys Gly Arg Phe Thr Ile Ser Arg Asp Asn Ser Lys
    50                  55                  60

Asn Thr Val Tyr Leu Gln Met Asn Ser Leu Arg Ala Glu Asp Thr Ala
65                  70                  75                  80

Thr Tyr Tyr Cys Ala Xaa Tyr Trp Gly Gln Gly Thr Gln Val Thr Val
                85                  90                  95

Ser Ser

<210> SEQ ID NO 185
<211> LENGTH: 99
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
<221> NAME/KEY: MISC_FEATURE
<222> LOCATION: (87)..(87)
<223> OTHER INFORMATION: Can be any amino acid or amino acids (e.g., any
      CDR3 described herein)

<400> SEQUENCE: 185

Glu Val Gln Leu Gln Ala Ser Gly Gly Gly Phe Val Gln Ala Gly Gly
1               5                   10                  15

Ser Leu Arg Leu Ser Cys Ala Ala Ser Gly Xaa Met Gly Trp Phe Arg
            20                  25                  30

Gln Ala Pro Gly Lys Glu Arg Glu Phe Val Ala Ala Ile Ser Xaa Tyr
        35                  40                  45

Tyr Ala Asp Ser Val Lys Gly Arg Phe Thr Ile Ser Arg Asp Asn Ala
    50                  55                  60

Lys Asn Thr Val Tyr Leu Gln Met Asn Ser Leu Lys Pro Glu Asp Thr
65                  70                  75                  80

Ala Thr Tyr Tyr Cys Ala Xaa Tyr Trp Gly Gln Gly Thr Gln Val Thr
                85                  90                  95

Val Ser Ser

<210> SEQ ID NO 186
<211> LENGTH: 99
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
<221> NAME/KEY: MISC_FEATURE
<222> LOCATION: (87)..(87)
<223> OTHER INFORMATION: Can be any amino acid or amino acids (e.g., any
      CDR3 described herein)

<400> SEQUENCE: 186

Glu Val Gln Leu Gln Ala Ser Gly Gly Gly Phe Val Gln Ala Gly Gly
1               5                   10                  15

Ser Leu Arg Leu Ser Cys Ala Ala Ser Gly Xaa Met Gly Trp Phe Arg
            20                  25                  30

Gln Ala Pro Gly Lys Glu Arg Glu Phe Val Ala Ala Ile Ser Xaa Tyr
        35                  40                  45

Tyr Ala Asp Ser Val Lys Gly Arg Phe Thr Ile Ser Arg Asp Asn Ala
    50                  55                  60

Lys Asn Thr Val Tyr Leu Gln Met Asn Ser Leu Lys Pro Glu Asp Thr
65                  70                  75                  80

Ala Thr Tyr Tyr Cys Ala Xaa Tyr Trp Gly Gln Gly Thr Gln Val Thr
```

-continued

```
                85                  90                  95

Val Ser Ser

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190
<211> LENGTH: 26
<212> TYPE: PRT
<213> ORGANISM: Artificial Sequence
<220> FEATURE:
<223> OTHER INFORMATION: Synthetic construct

<400> SEQUENCE: 190

Glu Val Gln Leu Gln Ala Ser Gly Gly Gly Phe Val Gln Ala Gly Gly
1               5                   10                  15

Ser Leu Arg Leu Ser Cys Ala Ala Ser Gly
            20                  25

<210> SEQ ID NO 191
<211> LENGTH: 26
<212> TYPE: PRT
<213> ORGANISM: Artificial Sequence
<220> FEATURE:
<223> OTHER INFORMATION: Synthetic construct

<400> SEQUENCE: 191

Glu Val Gln Leu Gln Ala Ser Gly Gly Gly Phe Val Gln Pro Gly Gly
1               5                   10                  15

Ser Leu Arg Leu Ser Cys Ala Ala Ser Gly
            20                  25

<210> SEQ ID NO 192
<211> LENGTH: 30
<212> TYPE: PRT
<213> ORGANISM: Artificial Sequence
<220> FEATURE:
<223> OTHER INFORMATION: Synthetic construct

<400> SEQUENCE: 192

Gln Val Gln Leu Val Glu Ser Gly Gly Gly Ser Val Gln Ala Gly Gly
1               5                   10                  15

Ser Leu Arg Leu Ser Cys Thr Ala Ser Gly Gly Ser Glu Tyr
            20                  25                  30

<210> SEQ ID NO 193
<211> LENGTH: 26
<212> TYPE: PRT
<213> ORGANISM: Artificial Sequence
<220> FEATURE:
```

<223> OTHER INFORMATION: Synthetic construct

<400> SEQUENCE: 193

Gln Val Gln Leu Val Glu Ser Gly Gly Gly Ser Val Gln Ala Gly Gly
1               5                   10                  15

Ser Leu Arg Leu Ser Cys Thr Ala Ser Gly
            20                  25

<210> SEQ ID NO 194
<211> LENGTH: 30
<212> TYPE: PRT
<213> ORGANISM: Artificial Sequence
<220> FEATURE:
<223> OTHER INFORMATION: Synthetic construct

<400> SEQUENCE: 194

Gln Val Gln Leu Val Glu Ser Gly Gly Gly Ser Val Gln Ala Gly Gly
1               5                   10                  15

Ser Leu Arg Leu Ser Cys Thr Ala Ser Gly Phe Ser Arg Glu
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Synthetic construct

<400> SEQUENCE: 195

Gln Val Gln Leu Gln Glu Ser Gly Pro Ser Leu Val Arg Pro Ser Gln
1               5                   10                  15

Thr Leu Ser Leu Thr Cys Thr Ile Ser Gly Phe Ser Arg Glu
            20                  25                  30

<210> SEQ ID NO 196
<211> LENGTH: 26
<212> TYPE: PRT
<213> ORGANISM: Artificial Sequence
<220> FEATURE:
<223> OTHER INFORMATION: Synthetic construct

<400> SEQUENCE: 196

Gln Val Gln Leu Gln Glu Ser Gly Pro Ser Leu Val Arg Pro Ser Gln
1               5                   10                  15

Thr Leu Ser Leu Thr Cys Thr Ile Ser Gly
            20                  25

<210> SEQ ID NO 197
<211> LENGTH: 30
<212> TYPE: PRT
<213> ORGANISM: Artificial Sequence
<220> FEATURE:
<223> OTHER INFORMATION: Synthetic construct

<400> SEQUENCE: 197

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 198
<211> LENGTH: 26
<212> TYPE: PRT
<213> ORGANISM: Artificial Sequence -continued

```
<220> FEATURE:
<223> OTHER INFORMATION: Synthetic construct

<400> SEQUENCE: 198

Gln Val Gln Leu Val Glu Ser Gly Gly Asn Leu Val Gln Pro Gly Gly
1               5                   10                  15

Ser Leu Arg Leu Ser Cys Ala Ala Ser Gly
            20                  25

<210> SEQ ID NO 199
<211> LENGTH: 30
<212> TYPE: PRT
<213> ORGANISM: Artificial Sequence
<220> FEATURE:
<223> OTHER INFORMATION: Synthetic construct

<400> SEQUENCE: 199

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn
            20                  25                  30

<210> SEQ ID NO 200
<211> LENGTH: 30
<212> TYPE: PRT
<213> ORGANISM: Artificial Sequence
<220> FEATURE:
<223> OTHER INFORMATION: Synthetic construct

<400> SEQUENCE: 200

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 201
<211> LENGTH: 30
<212> TYPE: PRT
<213> ORGANISM: Artificial Sequence
<220> FEATURE:
<223> OTHER INFORMATION: Synthetic construct

<400> SEQUENCE: 201

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 202
<211> LENGTH: 26
<212> TYPE: PRT
<213> ORGANISM: Artificial Sequence
<220> FEATURE:
<223> OTHER INFORMATION: Synthetic construct

<400> SEQUENCE: 202

Gln Val Gln Leu Val Glu Ser Gly Gly Ala Leu Val Gln Pro Gly Gly
1               5                   10                  15

Ser Leu Arg Leu Ser Cys Ala Ala Ser Gly
            20                  25

<210> SEQ ID NO 203
<211> LENGTH: 26
<212> TYPE: PRT
```

-continued

```
<213> ORGANISM: Artificial Sequence
<220> FEATURE:
<223> OTHER INFORMATION: Synthetic construct

<400> SEQUENCE: 203

Gln Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 204
<211> LENGTH: 26
<212> TYPE: PRT
<213> ORGANISM: Artificial Sequence
<220> FEATURE:
<223> OTHER INFORMATION: Synthetic construct

<400> SEQUENCE: 204

Gln Val Gln Leu Val Glu Ser Gly Gly Gly Leu Met Gln Ala Gly Gly
1               5                   10                  15

Ser Leu Arg Leu Ser Cys Ala Val Ser Gly
            20                  25

<210> SEQ ID NO 205
<211> LENGTH: 26
<212> TYPE: PRT
<213> ORGANISM: Artificial Sequence
<220> FEATURE:
<223> OTHER INFORMATION: Synthetic construct

<400> SEQUENCE: 205

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 206
<211> LENGTH: 26
<212> TYPE: PRT
<213> ORGANISM: Artificial Sequence
<220> FEATURE:
<223> OTHER INFORMATION: Synthetic construct

<400> SEQUENCE: 206

His Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 207
<211> LENGTH: 26
<212> TYPE: PRT
<213> ORGANISM: Artificial Sequence
<220> FEATURE:
<223> OTHER INFORMATION: Synthetic construct

<400> SEQUENCE: 207

Asp Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 208
<211> LENGTH: 26
```

```
<212> TYPE: PRT
<213> ORGANISM: Artificial Sequence
<220> FEATURE:
<223> OTHER INFORMATION: Synthetic construct

<400> SEQUENCE: 208

Glu Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 209
<211> LENGTH: 30
<212> TYPE: PRT
<213> ORGANISM: Artificial Sequence
<220> FEATURE:
<223> OTHER INFORMATION: Synthetic construct

<400> SEQUENCE: 209

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp
            20                  25                  30

<210> SEQ ID NO 210
<211> LENGTH: 26
<212> TYPE: PRT
<213> ORGANISM: Artificial Sequence
<220> FEATURE:
<223> OTHER INFORMATION: Synthetic construct

<400> SEQUENCE: 210

Glu Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 211
<211> LENGTH: 30
<212> TYPE: PRT
<213> ORGANISM: Artificial Sequence
<220> FEATURE:
<223> OTHER INFORMATION: Synthetic construct

<400> SEQUENCE: 211

Asp Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr
            20                  25                  30

<210> SEQ ID NO 212
<211> LENGTH: 26
<212> TYPE: PRT
<213> ORGANISM: Artificial Sequence
<220> FEATURE:
<223> OTHER INFORMATION: Synthetic construct

<400> SEQUENCE: 212

Asp Val Gln Leu Gln Ala Ser Gly Gly Gly Leu Val Gln Ala Gly Gly
1               5                   10                  15

Ser Leu Arg Leu Ser Cys Ala Ala Ser Gly
            20                  25

<210> SEQ ID NO 213
```

```
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid

<400> SEQUENCE: 213

Xaa Val Gln Leu Xaa Xaa Ser Gly Xaa Xaa Xaa Xaa Xaa Xaa Xaa
1               5                   10                  15

Xaa Leu Xaa Leu Xaa Cys Xaa Xaa Ser Gly Xaa Xaa Xaa Xaa
            20                  25                  30

<210> SEQ ID NO 214
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid

<400> SEQUENCE: 214

Xaa Xaa Xaa Leu Xaa Xaa Xaa Gly Xaa Xaa Xaa Xaa Xaa Xaa Xaa
1               5                   10                  15

Xaa Xaa Xaa Xaa Xaa Cys Xaa Xaa Xaa Xaa
            20                  25

<210> SEQ ID NO 215
<211> LENGTH: 26
<212> TYPE: PRT
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 215

Xaa Val Gln Leu Xaa Xaa Ser Gly Xaa Xaa Xaa Xaa Xaa Xaa Xaa
1               5                   10                  15

Xaa Leu Xaa Leu Xaa Cys Xaa Xaa Ser Gly
            20                  25

<210> SEQ ID NO 216
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid

<400> SEQUENCE: 216

Gln Val Gln Leu Val Glu Ser Gly Gly Gly Leu Val Gln Xaa Gly Gly
1               5                   10                  15

Ser Leu Arg Leu Ser Cys Ala Ala Ser Gly Xaa Xaa Xaa Xaa
            20                  25                  30

<210> SEQ ID NO 217
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(14)
<223> OTHER INFORMATION: Xaa can be any naturally occurring amino acid

<400> SEQUENCE: 217

Gln Val Gln Leu Val Glu Ser Gly Gly Gly Leu Val Gln Xaa Gly Gly
1               5                   10                  15

Ser Leu Arg Leu Ser Cys Ala Ala Ser Gly
            20                  25
```

```
<210> SEQ ID NO 218

<400> SEQUENCE: 218

000

<210> SEQ ID NO 219

<400> SEQUENCE: 219

000

<210> SEQ ID NO 220
<211> LENGTH: 19
<212> TYPE: PRT
<213> ORGANISM: Artificial Sequence
<220> FEATURE:
<223> OTHER INFORMATION: Synthetic construct

<400> SEQUENCE: 220

Met Gly Trp Phe Arg Gln Ala Pro Gly Lys Glu Arg Glu Phe Val Ala
1               5                   10                  15

Ala Ile Ser

<210> SEQ ID NO 221
<211> LENGTH: 19
<212> TYPE: PRT
<213> ORGANISM: Artificial Sequence
<220> FEATURE:
<223> OTHER INFORMATION: Synthetic construct

<400> SEQUENCE: 221

Met Gly Trp Phe Arg Gln Ala Pro Gly Lys Glu Arg Glu Phe Val Ser
1               5                   10                  15

Ala Ile Ser

<210> SEQ ID NO 222
<211> LENGTH: 14
<212> TYPE: PRT
<213> ORGANISM: Artificial Sequence
<220> FEATURE:
<223> OTHER INFORMATION: Synthetic construct

<400> SEQUENCE: 222

Trp Phe Arg Gln Ala Pro Gly Gln Glu Arg Glu Ala Val Ala
1               5                   10

<210> SEQ ID NO 223
<211> LENGTH: 17
<212> TYPE: PRT
<213> ORGANISM: Artificial Sequence
<220> FEATURE:
<223> OTHER INFORMATION: Synthetic construct

<400> SEQUENCE: 223

Trp Phe Arg Gln Ala Pro Gly Gln Glu Arg Glu Ala Val Ala Ala Ile
1               5                   10                  15

Ala

<210> SEQ ID NO 224
<211> LENGTH: 14
<212> TYPE: PRT
<213> ORGANISM: Artificial Sequence
<220> FEATURE:
<223> OTHER INFORMATION: Synthetic construct
```

```
<400> SEQUENCE: 224

Trp Val Arg Gln Ala Pro Gly Lys Ala Leu Glu Trp Leu Gly
1               5                   10

<210> SEQ ID NO 225
<211> LENGTH: 16
<212> TYPE: PRT
<213> ORGANISM: Artificial Sequence
<220> FEATURE:
<223> OTHER INFORMATION: Synthetic construct

<400> SEQUENCE: 225

Trp Val Arg Gln Ala Pro Gly Lys Ala Leu Glu Trp Leu Gly Arg Ile
1               5                   10                  15

<210> SEQ ID NO 226
<211> LENGTH: 14
<212> TYPE: PRT
<213> ORGANISM: Artificial Sequence
<220> FEATURE:
<223> OTHER INFORMATION: Synthetic construct

<400> SEQUENCE: 226

Trp Phe Arg Gln Ala Pro Gly Gln Glu Arg Glu Trp Leu Gly
1               5                   10

<210> SEQ ID NO 227
<211> LENGTH: 16
<212> TYPE: PRT
<213> ORGANISM: Artificial Sequence
<220> FEATURE:
<223> OTHER INFORMATION: Synthetic construct

<400> SEQUENCE: 227

Trp Phe Arg Gln Ala Pro Gly Gln Glu Arg Glu Trp Leu Gly Arg Ile
1               5                   10                  15

<210> SEQ ID NO 228
<211> LENGTH: 14
<212> TYPE: PRT
<213> ORGANISM: Artificial Sequence
<220> FEATURE:
<223> OTHER INFORMATION: Synthetic construct

<400> SEQUENCE: 228

Trp Val Arg Gln Ala Pro Gly Gly Gly Leu Glu Trp Val Ala
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Synthetic construct

<400> SEQUENCE: 229

Trp Tyr Arg Gln Ala Thr Gly Lys Glu Arg Glu Trp Val Ala
1               5                   10

<210> SEQ ID NO 230
<211> LENGTH: 16
<212> TYPE: PRT
<213> ORGANISM: Artificial Sequence
<220> FEATURE:
<223> OTHER INFORMATION: Synthetic construct
```

<400> SEQUENCE: 230

Met Ser Trp Tyr Arg Gln Ala Thr Gly Lys Glu Arg Glu Trp Val Ala
1               5                   10                  15

<210> SEQ ID NO 231
<211> LENGTH: 19
<212> TYPE: PRT
<213> ORGANISM: Artificial Sequence
<220> FEATURE:
<223> OTHER INFORMATION: Synthetic construct

<400> SEQUENCE: 231

Met Gly Trp Phe Arg Gln Ala Pro Gly Lys Glu Arg Glu Phe Val Ala
1               5                   10                  15

Ala Ile Arg

<210> SEQ ID NO 232
<211> LENGTH: 18
<212> TYPE: PRT
<213> ORGANISM: Artificial Sequence
<220> FEATURE:
<223> OTHER INFORMATION: Synthetic construct

<400> SEQUENCE: 232

Met Gly Trp Phe Arg Gln Ala Pro Gly Lys Glu Arg Glu Phe Val Ala
1               5                   10                  15

Ala Ile

<210> SEQ ID NO 233
<211> LENGTH: 16
<212> TYPE: PRT
<213> ORGANISM: Artificial Sequence
<220> FEATURE:
<223> OTHER INFORMATION: Synthetic construct

<400> SEQUENCE: 233

Met Gly Trp Phe Arg Gln Ala Pro Gly Lys Glu Arg Glu Phe Val Ala
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Synthetic construct

<400> SEQUENCE: 234

Met Gly Trp Tyr Arg Gln Ala Pro Gly Lys Glu Arg Glu Leu Val Ala
1               5                   10                  15

<210> SEQ ID NO 235
<211> LENGTH: 17
<212> TYPE: PRT
<213> ORGANISM: Artificial Sequence
<220> FEATURE:
<223> OTHER INFORMATION: Synthetic construct

<400> SEQUENCE: 235

Met Gly Trp Tyr Arg Gln Ala Pro Gly Lys Glu Arg Glu Leu Val Ala
1               5                   10                  15

Ala

<210> SEQ ID NO 236
<211> LENGTH: 19

```
<212> TYPE: PRT
<213> ORGANISM: Artificial Sequence
<220> FEATURE:
<223> OTHER INFORMATION: Synthetic construct

<400> SEQUENCE: 236

Met Gly Trp Tyr Arg Gln Ala Pro Gly Lys Glu Arg Glu Leu Val Ala
1               5                   10                  15

Ala Ile Asp

<210> SEQ ID NO 237
<211> LENGTH: 19
<212> TYPE: PRT
<213> ORGANISM: Artificial Sequence
<220> FEATURE:
<223> OTHER INFORMATION: Synthetic construct

<400> SEQUENCE: 237

Met Gly Trp Tyr Arg Gln Ala Pro Gly Lys Glu Arg Glu Leu Val Ala
1               5                   10                  15

Val Ile Ser

<210> SEQ ID NO 238
<211> LENGTH: 16
<212> TYPE: PRT
<213> ORGANISM: Artificial Sequence
<220> FEATURE:
<223> OTHER INFORMATION: Synthetic construct

<400> SEQUENCE: 238

Met Gly Trp Phe Arg Gln Ala Pro Gly Lys Glu Arg Glu Gly Val Ala
1               5                   10                  15

<210> SEQ ID NO 239
<211> LENGTH: 14
<212> TYPE: PRT
<213> ORGANISM: Artificial Sequence
<220> FEATURE:
<223> OTHER INFORMATION: Synthetic construct

<400> SEQUENCE: 239

Trp Phe Arg Gln Ala Pro Gly Lys Glu Arg Glu Gly Val Ala
1               5                   10

<210> SEQ ID NO 240
<211> LENGTH: 16
<212> TYPE: PRT
<213> ORGANISM: Artificial Sequence
<220> FEATURE:
<223> OTHER INFORMATION: Synthetic construct

<400> SEQUENCE: 240

Met Gly Trp Phe Arg Gln Ala Pro Gly Lys Glu Arg Glu Phe Val Ala
1               5                   10                  15

<210> SEQ ID NO 241
<211> LENGTH: 14
<212> TYPE: PRT
<213> ORGANISM: Artificial Sequence
<220> FEATURE:
<223> OTHER INFORMATION: Synthetic construct

<400> SEQUENCE: 241

Trp Phe Arg Gln Ala Pro Gly Lys Glu Arg Glu Phe Val Ala
1               5                   10
```

```
<210> SEQ ID NO 242
<211> LENGTH: 14
<212> TYPE: PRT
<213> ORGANISM: Artificial Sequence
<220> FEATURE:
<223> OTHER INFORMATION: Synthetic construct

<400> SEQUENCE: 242

Trp Val Arg Gln Ala Pro Gly Lys Gly Pro Glu Trp Val Ala
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Synthetic construct

<400> SEQUENCE: 243

Trp Phe Arg Gln Ala Pro Gly Lys Glu Arg Glu Phe Val Ser
1               5                   10

<210> SEQ ID NO 244
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(19)
<223> OTHER INFORMATION: Xaa can be any naturally occurring amino acid

<400> SEQUENCE: 244

Xaa Xaa Trp Xaa Xaa Xaa Xaa Xaa Xaa Xaa Xaa Xaa Xaa Xaa Xaa Xaa
1               5                   10                  15

Xaa Xaa Xaa

<210> SEQ ID NO 245
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(19)
<223> OTHER INFORMATION: Xaa can be any naturally occurring amino acid

<400> SEQUENCE: 245
```

```
Xaa Xaa Trp Xaa Arg Gln Ala Xaa Gly Xaa Xaa Xaa Glu Xaa Xaa Xaa
1               5                   10                  15

Xaa Xaa Xaa

<210> SEQ ID NO 246
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid

<400> SEQUENCE: 246

Xaa Xaa Trp Xaa Arg Gln Ala Xaa Gly Xaa Xaa Xaa Glu Xaa Xaa Xaa
1               5                   10                  15

<210> SEQ ID NO 247
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid

<400> SEQUENCE: 247

Met Xaa Trp Phe Arg Gln Ala Pro Gly Lys Glu Arg Glu Trp Val Ala
1               5                   10                  15

Xaa Xaa Xaa

<210> SEQ ID NO 248
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 248

Met Xaa Trp Phe Arg Gln Ala Pro Gly Lys Glu Arg Glu Trp Val Ala
1               5                   10                  15
```

-continued

<210> SEQ ID NO 249

<400> SEQUENCE: 249

000

<210> SEQ ID NO 250
<211> LENGTH: 38
<212> TYPE: PRT
<213> ORGANISM: Artificial Sequence
<220> FEATURE:
<223> OTHER INFORMATION: Synthetic construct

<400> SEQUENCE: 250

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Thr Tyr Tyr Cys Ala
        35

<210> SEQ ID NO 251
<211> LENGTH: 39
<212> TYPE: PRT
<213> ORGANISM: Artificial Sequence
<220> FEATURE:
<223> OTHER INFORMATION: Synthetic construct

<400> SEQUENCE: 251

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Thr Tyr Tyr Cys Ala
        35

<210> SEQ ID NO 252
<211> LENGTH: 38
<212> TYPE: PRT
<213> ORGANISM: Artificial Sequence
<220> FEATURE:
<223> OTHER INFORMATION: Synthetic construct

<400> SEQUENCE: 252

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Ala Glu Asp Thr
            20                  25                  30

Ala Thr Tyr Tyr Cys Ala
        35

<210> SEQ ID NO 253
<211> LENGTH: 39
<212> TYPE: PRT
<213> ORGANISM: Artificial Sequence
<220> FEATURE:
<223> OTHER INFORMATION: Synthetic construct

<400> SEQUENCE: 253

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

```
Thr Ala Thr Tyr Tyr Cys Ala
        35
```

<210> SEQ ID NO 254
<211> LENGTH: 31
<212> TYPE: PRT
<213> ORGANISM: Artificial Sequence
<220> FEATURE:
<223> OTHER INFORMATION: Synthetic construct

<400> SEQUENCE: 254

```
Arg Phe Thr Ile Ser Arg Asp Asn Ala Lys Asn Thr Val Thr Leu Gln
1               5                   10                  15

Met Asn Asn Leu Lys Pro Glu Asp Thr Ala Ile Tyr Tyr Cys Ala
            20                  25                  30
```

<210> SEQ ID NO 255
<211> LENGTH: 32
<212> TYPE: PRT
<213> ORGANISM: Artificial Sequence
<220> FEATURE:
<223> OTHER INFORMATION: Synthetic construct

<400> SEQUENCE: 255

```
Arg Phe Thr Ile Ser Arg Asp Asn Ala Lys Asn Thr Val Thr Leu Gln
1               5                   10                  15

Met Asn Asn Leu Lys Pro Glu Asp Thr Ala Ile Tyr Tyr Cys Ala Ala
            20                  25                  30
```

<210> SEQ ID NO 256
<211> LENGTH: 31
<212> TYPE: PRT
<213> ORGANISM: Artificial Sequence
<220> FEATURE:
<223> OTHER INFORMATION: Synthetic construct

<400> SEQUENCE: 256

```
Arg Leu Thr Ile Thr Arg Asp Ile Ser Lys Ser Gln Val Ser Leu Ser
1               5                   10                  15

Leu Ser Ser Val Thr Leu Glu Asp Thr Ala Glu Tyr Tyr Cys Val
            20                  25                  30
```

<210> SEQ ID NO 257
<211> LENGTH: 32
<212> TYPE: PRT
<213> ORGANISM: Artificial Sequence
<220> FEATURE:
<223> OTHER INFORMATION: Synthetic construct

<400> SEQUENCE: 257

```
Arg Leu Thr Ile Thr Arg Asp Ile Ser Lys Ser Gln Val Ser Leu Ser
1               5                   10                  15

Leu Ser Ser Val Thr Leu Glu Asp Thr Ala Glu Tyr Tyr Cys Val Tyr
            20                  25                  30
```

<210> SEQ ID NO 258
<211> LENGTH: 31
<212> TYPE: PRT
<213> ORGANISM: Artificial Sequence
<220> FEATURE:
<223> OTHER INFORMATION: Synthetic construct

<400> SEQUENCE: 258

```
Arg Phe Thr Ile Ser Arg Asp Ile Ala Lys Asn Thr Val Thr Leu Gln
1               5                   10                  15
```

Met Asn Asn Leu Lys Pro Glu Asp Thr Ala Ile Tyr Tyr Val Tyr
            20                  25                  30

<210> SEQ ID NO 259
<211> LENGTH: 32
<212> TYPE: PRT
<213> ORGANISM: Artificial Sequence
<220> FEATURE:
<223> OTHER INFORMATION: Synthetic construct

<400> SEQUENCE: 259

Arg Phe Thr Ile Ser Arg Asp Ile Ala Lys Asn Thr Val Thr Leu Gln
1               5                   10                  15

Met Asn Asn Leu Lys Pro Glu Asp Thr Ala Ile Tyr Tyr Val Tyr Ala
            20                  25                  30

<210> SEQ ID NO 260
<211> LENGTH: 39
<212> TYPE: PRT
<213> ORGANISM: Artificial Sequence
<220> FEATURE:
<223> OTHER INFORMATION: Synthetic construct

<400> SEQUENCE: 260

Tyr Tyr Ala Asp Ser Val Lys Gly Arg Phe Thr Ile Ser Arg Asp Asn
1               5                   10                  15

Ala Lys Asn Thr Val Thr Leu Gln Met Asn Asn Leu Lys Pro Glu Asp
            20                  25                  30

Thr Ala Ile Tyr Tyr Cys Ala
        35

<210> SEQ ID NO 261
<211> LENGTH: 40
<212> TYPE: PRT
<213> ORGANISM: Artificial Sequence
<220> FEATURE:
<223> OTHER INFORMATION: Synthetic construct

<400> SEQUENCE: 261

Tyr Tyr Ala Asp Ser Val Lys Gly Arg Phe Thr Ile Ser Arg Asp Asn
1               5                   10                  15

Ala Lys Asn Thr Val Thr Leu Gln Met Asn Asn Leu Lys Pro Glu Asp
            20                  25                  30

Thr Ala Ile Tyr Tyr Cys Ala Ala
        35                  40

<210> SEQ ID NO 262
<211> LENGTH: 39
<212> TYPE: PRT
<213> ORGANISM: Artificial Sequence
<220> FEATURE:
<223> OTHER INFORMATION: Synthetic construct

<400> SEQUENCE: 262

Tyr Glu Asp Ser Val Lys Gly Arg Phe Cys Ile Ser Arg Asp Asp Ala
1               5                   10                  15

Arg Asn Thr Val Tyr Leu Gln Met Asn Ser Leu Lys Pro Glu Asp Thr
            20                  25                  30

Ala Val Tyr Tyr Cys Asn Val
        35

<210> SEQ ID NO 263

```
<211> LENGTH: 38
<212> TYPE: PRT
<213> ORGANISM: Artificial Sequence
<220> FEATURE:
<223> OTHER INFORMATION: Synthetic construct

<400> SEQUENCE: 263

Tyr Glu Asp Ser Val Lys Gly Arg Phe Cys Ile Ser Arg Asp Asp Ala
1               5                   10                  15

Arg Asn Thr Val Tyr Leu Gln Met Asn Ser Leu Lys Pro Glu Asp Thr
            20                  25                  30

Ala Val Tyr Tyr Cys Asn
        35

<210> SEQ ID NO 264
<211> LENGTH: 39
<212> TYPE: PRT
<213> ORGANISM: Artificial Sequence
<220> FEATURE:
<223> OTHER INFORMATION: Synthetic construct

<400> SEQUENCE: 264

Tyr Ala Asp Ser Val Lys Gly Arg Phe Thr Ile Ser Arg Asp Asn Ala
1               5                   10                  15

Lys Asn Ser Val Tyr Leu Gln Met Asn Ser Leu Arg Val Glu Asp Thr
            20                  25                  30

Ala Val Tyr Tyr Cys Ala Arg
        35

<210> SEQ ID NO 265
<211> LENGTH: 38
<212> TYPE: PRT
<213> ORGANISM: Artificial Sequence
<220> FEATURE:
<223> OTHER INFORMATION: Synthetic construct

<400> SEQUENCE: 265

Tyr Ala Asp Ser Val Lys Gly Arg Phe Thr Ile Ser Arg Asp Asn Ala
1               5                   10                  15

Lys Asn Ser Val Tyr Leu Gln Met Asn Ser Leu Arg Val Glu Asp Thr
            20                  25                  30

Ala Val Tyr Tyr Cys Ala
        35

<210> SEQ ID NO 266
<211> LENGTH: 39
<212> TYPE: PRT
<213> ORGANISM: Artificial Sequence
<220> FEATURE:
<223> OTHER INFORMATION: Synthetic construct

<400> SEQUENCE: 266

Tyr Ala Asp Ser Val Lys Gly Arg Phe Thr Ile Ser Arg Asp Asn Ala
1               5                   10                  15

Arg Asn Thr Val Tyr Leu Gln Met Asn Ser Leu Lys Pro Glu Asp Thr
            20                  25                  30

Ala Val Tyr Tyr Cys Ala Arg
        35

<210> SEQ ID NO 267
<211> LENGTH: 38
<212> TYPE: PRT
<213> ORGANISM: Artificial Sequence
```

```
<220> FEATURE:
<223> OTHER INFORMATION: Synthetic construct

<400> SEQUENCE: 267

Tyr Ala Asp Ser Val Lys Gly Arg Phe Thr Ile Ser Arg Asp Asn Ala
1               5                   10                  15

Arg Asn Thr Val Tyr Leu Gln Met Asn Ser Leu Lys Pro Glu Asp Thr
            20                  25                  30

Ala Val Tyr Tyr Cys Ala
        35

<210> SEQ ID NO 268
<211> LENGTH: 39
<212> TYPE: PRT
<213> ORGANISM: Artificial Sequence
<220> FEATURE:
<223> OTHER INFORMATION: Synthetic construct

<400> SEQUENCE: 268

Tyr Ala Asp Ser Val Lys Gly Arg Phe Thr Ile Ser Arg Asp Asn Ala
1               5                   10                  15

Arg Asn Thr Val Tyr Leu Gln Met Asn Ser Leu Lys Pro Glu Asp Thr
            20                  25                  30

Ala Val Tyr Tyr Cys Ala Arg
        35

<210> SEQ ID NO 269
<211> LENGTH: 32
<212> TYPE: PRT
<213> ORGANISM: Artificial Sequence
<220> FEATURE:
<223> OTHER INFORMATION: Synthetic construct

<400> SEQUENCE: 269

Arg Phe Thr Ile Ser Arg Asp Asn Ala Arg Asn Thr Val Tyr Leu Gln
1               5                   10                  15

Met Asn Ser Leu Lys Pro Glu Asp Thr Ala Val Tyr Tyr Cys Ala Arg
            20                  25                  30

<210> SEQ ID NO 270
<211> LENGTH: 39
<212> TYPE: PRT
<213> ORGANISM: Artificial Sequence
<220> FEATURE:
<223> OTHER INFORMATION: Synthetic construct

<400> SEQUENCE: 270

Tyr Ala Asp Ser Val Lys Gly Arg Phe Thr Ile Ser Arg Asp Lys Gly
1               5                   10                  15

Lys Asn Thr Val Tyr Leu Gln Met Asp Ser Leu Lys Pro Glu Asp Thr
            20                  25                  30

Ala Thr Tyr Tyr Cys Ala Ala
        35

<210> SEQ ID NO 271
<211> LENGTH: 32
<212> TYPE: PRT
<213> ORGANISM: Artificial Sequence
<220> FEATURE:
<223> OTHER INFORMATION: Synthetic construct

<400> SEQUENCE: 271

Arg Phe Thr Ile Ser Arg Asp Lys Gly Lys Asn Thr Val Tyr Leu Gln
```

```
                1               5                  10                 15
Met Asp Ser Leu Lys Pro Glu Asp Thr Ala Thr Tyr Tyr Cys Ala Ala
                20                 25                 30
```

<210> SEQ ID NO 272
<211> LENGTH: 38
<212> TYPE: PRT
<213> ORGANISM: Artificial Sequence
<220> FEATURE:
<223> OTHER INFORMATION: Synthetic construct

<400> SEQUENCE: 272

```
Tyr Ala Asp Ser Val Lys Gly Arg Phe Thr Ile Ser Arg Asp Lys Gly
1               5                   10                  15
Lys Asn Thr Val Tyr Leu Gln Met Asp Ser Leu Lys Pro Glu Asp Thr
                20                  25                  30
Ala Thr Tyr Tyr Cys Ala
                35
```

<210> SEQ ID NO 273
<211> LENGTH: 31
<212> TYPE: PRT
<213> ORGANISM: Artificial Sequence
<220> FEATURE:
<223> OTHER INFORMATION: Synthetic construct

<400> SEQUENCE: 273

```
Arg Phe Thr Ile Ser Arg Asp Lys Gly Lys Asn Thr Val Tyr Leu Gln
1               5                   10                  15
Met Asp Ser Leu Lys Pro Glu Asp Thr Ala Thr Tyr Tyr Cys Ala
                20                  25                  30
```

<210> SEQ ID NO 274
<211> LENGTH: 39
<212> TYPE: PRT
<213> ORGANISM: Artificial Sequence
<220> FEATURE:
<223> OTHER INFORMATION: Synthetic construct

<400> SEQUENCE: 274

```
Tyr Tyr Ala Asp Ser Val Lys Gly Arg Phe Thr Ile Ser Arg Asp Lys
1               5                   10                  15
Ala Lys Asn Thr Val Tyr Leu Gln Met Asn Ser Leu Lys Tyr Glu Asp
                20                  25                  30
Thr Ala Val Tyr Tyr Cys Ala
                35
```

<210> SEQ ID NO 275
<211> LENGTH: 38
<212> TYPE: PRT
<213> ORGANISM: Artificial Sequence
<220> FEATURE:
<223> OTHER INFORMATION: Synthetic construct

<400> SEQUENCE: 275

```
Tyr Ala Asp Ser Val Lys Gly Arg Phe Thr Ile Ser Arg Asp Lys Ala
1               5                   10                  15
Lys Asn Thr Val Tyr Leu Gln Met Asn Ser Leu Lys Tyr Glu Asp Thr
                20                  25                  30
Ala Val Tyr Tyr Cys Ala
                35
```

```
<210> SEQ ID NO 276
<211> LENGTH: 39
<212> TYPE: PRT
<213> ORGANISM: Artificial Sequence
<220> FEATURE:
<223> OTHER INFORMATION: Synthetic construct

<400> SEQUENCE: 276

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala
        35

<210> SEQ ID NO 277
<211> LENGTH: 39
<212> TYPE: PRT
<213> ORGANISM: Artificial Sequence
<220> FEATURE:
<223> OTHER INFORMATION: Synthetic construct

<400> SEQUENCE: 277

Leu His Asn Pro Ala Leu Lys Ser Arg Leu Thr Ile Thr Arg Asp Ile
1               5                   10                  15

Ser Lys Ser Gln Val Ser Leu Ser Leu Ser Ser Val Thr Leu Glu Asp
            20                  25                  30

Thr Ala Glu Tyr Tyr Cys Val
        35

<210> SEQ ID NO 278
<211> LENGTH: 40
<212> TYPE: PRT
<213> ORGANISM: Artificial Sequence
<220> FEATURE:
<223> OTHER INFORMATION: Synthetic construct

<400> SEQUENCE: 278

Leu His Asn Pro Ala Leu Lys Ser Arg Leu Thr Ile Thr Arg Asp Ile
1               5                   10                  15

Ser Lys Ser Gln Val Ser Leu Ser Leu Ser Ser Val Thr Leu Glu Asp
            20                  25                  30

Thr Ala Glu Tyr Tyr Cys Val Tyr
        35                  40

<210> SEQ ID NO 279
<211> LENGTH: 40
<212> TYPE: PRT
<213> ORGANISM: Artificial Sequence
<220> FEATURE:
<223> OTHER INFORMATION: Synthetic construct

<400> SEQUENCE: 279

Leu His Asn Pro Ala Leu Lys Ser Arg Phe Thr Ile Ser Arg Asp Ile
1               5                   10                  15

Ala Lys Asn Thr Val Thr Leu Gln Met Asn Asn Leu Lys Pro Glu Asp
            20                  25                  30

Thr Ala Ile Tyr Tyr Val Tyr Ala
        35                  40

<210> SEQ ID NO 280
<211> LENGTH: 39
<212> TYPE: PRT
```

```
<213> ORGANISM: Artificial Sequence
<220> FEATURE:
<223> OTHER INFORMATION: Synthetic construct

<400> SEQUENCE: 280

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 281
<211> LENGTH: 38
<212> TYPE: PRT
<213> ORGANISM: Artificial Sequence
<220> FEATURE:
<223> OTHER INFORMATION: Synthetic construct

<400> SEQUENCE: 281

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala
        35

<210> SEQ ID NO 282
<211> LENGTH: 40
<212> TYPE: PRT
<213> ORGANISM: Artificial Sequence
<220> FEATURE:
<223> OTHER INFORMATION: Synthetic construct

<400> SEQUENCE: 282

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala Ala
        35                  40

<210> SEQ ID NO 283
<211> LENGTH: 32
<212> TYPE: PRT
<213> ORGANISM: Artificial Sequence
<220> FEATURE:
<223> OTHER INFORMATION: Synthetic construct

<400> SEQUENCE: 283

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 284
<211> LENGTH: 32
<212> TYPE: PRT
<213> ORGANISM: Artificial Sequence
<220> FEATURE:
<223> OTHER INFORMATION: Synthetic construct

<400> SEQUENCE: 284
```

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Asp Tyr Tyr Cys Ala Ala
            20                  25                  30

<210> SEQ ID NO 285
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(14)
<223> OTHER INFORMATION: Xaa can be any naturally occurring amino acid
<220> FEATURE:
<221> NAME/KEY: misc_feature
<222> LOCATION: (16)..(31)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid

<400> SEQUENCE: 285

Xaa Xaa Xaa Xaa Xaa Xaa Xaa Xaa Xaa Xaa Xaa Xaa Xaa Xaa Asp Xaa
1               5                   10                  15

Xaa Xaa Xaa Xaa Xaa Xaa Xaa Xaa Xaa Xaa Xaa Xaa Xaa Xaa Xaa Asp
            20                  25                  30

Xaa Xaa Xaa Tyr Xaa Cys Xaa Xaa
        35                  40

<210> SEQ ID NO 286
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(30)
<223> OTHER INFORMATION: Xaa can be any naturally occurring amino acid
<220> FEATURE:
<221> NAME/KEY: misc_feature
<222> LOCATION: (35)..(35)
```

```
<223> OTHER INFORMATION: Xaa can be any naturally occurring amino acid
<220> FEATURE:
<221> NAME/KEY: misc_feature
<222> LOCATION: (38)..(40)
<223> OTHER INFORMATION: Xaa can be any naturally occurring amino acid

<400> SEQUENCE: 286

Xaa Xaa Xaa Xaa Xaa Xaa Xaa Xaa Arg Xaa Xaa Ile Xaa Arg Asp Xaa
1               5                   10                  15

Xaa Xaa Xaa Xaa Val Xaa Leu Xaa Xaa Xaa Xaa Xaa Xaa Xaa Glu Asp
            20                  25                  30

Thr Ala Xaa Tyr Tyr Xaa Xaa Xaa
        35                  40

<210> SEQ ID NO 287
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid

<400> SEQUENCE: 287

Xaa Xaa Xaa Xaa Xaa Xaa Xaa Xaa Arg Xaa Xaa Ile Xaa Arg Asp Xaa
1               5                   10                  15

Xaa Xaa Xaa Xaa Val Xaa Leu Xaa Xaa Xaa Xaa Xaa Xaa Xaa Glu Asp
            20                  25                  30

Thr Ala Xaa Tyr Tyr Xaa Xaa
        35

<210> SEQ ID NO 288
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
```

-continued

```
<220> FEATURE:
<221> NAME/KEY: misc_feature
<222> LOCATION: (40)..(40)
<223> OTHER INFORMATION: Xaa can be any naturally occurring amino acid

<400> SEQUENCE: 288

Xaa Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala Xaa
        35                  40

<210> SEQ ID NO 289
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 289

Xaa Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala
        35

<210> SEQ ID NO 290
<211> LENGTH: 12
<212> TYPE: PRT
<213> ORGANISM: Artificial Sequence
<220> FEATURE:
<223> OTHER INFORMATION: Synthetic construct

<400> SEQUENCE: 290

Tyr Trp Gly Gln Gly Thr Gln Val Thr Val Ser Ser
1               5                   10

<210> SEQ ID NO 291
<211> LENGTH: 11
<212> TYPE: PRT
<213> ORGANISM: Artificial Sequence
<220> FEATURE:
<223> OTHER INFORMATION: Synthetic construct

<400> SEQUENCE: 291

Trp Gly Gln Gly Thr Gln Val Thr Val Ser Ser
1               5                   10

<210> SEQ ID NO 292
<211> LENGTH: 12
<212> TYPE: PRT
<213> ORGANISM: Artificial Sequence
<220> FEATURE:
<223> OTHER INFORMATION: Synthetic construct

<400> SEQUENCE: 292

Val Trp Gly Pro Gly Leu Leu Leu Thr Val Ser Ser
1               5                   10
```

<210> SEQ ID NO 293
<211> LENGTH: 11
<212> TYPE: PRT
<213> ORGANISM: Artificial Sequence
<220> FEATURE:
<223> OTHER INFORMATION: Synthetic construct

<400> SEQUENCE: 293

Trp Gly Pro Gly Leu Leu Thr Val Ser Ser
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Synthetic construct

<400> SEQUENCE: 294

Trp Gly Gln Gly Thr Leu Val Thr Val Ser
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Synthetic construct

<400> SEQUENCE: 295

Trp Gly Gln Gly Thr Leu Val Thr Val Ser Ser
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Synthetic construct

<400> SEQUENCE: 296

Trp Gly Gln Gly Thr Gln Val Thr Val Ser
1               5                   10

<210> SEQ ID NO 297
<211> LENGTH: 11
<212> TYPE: PRT
<213> ORGANISM: Artificial Sequence
<220> FEATURE:
<223> OTHER INFORMATION: Synthetic construct

<400> SEQUENCE: 297

Trp Gly Gln Gly Thr Gln Val Thr Val Ser Ser
1               5                   10

<210> SEQ ID NO 298
<211> LENGTH: 12
<212> TYPE: PRT
<213> ORGANISM: Artificial Sequence
<220> FEATURE:
<223> OTHER INFORMATION: Synthetic construct

<400> SEQUENCE: 298

Gln Trp Gly Gln Gly Thr Gln Val Thr Val Ser Ser
1               5                   10

<210> SEQ ID NO 299

```
<211> LENGTH: 11
<212> TYPE: PRT
<213> ORGANISM: Artificial Sequence
<220> FEATURE:
<223> OTHER INFORMATION: Synthetic construct

<400> SEQUENCE: 299

Tyr Trp Gly Gln Gly Thr Gln Val Thr Val Ser
1               5                   10

<210> SEQ ID NO 300
<211> LENGTH: 11
<212> TYPE: PRT
<213> ORGANISM: Artificial Sequence
<220> FEATURE:
<223> OTHER INFORMATION: Synthetic construct

<400> SEQUENCE: 300

Trp Gly Gln Gly Thr Thr Val Val Val Ser Ser
1               5                   10

<210> SEQ ID NO 301
<211> LENGTH: 11
<212> TYPE: PRT
<213> ORGANISM: Artificial Sequence
<220> FEATURE:
<223> OTHER INFORMATION: Synthetic construct

<400> SEQUENCE: 301

Trp Gly Lys Gly Thr Gln Val Thr Val Ser Ser
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 302

Xaa Trp Gly Xaa Gly Xaa Xaa Xaa Thr Val Ser Xaa
1               5                   10

<210> SEQ ID NO 303
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
```

```
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 303

Xaa Trp Gly Xaa Gly Xaa Xaa Xaa Thr Val Ser
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 304

Trp Gly Xaa Gly Xaa Xaa Xaa Thr Val Ser Xaa
1               5                   10

<210> SEQ ID NO 305
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 305

Xaa Xaa Gly Xaa Gly Thr Xaa Xaa Xaa Val Ser Xaa
1               5                   10

<210> SEQ ID NO 306
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 306
```

```
Xaa Trp Gly Gln Gly Thr Gln Val Thr Val Ser Ser
1               5                   10
```

```
<210> SEQ ID NO 307
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 307

Xaa Trp Gly Gln Gly Thr Gln Val Thr Val Ser
1               5                   10
```

```
<210> SEQ ID NO 308

<400> SEQUENCE: 308

000
```

```
<210> SEQ ID NO 309

<400> SEQUENCE: 309

000
```

```
<210> SEQ ID NO 310
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: any amino acid or can be absent

<400> SEQUENCE: 310

Gly Gly Gly Xaa
1
```

```
<210> SEQ ID NO 311
<211> LENGTH: 4
<212> TYPE: PRT
<213> ORGANISM: Artificial Sequence
<220> FEATURE:
<223> OTHER INFORMATION: Synthetic construct

<400> SEQUENCE: 311

Gly Gly Gly Ser
1
```

```
<210> SEQ ID NO 312
<211> LENGTH: 4
<212> TYPE: PRT
<213> ORGANISM: Artificial Sequence
<220> FEATURE:
<223> OTHER INFORMATION: Synthetic construct

<400> SEQUENCE: 312

Gly Gly Gly Gly
1
```

```
<210> SEQ ID NO 313
<211> LENGTH: 5
<212> TYPE: PRT
<213> ORGANISM: Artificial Sequence
<220> FEATURE:
<223> OTHER INFORMATION: Synthetic construct

<400> SEQUENCE: 313

Gly Gly Gly Gly Ser
1               5

<210> SEQ ID NO 314
<211> LENGTH: 4
<212> TYPE: PRT
<213> ORGANISM: Artificial Sequence
<220> FEATURE:
<223> OTHER INFORMATION: Synthetic construct

<400> SEQUENCE: 314

Gly Gly Ser Gly
1

<210> SEQ ID NO 315
<211> LENGTH: 10
<212> TYPE: PRT
<213> ORGANISM: Artificial Sequence
<220> FEATURE:
<223> OTHER INFORMATION: Synthetic construct

<400> SEQUENCE: 315

Gly Gly Gly Gly Ser Gly Gly Gly Gly Ser
1               5                   10

<210> SEQ ID NO 316
<211> LENGTH: 15
<212> TYPE: PRT
<213> ORGANISM: Artificial Sequence
<220> FEATURE:
<223> OTHER INFORMATION: Synthetic construct

<400> SEQUENCE: 316

Gly Gly Gly Gly Ser Gly Gly Gly Gly Ser Gly Gly Gly Gly Ser
1               5                   10                  15

<210> SEQ ID NO 317
<211> LENGTH: 20
<212> TYPE: PRT
<213> ORGANISM: Artificial Sequence
<220> FEATURE:
<223> OTHER INFORMATION: Synthetic construct

<400> SEQUENCE: 317

Gly Gly Gly Gly Ser Gly Gly Gly Gly Ser Gly Gly Gly Gly Ser Gly
1               5                   10                  15

Gly Gly Gly Ser
            20

<210> SEQ ID NO 318
<211> LENGTH: 8
<212> TYPE: PRT
<213> ORGANISM: Artificial Sequence
<220> FEATURE:
<223> OTHER INFORMATION: Synthetic construct

<400> SEQUENCE: 318

Gly Gly Ser Gly Gly Gly Ser Gly
1               5
```

```
<210> SEQ ID NO 319
<211> LENGTH: 12
<212> TYPE: PRT
<213> ORGANISM: Artificial Sequence
<220> FEATURE:
<223> OTHER INFORMATION: Synthetic construct

<400> SEQUENCE: 319

Gly Gly Ser Gly Gly Gly Ser Gly Gly Gly Ser Gly
1               5                   10

<210> SEQ ID NO 320
<211> LENGTH: 1273
<212> TYPE: PRT
<213> ORGANISM: Artificial Sequence
<220> FEATURE:
<223> OTHER INFORMATION: Synthetic construct

<400> SEQUENCE: 320

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
```

-continued

```
            290                 295                 300
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                    325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
                530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
                610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
                690                 695                 700

Val Ala Tyr Ser Asn Asn Ser Ile Ala Ile Pro Thr Asn Phe Thr Ile
705                 710                 715                 720
```

```
Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125
```

```
Val Ile Gly Ile Val Asn Asn Thr Val Tyr Asp Pro Leu Gln Pro
    1130            1135            1140

Glu Leu Asp Ser Phe Lys Glu Glu Leu Asp Lys Tyr Phe Lys Asn
    1145            1150            1155

His Thr Ser Pro Asp Val Asp Leu Gly Asp Ile Ser Gly Ile Asn
    1160            1165            1170

Ala Ser Val Val Asn Ile Gln Lys Glu Ile Asp Arg Leu Asn Glu
    1175            1180            1185

Val Ala Lys Asn Leu Asn Glu Ser Leu Ile Asp Leu Gln Glu Leu
    1190            1195            1200

Gly Lys Tyr Glu Gln Tyr Ile Lys Trp Pro Trp Tyr Ile Trp Leu
    1205            1210            1215

Gly Phe Ile Ala Gly Leu Ile Ala Ile Val Met Val Thr Ile Met
    1220            1225            1230

Leu Cys Cys Met Thr Ser Cys Cys Ser Cys Leu Lys Gly Cys Cys
    1235            1240            1245

Ser Cys Gly Ser Cys Cys Lys Phe Asp Glu Asp Asp Ser Glu Pro
    1250            1255            1260

Val Leu Lys Gly Val Lys Leu His Tyr Thr
    1265            1270

<210> SEQ ID NO 321
<211> LENGTH: 1269
<212> TYPE: PRT
<213> ORGANISM: Artificial Sequence
<220> FEATURE:
<223> OTHER INFORMATION: Synthetic construct

<400> SEQUENCE: 321

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ser
                20                  25                  30

Thr Arg Gly Val Tyr Tyr Pro Asp Lys Val Phe Arg Ser Ser Val Leu
            35                  40                  45

His Leu Thr Gln Asp Leu Phe Leu Pro Phe Phe Ser Asn Val Thr Trp
        50                  55                  60

Phe His Ala Ile His Val Ser Gly Thr Asn Gly Ile Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
            195                 200                 205
```

```
Pro Ile Asn Leu Val Arg Asp Leu Pro Pro Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Asp Ser Ile Val Arg Phe Pro Asn Ile Thr Asn Leu Cys
                325                 330                 335

Pro Phe Gly Glu Val Phe Asn Ala Thr Thr Phe Ala Ser Val Tyr Ala
                340                 345                 350

Trp Asn Arg Lys Arg Ile Ser Asn Cys Val Ala Asp Tyr Ser Val Leu
            355                 360                 365

Tyr Asn Ser Thr Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Thr Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Lys His Ile Asp Ala Lys Glu Gly Gly Asn
            435                 440                 445

Phe Asn Tyr Leu Tyr Arg Leu Phe Arg Lys Ala Asn Leu Lys Pro Phe
    450                 455                 460

Glu Arg Asp Ile Ser Thr Glu Ile Tyr Gln Ala Gly Ser Lys Pro Cys
465                 470                 475                 480

Asn Gly Gln Thr Gly Leu Asn Cys Tyr Tyr Pro Leu Tyr Arg Tyr Gly
                485                 490                 495

Phe Tyr Pro Thr Asp Gly Val Gly His Gln Pro Tyr Arg Val Val Val
            500                 505                 510

Leu Ser Phe Glu Leu Leu Asn Ala Pro Ala Thr Val Cys Gly Pro Lys
    515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Ala Ser Asn Gln Val
            595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
```

```
            625                 630                 635                 640
        Asn Val Phe Gln Thr Arg Ala Gly Cys Leu Ile Gly Ala Glu His Val
                        645                 650                 655
        Asn Asn Ser Tyr Glu Cys Asp Ile Pro Ile Gly Ala Gly Ile Cys Ala
                        660                 665                 670
        Ser Tyr Gln Thr Gln Thr Asn Ser Arg Ser Val Ala Ser Gln Ser Ile
                        675                 680                 685
        Ile Ala Tyr Thr Met Ser Leu Gly Ala Glu Asn Ser Val Ala Tyr Ser
                        690                 695                 700
        Asn Asn Ser Ile Ala Ile Pro Thr Asn Phe Thr Ile Ser Val Thr Thr
        705                 710                 715                 720
        Glu Ile Leu Pro Val Ser Met Thr Lys Thr Ser Val Asp Cys Thr Met
                        725                 730                 735
        Tyr Ile Cys Gly Asp Ser Thr Glu Cys Ser Asn Leu Leu Leu Gln Tyr
                        740                 745                 750
        Gly Ser Phe Cys Thr Gln Leu Asn Arg Ala Leu Thr Gly Ile Ala Val
                        755                 760                 765
        Glu Gln Asp Lys Asn Thr Gln Glu Val Phe Ala Gln Val Lys Gln Ile
                        770                 775                 780
        Tyr Lys Thr Pro Pro Ile Lys Asp Phe Gly Gly Phe Asn Phe Ser Gln
        785                 790                 795                 800
        Ile Leu Pro Asp Pro Ser Lys Pro Ser Lys Arg Ser Phe Ile Glu Asp
                        805                 810                 815
        Leu Leu Phe Asn Lys Val Thr Leu Ala Asp Ala Gly Phe Ile Lys Gln
                        820                 825                 830
        Tyr Gly Asp Cys Leu Gly Asp Ile Ala Ala Arg Asp Leu Ile Cys Ala
                        835                 840                 845
        Gln Lys Phe Asn Gly Leu Thr Val Leu Pro Pro Leu Leu Thr Asp Glu
                        850                 855                 860
        Met Ile Ala Gln Tyr Thr Ser Ala Leu Leu Ala Gly Thr Ile Thr Ser
        865                 870                 875                 880
        Gly Trp Thr Phe Gly Ala Gly Ala Ala Leu Gln Ile Pro Phe Ala Met
                        885                 890                 895
        Gln Met Ala Tyr Arg Phe Asn Gly Ile Gly Val Thr Gln Asn Val Leu
                        900                 905                 910
        Tyr Glu Asn Gln Lys Leu Ile Ala Asn Gln Phe Asn Ser Ala Ile Gly
                        915                 920                 925
        Lys Ile Gln Asp Ser Leu Ser Ser Thr Ala Ser Ala Leu Gly Lys Leu
                        930                 935                 940
        Gln Asp Val Val Asn Gln Asn Ala Gln Ala Leu Asn Thr Leu Val Lys
        945                 950                 955                 960
        Gln Leu Ser Ser Asn Phe Gly Ala Ile Ser Ser Val Leu Asn Asp Ile
                        965                 970                 975
        Leu Ser Arg Leu Asp Lys Val Glu Ala Glu Val Gln Ile Asp Arg Leu
                        980                 985                 990
        Ile Thr Gly Arg Leu Gln Ser Leu  Gln Thr Tyr Val Thr  Gln Gln Leu
                        995                 1000                1005
        Ile Arg  Ala Ala Glu Ile Arg  Ala Ser Ala Asn Leu  Ala Ala Thr
                        1010                1015                1020
        Lys Met  Ser Glu Cys Val Leu  Gly Gln Ser Lys Arg  Val Asp Phe
                        1025                1030                1035
        Cys Gly  Lys Gly Tyr His Leu  Met Ser Phe Pro Gln  Ser Ala Pro
                        1040                1045                1050
```

```
His Gly Val Val Phe Leu His Val Thr Tyr Val Pro Ala Gln Glu
    1055                1060                1065

Lys Asn Phe Thr Thr Ala Pro Ala Ile Cys His Asp Gly Lys Ala
    1070                1075                1080

His Phe Pro Arg Glu Gly Val Phe Val Ser Asn Gly Thr His Trp
    1085                1090                1095

Phe Val Thr Gln Arg Asn Phe Tyr Glu Pro Gln Ile Ile Thr Thr
    1100                1105                1110

Asp Asn Thr Phe Val Ser Gly Ser Cys Asp Val Ile Gly Ile
    1115                1120                1125

Val Asn Asn Thr Val Tyr Asp Pro Leu Gln Pro Glu Leu Asp Ser
    1130                1135                1140

Phe Lys Glu Glu Leu Asp Lys Tyr Phe Lys Asn His Thr Ser Pro
    1145                1150                1155

Asp Val Asp Leu Gly Asp Ile Ser Gly Ile Asn Ala Ser Val Val
    1160                1165                1170

Asn Ile Gln Lys Glu Ile Asp Arg Leu Asn Glu Val Ala Lys Asn
    1175                1180                1185

Leu Asn Glu Ser Leu Ile Asp Leu Gln Glu Leu Gly Lys Tyr Glu
    1190                1195                1200

Gln Tyr Ile Lys Trp Pro Trp Tyr Ile Trp Leu Gly Phe Ile Ala
    1205                1210                1215

Gly Leu Ile Ala Ile Ile Met Val Thr Ile Met Leu Cys Cys Met
    1220                1225                1230

Thr Ser Cys Cys Ser Cys Leu Lys Gly Cys Cys Ser Cys Gly Ser
    1235                1240                1245

Cys Cys Lys Phe Asp Glu Asp Asp Ser Glu Pro Val Leu Lys Gly
    1250                1255                1260

Val Lys Leu His Tyr Thr
    1265

<210> SEQ ID NO 322
<211> LENGTH: 1255
<212> TYPE: PRT
<213> ORGANISM: Artificial Sequence
<220> FEATURE:
<223> OTHER INFORMATION: Synthetic construct

<400> SEQUENCE: 322

Met Phe Ile Phe Leu Leu Phe Leu Thr Leu Thr Ser Gly Ser Asp Leu
1                5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125
```

```
Asn Phe Glu Leu Cys Asp Asn Pro Phe Phe Ala Val Ser Lys Pro Met
            130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
                195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
                355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
530                 535                 540
```

-continued

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
        690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
        770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
        850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp

```
                965                 970                 975
Arg Leu Ile Thr Gly Arg Leu Gln Ser Leu Gln Thr Tyr Val Thr Gln
                980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
        1010                1015                1020

Phe Cys Gly Lys Gly Tyr His Leu Met Ser Phe Pro Gln Ala Ala
        1025                1030                1035

Pro His Gly Val Val Phe Leu His Val Thr Tyr Val Pro Ser Gln
        1040                1045                1050

Glu Arg Asn Phe Thr Thr Ala Pro Ala Ile Cys His Glu Gly Lys
        1055                1060                1065

Ala Tyr Phe Pro Arg Glu Gly Val Phe Val Phe Asn Gly Thr Ser
        1070                1075                1080

Trp Phe Ile Thr Gln Arg Asn Phe Phe Ser Pro Gln Ile Ile Thr
        1085                1090                1095

Thr Asp Asn Thr Phe Val Ser Gly Asn Cys Asp Val Val Ile Gly
        1100                1105                1110

Ile Ile Asn Asn Thr Val Tyr Asp Pro Leu Gln Pro Glu Leu Asp
        1115                1120                1125

Ser Phe Lys Glu Glu Leu Asp Lys Tyr Phe Lys Asn His Thr Ser
        1130                1135                1140

Pro Asp Val Asp Leu Gly Asp Ile Ser Gly Ile Asn Ala Ser Val
        1145                1150                1155

Val Asn Ile Gln Lys Glu Ile Asp Arg Leu Asn Glu Val Ala Lys
        1160                1165                1170

Asn Leu Asn Glu Ser Leu Ile Asp Leu Gln Glu Leu Gly Lys Tyr
        1175                1180                1185

Glu Gln Tyr Ile Lys Trp Pro Trp Tyr Val Trp Leu Gly Phe Ile
        1190                1195                1200

Ala Gly Leu Ile Ala Ile Val Met Val Thr Ile Leu Leu Cys Cys
        1205                1210                1215

Met Thr Ser Cys Cys Ser Cys Leu Lys Gly Ala Cys Ser Cys Gly
        1220                1225                1230

Ser Cys Cys Lys Phe Asp Glu Asp Asp Ser Glu Pro Val Leu Lys
        1235                1240                1245

Gly Val Lys Leu His Tyr Thr
        1250                1255

<210> SEQ ID NO 323
<211> LENGTH: 1255
<212> TYPE: PRT
<213> ORGANISM: Artificial Sequence
<220> FEATURE:
<223> OTHER INFORMATION: Synthetic construct

<400> SEQUENCE: 323

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
```

```
                50              55              60
Asn Val Thr Gly Phe His Thr Ile Asn His Thr Phe Asp Asn Pro Val
65                      70                  75                  80
Ile Pro Phe Lys Asp Gly Ile Tyr Phe Ala Ala Thr Glu Lys Ser Asn
                    85                  90                  95
Val Val Arg Gly Trp Val Phe Gly Ser Thr Met Asn Asn Lys Ser Gln
                100                 105                 110
Ser Val Ile Ile Ile Asn Asn Ser Thr Asn Val Val Ile Arg Ala Cys
            115                 120                 125
Asn Phe Glu Leu Cys Asp Asn Pro Phe Phe Val Val Ser Lys Pro Met
        130                 135                 140
Gly Thr Arg Thr His Thr Met Ile Phe Asp Asn Ala Phe Asn Cys Thr
145                 150                 155                 160
Phe Glu Tyr Ile Ser Asp Ala Phe Ser Leu Asp Val Ser Glu Lys Ser
                165                 170                 175
Gly Asn Phe Lys His Leu Arg Glu Phe Val Phe Lys Asn Lys Asp Gly
                180                 185                 190
Phe Leu Tyr Val Tyr Lys Gly Tyr Gln Pro Ile Asp Val Val Arg Asp
            195                 200                 205
Leu Pro Ser Gly Phe Asn Thr Leu Lys Pro Ile Phe Lys Leu Pro Leu
210                 215                 220
Gly Ile Asn Ile Thr Asn Phe Arg Ala Ile Leu Thr Ala Phe Ser Pro
225                 230                 235                 240
Ala Gln Asp Thr Trp Gly Thr Ser Ala Ala Tyr Phe Val Gly Tyr
                245                 250                 255
Leu Lys Pro Thr Thr Phe Met Leu Lys Tyr Asp Glu Asn Gly Thr Ile
                260                 265                 270
Thr Asp Ala Val Asp Cys Ser Gln Asn Pro Leu Ala Glu Leu Lys Cys
                275                 280                 285
Ser Val Lys Ser Phe Glu Ile Asp Lys Gly Ile Tyr Gln Thr Ser Asn
            290                 295                 300
Phe Arg Val Val Pro Ser Gly Asp Val Val Arg Phe Pro Asn Ile Thr
305                 310                 315                 320
Asn Leu Cys Pro Phe Gly Glu Val Phe Asn Ala Thr Lys Phe Pro Ser
                325                 330                 335
Val Tyr Ala Trp Glu Arg Lys Arg Ile Ser Asn Cys Val Ala Asp Tyr
                340                 345                 350
Ser Val Leu Tyr Asn Ser Thr Ser Phe Ser Thr Phe Lys Cys Tyr Gly
            355                 360                 365
Val Ser Ala Thr Lys Leu Asn Asp Leu Cys Phe Ser Asn Val Tyr Ala
        370                 375                 380
Asp Ser Phe Val Val Lys Gly Asp Val Arg Gln Ile Ala Pro Gly
385                 390                 395                 400
Gln Thr Gly Val Ile Ala Asp Tyr Asn Tyr Lys Leu Pro Asp Asp Phe
                405                 410                 415
Met Gly Cys Val Leu Ala Trp Asn Thr Arg Asn Ile Asp Ala Thr Ser
                420                 425                 430
Thr Gly Asn Tyr Asn Tyr Lys Tyr Arg Tyr Leu Arg His Gly Lys Leu
            435                 440                 445
Arg Pro Phe Glu Arg Asp Ile Ser Asn Val Pro Phe Ser Pro Asp Gly
        450                 455                 460
Lys Pro Cys Thr Pro Pro Ala Pro Asn Cys Tyr Trp Pro Leu Asn Gly
465                 470                 475                 480
```

-continued

Tyr Gly Phe Tyr Thr Thr Ser Gly Ile Gly Tyr Gln Pro Tyr Arg Val
                    485             490             495

Val Val Leu Ser Phe Glu Leu Leu Asn Ala Pro Ala Thr Val Cys Gly
                500             505             510

Pro Lys Leu Ser Thr Asp Leu Ile Lys Asn Gln Cys Val Asn Phe Asn
                515             520             525

Phe Asn Gly Leu Thr Gly Thr Gly Val Leu Thr Pro Ser Ser Lys Arg
                530             535             540

Phe Gln Pro Phe Gln Gln Phe Gly Arg Asp Val Ser Asp Phe Thr Asp
545             550             555             560

Ser Val Arg Asp Pro Lys Thr Ser Glu Ile Leu Asp Ile Ser Pro Cys
                565             570             575

Ser Phe Gly Gly Val Ser Val Ile Thr Pro Gly Thr Asn Ala Ser Ser
                580             585             590

Glu Val Ala Val Leu Tyr Gln Asp Val Asn Cys Thr Asp Val Ser Thr
                595             600             605

Leu Ile His Ala Glu Gln Leu Thr Pro Ala Trp Arg Ile Tyr Ser Thr
                610             615             620

Gly Asn Asn Val Phe Gln Thr Gln Ala Gly Cys Leu Ile Gly Ala Glu
625             630             635             640

His Val Asp Thr Ser Tyr Glu Cys Asp Ile Pro Ile Gly Ala Gly Ile
                645             650             655

Cys Ala Ser Tyr His Thr Val Ser Ser Leu Arg Ser Thr Ser Gln Lys
                660             665             670

Ser Ile Val Ala Tyr Thr Met Ser Leu Gly Ala Asp Ser Ser Ile Ala
                675             680             685

Tyr Ser Asn Asn Thr Ile Ala Ile Pro Thr Asn Phe Ser Ile Ser Ile
                690             695             700

Thr Thr Glu Val Met Pro Val Ser Met Ala Lys Thr Ser Val Asp Cys
705             710             715             720

Asn Met Tyr Ile Cys Gly Asp Ser Thr Glu Cys Ala Asn Leu Leu Leu
                725             730             735

Gln Tyr Gly Ser Phe Cys Arg Gln Leu Asn Arg Ala Leu Ser Gly Ile
                740             745             750

Ala Ala Glu Gln Asp Arg Asn Thr Arg Glu Val Phe Val Gln Val Lys
                755             760             765

Gln Met Tyr Lys Thr Pro Thr Leu Lys Asp Phe Gly Gly Phe Asn Phe
                770             775             780

Ser Gln Ile Leu Pro Asp Pro Leu Lys Pro Thr Lys Arg Ser Phe Ile
785             790             795             800

Glu Asp Leu Leu Phe Asn Lys Val Thr Leu Ala Asp Ala Gly Phe Met
                805             810             815

Lys Gln Tyr Gly Glu Cys Leu Gly Asp Ile Asn Ala Arg Asp Leu Ile
                820             825             830

Cys Ala Gln Lys Phe Asn Gly Leu Thr Val Leu Pro Pro Leu Leu Thr
                835             840             845

Asp Asp Met Ile Ala Ala Tyr Thr Ala Ala Leu Val Ser Gly Thr Ala
                850             855             860

Thr Ala Gly Trp Thr Phe Gly Ala Gly Ala Ala Leu Gln Ile Pro Phe
865             870             875             880

Ala Met Gln Met Ala Tyr Arg Phe Asn Gly Ile Gly Val Thr Gln Asn
                885             890             895

Val Leu Tyr Glu Asn Gln Lys Gln Ile Ala Asn Gln Phe Asn Lys Ala
              900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Glu Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 324
<211> LENGTH: 1242
<212> TYPE: PRT
<213> ORGANISM: Artificial Sequence
<220> FEATURE:
<223> OTHER INFORMATION: Synthetic construct

<400> SEQUENCE: 324

| | | | | | | | | | | | | | | |
|---|---|---|---|---|---|---|---|---|---|---|---|---|---|---|
|Met|Lys|Ile|Leu|Ile|Phe|Ala|Phe|Leu|Ala|Asn|Leu|Ala|Lys|Ala|Gln|
|1| | | |5| | | | |10| | | | |15| |
|Glu|Gly|Cys|Gly|Ile|Ile|Ser|Arg|Lys|Pro|Gln|Pro|Lys|Met|Ala|Gln|
| | | |20| | | | |25| | | | |30| | |
|Val|Ser|Ser|Ser|Arg|Arg|Gly|Val|Tyr|Tyr|Asn|Asp|Ile|Phe|Arg| |
| | |35| | | | |40| | | | |45| | | |
|Ser|Asp|Val|Leu|His|Leu|Thr|Gln|Asp|Tyr|Phe|Leu|Pro|Phe|Asp|Ser|
| |50| | | | |55| | | | |60| | | | |
|Asn|Leu|Thr|Gln|Tyr|Phe|Ser|Leu|Asn|Val|Asp|Ser|Asp|Arg|Tyr|Thr|
|65| | | | |70| | | | |75| | | | |80|
|Tyr|Phe|Asp|Asn|Pro|Ile|Leu|Asp|Phe|Gly|Asp|Gly|Val|Tyr|Phe|Ala|
| | | | |85| | | | |90| | | | |95| |
|Ala|Thr|Glu|Lys|Ser|Asn|Val|Ile|Arg|Gly|Trp|Ile|Phe|Gly|Ser|Ser|
| | | |100| | | | |105| | | | |110| | |
|Phe|Asp|Asn|Thr|Thr|Gln|Ser|Ala|Val|Ile|Val|Asn|Asn|Ser|Thr|His|
| | |115| | | | |120| | | | |125| | | |
|Ile|Ile|Ile|Arg|Val|Cys|Asn|Phe|Asn|Leu|Cys|Lys|Glu|Pro|Met|Tyr|
|130| | | | |135| | | | |140| | | | | |
|Thr|Val|Ser|Arg|Gly|Thr|Gln|Gln|Asn|Ala|Trp|Val|Tyr|Gln|Ser|Ala|
|145| | | | |150| | | | |155| | | | |160|
|Phe|Asn|Cys|Thr|Tyr|Asp|Arg|Val|Glu|Lys|Ser|Phe|Gln|Leu|Asp|Thr|
| | | | |165| | | | |170| | | | |175| |
|Thr|Pro|Lys|Thr|Gly|Asn|Phe|Lys|Asp|Leu|Arg|Glu|Tyr|Val|Phe|Lys|
| | | |180| | | | |185| | | | |190| | |
|Asn|Arg|Asp|Gly|Phe|Leu|Ser|Val|Tyr|Gln|Thr|Tyr|Thr|Ala|Val|Asn|
| | |195| | | | |200| | | | |205| | | |
|Leu|Pro|Arg|Gly|Leu|Pro|Thr|Gly|Phe|Ser|Val|Leu|Lys|Pro|Ile|Leu|
|210| | | | |215| | | | |220| | | | | |
|Lys|Leu|Pro|Phe|Gly|Ile|Asn|Ile|Thr|Ser|Tyr|Arg|Val|Val|Met|Ala|
|225| | | | |230| | | | |235| | | | |240|
|Met|Phe|Ser|Gln|Thr|Thr|Ser|Asn|Phe|Leu|Pro|Glu|Ser|Ala|Ala|Tyr|
| | | | |245| | | | |250| | | | |255| |
|Tyr|Val|Gly|Asn|Leu|Lys|Tyr|Ser|Thr|Phe|Met|Leu|Arg|Phe|Asn|Glu|
| | | |260| | | | |265| | | | |270| | |
|Asn|Gly|Thr|Ile|Thr|Asp|Ala|Val|Asp|Cys|Ser|Gln|Asn|Pro|Leu|Ala|
| | |275| | | | |280| | | | |285| | | |
|Glu|Leu|Lys|Cys|Thr|Ile|Lys|Asn|Phe|Asn|Val|Asp|Lys|Gly|Ile|Tyr|
|290| | | | |295| | | | |300| | | | | |
|Gln|Thr|Ser|Asn|Phe|Arg|Val|Ser|Pro|Thr|Gln|Glu|Val|Ile|Arg|Phe|
|305| | | | |310| | | | |315| | | | |320|
|Pro|Asn|Ile|Thr|Asn|Arg|Cys|Pro|Phe|Asp|Lys|Val|Phe|Asn|Ala|Thr|
| | | | |325| | | | |330| | | | |335| |
|Arg|Phe|Pro|Asn|Val|Tyr|Ala|Trp|Glu|Arg|Thr|Lys|Ile|Ser|Asp|Cys|
| | | |340| | | | |345| | | | |350| | |
|Val|Ala|Asp|Tyr|Thr|Val|Leu|Tyr|Asn|Ser|Thr|Ser|Phe|Ser|Thr|Phe|
| | |355| | | | |360| | | | |365| | | |
|Lys|Cys|Tyr|Gly|Val|Ser|Pro|Ser|Lys|Leu|Ile|Asp|Leu|Cys|Phe|Thr|
| |370| | | | |375| | | | |380| | | | |
|Ser|Val|Tyr|Ala|Asp|Thr|Phe|Leu|Ile|Arg|Ser|Ser|Glu|Val|Arg|Gln|
|385| | | | |390| | | | |395| | | | |400|
|Val|Ala|Pro|Gly|Glu|Thr|Gly|Val|Ile|Ala|Asp|Tyr|Asn|Tyr|Lys|Leu|

```
                405                 410                 415
Pro Asp Asp Phe Thr Gly Cys Val Ile Ala Trp Asn Thr Ala Lys His
            420                 425                 430

Asp Thr Gly Asn Tyr Tyr Tyr Arg Ser His Arg Lys Thr Lys Leu Lys
            435                 440                 445

Pro Phe Glu Arg Asp Leu Ser Asp Asp Gly Asn Gly Val Tyr Thr
450                 455                 460

Leu Ser Thr Tyr Asp Phe Asn Pro Asn Val Pro Val Ala Tyr Gln Ala
465                 470                 475                 480

Thr Arg Val Val Val Leu Ser Phe Glu Leu Leu Asn Ala Pro Ala Thr
            485                 490                 495

Val Cys Gly Pro Lys Leu Ser Thr Glu Leu Val Lys Asn Gln Cys Val
            500                 505                 510

Asn Phe Asn Phe Asn Gly Leu Lys Gly Thr Gly Val Leu Thr Ser Ser
            515                 520                 525

Ser Lys Arg Phe Gln Ser Phe Gln Gln Phe Gly Arg Asp Thr Ser Asp
530                 535                 540

Phe Thr Asp Ser Val Arg Asp Pro Gln Thr Leu Glu Ile Leu Asp Ile
545                 550                 555                 560

Ser Pro Cys Ser Phe Gly Gly Val Ser Val Ile Thr Pro Gly Thr Asn
                565                 570                 575

Ala Ser Ser Glu Val Ala Val Leu Tyr Gln Asp Val Asn Cys Thr Asp
            580                 585                 590

Val Pro Thr Ala Ile Arg Ala Asp Gln Leu Thr Pro Ala Trp Arg Val
            595                 600                 605

Tyr Ser Thr Gly Val Asn Val Phe Gln Thr Gln Ala Gly Cys Leu Ile
610                 615                 620

Gly Ala Glu His Val Asn Ala Ser Tyr Glu Cys Asp Ile Pro Ile Gly
625                 630                 635                 640

Ala Gly Ile Cys Ala Ser Tyr His Thr Ala Ser Val Leu Arg Ser Thr
                645                 650                 655

Gly Gln Lys Ser Ile Val Ala Tyr Thr Met Ser Leu Gly Ala Glu Asn
            660                 665                 670

Ser Ile Ala Tyr Ala Asn Asn Ser Ile Ala Ile Pro Thr Asn Phe Ser
            675                 680                 685

Ile Ser Val Thr Thr Glu Val Met Pro Val Ser Met Ala Lys Thr Ala
            690                 695                 700

Val Asp Cys Thr Met Tyr Ile Cys Gly Asp Ser Leu Glu Cys Ser Asn
705                 710                 715                 720

Leu Leu Leu Gln Tyr Gly Ser Phe Cys Thr Gln Leu Asn Arg Ala Leu
                725                 730                 735

Thr Gly Ile Ala Ile Glu Gln Asp Lys Asn Thr Gln Glu Val Phe Ala
            740                 745                 750

Gln Val Lys Gln Met Tyr Lys Thr Pro Ala Ile Lys Asp Phe Gly Gly
            755                 760                 765

Phe Asn Phe Ser Gln Ile Leu Pro Asp Pro Ser Lys Pro Thr Lys Arg
770                 775                 780

Ser Phe Ile Glu Asp Leu Leu Phe Asn Lys Val Thr Leu Ala Asp Ala
785                 790                 795                 800

Gly Phe Met Lys Gln Tyr Gly Asp Cys Leu Gly Asp Val Ser Ala Arg
                805                 810                 815

Asp Leu Ile Cys Ala Gln Lys Phe Asn Gly Leu Thr Val Leu Pro Pro
            820                 825                 830
```

```
Leu Leu Thr Asp Glu Met Val Ala Ala Tyr Thr Ala Ala Leu Val Ser
        835                 840                 845

Gly Thr Ala Thr Ala Gly Trp Thr Phe Gly Ala Gly Ala Ala Leu Gln
    850                 855                 860

Ile Pro Phe Ala Met Gln Met Ala Tyr Arg Phe Asn Gly Ile Gly Val
865                 870                 875                 880

Thr Gln Asn Val Leu Tyr Glu Asn Gln Lys Leu Ile Ala Asn Gln Phe
                885                 890                 895

Asn Ser Ala Ile Gly Lys Ile Gln Glu Ser Leu Ser Ser Thr Ala Ser
            900                 905                 910

Ala Leu Gly Lys Leu Gln Asp Val Val Asn Gln Asn Ala Gln Ala Leu
        915                 920                 925

Asn Thr Leu Val Lys Gln Leu Ser Ser Asn Phe Gly Ala Ile Ser Ser
    930                 935                 940

Val Leu Asn Asp Ile Leu Ser Arg Leu Asp Lys Val Glu Ala Glu Val
945                 950                 955                 960

Gln Ile Asp Arg Leu Ile Thr Gly Arg Leu Gln Ser Leu Gln Thr Tyr
                965                 970                 975

Val Thr Gln Gln Leu Ile Arg Ala Ala Glu Ile Arg Ala Ser Ala Asn
            980                 985                 990

Leu Ala Ala Thr Lys Met Ser Glu Cys Val Leu Gly Gln Ser Lys Arg
        995                 1000                1005

Val Asp Phe Cys Gly Lys Gly Tyr His Leu Met Ser Phe Pro Gln
    1010                1015                1020

Ser Ala Pro His Gly Val Val Phe Leu His Val Thr Tyr Val Pro
    1025                1030                1035

Ser Gln Glu Lys Asn Phe Thr Thr Ala Pro Ala Ile Cys His Glu
    1040                1045                1050

Gly Lys Ala Tyr Phe Pro Arg Glu Gly Val Phe Val Ser Asn Gly
    1055                1060                1065

Thr Ser Trp Phe Ile Thr Gln Arg Asn Phe Tyr Ser Pro Gln Leu
    1070                1075                1080

Ile Thr Thr Asp Asn Thr Phe Val Ser Gly Asn Cys Asp Val Val
    1085                1090                1095

Ile Gly Ile Ile Asn Asn Thr Val Tyr Asp Pro Leu Gln Pro Glu
    1100                1105                1110

Leu Asp Ser Phe Lys Glu Glu Leu Asp Lys Tyr Phe Lys Asn His
    1115                1120                1125

Thr Ser Pro Asp Val Asp Leu Gly Asp Ile Ser Gly Ile Asn Ala
    1130                1135                1140

Ser Val Val Asn Ile Gln Lys Glu Ile Asp Arg Leu Asn Glu Val
    1145                1150                1155

Ala Lys Asn Leu Asn Glu Ser Leu Ile Asp Leu Gln Glu Leu Gly
    1160                1165                1170

Lys Tyr Glu Gln Tyr Ile Lys Trp Pro Trp Tyr Val Trp Leu Gly
    1175                1180                1185

Phe Ile Ala Gly Leu Ile Ala Ile Val Met Val Thr Ile Leu Leu
    1190                1195                1200

Cys Cys Met Thr Ser Cys Cys Ser Cys Leu Lys Gly Ala Cys Ser
    1205                1210                1215

Cys Gly Ser Cys Cys Lys Phe Asp Glu Asp Asp Ser Glu Pro Val
    1220                1225                1230
```

-continued

```
Leu Lys Gly Val Lys Leu His Tyr Thr
    1235            1240
```

```
<210> SEQ ID NO 325
<211> LENGTH: 1241
<212> TYPE: PRT
<213> ORGANISM: Artificial Sequence
<220> FEATURE:
<223> OTHER INFORMATION: Synthetic construct

<400> SEQUENCE: 325

Met Lys Ile Leu Ile Leu Ala Phe Leu Ala Ser Leu Ala Lys Ala Gln
1               5                   10                  15

Glu Gly Cys Gly Ile Ile Ser Arg Lys Pro Gln Pro Lys Met Ala Gln
            20                  25                  30

Val Ser Ser Ser Arg Arg Gly Val Tyr Tyr Asn Asp Asp Ile Phe Arg
        35                  40                  45

Ser Asn Val Leu His Leu Thr Gln Asp Tyr Phe Leu Pro Phe Asp Ser
50                  55                  60

Asn Leu Thr Gln Tyr Phe Ser Leu Asn Val Asp Ser Asp Arg Phe Thr
65                  70                  75                  80

Tyr Phe Asp Asn Pro Ile Leu Asp Phe Gly Asp Gly Val Tyr Phe Ala
                85                  90                  95

Ala Thr Glu Lys Ser Asn Val Ile Arg Gly Trp Ile Phe Gly Ser Thr
            100                 105                 110

Phe Asp Asn Thr Thr Gln Ser Ala Val Ile Val Asn Asn Ser Thr His
        115                 120                 125

Ile Ile Ile Arg Val Cys Asn Phe Asn Leu Cys Lys Glu Pro Met Tyr
130                 135                 140

Thr Val Ser Arg Gly Ala Gln Gln Ser Ser Trp Val Tyr Gln Ser Ala
145                 150                 155                 160

Phe Asn Cys Thr Tyr Asp Arg Val Glu Lys Ser Phe Gln Leu Asp Thr
                165                 170                 175

Ala Pro Lys Thr Gly Asn Phe Lys Asp Leu Arg Glu Tyr Val Phe Lys
            180                 185                 190

Asn Arg Asp Gly Phe Leu Ser Val Tyr Gln Thr Tyr Thr Ala Val Asn
        195                 200                 205

Leu Pro Arg Gly Leu Pro Ile Gly Phe Ser Val Leu Arg Pro Ile Leu
210                 215                 220

Lys Leu Pro Phe Gly Ile Asn Ile Thr Ser Tyr Arg Val Val Met Ala
225                 230                 235                 240

Met Phe Ser Gln Thr Thr Ser Asn Phe Leu Pro Glu Ser Ala Ala Tyr
                245                 250                 255

Tyr Val Gly Asn Leu Lys Tyr Thr Thr Phe Met Leu Ser Phe Asn Glu
            260                 265                 270

Asn Gly Thr Ile Thr Asn Ala Ile Asp Cys Ala Gln Asn Pro Leu Ala
        275                 280                 285

Glu Leu Lys Cys Thr Ile Lys Asn Phe Asn Val Ser Lys Gly Ile Tyr
290                 295                 300

Gln Thr Ser Asn Phe Arg Val Ser Pro Thr Gln Glu Val Ile Arg Phe
305                 310                 315                 320

Pro Asn Ile Thr Asn Arg Cys Pro Phe Asp Lys Val Phe Asn Ala Thr
                325                 330                 335

Arg Phe Pro Asn Val Tyr Ala Trp Glu Arg Thr Lys Ile Ser Asp Cys
            340                 345                 350
```

```
Val Ala Asp Tyr Thr Val Leu Tyr Asn Ser Thr Ser Phe Ser Thr Phe
            355                 360                 365

Lys Cys Tyr Gly Val Ser Pro Ser Lys Leu Ile Asp Leu Cys Phe Thr
370                 375                 380

Ser Val Tyr Ala Asp Thr Phe Leu Ile Arg Ser Ser Glu Val Arg Gln
385                 390                 395                 400

Val Ala Pro Gly Glu Thr Gly Val Ile Ala Asp Tyr Asn Tyr Lys Leu
                405                 410                 415

Pro Asp Asp Phe Thr Gly Cys Val Ile Ala Trp Asn Thr Ala Lys Gln
            420                 425                 430

Asp Gln Gly Gln Tyr Tyr Arg Ser His Arg Lys Thr Lys Leu Lys
        435                 440                 445

Pro Phe Glu Arg Asp Leu Ser Ser Asp Glu Asn Gly Val Arg Thr Leu
    450                 455                 460

Ser Thr Tyr Asp Phe Tyr Pro Ser Val Pro Val Ala Tyr Gln Ala Thr
465                 470                 475                 480

Arg Val Val Val Leu Ser Phe Glu Leu Leu Asn Ala Pro Ala Thr Val
                485                 490                 495

Cys Gly Pro Lys Leu Ser Thr Gln Leu Val Lys Asn Gln Cys Val Asn
            500                 505                 510

Phe Asn Phe Asn Gly Leu Lys Gly Thr Gly Val Leu Thr Glu Ser Ser
        515                 520                 525

Lys Arg Phe Gln Ser Phe Gln Gln Phe Gly Arg Asp Thr Ser Asp Phe
    530                 535                 540

Thr Asp Ser Val Arg Asp Pro Gln Thr Leu Glu Ile Leu Asp Ile Ser
545                 550                 555                 560

Pro Cys Ser Phe Gly Gly Val Ser Val Ile Thr Pro Gly Thr Asn Ala
                565                 570                 575

Ser Ser Glu Val Ala Val Leu Tyr Gln Asp Val Asn Cys Thr Asp Val
            580                 585                 590

Pro Ala Ala Ile His Ala Asp Gln Leu Thr Pro Ala Trp Arg Val Tyr
        595                 600                 605

Ser Thr Gly Thr Asn Val Phe Gln Thr Gln Ala Gly Cys Leu Ile Gly
    610                 615                 620

Ala Glu His Val Asn Ala Ser Tyr Glu Cys Asp Ile Pro Ile Gly Ala
625                 630                 635                 640

Gly Ile Cys Ala Ser Tyr His Thr Ala Ser Thr Leu Arg Ser Val Gly
                645                 650                 655

Gln Lys Ser Ile Val Ala Tyr Thr Met Ser Leu Gly Ala Glu Asn Ser
            660                 665                 670

Ile Ala Tyr Ala Asn Asn Ser Ile Ala Ile Pro Thr Asn Phe Ser Ile
        675                 680                 685

Ser Val Thr Thr Glu Val Met Pro Val Ser Met Ala Lys Thr Ser Val
    690                 695                 700

Asp Cys Thr Met Tyr Ile Cys Gly Asp Ser Leu Glu Cys Ser Asn Leu
705                 710                 715                 720

Leu Leu Gln Tyr Gly Ser Phe Cys Thr Gln Leu Asn Arg Ala Leu Ser
                725                 730                 735

Gly Ile Ala Ile Glu Gln Asp Lys Asn Thr Gln Glu Val Phe Ala Gln
            740                 745                 750

Val Lys Gln Met Tyr Lys Thr Pro Ala Ile Lys Asp Phe Gly Gly Phe
        755                 760                 765

Asn Phe Ser Gln Ile Leu Pro Asp Pro Ser Lys Pro Thr Lys Arg Ser
```

```
            770              775               780
    Phe Ile Glu Asp Leu Leu Phe Asn Lys Val Thr Leu Ala Asp Ala Gly
    785              790              795               800

Phe Met Lys Gln Tyr Gly Glu Cys Leu Gly Asp Ile Ser Ala Arg Asp
                     805              810              815

Leu Ile Cys Ala Gln Lys Phe Asn Gly Leu Thr Val Leu Pro Pro Leu
                820              825              830

Leu Thr Asp Glu Met Ile Ala Ala Tyr Thr Ala Ala Leu Val Ser Gly
                835              840              845

Thr Ala Thr Ala Gly Trp Thr Phe Gly Ala Gly Ser Ala Leu Gln Ile
            850              855              860

Pro Phe Ala Met Gln Met Ala Tyr Arg Phe Asn Gly Ile Gly Val Thr
    865              870              875              880

Gln Asn Val Leu Tyr Glu Asn Gln Lys Gln Ile Ala Asn Gln Phe Asn
                     885              890              895

Lys Ala Ile Ser Gln Ile Gln Glu Ser Leu Thr Thr Thr Ser Thr Ala
                900              905              910

Leu Gly Lys Leu Gln Asp Val Val Asn Gln Asn Ala Gln Ala Leu Asn
                915              920              925

Thr Leu Val Lys Gln Leu Ser Ser Asn Phe Gly Ala Ile Ser Ser Val
                930              935              940

Leu Asn Asp Ile Leu Ser Arg Leu Asp Lys Val Glu Ala Glu Val Gln
    945              950              955              960

Ile Asp Arg Leu Ile Thr Gly Arg Leu Gln Ser Leu Gln Thr Tyr Val
                     965              970              975

Thr Gln Gln Leu Ile Arg Ala Ala Glu Ile Arg Ala Ser Ala Asn Leu
                980              985              990

Ala Ala Thr Lys Met Ser Glu Cys Val Leu Gly Gln Ser  Lys Arg Val
                995              1000             1005

Asp Phe  Cys Gly Lys Gly Tyr  His Leu Met Ser Phe  Pro Gln Ala
        1010             1015              1020

Ala Pro  His Gly Val Val Phe  Leu His Val Thr Tyr  Val Pro Ser
        1025             1030              1035

Gln Glu  Arg Asn Phe Thr Thr  Ala Pro Ala Ile Cys  His Glu Gly
        1040             1045              1050

Lys Ala  Tyr Phe Pro Arg Glu  Gly Val Phe Val Ser  Asn Gly Thr
        1055             1060              1065

Ser Trp  Phe Ile Thr Gln Arg  Asn Phe Tyr Ser Pro  Gln Ile Ile
        1070             1075              1080

Thr Thr  Asp Asn Thr Phe Val  Ala Gly Ser Cys Asp  Val Val Ile
        1085             1090              1095

Gly Ile  Ile Asn Asn Thr Val  Tyr Asp Pro Leu Gln  Pro Glu Leu
        1100             1105              1110

Asp Ser  Phe Lys Glu Glu Leu  Asp Lys Tyr Phe Lys  Asn His Thr
        1115             1120              1125

Ser Pro  Asp Val Asp Leu Gly  Asp Ile Ser Gly Ile  Asn Ala Ser
        1130             1135              1140

Val Val  Asn Ile Gln Lys Glu  Ile Asp Arg Leu Asn  Glu Val Ala
        1145             1150              1155

Lys Asn  Leu Asn Glu Ser Leu  Ile Asp Leu Gln Glu  Leu Gly Lys
        1160             1165              1170

Tyr Glu  Gln Tyr Ile Lys Trp  Pro Trp Tyr Val Trp  Leu Gly Phe
        1175             1180              1185
```

-continued

```
Ile Ala Gly Leu Ile Ala Ile Val Met Val Thr Ile Leu Leu Cys
    1190            1195                1200

Cys Met Thr Ser Cys Cys Ser Cys Leu Lys Gly Ala Cys Ser Cys
    1205            1210                1215

Gly Ser Cys Cys Lys Phe Asp Glu Asp Asp Ser Glu Pro Val Leu
    1220            1225                1230

Lys Gly Val Lys Leu His Tyr Thr
    1235            1240

<210> SEQ ID NO 326
<211> LENGTH: 1241
<212> TYPE: PRT
<213> ORGANISM: Artificial Sequence
<220> FEATURE:
<223> OTHER INFORMATION: Synthetic construct

<400> SEQUENCE: 326

Met Lys Val Leu Ile Phe Ala Leu Leu Phe Ser Leu Ala Lys Ala Gln
1               5                   10                  15

Glu Gly Cys Gly Ile Ile Ser Arg Lys Pro Gln Pro Lys Met Glu Lys
            20                  25                  30

Val Ser Ser Arg Arg Gly Val Tyr Tyr Asn Asp Ile Phe Arg
        35                  40                  45

Ser Asp Val Leu His Leu Thr Gln Asp Tyr Phe Leu Pro Phe Asp Ser
50                  55                  60

Asn Leu Thr Gln Tyr Phe Ser Leu Asn Ile Asp Ser Asn Lys Tyr Thr
65                  70                  75                  80

Tyr Phe Asp Asn Pro Ile Leu Asp Phe Gly Asp Gly Val Tyr Phe Ala
                85                  90                  95

Ala Thr Glu Lys Ser Asn Val Ile Arg Gly Trp Ile Phe Gly Ser Ser
            100                 105                 110

Phe Asp Asn Thr Thr Gln Ser Ala Ile Ile Val Asn Asn Ser Thr His
        115                 120                 125

Ile Ile Ile Arg Val Cys Asn Phe Asn Leu Cys Lys Glu Pro Met Tyr
130                 135                 140

Thr Val Ser Lys Gly Thr Gln Gln Ser Ser Trp Val Tyr Gln Ser Ala
145                 150                 155                 160

Phe Asn Cys Thr Tyr Asp Arg Val Glu Lys Ser Phe Gln Leu Asp Thr
                165                 170                 175

Ala Pro Lys Thr Gly Asn Phe Lys Asp Leu Arg Glu Tyr Val Phe Lys
            180                 185                 190

Asn Arg Asp Gly Phe Leu Ser Val Tyr Gln Thr Tyr Thr Ala Val Asn
        195                 200                 205

Leu Pro Arg Gly Phe Pro Ala Gly Phe Ser Val Leu Arg Pro Ile Leu
    210                 215                 220

Lys Leu Pro Phe Gly Ile Asn Ile Thr Ser Tyr Arg Val Val Met Thr
225                 230                 235                 240

Met Phe Ser Gln Phe Asn Ser Asn Phe Leu Pro Glu Ser Ala Ala Tyr
                245                 250                 255

Tyr Val Gly Asn Leu Lys Tyr Thr Thr Phe Met Leu Ser Phe Asn Glu
            260                 265                 270

Asn Gly Thr Ile Thr Asp Ala Val Asp Cys Ser Gln Asn Pro Leu Ala
        275                 280                 285

Glu Leu Lys Cys Thr Ile Lys Asn Phe Asn Val Ser Lys Gly Ile Tyr
    290                 295                 300
```

```
Gln Thr Ser Asn Phe Arg Val Thr Pro Thr Gln Glu Val Val Arg Phe
305                 310                 315                 320

Pro Asn Ile Thr Asn Arg Cys Pro Phe Asp Lys Val Phe Asn Ala Ser
                325                 330                 335

Arg Phe Pro Asn Val Tyr Ala Trp Glu Arg Thr Lys Ile Ser Asp Cys
            340                 345                 350

Val Ala Asp Tyr Thr Val Leu Tyr Asn Ser Thr Ser Phe Ser Thr Phe
        355                 360                 365

Lys Cys Tyr Gly Val Ser Pro Ser Lys Leu Ile Asp Leu Cys Phe Thr
    370                 375                 380

Ser Val Tyr Ala Asp Thr Phe Leu Ile Arg Ser Ser Glu Val Arg Gln
385                 390                 395                 400

Val Ala Pro Gly Glu Thr Gly Val Ile Ala Asp Tyr Asn Tyr Lys Leu
                405                 410                 415

Pro Asp Asp Phe Thr Gly Cys Val Ile Ala Trp Asn Thr Ala Gln Gln
            420                 425                 430

Asp Gln Gly Gln Tyr Tyr Arg Ser Tyr Arg Lys Glu Lys Leu Lys
        435                 440                 445

Pro Phe Glu Arg Asp Leu Ser Ser Asp Glu Asn Gly Val Tyr Thr Leu
    450                 455                 460

Ser Thr Tyr Asp Phe Tyr Pro Ser Ile Pro Val Glu Tyr Gln Ala Thr
465                 470                 475                 480

Arg Val Val Val Leu Ser Phe Glu Leu Leu Asn Ala Pro Ala Thr Val
                485                 490                 495

Cys Gly Pro Lys Leu Ser Thr Gln Leu Val Lys Asn Gln Cys Val Asn
            500                 505                 510

Phe Asn Phe Asn Gly Leu Arg Gly Thr Gly Val Leu Thr Thr Ser Ser
        515                 520                 525

Lys Arg Phe Gln Ser Phe Gln Gln Phe Gly Arg Asp Thr Ser Asp Phe
    530                 535                 540

Thr Asp Ser Val Arg Asp Pro Gln Thr Leu Glu Ile Leu Asp Ile Ser
545                 550                 555                 560

Pro Cys Ser Phe Gly Gly Val Ser Val Ile Thr Pro Gly Thr Asn Ala
                565                 570                 575

Ser Ser Glu Val Ala Val Leu Tyr Gln Asp Val Asn Cys Thr Asp Val
            580                 585                 590

Pro Thr Ser Ile His Ala Asp Gln Leu Thr Pro Ala Trp Arg Val Tyr
        595                 600                 605

Ser Thr Gly Val Asn Val Phe Gln Thr Gln Ala Gly Cys Leu Ile Gly
    610                 615                 620

Ala Glu His Val Asn Ala Ser Tyr Glu Cys Asp Ile Pro Ile Gly Ala
625                 630                 635                 640

Gly Ile Cys Ala Ser Tyr His Thr Ala Ser Val Leu Arg Ser Thr Gly
                645                 650                 655

Gln Lys Ser Ile Val Ala Tyr Thr Met Ser Leu Gly Ala Glu Asn Ser
            660                 665                 670

Ile Ala Tyr Ala Asn Asn Ser Ile Ala Ile Pro Thr Asn Phe Ser Ile
        675                 680                 685

Ser Val Thr Thr Glu Val Met Pro Val Ser Ile Ala Lys Thr Ser Val
    690                 695                 700

Asp Cys Thr Met Tyr Ile Cys Gly Asp Ser Leu Glu Cys Ser Asn Leu
705                 710                 715                 720
```

-continued

Leu Leu Gln Tyr Gly Ser Phe Cys Thr Gln Leu Asn Arg Ala Leu Thr
            725                 730                 735
Gly Ile Ala Ile Glu Gln Asp Lys Asn Thr Gln Glu Val Phe Ala Gln
            740                 745                 750
Val Lys Gln Met Tyr Lys Thr Pro Ala Ile Lys Asp Phe Gly Gly Phe
            755                 760                 765
Asn Phe Ser Gln Ile Leu Pro Asp Pro Ser Lys Pro Thr Lys Arg Ser
            770                 775                 780
Phe Ile Glu Asp Leu Leu Phe Asn Lys Val Thr Leu Ala Asp Ala Gly
785                 790                 795                 800
Phe Met Lys Gln Tyr Gly Glu Cys Leu Gly Asp Ile Ser Ala Arg Asp
            805                 810                 815
Leu Ile Cys Ala Gln Lys Phe Asn Gly Leu Thr Val Leu Pro Pro Leu
            820                 825                 830
Leu Thr Asp Glu Met Ile Ala Ala Tyr Thr Ala Ala Leu Val Ser Gly
            835                 840                 845
Thr Ala Thr Ala Gly Trp Thr Phe Gly Ala Gly Ser Ala Leu Gln Ile
850                 855                 860
Pro Phe Ala Met Gln Met Ala Tyr Arg Phe Asn Gly Ile Gly Val Thr
865                 870                 875                 880
Gln Asn Val Leu Tyr Glu Asn Gln Lys Gln Ile Ala Asn Gln Phe Asn
            885                 890                 895
Lys Ala Ile Ser Gln Ile Gln Glu Ser Leu Thr Thr Thr Ser Thr Ala
            900                 905                 910
Leu Gly Lys Leu Gln Asp Val Val Asn Asp Asn Ala Gln Ala Leu Asn
            915                 920                 925
Thr Leu Val Lys Gln Leu Ser Ser Asn Phe Gly Ala Ile Ser Ser Val
930                 935                 940
Leu Asn Asp Ile Leu Ser Arg Leu Asp Lys Val Glu Ala Glu Val Gln
945                 950                 955                 960
Ile Asp Arg Leu Ile Thr Gly Arg Leu Gln Ser Leu Gln Thr Tyr Val
            965                 970                 975
Thr Gln Gln Leu Ile Arg Ala Ala Glu Ile Arg Ala Ser Ala Asn Leu
            980                 985                 990
Ala Ala Thr Lys Met Ser Glu Cys Val Leu Gly Gln Ser Lys Arg Val
            995                1000                1005
Asp Phe Cys Gly Lys Gly Tyr His Leu Met Ser Phe Pro Gln Ala
            1010                1015                1020
Ala Pro His Gly Val Val Phe Leu His Val Thr Tyr Val Pro Ser
            1025                1030                1035
Gln Glu Arg Asn Phe Thr Thr Ala Pro Ala Ile Cys His Glu Gly
            1040                1045                1050
Lys Ala Tyr Phe Pro Arg Glu Gly Val Phe Val Ser Asn Gly Thr
            1055                1060                1065
Ser Trp Phe Ile Thr Gln Arg Asn Phe Tyr Ser Pro Gln Ile Ile
            1070                1075                1080
Thr Thr Asp Asn Thr Phe Val Ala Gly Asn Cys Asp Val Val Ile
            1085                1090                1095
Gly Ile Ile Asn Asn Thr Val Tyr Asp Pro Leu Gln Pro Glu Leu
            1100                1105                1110
Asp Ser Phe Lys Glu Glu Leu Asp Lys Tyr Phe Lys Asn His Thr
            1115                1120                1125
Ser Pro Asp Val Asp Leu Gly Asp Ile Ser Gly Ile Asn Ala Ser

```
                 1130                1135                1140

Val Val  Asn Ile Gln Lys  Glu Ile Asp Arg  Leu Asn Glu Val Ala
             1145                 1150                1155

Lys Asn  Leu Asn Glu Ser  Leu Ile Asp Leu  Gln Glu Leu Gly Lys
             1160                 1165                1170

Tyr Glu  Gln Tyr Ile Lys  Trp Pro Trp Tyr  Val Trp Leu Gly Phe
             1175                 1180                1185

Ile Ala  Gly Leu Ile Ala  Ile Val Met Val  Thr Ile Leu Leu Cys
             1190                 1195                1200

Cys Met  Thr Ser Cys Cys  Ser Cys Leu Lys  Gly Ala Cys Ser Cys
             1205                 1210                1215

Gly Ser  Cys Cys Lys Phe  Asp Glu Asp Ser  Glu Pro Val Leu
             1220                 1225                1230

Lys Gly  Val Lys Leu His  Tyr Thr
             1235                 1240

<210> SEQ ID NO 327
<211> LENGTH: 1264
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
```

```
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(105)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (128)..(129)
<223> OTHER INFORMATION: Xaa can be any naturally occurring amino acid
<220> FEATURE:
<221> NAME/KEY: misc_feature
<222> LOCATION: (131)..(133)
<223> OTHER INFORMATION: Xaa can be any naturally occurring amino acid
<220> FEATURE:
<221> NAME/KEY: misc_feature
<222> LOCATION: (135)..(153)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (159)..(165)
<223> OTHER INFORMATION: Xaa can be any naturally occurring amino acid
<220> FEATURE:
<221> NAME/KEY: misc_feature
<222> LOCATION: (167)..(168)
<223> OTHER INFORMATION: Xaa can be any naturally occurring amino acid
```

```
<220> FEATURE:
<221> NAME/KEY: misc_feature
<222> LOCATION: (170)..(172)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (191)..(194)
<223> OTHER INFORMATION: Xaa can be any naturally occurring amino acid
<220> FEATURE:
<221> NAME/KEY: misc_feature
<222> LOCATION: (196)..(204)
<223> OTHER INFORMATION: Xaa can be any naturally occurring amino acid
<220> FEATURE:
<221> NAME/KEY: misc_feature
<222> LOCATION: (206)..(207)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (212)..(213)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (217)..(219)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (228)..(253)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (262)..(264)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (269)..(271)
<223> OTHER INFORMATION: Xaa can be any naturally occurring amino acid
<220> FEATURE:
<221> NAME/KEY: misc_feature
<222> LOCATION: (278)..(278)
```

```
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (283)..(285)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (298)..(300)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (314)..(318)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (330)..(331)
<223> OTHER INFORMATION: Xaa can be any naturally occurring amino acid
<220> FEATURE:
<221> NAME/KEY: misc_feature
<222> LOCATION: (336)..(337)
<223> OTHER INFORMATION: Xaa can be any naturally occurring amino acid
<220> FEATURE:
<221> NAME/KEY: misc_feature
<222> LOCATION: (339)..(340)
<223> OTHER INFORMATION: Xaa can be any naturally occurring amino acid
<220> FEATURE:
<221> NAME/KEY: misc_feature
<222> LOCATION: (345)..(345)
<223> OTHER INFORMATION: Xaa can be any naturally occurring amino acid
<220> FEATURE:
<221> NAME/KEY: misc_feature
<222> LOCATION: (347)..(348)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (363)..(364)
<223> OTHER INFORMATION: Xaa can be any naturally occurring amino acid
<220> FEATURE:
<221> NAME/KEY: misc_feature
<222> LOCATION: (375)..(376)
<223> OTHER INFORMATION: Xaa can be any naturally occurring amino acid
<220> FEATURE:
<221> NAME/KEY: misc_feature
```

```
<222> LOCATION: (379)..(379)
<223> OTHER INFORMATION: Xaa can be any naturally occurring amino acid
<220> FEATURE:
<221> NAME/KEY: misc_feature
<222> LOCATION: (384)..(385)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (392)..(397)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (408)..(408)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:
<221> NAME/KEY: misc_feature
<222> LOCATION: (429)..(432)
<223> OTHER INFORMATION: Xaa can be any naturally occurring amino acid
<220> FEATURE:
<221> NAME/KEY: misc_feature
<222> LOCATION: (434)..(437)
<223> OTHER INFORMATION: Xaa can be any naturally occurring amino acid
<220> FEATURE:
<221> NAME/KEY: misc_feature
<222> LOCATION: (439)..(441)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid
<220> FEATURE:
<221> NAME/KEY: misc_feature
<222> LOCATION: (446)..(447)
<223> OTHER INFORMATION: Xaa can be any naturally occurring amino acid
<220> FEATURE:
<221> NAME/KEY: misc_feature
<222> LOCATION: (449)..(451)
<223> OTHER INFORMATION: Xaa can be any naturally occurring amino acid
<220> FEATURE:
<221> NAME/KEY: misc_feature
<222> LOCATION: (453)..(453)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (461)..(477)
<223> OTHER INFORMATION: Xaa can be any naturally occurring amino acid
<220> FEATURE:
<221> NAME/KEY: misc_feature
<222> LOCATION: (479)..(482)
<223> OTHER INFORMATION: Xaa can be any naturally occurring amino acid
<220> FEATURE:
<221> NAME/KEY: misc_feature
<222> LOCATION: (484)..(485)
<223> OTHER INFORMATION: Xaa can be any naturally occurring amino acid
<220> FEATURE:
```

```
<221> NAME/KEY: misc_feature
<222> LOCATION: (487)..(487)
<223> OTHER INFORMATION: Xaa can be any naturally occurring amino acid
<220> FEATURE:
<221> NAME/KEY: misc_feature
<222> LOCATION: (489)..(496)
<223> OTHER INFORMATION: Xaa can be any naturally occurring amino acid
<220> FEATURE:
<221> NAME/KEY: misc_feature
<222> LOCATION: (498)..(499)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (520)..(520)
<223> OTHER INFORMATION: Xaa can be any naturally occurring amino acid
<220> FEATURE:
<221> NAME/KEY: misc_feature
<222> LOCATION: (523)..(523)
<223> OTHER INFORMATION: Xaa can be any naturally occurring amino acid
<220> FEATURE:
<221> NAME/KEY: misc_feature
<222> LOCATION: (525)..(525)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid
<220> FEATURE:
<221> NAME/KEY: misc_feature
<222> LOCATION: (538)..(538)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (549)..(549)
<223> OTHER INFORMATION: Xaa can be any naturally occurring amino acid
<220> FEATURE:
<221> NAME/KEY: misc_feature
<222> LOCATION: (551)..(552)
<223> OTHER INFORMATION: Xaa can be any naturally occurring amino acid
<220> FEATURE:
<221> NAME/KEY: misc_feature
<222> LOCATION: (560)..(561)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (566)..(566)
<223> OTHER INFORMATION: Xaa can be any naturally occurring amino acid
<220> FEATURE:
<221> NAME/KEY: misc_feature
<222> LOCATION: (571)..(571)
<223> OTHER INFORMATION: Xaa can be any naturally occurring amino acid
<220> FEATURE:
<221> NAME/KEY: misc_feature
<222> LOCATION: (573)..(573)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (595)..(595)
<223> OTHER INFORMATION: Xaa can be any naturally occurring amino acid
```

-continued

```
<220> FEATURE:
<221> NAME/KEY: misc_feature
<222> LOCATION: (597)..(598)
<223> OTHER INFORMATION: Xaa can be any naturally occurring amino acid
<220> FEATURE:
<221> NAME/KEY: misc_feature
<222> LOCATION: (610)..(610)
<223> OTHER INFORMATION: Xaa can be any naturally occurring amino acid
<220> FEATURE:
<221> NAME/KEY: misc_feature
<222> LOCATION: (612)..(614)
<223> OTHER INFORMATION: Xaa can be any naturally occurring amino acid
<220> FEATURE:
<221> NAME/KEY: misc_feature
<222> LOCATION: (616)..(616)
<223> OTHER INFORMATION: Xaa can be any naturally occurring amino acid
<220> FEATURE:
<221> NAME/KEY: misc_feature
<222> LOCATION: (618)..(618)
<223> OTHER INFORMATION: Xaa can be any naturally occurring amino acid
<220> FEATURE:
<221> NAME/KEY: misc_feature
<222> LOCATION: (623)..(623)
<223> OTHER INFORMATION: Xaa can be any naturally occurring amino acid
<220> FEATURE:
<221> NAME/KEY: misc_feature
<222> LOCATION: (626)..(626)
<223> OTHER INFORMATION: Xaa can be any naturally occurring amino acid
<220> FEATURE:
<221> NAME/KEY: misc_feature
<222> LOCATION: (631)..(631)
<223> OTHER INFORMATION: Xaa can be any naturally occurring amino acid
<220> FEATURE:
<221> NAME/KEY: misc_feature
<222> LOCATION: (637)..(637)
<223> OTHER INFORMATION: Xaa can be any naturally occurring amino acid
<220> FEATURE:
<221> NAME/KEY: misc_feature
<222> LOCATION: (648)..(649)
<223> OTHER INFORMATION: Xaa can be any naturally occurring amino acid
<220> FEATURE:
<221> NAME/KEY: misc_feature
<222> LOCATION: (666)..(666)
<223> OTHER INFORMATION: Xaa can be any naturally occurring amino acid
<220> FEATURE:
<221> NAME/KEY: misc_feature
<222> LOCATION: (668)..(675)
<223> OTHER INFORMATION: Xaa can be any naturally occurring amino acid
<220> FEATURE:
<221> NAME/KEY: misc_feature
<222> LOCATION: (678)..(681)
<223> OTHER INFORMATION: Xaa can be any naturally occurring amino acid
<220> FEATURE:
<221> NAME/KEY: misc_feature
<222> LOCATION: (684)..(684)
<223> OTHER INFORMATION: Xaa can be any naturally occurring amino acid
<220> FEATURE:
<221> NAME/KEY: misc_feature
<222> LOCATION: (693)..(694)
<223> OTHER INFORMATION: Xaa can be any naturally occurring amino acid
<220> FEATURE:
<221> NAME/KEY: misc_feature
<222> LOCATION: (696)..(696)
<223> OTHER INFORMATION: Xaa can be any naturally occurring amino acid
<220> FEATURE:
<221> NAME/KEY: misc_feature
<222> LOCATION: (699)..(699)
<223> OTHER INFORMATION: Xaa can be any naturally occurring amino acid
<220> FEATURE:
<221> NAME/KEY: misc_feature
<222> LOCATION: (702)..(702)
<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
<221> NAME/KEY: misc_feature
<222> LOCATION: (713)..(713)
```

-continued

```
<223> OTHER INFORMATION: Xaa can be any naturally occurring amino acid
<220> FEATURE:
<221> NAME/KEY: misc_feature
<222> LOCATION: (717)..(718)
<223> OTHER INFORMATION: Xaa can be any naturally occurring amino acid
<220> FEATURE:
<221> NAME/KEY: misc_feature
<222> LOCATION: (722)..(723)
<223> OTHER INFORMATION: Xaa can be any naturally occurring amino acid
<220> FEATURE:
<221> NAME/KEY: misc_feature
<222> LOCATION: (726)..(726)
<223> OTHER INFORMATION: Xaa can be any naturally occurring amino acid
<220> FEATURE:
<221> NAME/KEY: misc_feature
<222> LOCATION: (730)..(730)
<223> OTHER INFORMATION: Xaa can be any naturally occurring amino acid
<220> FEATURE:
<221> NAME/KEY: misc_feature
<222> LOCATION: (738)..(738)
<223> OTHER INFORMATION: Xaa can be any naturally occurring amino acid
<220> FEATURE:
<221> NAME/KEY: misc_feature
<222> LOCATION: (741)..(741)
<223> OTHER INFORMATION: Xaa can be any naturally occurring amino acid
<220> FEATURE:
<221> NAME/KEY: misc_feature
<222> LOCATION: (752)..(752)
<223> OTHER INFORMATION: Xaa can be any naturally occurring amino acid
<220> FEATURE:
<221> NAME/KEY: misc_feature
<222> LOCATION: (759)..(759)
<223> OTHER INFORMATION: Xaa can be any naturally occurring amino acid
<220> FEATURE:
<221> NAME/KEY: misc_feature
<222> LOCATION: (763)..(763)
<223> OTHER INFORMATION: Xaa can be any naturally occurring amino acid
<220> FEATURE:
<221> NAME/KEY: misc_feature
<222> LOCATION: (767)..(767)
<223> OTHER INFORMATION: Xaa can be any naturally occurring amino acid
<220> FEATURE:
<221> NAME/KEY: misc_feature
<222> LOCATION: (770)..(770)
<223> OTHER INFORMATION: Xaa can be any naturally occurring amino acid
<220> FEATURE:
<221> NAME/KEY: misc_feature
<222> LOCATION: (774)..(774)
<223> OTHER INFORMATION: Xaa can be any naturally occurring amino acid
<220> FEATURE:
<221> NAME/KEY: misc_feature
<222> LOCATION: (779)..(779)
<223> OTHER INFORMATION: Xaa can be any naturally occurring amino acid
<220> FEATURE:
<221> NAME/KEY: misc_feature
<222> LOCATION: (784)..(785)
<223> OTHER INFORMATION: Xaa can be any naturally occurring amino acid
<220> FEATURE:
<221> NAME/KEY: misc_feature
<222> LOCATION: (787)..(787)
<223> OTHER INFORMATION: Xaa can be any naturally occurring amino acid
<220> FEATURE:
<221> NAME/KEY: misc_feature
<222> LOCATION: (801)..(801)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (825)..(825)
<223> OTHER INFORMATION: Xaa can be any naturally occurring amino acid
<220> FEATURE:
<221> NAME/KEY: misc_feature
<222> LOCATION: (830)..(830)
<223> OTHER INFORMATION: Xaa can be any naturally occurring amino acid
<220> FEATURE:
<221> NAME/KEY: misc_feature
```

```
<222> LOCATION: (835)..(836)
<223> OTHER INFORMATION: Xaa can be any naturally occurring amino acid
<220> FEATURE:
<221> NAME/KEY: misc_feature
<222> LOCATION: (859)..(859)
<223> OTHER INFORMATION: Xaa can be any naturally occurring amino acid
<220> FEATURE:
<221> NAME/KEY: misc_feature
<222> LOCATION: (861)..(861)
<223> OTHER INFORMATION: Xaa can be any naturally occurring amino acid
<220> FEATURE:
<221> NAME/KEY: misc_feature
<222> LOCATION: (863)..(863)
<223> OTHER INFORMATION: Xaa can be any naturally occurring amino acid
<220> FEATURE:
<221> NAME/KEY: misc_feature
<222> LOCATION: (866)..(866)
<223> OTHER INFORMATION: Xaa can be any naturally occurring amino acid
<220> FEATURE:
<221> NAME/KEY: misc_feature
<222> LOCATION: (869)..(870)
<223> OTHER INFORMATION: Xaa can be any naturally occurring amino acid
<220> FEATURE:
<221> NAME/KEY: misc_feature
<222> LOCATION: (873)..(873)
<223> OTHER INFORMATION: Xaa can be any naturally occurring amino acid
<220> FEATURE:
<221> NAME/KEY: misc_feature
<222> LOCATION: (875)..(875)
<223> OTHER INFORMATION: Xaa can be any naturally occurring amino acid
<220> FEATURE:
<221> NAME/KEY: misc_feature
<222> LOCATION: (883)..(883)
<223> OTHER INFORMATION: Xaa can be any naturally occurring amino acid
<220> FEATURE:
<221> NAME/KEY: misc_feature
<222> LOCATION: (913)..(913)
<223> OTHER INFORMATION: Xaa can be any naturally occurring amino acid
<220> FEATURE:
<221> NAME/KEY: misc_feature
<222> LOCATION: (920)..(920)
<223> OTHER INFORMATION: Xaa can be any naturally occurring amino acid
<220> FEATURE:
<221> NAME/KEY: misc_feature
<222> LOCATION: (923)..(924)
<223> OTHER INFORMATION: Xaa can be any naturally occurring amino acid
<220> FEATURE:
<221> NAME/KEY: misc_feature
<222> LOCATION: (927)..(927)
<223> OTHER INFORMATION: Xaa can be any naturally occurring amino acid
<220> FEATURE:
<221> NAME/KEY: misc_feature
<222> LOCATION: (930)..(931)
<223> OTHER INFORMATION: Xaa can be any naturally occurring amino acid
<220> FEATURE:
<221> NAME/KEY: misc_feature
<222> LOCATION: (933)..(934)
<223> OTHER INFORMATION: Xaa can be any naturally occurring amino acid
<220> FEATURE:
<221> NAME/KEY: misc_feature
<222> LOCATION: (945)..(945)
<223> OTHER INFORMATION: Xaa can be any naturally occurring amino acid
<220> FEATURE:
<221> NAME/KEY: misc_feature
<222> LOCATION: (1046)..(1046)
<223> OTHER INFORMATION: Xaa can be any naturally occurring amino acid
<220> FEATURE:
<221> NAME/KEY: misc_feature
<222> LOCATION: (1061)..(1061)
<223> OTHER INFORMATION: Xaa can be any naturally occurring amino acid
<220> FEATURE:
<221> NAME/KEY: misc_feature
<222> LOCATION: (1064)..(1064)
<223> OTHER INFORMATION: Xaa can be any naturally occurring amino acid
<220> FEATURE:
<221> NAME/KEY: misc_feature
<222> LOCATION: (1075)..(1075)
<223> OTHER INFORMATION: Xaa can be any naturally occurring amino acid
<220> FEATURE:
```

```
<221> NAME/KEY: misc_feature
<222> LOCATION: (1079)..(1079)
<223> OTHER INFORMATION: Xaa can be any naturally occurring amino acid
<220> FEATURE:
<221> NAME/KEY: misc_feature
<222> LOCATION: (1088)..(1088)
<223> OTHER INFORMATION: Xaa can be any naturally occurring amino acid
<220> FEATURE:
<221> NAME/KEY: misc_feature
<222> LOCATION: (1092)..(1092)
<223> OTHER INFORMATION: Xaa can be any naturally occurring amino acid
<220> FEATURE:
<221> NAME/KEY: misc_feature
<222> LOCATION: (1095)..(1095)
<223> OTHER INFORMATION: Xaa can be any naturally occurring amino acid
<220> FEATURE:
<221> NAME/KEY: misc_feature
<222> LOCATION: (1101)..(1102)
<223> OTHER INFORMATION: Xaa can be any naturally occurring amino acid
<220> FEATURE:
<221> NAME/KEY: misc_feature
<222> LOCATION: (1105)..(1105)
<223> OTHER INFORMATION: Xaa can be any naturally occurring amino acid
<220> FEATURE:
<221> NAME/KEY: misc_feature
<222> LOCATION: (1114)..(1114)
<223> OTHER INFORMATION: Xaa can be any naturally occurring amino acid
<220> FEATURE:
<221> NAME/KEY: misc_feature
<222> LOCATION: (1116)..(1116)
<223> OTHER INFORMATION: Xaa can be any naturally occurring amino acid
<220> FEATURE:
<221> NAME/KEY: misc_feature
<222> LOCATION: (1124)..(1124)
<223> OTHER INFORMATION: Xaa can be any naturally occurring amino acid
<220> FEATURE:
<221> NAME/KEY: misc_feature
<222> LOCATION: (1172)..(1172)
<223> OTHER INFORMATION: Xaa can be any naturally occurring amino acid
<220> FEATURE:
<221> NAME/KEY: misc_feature
<222> LOCATION: (1207)..(1207)
<223> OTHER INFORMATION: Xaa can be any naturally occurring amino acid
<220> FEATURE:
<221> NAME/KEY: misc_feature
<222> LOCATION: (1219)..(1219)
<223> OTHER INFORMATION: Xaa can be any naturally occurring amino acid
<220> FEATURE:
<221> NAME/KEY: misc_feature
<222> LOCATION: (1224)..(1224)
<223> OTHER INFORMATION: Xaa can be any naturally occurring amino acid
<220> FEATURE:
<221> NAME/KEY: misc_feature
<222> LOCATION: (1238)..(1238)
<223> OTHER INFORMATION: Xaa can be any naturally occurring amino acid

<400> SEQUENCE: 327

Xaa Xaa Xaa Xaa Xaa Cys Xaa Xaa Xaa Xaa Xaa Xaa Xaa Xaa Xaa
1               5                   10                  15

Xaa Xaa Xaa Xaa Xaa Ser Xaa Xaa Arg Gly Val Tyr Tyr Xaa Asp Xaa
            20                  25                  30

Xaa Phe Arg Ser Xaa Xaa Leu Xaa Xaa Thr Gln Asp Xaa Phe Leu Pro
        35                  40                  45

Phe Xaa Ser Asn Xaa Thr Xaa Xaa Xaa Xaa Xaa Xaa Xaa Xaa Xaa
    50                  55                  60

Xaa Xaa Xaa Xaa Xaa Phe Xaa Asn Pro Xaa Xaa Xaa Phe Xaa Asp Gly
65                  70                  75                  80

Xaa Tyr Phe Ala Xaa Thr Glu Lys Ser Asn Xaa Xaa Arg Gly Trp Xaa
            85                  90                  95

Phe Gly Xaa Xaa Xaa Xaa Xaa Xaa Xaa Gln Ser Xaa Xaa Ile Xaa Asn
            100                 105                 110
```

-continued

```
Asn Xaa Thr Xaa Xaa Xaa Ile Xaa Xaa Cys Xaa Phe Xaa Xaa Cys Xaa
        115                 120                 125

Xaa Pro Xaa Xaa Xaa Val Xaa Xaa Xaa Xaa Xaa Xaa Xaa Xaa Xaa Xaa
    130                 135                 140

Xaa Xaa Xaa Xaa Xaa Xaa Xaa Xaa Xaa Ala Xaa Asn Cys Thr Xaa Xaa
145                 150                 155                 160

Xaa Xaa Xaa Xaa Xaa Phe Xaa Xaa Asp Xaa Xaa Xaa Lys Xaa Gly Asn
                165                 170                 175

Phe Lys Xaa Leu Arg Glu Xaa Val Phe Lys Asn Xaa Asp Gly Xaa Xaa
            180                 185                 190

Xaa Xaa Tyr Xaa Xaa Xaa Xaa Xaa Xaa Xaa Xaa Xaa Arg Xaa Xaa Pro
        195                 200                 205

Xaa Gly Phe Xaa Xaa Leu Xaa Pro Xaa Xaa Xaa Leu Pro Xaa Gly Ile
    210                 215                 220

Asn Ile Thr Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Ala Ala Tyr
                245                 250                 255

Xaa Val Gly Xaa Leu Xaa Xaa Xaa Thr Phe Xaa Leu Xaa Xaa Xaa Glu
            260                 265                 270

Asn Gly Thr Ile Thr Xaa Ala Xaa Asp Cys Xaa Xaa Xaa Pro Leu Xaa
        275                 280                 285

Glu Xaa Lys Cys Xaa Xaa Lys Xaa Phe Xaa Xaa Xaa Lys Gly Ile Tyr
    290                 295                 300

Gln Thr Ser Asn Phe Arg Val Xaa Pro Xaa Xaa Xaa Xaa Xaa Arg Phe
305                 310                 315                 320

Pro Asn Ile Thr Asn Xaa Cys Pro Phe Xaa Xaa Val Phe Asn Ala Xaa
                325                 330                 335

Xaa Phe Xaa Xaa Val Tyr Ala Trp Xaa Arg Xaa Xaa Ile Ser Xaa Cys
            340                 345                 350

Val Ala Asp Tyr Xaa Val Leu Tyr Asn Ser Xaa Xaa Phe Ser Thr Phe
        355                 360                 365

Lys Cys Tyr Gly Val Ser Xaa Xaa Lys Leu Xaa Asp Leu Cys Phe Xaa
    370                 375                 380

Xaa Val Tyr Ala Asp Xaa Phe Xaa Xaa Xaa Xaa Xaa Xaa Val Arg Gln
385                 390                 395                 400

Xaa Ala Pro Gly Xaa Thr Gly Xaa Ile Ala Asp Tyr Asn Tyr Lys Leu
                405                 410                 415

Pro Asp Asp Phe Xaa Gly Cys Val Xaa Ala Trp Asn Xaa Xaa Xaa Xaa
            420                 425                 430

Asp Xaa Xaa Xaa Xaa Gly Xaa Xaa Xaa Tyr Xaa Tyr Arg Xaa Xaa Arg
        435                 440                 445

Xaa Xaa Xaa Leu Xaa Pro Phe Glu Arg Asp Xaa Ser Xaa Xaa Xaa Xaa
    450                 455                 460

Xaa Xaa Xaa Xaa Xaa Xaa Xaa Xaa Xaa Xaa Xaa Xaa Xaa Asn Xaa Xaa
465                 470                 475                 480

Xaa Xaa Leu Xaa Xaa Tyr Xaa Phe Xaa Xaa Xaa Xaa Xaa Xaa Xaa Xaa
                485                 490                 495

Gln Xaa Xaa Arg Val Val Val Leu Ser Phe Glu Leu Leu Xaa Ala Pro
            500                 505                 510

Ala Thr Val Cys Gly Pro Lys Xaa Ser Thr Xaa Leu Xaa Lys Asn Xaa
        515                 520                 525

Cys Val Asn Phe Asn Phe Asn Gly Leu Xaa Gly Thr Gly Val Leu Thr
```

-continued

```
    530                 535                 540

Xaa Ser Xaa Lys Xaa Phe Xaa Xaa Phe Gln Gln Phe Gly Arg Asp Xaa
545                 550                 555                 560

Xaa Asp Xaa Thr Asp Xaa Val Arg Asp Pro Xaa Thr Xaa Glu Ile Leu
                565                 570                 575

Asp Ile Xaa Pro Cys Ser Phe Gly Gly Val Ser Val Ile Thr Pro Gly
            580                 585                 590

Thr Asn Xaa Ser Xaa Xaa Val Ala Val Leu Tyr Gln Asp Val Asn Cys
        595                 600                 605

Thr Xaa Val Xaa Xaa Xaa Ile Xaa Ala Xaa Gln Leu Thr Pro Xaa Trp
    610                 615                 620

Arg Xaa Tyr Ser Thr Gly Xaa Asn Val Phe Gln Thr Xaa Ala Gly Cys
625                 630                 635                 640

Leu Ile Gly Ala Glu His Val Xaa Xaa Ser Tyr Glu Cys Asp Ile Pro
                645                 650                 655

Ile Gly Ala Gly Ile Cys Ala Ser Tyr Xaa Thr Xaa Xaa Xaa Xaa Xaa
            660                 665                 670

Xaa Xaa Xaa Arg Ser Xaa Xaa Xaa Xaa Ser Ile Xaa Ala Tyr Thr Met
        675                 680                 685

Ser Leu Gly Ala Xaa Xaa Ser Xaa Ala Tyr Xaa Asn Asn Xaa Ile Ala
    690                 695                 700

Ile Pro Thr Asn Phe Xaa Ile Ser Xaa Thr Thr Glu Xaa Xaa Pro Val
705                 710                 715                 720

Ser Xaa Xaa Lys Thr Xaa Val Asp Cys Xaa Met Tyr Ile Cys Gly Asp
                725                 730                 735

Ser Xaa Glu Cys Xaa Asn Leu Leu Leu Gln Tyr Gly Ser Phe Cys Xaa
            740                 745                 750

Gln Leu Asn Arg Ala Leu Xaa Gly Ile Ala Xaa Glu Gln Asp Xaa Asn
        755                 760                 765

Thr Xaa Glu Val Phe Xaa Gln Val Lys Gln Xaa Tyr Lys Thr Pro Xaa
    770                 775                 780

Xaa Lys Xaa Phe Gly Gly Phe Asn Phe Ser Gln Ile Leu Pro Asp Pro
785                 790                 795                 800

Xaa Lys Pro Xaa Lys Arg Ser Phe Ile Glu Asp Leu Leu Phe Asn Lys
                805                 810                 815

Val Thr Leu Ala Asp Ala Gly Phe Xaa Lys Gln Tyr Gly Xaa Cys Leu
            820                 825                 830

Gly Asp Xaa Xaa Ala Arg Asp Leu Ile Cys Ala Gln Lys Phe Asn Gly
        835                 840                 845

Leu Thr Val Leu Pro Pro Leu Leu Thr Asp Xaa Met Xaa Ala Xaa Tyr
    850                 855                 860

Thr Xaa Ala Leu Xaa Xaa Gly Thr Xaa Thr Xaa Gly Trp Thr Phe Gly
865                 870                 875                 880

Ala Gly Xaa Ala Leu Gln Ile Pro Phe Ala Met Gln Met Ala Tyr Arg
                885                 890                 895

Phe Asn Gly Ile Gly Val Thr Gln Asn Val Leu Tyr Glu Asn Gln Lys
            900                 905                 910

Xaa Ile Ala Asn Gln Phe Asn Xaa Ala Ile Xaa Xaa Ile Gln Xaa Ser
        915                 920                 925

Leu Xaa Xaa Thr Xaa Xaa Ala Leu Gly Lys Leu Gln Asp Val Val Asn
    930                 935                 940

Xaa Asn Ala Gln Ala Leu Asn Thr Leu Val Lys Gln Leu Ser Ser Asn
945                 950                 955                 960
```

Phe Gly Ala Ile Ser Ser Val Leu Asn Asp Ile Leu Ser Arg Leu Asp
            965                 970                 975

Lys Val Glu Ala Glu Val Gln Ile Asp Arg Leu Ile Thr Gly Arg Leu
        980                 985                 990

Gln Ser Leu Gln Thr Tyr Val Thr Gln Gln Leu Ile Arg Ala Ala Glu
    995                 1000                1005

Ile Arg Ala Ser Ala Asn Leu Ala Ala Thr Lys Met Ser Glu Cys
1010                1015                1020

Val Leu Gly Gln Ser Lys Arg Val Asp Phe Cys Gly Lys Gly Tyr
    1025                1030                1035

His Leu Met Ser Phe Pro Gln Xaa Ala Pro His Gly Val Val Phe
    1040                1045                1050

Leu His Val Thr Tyr Val Pro Xaa Gln Glu Xaa Asn Phe Thr Thr
    1055                1060                1065

Ala Pro Ala Ile Cys His Xaa Gly Lys Ala Xaa Phe Pro Arg Glu
    1070                1075                1080

Gly Val Phe Val Xaa Asn Gly Thr Xaa Trp Phe Xaa Thr Gln Arg
    1085                1090                1095

Asn Phe Xaa Xaa Pro Gln Xaa Ile Thr Thr Asp Asn Thr Phe Val
    1100                1105                1110

Xaa Gly Xaa Cys Asp Val Val Ile Gly Ile Xaa Asn Asn Thr Val
    1115                1120                1125

Tyr Asp Pro Leu Gln Pro Glu Leu Asp Ser Phe Lys Glu Glu Leu
    1130                1135                1140

Asp Lys Tyr Phe Lys Asn His Thr Ser Pro Asp Val Asp Leu Gly
    1145                1150                1155

Asp Ile Ser Gly Ile Asn Ala Ser Val Val Asn Ile Gln Xaa Glu
    1160                1165                1170

Ile Asp Arg Leu Asn Glu Val Ala Lys Asn Leu Asn Glu Ser Leu
    1175                1180                1185

Ile Asp Leu Gln Glu Leu Gly Lys Tyr Glu Gln Tyr Ile Lys Trp
    1190                1195                1200

Pro Trp Tyr Xaa Trp Leu Gly Phe Ile Ala Gly Leu Ile Ala Ile
    1205                1210                1215

Xaa Met Val Thr Ile Xaa Leu Cys Cys Met Thr Ser Cys Cys Ser
    1220                1225                1230

Cys Leu Lys Gly Xaa Cys Ser Cys Gly Ser Cys Cys Lys Phe Asp
    1235                1240                1245

Glu Asp Asp Ser Glu Pro Val Leu Lys Gly Val Lys Leu His Tyr
    1250                1255                1260

Thr

<210> SEQ ID NO 328
<211> LENGTH: 223
<212> TYPE: PRT
<213> ORGANISM: Artificial Sequence
<220> FEATURE:
<223> OTHER INFORMATION: Synthetic construct

<400> SEQUENCE: 328

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
 50                  55                  60

Ser Pro Thr Lys Leu Asn Asp Leu Cys Phe Thr Asn Val Tyr Ala Asp
 65                  70                  75                  80

Ser Phe Val Ile Arg Gly Asp Glu Val Arg Gln Ile Ala Pro Gly Gln
                 85                  90                  95

Thr Gly Lys Ile Ala Asp Tyr Asn Tyr Lys Leu Pro Asp Asp Phe Thr
             100                 105                 110

Gly Cys Val Ile Ala Trp Asn Ser Asn Asn Leu Asp Ser Lys Val Gly
             115                 120                 125

Gly Asn Tyr Asn Tyr Leu Tyr Arg Leu Phe Arg Lys Ser Asn Leu Lys
130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
             180                 185                 190

Val Val Leu Ser Phe Glu Leu Leu His Ala Pro Ala Thr Val Cys Gly
             195                 200                 205

Pro Lys Lys Ser Thr Asn Leu Val Lys Asn Lys Cys Val Asn Phe
         210                 215                 220

<210> SEQ ID NO 329
<211> LENGTH: 223
<212> TYPE: PRT
<213> ORGANISM: Artificial Sequence
<220> FEATURE:
<223> OTHER INFORMATION: Synthetic construct

<400> SEQUENCE: 329

Arg Val Gln Pro Thr Asp Ser Ile Val Arg Phe Pro Asn Ile Thr Asn
1               5                   10                  15

Leu Cys Pro Phe Gly Glu Val Phe Asn Ala Thr Thr Phe Ala Ser Val
             20                  25                  30

Tyr Ala Trp Asn Arg Lys Arg Ile Ser Asn Cys Val Ala Asp Tyr Ser
            35                  40                  45

Val Leu Tyr Asn Ser Thr Ser Phe Ser Thr Phe Lys Cys Tyr Gly Val
 50                  55                  60

Ser Pro Thr Lys Leu Asn Asp Leu Cys Phe Thr Asn Val Tyr Ala Asp
 65                  70                  75                  80

Ser Phe Val Ile Thr Gly Asp Glu Val Arg Gln Ile Ala Pro Gly Gln
                 85                  90                  95

Thr Gly Lys Ile Ala Asp Tyr Asn Tyr Lys Leu Pro Asp Asp Phe Thr
             100                 105                 110

Gly Cys Val Ile Ala Trp Asn Ser Lys His Ile Asp Ala Lys Glu Gly
             115                 120                 125

Gly Asn Phe Asn Tyr Leu Tyr Arg Leu Phe Arg Lys Ala Asn Leu Lys
130                 135                 140

Pro Phe Glu Arg Asp Ile Ser Thr Glu Ile Tyr Gln Ala Gly Ser Lys
145                 150                 155                 160

Pro Cys Asn Gly Gln Thr Gly Leu Asn Cys Tyr Tyr Pro Leu Tyr Arg
                165                 170                 175

-continued

```
Tyr Gly Phe Tyr Pro Thr Asp Gly Val Gly His Gln Pro Tyr Arg Val
            180                 185                 190

Val Val Leu Ser Phe Glu Leu Leu Asn Ala Pro Ala Thr Val Cys Gly
        195                 200                 205

Pro Lys Lys Ser Thr Asn Leu Val Lys Asn Lys Cys Val Asn Phe
210                 215                 220

<210> SEQ ID NO 330
<211> LENGTH: 222
<212> TYPE: PRT
<213> ORGANISM: Artificial Sequence
<220> FEATURE:
<223> OTHER INFORMATION: Synthetic construct

<400> SEQUENCE: 330

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220

<210> SEQ ID NO 331
<211> LENGTH: 222
<212> TYPE: PRT
<213> ORGANISM: Artificial Sequence
<220> FEATURE:
<223> OTHER INFORMATION: Synthetic construct

<400> SEQUENCE: 331

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Arg Ile Ser Asn Cys Val Ala Asp Tyr Ser
        35                  40                  45
```

Val Leu Tyr Asn Ser Thr Ser Phe Ser Thr Phe Lys Cys Tyr Gly Val
 50                  55                  60

Ser Ala Thr Lys Leu Asn Asp Leu Cys Phe Ser Asn Val Tyr Ala Asp
 65                  70                  75                  80

Ser Phe Val Val Lys Gly Asp Val Arg Gln Ile Ala Pro Gly Gln
                 85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
                115                 120                 125

Gly Asn Tyr Asn Tyr Lys Tyr Arg Tyr Leu Arg His Gly Lys Leu Arg
            130                 135                 140

Pro Phe Glu Arg Asp Ile Ser Asn Val Pro Phe Ser Pro Asp Gly Lys
145                 150                 155                 160

Pro Cys Thr Pro Pro Ala Pro Asn Cys Tyr Trp Pro Leu Asn Gly Tyr
                165                 170                 175

Gly Phe Tyr Thr Thr Ser Gly Ile Gly Tyr Gln Pro Tyr Arg Val Val
                180                 185                 190

Val Leu Ser Phe Glu Leu Leu Asn Ala Pro Ala Thr Val Cys Gly Pro
            195                 200                 205

Lys Leu Ser Thr Asp Leu Ile Lys Asn Gln Cys Val Asn Phe
            210                 215                 220

<210> SEQ ID NO 332
<211> LENGTH: 205
<212> TYPE: PRT
<213> ORGANISM: Artificial Sequence
<220> FEATURE:
<223> OTHER INFORMATION: Synthetic construct

<400> SEQUENCE: 332

Arg Val Ser Pro Thr Gln Glu Val Ile Arg Phe Pro Asn Ile Thr Asn
1               5                   10                  15

Arg Cys Pro Phe Asp Lys Val Phe Asn Ala Thr Arg Phe Pro Asn Val
                20                  25                  30

Tyr Ala Trp Glu Arg Thr Lys Ile Ser Asp Cys Val Ala Asp Tyr Thr
            35                  40                  45

Val Leu Tyr Asn Ser Thr Ser Phe Ser Thr Phe Lys Cys Tyr Gly Val
 50                  55                  60

Ser Pro Ser Lys Leu Ile Asp Leu Cys Phe Thr Ser Val Tyr Ala Asp
 65                  70                  75                  80

Thr Phe Leu Ile Arg Ser Ser Glu Val Arg Gln Val Ala Pro Gly Glu
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Ala Lys His Asp Thr Gly Asn Tyr
                115                 120                 125

Tyr Tyr Arg Ser His Arg Lys Thr Lys Leu Lys Pro Phe Glu Arg Asp
            130                 135                 140

Leu Ser Ser Asp Asp Gly Asn Gly Val Tyr Thr Leu Ser Thr Tyr Asp
145                 150                 155                 160

Phe Asn Pro Asn Val Pro Val Ala Tyr Gln Ala Thr Arg Val Val Val
                165                 170                 175

Leu Ser Phe Glu Leu Leu Asn Ala Pro Ala Thr Val Cys Gly Pro Lys
            180                 185                 190

```
Leu Ser Thr Glu Leu Val Lys Asn Gln Cys Val Asn Phe
        195                 200                 205
```

<210> SEQ ID NO 333
<211> LENGTH: 204
<212> TYPE: PRT
<213> ORGANISM: Artificial Sequence
<220> FEATURE:
<223> OTHER INFORMATION: Synthetic construct

<400> SEQUENCE: 333

```
Arg Val Ser Pro Thr Gln Glu Val Ile Arg Phe Pro Asn Ile Thr Asn
1               5                   10                  15

Arg Cys Pro Phe Asp Lys Val Phe Asn Ala Thr Arg Phe Pro Asn Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Ser Ser Glu Val Arg Gln Val Ala Pro Gly Glu
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Ala Lys Gln Asp Gln Gly Gln Tyr
        115                 120                 125

Tyr Tyr Arg Ser His Arg Lys Thr Lys Leu Lys Pro Phe Glu Arg Asp
    130                 135                 140

Leu Ser Ser Asp Glu Asn Gly Val Arg Thr Leu Ser Thr Tyr Asp Phe
145                 150                 155                 160

Tyr Pro Ser Val Pro Val Ala Tyr Gln Ala Thr Arg Val Val Val Leu
                165                 170                 175

Ser Phe Glu Leu Leu Asn Ala Pro Ala Thr Val Cys Gly Pro Lys Leu
            180                 185                 190

Ser Thr Gln Leu Val Lys Asn Gln Cys Val Asn Phe
        195                 200
```

<210> SEQ ID NO 334
<211> LENGTH: 204
<212> TYPE: PRT
<213> ORGANISM: Artificial Sequence
<220> FEATURE:
<223> OTHER INFORMATION: Synthetic construct

<400> SEQUENCE: 334

```
Arg Val Thr Pro Thr Gln Glu Val Val Arg Phe Pro Asn Ile Thr Asn
1               5                   10                  15

Arg Cys Pro Phe Asp Lys Val Phe Asn Ala Ser Arg Phe Pro Asn Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Ser Ser Glu Val Arg Gln Val Ala Pro Gly Glu
```

85                  90                  95
Thr Gly Val Ile Ala Asp Tyr Asn Tyr Lys Leu Pro Asp Asp Phe Thr
                100                 105                 110
Gly Cys Val Ile Ala Trp Asn Thr Ala Gln Gln Asp Gln Gly Gln Tyr
            115                 120                 125
Tyr Tyr Arg Ser Tyr Arg Lys Glu Lys Leu Lys Pro Phe Glu Arg Asp
        130                 135                 140
Leu Ser Ser Asp Glu Asn Gly Val Tyr Thr Leu Ser Thr Tyr Asp Phe
145                 150                 155                 160
Tyr Pro Ser Ile Pro Val Glu Tyr Gln Ala Thr Arg Val Val Leu
                165                 170                 175
Ser Phe Glu Leu Leu Asn Ala Pro Ala Thr Val Cys Gly Pro Lys Leu
                180                 185                 190
Ser Thr Gln Leu Val Lys Asn Gln Cys Val Asn Phe
            195                 200

<210> SEQ ID NO 335
<211> LENGTH: 223
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:

-continued

```
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (83)..(88)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (120)..(123)
<223> OTHER INFORMATION: Xaa can be any naturally occurring amino acid
<220> FEATURE:
<221> NAME/KEY: misc_feature
<222> LOCATION: (125)..(128)
<223> OTHER INFORMATION: Xaa can be any naturally occurring amino acid
<220> FEATURE:
<221> NAME/KEY: misc_feature
<222> LOCATION: (130)..(132)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (137)..(138)
<223> OTHER INFORMATION: Xaa can be any naturally occurring amino acid
<220> FEATURE:
<221> NAME/KEY: misc_feature
<222> LOCATION: (140)..(142)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (152)..(168)
<223> OTHER INFORMATION: Xaa can be any naturally occurring amino acid
<220> FEATURE:
<221> NAME/KEY: misc_feature
<222> LOCATION: (170)..(173)
<223> OTHER INFORMATION: Xaa can be any naturally occurring amino acid
<220> FEATURE:
<221> NAME/KEY: misc_feature
<222> LOCATION: (175)..(176)
<223> OTHER INFORMATION: Xaa can be any naturally occurring amino acid
```

```
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (180)..(187)
<223> OTHER INFORMATION: Xaa can be any naturally occurring amino acid
<220> FEATURE:
<221> NAME/KEY: misc_feature
<222> LOCATION: (189)..(190)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid

<400> SEQUENCE: 335

Arg Val Xaa Pro Xaa Xaa Xaa Xaa Arg Phe Pro Asn Ile Thr Asn
1               5                   10                  15

Xaa Cys Pro Phe Xaa Xaa Xaa Phe Asn Ala Xaa Xaa Phe Xaa Xaa Val
                20                  25                  30

Tyr Ala Trp Xaa Arg Xaa Xaa Ile Ser Xaa Cys Val Ala Asp Tyr Xaa
            35                  40                  45

Val Leu Tyr Asn Ser Xaa Xaa Phe Ser Thr Phe Lys Cys Tyr Gly Val
50                  55                  60

Ser Xaa Xaa Lys Leu Xaa Asp Leu Cys Phe Xaa Xaa Val Tyr Ala Asp
65                  70                  75                  80

Xaa Phe Xaa Xaa Xaa Xaa Xaa Val Arg Gln Xaa Ala Pro Gly Xaa
                85                  90                  95

Thr Gly Xaa Ile Ala Asp Tyr Asn Tyr Lys Leu Pro Asp Asp Phe Xaa
            100                 105                 110

Gly Cys Val Xaa Xaa Trp Asn Xaa Xaa Xaa Asp Xaa Xaa Xaa Xaa
            115                 120                 125

Gly Xaa Xaa Xaa Tyr Xaa Tyr Arg Xaa Xaa Arg Xaa Xaa Xaa Leu Xaa
            130                 135                 140

Pro Phe Glu Arg Asp Xaa Ser Xaa Xaa Xaa Xaa Xaa Xaa Xaa Xaa
145                 150                 155                 160

Xaa Xaa Xaa Xaa Xaa Xaa Xaa Xaa Asn Xaa Xaa Xaa Xaa Leu Xaa Xaa
            165                 170                 175

Tyr Xaa Phe Xaa Xaa Xaa Xaa Xaa Xaa Xaa Gln Xaa Xaa Arg Val
            180                 185                 190

Val Val Leu Ser Phe Glu Leu Leu Xaa Ala Pro Ala Thr Val Cys Gly
            195                 200                 205

Pro Lys Xaa Ser Thr Xaa Leu Xaa Lys Asn Xaa Cys Val Asn Phe
210                 215                 220

<210> SEQ ID NO 336
```

```
<211> LENGTH: 72
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(50)
<223> OTHER INFORMATION: Xaa can be any naturally occurring amino acid
<220> FEATURE:
<221> NAME/KEY: misc_feature
<222> LOCATION: (52)..(55)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid

<400> SEQUENCE: 336

Asn Xaa Xaa Xaa Xaa Asp Xaa Xaa Xaa Gly Xaa Xaa Xaa Tyr Xaa
1               5                   10                  15

Tyr Arg Xaa Xaa Arg Xaa Xaa Xaa Leu Xaa Pro Phe Glu Arg Asp Xaa
            20                  25                  30

Ser Xaa Xaa Xaa Xaa Xaa Xaa Xaa Xaa Xaa Xaa Xaa Xaa Xaa Xaa
        35                  40                  45

Xaa Xaa Asn Xaa Xaa Xaa Xaa Leu Xaa Xaa Tyr Xaa Phe Xaa Xaa Xaa
    50                  55                  60

Xaa Xaa Xaa Xaa Xaa Gln Xaa Xaa
65                  70
```